United States Patent
Labelle et al.

(10) Patent No.: US 9,221,801 B2
(45) Date of Patent: Dec. 29, 2015

(54) INHIBITORS OF HISTONE DEMETHYLASES

(71) Applicant: EpiTherapeutics ApS, København N (DK)

(72) Inventors: Marc Labelle, Basking Ridge, NJ (US); Thomas Boesen, København Ø (DK); Qasim Khan, Winnipeg (CA); Ramkrishna Reddy Vakiti, Winnipeg (CA); Utpal Sharma, Brampton (CA); Ying Yang, Winnipeg (CA); Mukund Mehrotra, Winnipeg (CA); Neerja Saraswat, Winnipeg (CA); Farman Ullah, Winnipeg (CA)

(73) Assignee: Epitherapeutics APS, Copenhagen N (DK)

( * ) Notice: Subject to any disclaimer, the term of this patent is extended or adjusted under 35 U.S.C. 154(b) by 0 days.

(21) Appl. No.: 14/472,065

(22) Filed: Aug. 28, 2014

(65) Prior Publication Data
US 2014/0371214 A1    Dec. 18, 2014

Related U.S. Application Data

(63) Continuation of application No. 14/381,556, filed as application No. PCT/EP2014/053674 on Feb. 26, 2014.

(60) Provisional application No. 61/770,058, filed on Feb. 27, 2013, provisional application No. 61/770,065, filed on Feb. 27, 2013, provisional application No. 61/770,067, filed on Feb. 27, 2013, provisional application No. 61/931,126, filed on Jan. 24, 2014.

(30) Foreign Application Priority Data

Feb. 27, 2013  (DK) ............................. 2013 70113
Feb. 27, 2013  (DK) ............................. 2013 70114
Feb. 27, 2013  (DK) ............................. 2013 70115

(51) Int. Cl.
| | |
|---|---|
| C07D 413/04 | (2006.01) |
| C07D 213/56 | (2006.01) |
| C07D 401/04 | (2006.01) |
| C07D 401/12 | (2006.01) |
| C07D 213/38 | (2006.01) |
| C07D 213/48 | (2006.01) |
| C07C 55/06 | (2006.01) |
| C07C 309/30 | (2006.01) |

(52) U.S. Cl.
CPC .............. *C07D 413/04* (2013.01); *C07C 55/06* (2013.01); *C07C 309/30* (2013.01); *C07D 213/38* (2013.01); *C07D 213/48* (2013.01); *C07D 213/56* (2013.01); *C07D 401/04* (2013.01); *C07D 401/12* (2013.01)

(58) Field of Classification Search
CPC ............................. C07D 413/04; C07D 213/56
USPC .................. 514/228.8, 357; 546/336; 544/71
See application file for complete search history.

(56) References Cited

U.S. PATENT DOCUMENTS

| | | | |
|---|---|---|---|
| 4,100,274 A | 7/1978 | Dutta et al. | |
| 4,636,505 A | 1/1987 | Tucker | |
| 4,659,516 A | 4/1987 | Bowler et al. | |
| 5,010,099 A | 4/1991 | Gunasekera et al. | |
| 5,843,901 A | 12/1998 | Roeske | |
| 5,874,438 A | 2/1999 | Schohe-Loop et al. | |
| 6,194,181 B1 | 2/2001 | Hofmann et al. | |
| 2008/0177082 A1 | 7/2008 | Wallace et al. | |
| 2009/0246274 A1 | 10/2009 | Bateman et al. | |
| 2011/0224190 A1 | 9/2011 | Huang et al. | |
| 2012/0282179 A1 | 11/2012 | Aftab et al. | |
| 2014/0171432 A1 | 6/2014 | Kanouni et al. | |
| 2014/0371195 A1 | 12/2014 | Labelle et al. | |

(Continued)

FOREIGN PATENT DOCUMENTS

| | | |
|---|---|---|
| CN | 102585150 | 7/2012 |
| EP | 2578569 | 4/2013 |
| WO | WO 98/08849 | 3/1998 |

(Continued)

OTHER PUBLICATIONS

Cloos et al., "Erasing the Methyl Mark: Histone Demethylases at the Center of Cellular Differentiation and Disease" Genes & Development 22, 1115-1140, 2008.

Morton, C. and Houghton, P. "Establishment of Human Tumor Xenografts in Immunodeficient Mice", Nature Protocols, 2(2) 247-250, 2007.

Queguiner, G. and Pastour, P. "Reduction Selective des Pyridinedicarboxylates d'Ethyle Dissymetriques" Comptes Rendus des Seances de l'Academie des Sciences Chimiques (1969), 268(2), 182-185 (with English translation).

(Continued)

*Primary Examiner* — Kahsay Habte
(74) *Attorney, Agent, or Firm* — Cooley LLP; Heidi A. Erlacher; Ivor R. Elrifi

(57) ABSTRACT

Compounds of the form

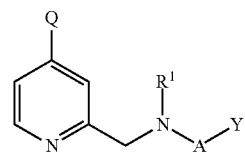

In which Q is selected from —CH═NR$^{12}$, —W, —CH$_2$NHR$^{13}$, —CH═O and —CH(OR$^{17}$)$_2$ capable of modulating the activity of histone demethylases (HDMEs), which are useful for prevention and/or treatment of diseases in which genomic dysregulation is involved in the pathogenesis, such as e.g. cancer and formulations and methods of use of such compounds.

23 Claims, No Drawings

(56) References Cited

U.S. PATENT DOCUMENTS

| | | |
|---|---|---|
| 2015/0065522 A1 | 3/2015 | Albrecht et al. |
| 2015/0203453 A1 | 7/2015 | Labelle |

FOREIGN PATENT DOCUMENTS

| | | |
|---|---|---|
| WO | WO 98/10121 | 3/1998 |
| WO | WO 98/22461 | 5/1998 |
| WO | WO 98/25929 | 6/1998 |
| WO | WO 99/17804 | 4/1999 |
| WO | WO 99/43653 | 9/1999 |
| WO | WO 00/31247 | 6/2000 |
| WO | WO 02/22577 | 3/2002 |
| WO | WO 2008/002671 | 1/2008 |
| WO | WO 2010/056549 | 5/2010 |
| WO | WO 2011/017583 | 2/2011 |
| WO | WO 2012/007007 | 1/2012 |
| WO | WO 2012/042042 | 4/2012 |
| WO | WO 2012/071469 | 5/2012 |
| WO | WO 2012/135113 | 10/2012 |
| WO | WO 2013/025805 | 2/2013 |
| WO | WO 2013/123411 | 8/2013 |
| WO | WO 2014/053491 | 4/2014 |
| WO | WO 2014/089364 | 6/2014 |
| WO | WO 2014/100818 | 6/2014 |
| WO | WO 2014/151106 | 9/2014 |
| WO | WO 2015/153498 | 10/2015 |

OTHER PUBLICATIONS

Roy, M. et al. "AlphaLISA JMJD2A Histone H3-Lysine 9 Demethylase Assay", PerkinElmer Technical Note: AlphaLISA #12, Apr. 2011, 2 pages.

Rehse, K. and Mletzko, S. "Antiaggregatorische Und Anticoagulante Eigenschaften Von Oligoaminen. 8. Mitt.: Oligoamine Mit N-Heterocyclischen Teilstrukturen" Arch Pharm. (Weinheim), (1988) 321(9) p. 533-536 (with English translation).

Lohse, B. et al. "Inhibitors of Histone Demethylases", Bioorganic & Medicinal Chemistry, (2011) 19(12) p. 3625-3636.

Chang, K. et al. "Inhibition of Histone Demethylases by 4-Carboxy-2.2'-Bipyridyl Compounds" ChemMedChem, (2011) 6(5) p. 759-764.

International Search Report issued by the International Searching Authority for PCT/EP2013/070457, mailed Jan. 14, 2014, 4 pages.

International Search Report issued by the International Searching Authority for PCT/EP2014/053674, mailed Mar. 31, 2014, 4 pages.

Written Opinion issued by the International Searching Authority for PCT/EP2013/070457, mailed Jan. 14, 2014, 7 pages.

International Search Report issued by the International Searching Authority for PCT/US2015/023407, mailed Jul. 31, 2015, 4 pages.

Written Opinion issued by the International Searching Authority for PCT/US2015/023407, mailed Jul. 31, 2015, 10 pages.

Written Opinion issued by the International Searching Authority for PCT/EP2014/053674, mailed Aug. 27, 2015, 7 pages.

International Search Report and Written Opinion issued by the International Searching Authority for Application No. PCT/US2015/046921, dated Nov. 2, 2015, 13 pages.

SEQUENCE LISTING

```
<160> NUMBER OF SEQ ID NOS: 6

<210> SEQ ID NO 1
<211> LENGTH: 19
<212> TYPE: PRT
<213> ORGANISM: Homo sapiens
<220> FEATURE:
<221> NAME/KEY: MOD_RES
<222> LOCATION: 1
<223> OTHER INFORMATION: Biotin
<220> FEATURE:
<221> NAME/KEY: MOD_RES
<222> LOCATION: 9
<223> OTHER INFORMATION: trimethylated

<400> SEQUENCE: 1

Ala Arg Thr Lys Gln Thr Ala Arg Lys Ser Thr Gly Gly Lys Ala Pro
1               5                   10                  15

Arg Lys Gln

<210> SEQ ID NO 2
<211> LENGTH: 19
<212> TYPE: PRT
<213> ORGANISM: Homo sapiens
<220> FEATURE:
<221> NAME/KEY: MOD_RES
<222> LOCATION: 1
<223> OTHER INFORMATION: Biotin
<220> FEATURE:
<221> NAME/KEY: MOD_RES
<222> LOCATION: 9
<223> OTHER INFORMATION: dimethylated

<400> SEQUENCE: 2

Ala Arg Thr Lys Gln Thr Ala Arg Lys Ser Thr Gly Gly Lys Ala Pro
1               5                   10                  15

Arg Lys Gln

<210> SEQ ID NO 3
<211> LENGTH: 19
<212> TYPE: PRT
<213> ORGANISM: Homo sapiens
<220> FEATURE:
<221> NAME/KEY: MOD_RES
<222> LOCATION: 1
<223> OTHER INFORMATION: Biotin
<220> FEATURE:
<221> NAME/KEY: MOD_RES
<222> LOCATION: 9
<223> OTHER INFORMATION: methylation

<400> SEQUENCE: 3

Ala Arg Thr Lys Gln Thr Ala Arg Lys Ser Thr Gly Gly Lys Ala Pro
1               5                   10                  15

Arg Lys Gln

<210> SEQ ID NO 4
<211> LENGTH: 21
<212> TYPE: PRT
<213> ORGANISM: Homo sapiens
```

```
<220> FEATURE:
<221> NAME/KEY: MOD_RES
<222> LOCATION: 4
<223> OTHER INFORMATION: trimethylated
<220> FEATURE:
<221> NAME/KEY: MOD_RES
<222> LOCATION: 21
<223> OTHER INFORMATION: Biotin

<400> SEQUENCE: 4

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 5
<211> LENGTH: 21
<212> TYPE: PRT
<213> ORGANISM: Homo sapiens
<220> FEATURE:
<221> NAME/KEY: MOD_RES
<222> LOCATION: 1
<223> OTHER INFORMATION: Biotin
<220> FEATURE:
<221> NAME/KEY: MOD_RES
<222> LOCATION: 7
<223> OTHER INFORMATION: trimethylated

<400> SEQUENCE: 5

Ala Thr Lys Ala Ala Arg Lys Ser Ala Pro Ala Thr Gly Gly Val Lys
1               5                   10                  15

Lys Pro His Arg Tyr
            20

<210> SEQ ID NO 6
<211> LENGTH: 22
<212> TYPE: PRT
<213> ORGANISM: Homo sapiens
<220> FEATURE:
<221> NAME/KEY: MOD_RES
<222> LOCATION: 11
<223> OTHER INFORMATION: dimethylated
<220> FEATURE:
<221> NAME/KEY: MOD_RES
<222> LOCATION: 22
<223> OTHER INFORMATION: Biotin

<400> SEQUENCE: 6

Arg Lys Ala Ala Pro Ala Thr Gly Gly Val Lys Lys Pro His Arg Tyr
1               5                   10                  15

Arg Pro Gly Thr Val Lys
            20
```

INHIBITORS OF HISTONE DEMETHYLASES

RELATED APPLICATIONS

This application is a Continuation of U.S. application Ser. No. 14/381,556, filed Aug. 27, 2014, which is a U.S. National Phase application of International Application No. PCT/EP2014/053674, filed Feb. 26, 2014, which claims priority to and the benefit of U.S. Provisional Application No. 61/770,058, filed Feb. 27, 2013; Danish Application No. PA 2013 70113, filed Feb. 27, 2013; U.S. Provisional Application No. 61/770,065, filed Feb. 27, 2013; Danish Application No. PA 2013 70114, filed Feb. 27, 2013, U.S. Provisional Application No. 61/770,067, filed Feb. 27, 2013; Danish Application No. PA 2013 70115, filed Feb. 27, 2013; and U.S. Provisional Application No. 61/931,126, filed Jan. 24, 2014; the contents of each of which are incorporated by reference herein in their entireties.

INCORPORATION BY REFERENCE OF SEQUENCE LISTING

The contents of the text file named "EPIZ002C01US_SEQ_LIST.txt", which was created on Aug. 28, 2014 and is 2.4 KB in size, are hereby incorporated by reference in their entireties.

FIELD OF THE INVENTION

The present invention relates to compounds capable of modulating the activity of histone demethylases (HDMEs), which compounds are useful for the prevention and/or the treatment of diseases in which genomic dysregulation is involved in the pathogenesis, such as e.g. cancer.

BACKGROUND OF THE INVENTION

The DNA of eukaryotic cells is packaged into chromatin by winding of the DNA around histone proteins to form nucleosomes, the basic unit of chromatin. One of the important functions of chromatin is to determine regions of active and silenced transcription by changing the ordered chromatin structure. Such changes have profound effects on cellular function since they affect fundamental processes as differentiation, proliferation and apoptosis, and are often referred collectively to as "epigenetic" since they can lead to heritable changes that do not involve changes in gene sequences (Quina, A. S. et al. (2006), Biochem. Pharmacol. 72; 1563-1569)

These highly controlled chromatin changes are mediated by alterations histone proteins associated with DNA in the nucleosome. Most notably, the N-terminal histone tail of Histone H3 and histone H4 are subject to such covalent changes, which include changes in methylation, acetylation, phosphorylation and ubiquitination. The addition or removal of these groups on histones is mediated by specific enzymes, e.g. histone methyl transferases and histone demethylases for methyl groups, histone acetyltransferases and histone deacetylases for acetyl groups, etc. In the event that the activity or expression of these "epigenetic" enzymes is not correctly controlled and regulated it may lead to disease. Cancer, in particular, is an area of high importance in relation to dysregulated epigenetic enzyme activity due to the role of epigenetics in cell differentiation, proliferation and apoptosis, but epigenetics may also play a role in other diseases like metabolic, inflammatory, neurodegenerative and cardiovascular diseases. Therefore the selective modulation of aberrant action of epigenetic enzymes may hold great promise for the treatment of human disease (Kelly, T. K. et al. (2010), Nat. Biotechnol. 28; 1069-1078, and Cloos, P. a. C. et al. (2008), Genes. Dev. 22; 115-1140).

Methylation and demethylation of lysine residues on the histone H3 tail constitute important epigenetic marks delineating transcriptionally active and inactive chromatin. For example, methylation of lysine 9 on histone H3 (H3K9) is usually associated with epigenetically silenced chromatin (Fischle, W., et. al. (2003), Curr. Opinion Cell Biol. 15, 172-83; Margueron, R., et al. (2005), Curr. Opinion Genet. Dev. 15, 163-76) while methylation of lysine 4 on histone 3 is associated with transcriptionally active chromatin. Similarly, the lysine 27 histone H3 (H3K27) mark is repressive in its di- and tri-methylated states whereas the lysine 36 histone H3 mark is found in association with gene activation (Barski, A. et al. (2007), Cell, 129, 823-37; Vakoc, C. et al. (2006) Mol. Cell. Biol. 26, 9185-95; Wagner, E. J. & Carpenter, P. B. (2012) Nature Mol. Cell Biol 13, 115-26). There are, however, many exemptions from these general rules of association between methylation states of epigenetic marks and the effect they have on transcription.

As documented by studies of the SUV39H1 knockout mouse, loss of the tri-methyl variant of the H3K9 mark results in chromosomal aberrations and predisposes to cancer (Peters, A. H. et al., Cell 107, 323-37, 2001). The JMJD2C protein (KDM4C, GASC1) has been identified as an eraser of the H3K9 mark (a histone demethylase) and may therefore promote cancer if its expression and activity is not tightly controlled (Cloos, P. et al. (2006), Nature 442, 307-11; Klose, R. J. et al. (2006), Nature 442, 312-16; Liu, G. et al. (2009), Oncogene 28, 4491-500). For example, JMJD2C has been shown to induce transformed phenotypes like growth factor independent growth, anchorage independent growth and mammosphere formation, if it is overexpressed in cells (Liu, G. et al. (2009), Oncogene 28, 4491-500). These findings are supported by the overexpression of JMJD2C in a range of human tumours like squamous cell carcinoma, metastatic lung carcinoma, prostate cancer, breast cancer and several others (Yang, Z. Q. et al. (2000) Cancer Res. 60, 4735-39; Yang, Z. Q. et al. (2001) Jpn. J. Cancer Res. 92, 423-28; Hu, N. et al. (2005) Cancer Res. 65, 2542-46; Liu, G. et al. (2009) Oncogene 28, 4491-500; Wissmann, M. et al. (2007) Nat. Cell Biol. 9, 347-53), indicating the potential importance of JMJD2C as an oncogene.

The JMJD2A protein (KDM4A, JHDM3A) shows similar properties to JMJD2C. JMJD2A shows high sequence identity to JMJD2C in its JmjC catalytic domain, is an eraser of the H3K9 mark and has also been shown to be overexpressed in prostate cancer (Cloos, P. Et al., Nature 442, 307-11, 2006). JMJD2A has been shown to interact with the estrogen receptor alpha (ER-alpha) and overexpression of JMJD2A enhances estrogen-dependent transcription and the downregulation of JMJD2A reduced transcription of a seminal ER-alpha target gene, cyclin D1 (Kawazu et al., (2011) PLoS One 6; Berry et al., (2012) Int J Oncol 41). Additionally, it has been shown that catalytically inactive JMJD2A is compromised in its ability to stimulate ER-alpha mediated transcription, suggesting that inhibitors of JMJD2A may be beneficial for the treatment of ER-alpha positive breast tumours (Berry et al., (2012) Int J Oncol 41).

Likewise, an eraser of the tri-methyl variant of the H3K4 mark, JARID1B (KDM5B, PLU1) has also been identified as potential oncogene. In cancer JARID1B most likely acts as a repressor of tumour repressor genes via removal of the H3K4 tri-methylation leading to decreased transcriptional activation in the affected chromatin regions. The oncogenic potential of JARID1B is demonstrated by its stimulation of proliferation in cell lines and further validated by shRNA knockdown studies of JARID1B expression showing inhibition of proliferation in MCF7 human breast cancer cells, in SW780 and RT4 bladder cancer cells, in A549 and LC319 lung cancer cells and in 4T1 mouse tumour cells in vitro and/or in mouse xenograft experiments (Yamane K. et al. (2007), Mol. Cell 25, 801-12; Hayami S. et al. (2010) Mol. Cancer 9, 59; Catchpole S et al. (2011), Int. J. Oncol. 38, 1267-77). Finally, JARID1B is overexpressed in prostate cancer and is associated with malignancy and poor prognosis (Xiang Y. et al. (2007) PNAS 104).

JARID1A (KDM5A, RBP2) is also an eraser of the tri- and di-methyl variant of the H3K4 mark. JARID1A is overexpressed in gastric cancer (Zeng et al., (2010) Gastroenterology 138) and its gene is amplified in cervix carcinoma (Hidalgo et al, (2005) BMC Cancer 5). It has been suggested that JARID1A is fine-tuning progesterone receptor expression control by estrogens (Stratmann and Haendler (2011) FEBS J 278). Together with JARID1B, JARID1A has been implicated in the maintenance of a slow-growing population of cancer cells that are required for continuous tumor growth and that are resistant to cytotoxic and targeted therapy (Roesch, et al, (2010) Cell 141; Sharma, et al., (2010) Cell 141). JARID1A is required for the tumor initiation and progression in Rb+/– and Men1-defective mice (Lin, et al., (2011) PNAS 108). Data from Pasini show that JARID1A binds to Polycomb group protein target genes which are involved in regulating important cellular processes such as embryogenesis, cell proliferation, and stem cell self-renewal through the transcriptional repression of genes determining cell fate decisions (Pasini et al., (2008) Genes & Dev 22). Additionally, JARID1A were also shown to binds the PRC2 complex and being regulator of PRC2 target genes (Pasini et al., (2008) Genes & Dev 22).

Another potential oncogene, an eraser of the di-methyl variant of the H3K36 mark, JHDM1B (KDM2B, FBXL10) has been shown to be highly expressed in human cancers (Tzatsos A et al. (2009), PNAS 106 (8), 2641-6; He, J. et al. (2011), Blood 117 (14), 3869-80). Knock-down of FBXL10 causes senescence in mouse embryonic fibroblasts (MEFs), which can be rescued by expression of catalytic active (but not catalytic inactive) JHDM1B (Pfau R et al. (2008), PNAS 105(6), 1907-12; He J et al. (2008), Nat Struct Mol Biol 15, 1169-75). JHDM1B demethylates H3K36me2 on the tumor-suppressor gene Ink4b (p15$^{Ink4b}$), and thereby silences the expression of this senescence-mediating gene in MEFs and in leukemic cells (He, J. et al. (2008), Nat Struct Mol Biol 15, 1169-75; He, J. et al. (2011), Blood 117 (14), 3869-80). The catalytic dependency of JHDM1B is further shown by He et al. as catalytic activity is required for development of leukemia in a mouse AML model.

Inhibitors of the histone demethylase class of epigenetic enzymes, and in particular the potential oncogenes JARID1B, JARID1A, JMJD2C, JMJD2A, and JHDM1B, would present a novel approach for intervention in cancers and other proliferative diseases. Being one of the most devastating diseases, affecting millions of people worldwide, there remains a high need for efficacious and specific compounds against cancer.

PCT/EP2013/070457 discloses histone demethylase (HDME) inhibitors or activity modulators.

Embodiments of the invention provide novel series of compounds capable of modulating the activity of histone demethylases, at least some of which compounds are useful for the prevention and/or the treatment of diseases in which genomic disregulation is involved in the pathogenesis, such as e.g. cancer. By way of the invention The inventors have surprisingly found that novel compounds of Formula (I) as defined herein can be used in the treatment of HDME dependent diseases by inhibiting HDMEs. Inhibiting HDMEs would provide a novel approach to the prevention and treatment of cancer and other proliferative diseases. Accordingly, it is an object of the present invention to provide compounds that when administered alone or optionally in combination with anti-neoplastic compounds, increases the efficacy of the treatment of HDME dependent diseases.

Accordingly, a first aspect of the present invention relates to a compound of the Formula (I)

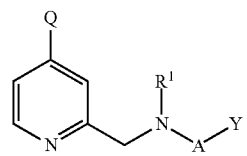

wherein
Q is selected from —CH=NR$^{12}$, —W, —CH$_2$NHR$^{13}$, —CH=O and —CH(OR$^{17}$)$_2$;
A is selected from —CHR$^2$C(O)—, C$_{1-8}$ alkylene, C$_{2-8}$ alkenylene, C$_{2-8}$ alkynylene, C$_{3-10}$ cycloalkylene, heterocyclylene, heteroarylene and arylene, which alkylene, alkenylene, alkynylene, cycloalkylene, heterocyclylene, heteroarylene and arylene may optionally be substituted with one or more R$^3$; with the proviso that when Q is —CH=O, A is not alkynylene;
Y is selected from —H, —NR$^6$R$^7$, C$_{1-8}$ alkyl, C$_{2-8}$ alkenyl, C$_{2-8}$ alkynyl, C$_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more R$^3$ and may form a cyclic structure with R$^2$; with the proviso that when Q is —CH=O, Y is not alkynyl;
R$^1$ is selected from —H, C$_{1-8}$ alkyl, C$_{2-8}$ alkenyl, C$_{2-8}$ alkynyl, C$_{3-10}$ cycloalkyl, which alkyl, alkenyl, alkynyl and cycloalkyl may be optionally substituted with one or more selected from —OH, aryl, C$_{1-6}$ alkoxy, heteroaryl, aryloxy, heteroaryloxy, F, and C$_{3-6}$ cycloalkyl; or more preferably is selected from —H and C$_{1-4}$ alkyl; or with -A-Y forms a nitrogen containing optionally substituted heterocyclic group where the optional substitution may be C$_{1-8}$ alkyl, C$_{2-8}$ alkenyl, C$_{2-8}$ alkynyl, or C$_{3-10}$ cycloalkyl, which alkyl, alkenyl, alkynyl and cycloalkyl may be optionally substituted with one or more selected from —OH, aryl, C$_{1-6}$ alkoxy, heteroaryl, aryloxy, heteroaryloxy, F, and C$_{3-6}$ cycloalkyl;
R$^2$ is selected from —H, C$_{1-8}$ alkyl, C$_{2-8}$ alkenyl, C$_{2-8}$ alkynyl, and C$_{3-10}$ cycloalkyl, which alkyl, alkenyl, alkynyl and cycloalkyl may be optionally substituted with one or more selected from —OH, aryl, C$_{1-6}$ alkoxy, heteroaryl, aryloxy, heteroaryloxy, F, and C$_{3-6}$ cycloalkyl, and may form a cyclic structure with Y;
each R$^3$ is independently selected from C$_{1-6}$ alkyl, C$_{1-4}$ fluoroalkyl, C$_{1-4}$ hydroxyalkyl, C$_{2-6}$ alkenyl, C$_{2-6}$ alkynyl, C$_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$, —Z—SO$_2$NR$^6$R$^7$ and —Z—COOR$^7$, wherein any heterocyclyl may be substituted with one or more R$^4$, and wherein any heteroaryl and any aryl may be substituted with one or more R$^5$;
Z is selected from a single bond, C$_{1-4}$ alkylene, heterocyclylene and C$_{3-6}$ cycloalkylene;

each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —N($R^1$)$_2$, carbamoyl, and —OH;

each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH;

each of $R^6$ and $R^7$ is independently selected from $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$; or, alternatively, $R^6$ and $R^7$ may together with the N-atom to which they are attached form an N-heterocyclic ring optionally substituted with one or more independently selected $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$; wherein any heterocyclyl may be further substituted with one or more $R^4$ as defined above, and wherein any heteroaryl and any aryl may be further substituted with one or more $R^5$ as defined above, and each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein any heterocyclyl may be substituted with one or more $R^4$ as defined above, and wherein any heteroaryl and any aryl may be substituted with one or more $R^5$ as defined above;

each of $R^{10}$ and $R^{11}$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more $R^4$ as defined above, and wherein any heteroaryl and any aryl may be substituted with one or more $R^5$ as defined above, or, alternatively, $R^{10}$ and $R^{11}$ may together with the N-atom to which they are attached form an optionally 5 to 7 membered, N-heterocyclic ring optionally substituted with one or more $R^4$ as defined above;

with the proviso that Y is not H when A is —CH$_2$—;

when Q is —CH=NR$^{12}$, R$^{12}$ is selected from $C_{1-10}$ alkyl, $C_{2-10}$ alkenyl, $C_{2-10}$ alkynyl, $C_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$ and —Z—COOR$^7$, which alkyl, alkenyl, alkynyl, cycloalkyl, heterocyclyl, heteroaryl and aryl may optionally be substituted with one or more $R^3$;

when Q is —CH$_2$NHR$^{13}$, R$^{13}$ is selected from hydrogen, —C(O)R$^7$, —C(O)C(O)R$^7$, —C(O)C(O)OR$^7$, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, and —Z-monocyclic-heteroaryl, which alkyl, alkenyl, alkynyl, cycloalkyl, heterocyclyl, and moncyclic-heteroaryl may optionally be substituted with one or more independently selected $R^8$, or is —CR$^{14}$R$^{15}$—NR$^6$R$^7$, —CR$^{14}$R$^{15}$CN, or —CR$^{14}$R$^{15}$OR$^7$, wherein each of $R^{14}$ and $R^{15}$ is independently selected from —H, $C_{1-8}$ alkyl, $C_{2-8}$ alkenyl, $C_{2-8}$ alkynyl, $C_{3-10}$ cycloalkyl, heterocyclyl, heteroaryl and aryl, and wherein $R^{14}$ and $R^{15}$ together with the intervening carbon atom may designate a $C_{3-10}$ cycloalkyl or $C_{5-10}$-cycloalkenyl ring, which alkyl, alkenyl, alkynyl, cycloalkyl (ring), cycloalkenyl ring, heterocyclyl, heteroaryl and aryl may optionally be substituted with one or more $R^3$;

when Q is W, W is selected from an 1,3-diaza-$C_{5-7}$-cycloalk-2-yl group which is N-substituted with $R^{16}$ and optionally further substituted with one or more $R^3$, and optionally containing one or two oxo groups; a 1,3-thiaza-$C_{5-7}$-cycloalk-2-yl group which is N-substituted with $R^{16}$ and optionally further substituted with one or more $R^3$ and optionally containing one or two oxo groups; an 1,3-oxaza-$C_{5-7}$-cycloalk-2-yl group which is N-substituted with $R^{16}$ and optionally further substituted with one or more $R^3$, and optionally containing one or two oxo groups, wherein in all three instances two $R^3$'s on the same carbon atom may together form a spiro group;

$R^{16}$ is selected from hydrogen, —C(O)R$^7$, —C(O)C(O)R$^7$ and —C(O)C(O)OR$^7$; when Q is —CH(OR$^{17}$)$_2$, each $R^{17}$ independently is $R^3$, or wherein two $R^{17}$ substituents together with the intervening —O—CH(-)—O— may form a heterocyclyl optionally substituted with one or more $R^3$ and containing up to two oxo groups;

or an isomer or a mixture of isomers thereof, or a pharmaceutically acceptable salt, or solvate or prodrug thereof.

It is considered to be probable that each of the groups Q is converted in vivo to produce the corresponding acid (Q=—C(O)OH) by processes which possibly include or consist of enzymatic processing. Accordingly, many or all of the compounds of this invention may act in vivo at least principally in the form of corresponding acid derivatives described in PCT/EP2013/070457. It is thought likely that the enzymatic processing takes place partly or entirely within cells into which the respective compound of the invention has penetrated. In view of this, it is probable that differences in activity in vitro seen in compounds of the invention that have the same -A-Y substituent but differ in the group Q are due to the influence of the different groups Q on cell penetration and/or the efficiency of conversion to the acid form within the cell. This tentative conclusion is based on detection of the corresponding acid within cells following administration of certain compounds according to the invention and molecular modelling of the interaction of the acids with relevant enzymes.

Accordingly, in an alternative aspect, the invention provides a compound of the general Formula

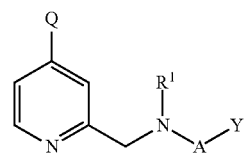

wherein $R^1$, A, and Y are as defined above or below herein and Q is a group that is converted to —COOH or COO$^-$ upon administration of said compound to a human, provided that Q is not an amide or an ester of such a —COOH group.

According to a first set of embodiments, the invention provides a compound of the Formula (I)

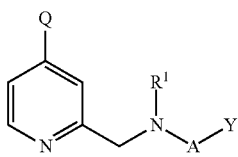

wherein
Q is selected from —CH=NR$^{12}$ and —W;
A is selected from —CHR$^2$C(O)—, C$_{1-8}$ alkylene, C$_{2-8}$ alkenylene, C$_{2-8}$ alkynylene, C$_{3-10}$ cycloalkylene, heterocyclylene, heteroarylene and arylene, which alkylene, alkenylene, alkynylene, cycloalkylene, heterocyclylene, heteroarylene and arylene may optionally be substituted with one or more R$^3$;
Y is selected from —H, —NR$^6$R$^7$, —OR$^7$, C$_{1-8}$ alkyl, C$_{2-8}$ alkenyl, C$_{2-8}$ alkynyl, C$_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more R$^3$;
R$^1$ is selected from —H and C$_{1-4}$ alkyl;
R$^2$ is selected from —H, C$_{1-8}$ alkyl, C$_{2-8}$ alkenyl, C$_{2-8}$ alkynyl, C$_{3-10}$ cycloalkyl, which alkyl, alkenyl, alkynyl and cycloalkyl may be optionally substituted with one or more selected from —OH, aryl, C$_{1-6}$ alkoxy, heteroaryl, aryloxy, heteroaryloxy, F, and C$_{3-6}$ cycloalkyl;
each R$^3$ is independently selected from C$_{1-6}$ alkyl, C$_{1-4}$ fluoroalkyl, C$_{1-4}$ hydroxyalkyl, C$_{2-6}$ alkenyl, C$_{2-6}$ alkynyl, C$_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$, —Z—SO$_2$NR$^6$R$^7$ and —Z—COOR$^7$, wherein any heterocyclyl may be substituted with one or more R$^4$, and wherein any heteroaryl and any aryl may be substituted with one or more R$^5$;
Z is selected from a single bond, C$_{1-4}$ alkylene, heterocyclylene and C$_{3-6}$ cycloalkylene;
each R$^4$ is independently selected from C$_{1-6}$ alkyl, C$_{1-4}$ fluoroalkyl, C$_{1-4}$ hydroxyalkyl, C$_{1-4}$ alkoxy, C$_{3-10}$ cycloalkyl, —N(R$^1$)$_2$, carbamoyl, and —OH;
each R$^5$ is independently selected from C$_{1-6}$ alkyl, C$_{1-4}$ fluoroalkyl, C$_{1-4}$ hydroxyalkyl, C$_{1-4}$ alkoxy, C$_{3-6}$ cycloalkyl, —CN, —F, —Cl, —Br, carbamoyl and —OH;
each of R$^6$ and R$^7$ is independently selected from —H, C$_{1-8}$ alkyl, C$_{1-4}$ fluoroalkyl, C$_{1-4}$ perfluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected R$^8$; or, alternatively, R$^6$ and R$^7$ may together with the N-atom to which they are attached form an N-heterocyclic ring optionally substituted with one or more independently selected R$^8$;
each R$^8$ is independently selected from C$_{1-6}$ alkyl, C$_{1-4}$ fluoroalkyl, C$_{1-4}$ hydroxyalkyl, C$_{2-6}$ alkenyl, C$_{2-6}$ alkynyl, C$_{3-10}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$, which alkyl, alkenyl, alkynyl, cycloalkyl, heterocyclics, heteroaryl and aryl may optionally be substituted with one or more selected from C$_{1-4}$ alkyl, C$_{1-4}$ fluoroalkyl, C$_{1-4}$ hydroxyalkyl, C$_{3-6}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$; wherein any heterocyclyl may be further substituted with one or more R$^4$ as defined above, and wherein any heteroaryl and any aryl may be further substituted with one or more R$^5$ as defined above, and each R$^9$ is independently selected from —H, C$_{1-8}$ alkyl, C$_{1-4}$ fluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, —Z-aryl, and —Z-heteroaryl, wherein any heterocyclyl may be substituted with one or more R$^4$ as defined above, and wherein any heteroaryl and any aryl may be substituted with one or more R$^5$ as defined above;
each of R$^{10}$ and R$^{11}$ is independently selected from —H, C$_{1-6}$ alkyl, C$_{1-4}$ fluoroalkyl, C$_{1-4}$ hydroxyalkyl, C$_{2-8}$ alkenyl, C$_{2-8}$ alkynyl, C$_{3-10}$ cycloalkyl, heterocyclyl, heteroaryl, and aryl, wherein any heterocyclyl may be substituted with one or more R$^4$ as defined above, and wherein any heteroaryl and any aryl may be substituted with one or more R$^5$ as defined above, or, alternatively, R$^{10}$ and R$^{11}$ may together with the N-atom to which they are attached form an N-heterocyclic ring optionally substituted with one or more R$^4$ as defined above;
R$^{12}$ is selected from C$_{1-10}$ alkyl, C$_{2-10}$ alkenyl, C$_{2-10}$ alkynyl, C$_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$ and —Z—COOR$^7$, which alkyl, alkenyl, alkynyl, cycloalkyl, heterocyclyl, heteroaryl and aryl may optionally be substituted with one or more R$^3$;
W is selected from an 1,3-diaza-C$_{5-7}$-cycloalk-2-yl group which is N-substituted with R$^{16}$ and optionally further substituted with one or more R$^3$, and an 1,3-oxaza-C$_{5-7}$-cycloalk-2-yl group which is N-substituted with R$^{16}$ and optionally further substituted with one or more R$^3$, wherein in both instances two R$^3$'s on the same carbon atom may together form a spiro group;
R$^{16}$ is selected from hydrogen, —C(O)R$^7$, and —C(O)C(O)R$^7$;
with the proviso that Y is not H when A is —CH$_2$—;
or an isomer or a mixture of isomers thereof, or a pharmaceutically acceptable salt, solvate or prodrug thereof.

According to a second set of embodiments, the invention provides a compound of the Formula (I)

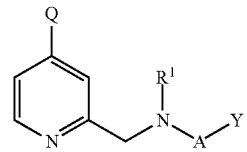

wherein
Q is —CH$_2$NHR$^{13}$;
A is selected from —CHR$^2$C(O)—, C$_{1-8}$ alkylene, C$_{2-8}$ alkenylene, C$_{2-8}$ alkynylene, C$_{3-10}$ cycloalkylene, heterocyclylene, heteroarylene and arylene, which alkylene, alkenylene, alkynylene, cycloalkylene, heterocyclylene, heteroarylene and arylene may optionally be substituted with one or more R$^3$;
Y is selected from —H, —NR$^6$R$^7$, —OR$^7$, C$_{1-8}$ alkyl, C$_{2-8}$ alkenyl, C$_{2-8}$ alkynyl, C$_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more R$^3$;
R$^1$ is selected from —H and C$_{1-4}$ alkyl;
R$^2$ is selected from —H, C$_{1-8}$ alkyl, C$_{2-8}$ alkenyl, C$_{2-8}$ alkynyl, C$_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl;

each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein any heterocyclyl may be substituted with one or more $R^4$, and wherein any heteroaryl and any aryl may be substituted with one or more $R^5$;

Z is selected from a single bond, $C_{1-4}$ alkylene, heterocyclylene and $C_{3-6}$ cycloalkylene;

each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —$N(R^1)_2$, carbamoyl, and —OH;

each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH;

each of $R^6$ and $R^7$ is independently selected from —H, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$; or, alternatively, $R^6$ and $R^7$ may together with the N-atom to which they are attached form an N-heterocyclic ring optionally substituted with one or more independently selected $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$; wherein any heterocyclyl may be further substituted with one or more $R^4$ as defined above, and wherein any heteroaryl and any aryl may be further substituted with one or more $R^5$ as defined above, and each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein any heterocyclyl may be substituted with one or more $R^4$ as defined above, and wherein any heteroaryl and any aryl may be substituted with one or more $R^5$ as defined above;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more $R^4$ as defined above, and wherein any heteroaryl and any aryl may be substituted with one or more $R^5$ as defined above, or, alternatively, $R^{10}$ and $R^{11}$ may together with the N-atom to which they are attached form an N-heterocyclic ring optionally substituted with one or more $R^4$ as defined above;

$R^{13}$ is selected from hydrogen, —C(O)$R^7$, —C(O)C(O)$R^7$, —$R^7$, —$CR^{14}R^{15}$—$NR^6R^7$, —$CR^{14}R^{15}$CN, —$CR^{14}R^{15}OR^7$, wherein each of $R^{14}$ and $R^{15}$ is independently selected from —H, $C_{1-8}$ alkyl, $C_{2-8}$ alkenyl, $C_{2-8}$ alkynyl, $C_{3-10}$ cycloalkyl, heterocyclyl, heteroaryl and aryl, and wherein $R^{14}$ and $R^{15}$ together with the intervening carbon atom may designate a $C_{3-10}$ cycloalkyl or $C_{5-10}$-cycloalkenyl ring, which alkyl, alkenyl, alkynyl, cycloalkyl (ring), cycloalkenyl ring, heterocyclyl, heteroaryl and aryl may optionally be substituted with one or more $R^3$;

with the proviso that Y is not H when A is —$CH_2$—;

or an isomer or a mixture of isomers thereof, or a pharmaceutically acceptable salt, solvate or prodrug thereof.

Optionally, Q is required to be different from -A-Y. Optionally, at least one of Q and -A-Y is not of the form -alkylene-NH-alkylene-aryl, or more specifically is not of the form -alkylene-NH-alkylene-phenyl. For example, one or both of Q and -A-Y may be not of the form —$CH_2$—NH—$(CH_2)_x$-phenyl, where x is 1-6 and may in particular be 4.

Optionally, Q does not comprise a polycyclic heteroaryl group, and in particular, Q may not comprise

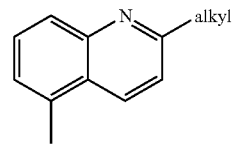

and optionally may not be

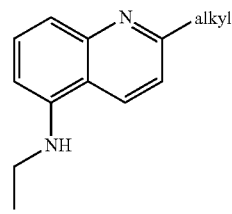

where 'alkyl' may be methyl.

According to a third set of embodiments, the invention provides a compound of the Formula (I)

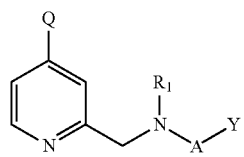

wherein

Q is selected from —CH=O and —CH(OR$^{17}$)$_2$;

A is selected from —CHR$^2$C(O)—, $C_{1-8}$ alkylene, $C_{2-8}$ alkenylene, $C_{2-8}$ alkynylene, $C_{3-10}$ cycloalkylene, heterocyclylene, heteroarylene and arylene, which alkylene, alkenylene, alkynylene, cycloalkylene, heterocyclylene, heteroarylene and arylene may optionally be substituted with one or more $R^3$;

Y is selected from —H, —$NR^6R^7$, —$OR^7$, $C_{1-8}$ alkyl, $C_{2-8}$ alkenyl, $C_{2-8}$ alkynyl, $C_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more $R^3$;

$R^1$ is selected from —H and $C_{1-4}$ alkyl;

$R^2$ is selected from —H, $C_{1-8}$ alkyl, $C_{2-8}$ alkenyl, $C_{2-8}$ alkynyl, $C_{3-10}$ cycloalkyl, which alkyl, alkenyl, alkynyl and cycloalkyl may be optionally substituted with one or more selected from —OH, aryl, $C_{1-8}$ alkoxy, heteroaryl, aryloxy, heteroaryloxy, F, and $C_{3-6}$ cycloalkyl;

each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein any heterocyclyl may be substituted with one or more $R^4$, and wherein any heteroaryl and any aryl may be substituted with one or more $R^5$;

Z is selected from a single bond, $C_{1-4}$ alkylene, heterocyclylene and $C_{3-6}$ cycloalkylene, each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —$N(R^1)_2$, carbamoyl, and —OH;

each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH;

each of $R^6$ and $R^7$ is independently selected from —H, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$; or, alternatively, $R^6$ and $R^7$ may together with the N-atom to which they are attached form an N-heterocyclic ring optionally substituted with one or more independently selected $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$; wherein any heterocyclyl may be further substituted with one or more $R^4$ as defined above, and wherein any heteroaryl and any aryl may be further substituted with one or more $R^5$ as defined above, and each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein any heterocyclyl may be substituted with one or more $R^4$ as defined above, and wherein any heteroaryl and any aryl may be substituted with one or more $R^5$ as defined above;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more $R^4$ as defined above, and wherein any heteroaryl and any aryl may be substituted with one or more $R^5$ as defined above, or, alternatively, $R^{10}$ and $R^{11}$ may together with the N-atom to which they are attached form an N-heterocyclic ring optionally substituted with one or more $R^4$ as defined above;

each $R^{17}$ independently is $R^3$, or wherein two $R^{17}$ substituents together with the intervening —O—CH(-)—O— may form a heterocyclyl optionally substituted with one or more $R^3$ and containing up to two oxo groups;

with the proviso that Y is not H when A is —$CH_2$—;

or an isomer or a mixture of isomers thereof, or a pharmaceutically acceptable salt, solvate or prodrug thereof.

In this set of embodiments of the invention, optionally -A-Y does not include an alkynylene moiety. Optionally, -A-Y does not comprise a moiety of the formula

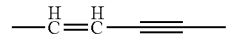

or more particularly a moiety of the formula

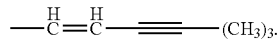

A in any of the compounds defined by general formula herein may be selected from —$CHR^2C(O)$—, or $C_{1-8}$ alkylene, or heterocyclylene.

Y in any of the compounds defined by general formula herein may be —$NR^6R^7$.

A in any of the compounds defined by general formula herein may be —$CHR^2C(O)$—.

A in any of the compounds defined by general formula herein may be —$CH_2$—C(O)—.

Y in any of the compounds defined by general formula herein may be

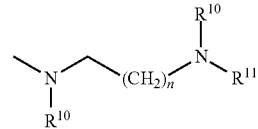

wherein n is from 1 to 3 and each of $R^{10}$ and $R^{11}$ independently is as defined in claim 1.

Y in any of the compounds defined by general formula herein may be

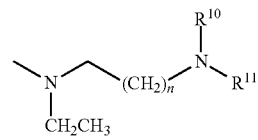

for instance

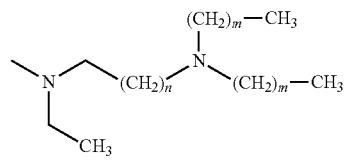

wherein n is from 1 to 3 and each m independently is from 0 to 2.

Y in any of the compounds defined by general formula herein may be selected from heterocyclyl, heteroaryl and aryl, which may be optionally substituted with one or more $R^3$.

$R^{13}$ may be H in any of the compounds defined by general formula herein.

Q may be of the formula:

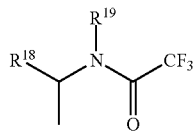

wherein R18 and R19 are hydrogen, or together form a 1,3-diaza-$C_{5-7}$-cycloalk-2-yl group which is N-substituted with $R^{16}$ and optionally further substituted with one or more $R^3$, and optionally containing one or two oxo groups; a 1,3-thiaza-$C_{5-7}$-cycloalk-2-yl group which is N-substituted with $R^{16}$ and optionally further substituted with one or more $R^3$ and optionally containing one or two oxo groups; an 1,3-oxaza-$C_{5-7}$-cycloalk-2-yl group which is N-substituted with $R^{16}$ and optionally further substituted with one or more $R^3$, and optionally containing one or two oxo groups, wherein in all three instances two $R^3$'s on the same carbon atom may together form a spiro group.

In some preferred instances, the compound may be one wherein the moiety -A-Y includes 1-3 cyclic moieties selected from monocylic cycloalkyl, monocyclic heterocyclyl, monocylic heteroaryl, dicyclic heteroaryl and monocyclic aryl.

In preferred aspects of the invention, the compound may be as shown in Table 1 in the Examples section below.

A compound according to the invention may have a molecular weight of 130-1,000 g/mol, such as 180-800 g/mol, e.g. 225-600 g/mol or 250-500 g/mol.

The invention includes a pharmaceutical composition comprising at least one compound of Formula (I) as defined in any paragraph herein containing such a definition and optionally one or more pharmaceutically acceptable excipients, diluents or carriers.

The invention includes such a pharmaceutical composition, which comprises one or more further active substances.

The invention includes a compound for use as a medicament which is a compound of the Formula (I)

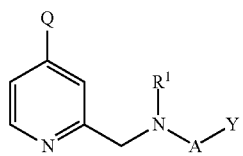

wherein
Q is selected from —CH=$NR^{12}$, —W, —$CH_2NHR^{13}$, —CH=O and —CH($OR^{17}$)$_2$;
A is selected from —$CHR^2C(O)$—, $C_{1-8}$ alkylene, $C_{2-8}$ alkenylene, $C_{2-8}$ alkynylene, $C_{3-10}$ cycloalkylene, heterocyclylene, heteroarylene and arylene, which alkylene, alkenylene, alkynylene, cycloalkylene, heterocyclylene, heteroarylene and arylene may optionally be substituted with one or more $R^3$; with the proviso that when Q is —CH=O, A is not alkynylene;
Y is selected from —H, —$NR^6R^7$, —$OR^7$, $C_{1-8}$ alkyl, $C_{2-8}$ alkenyl, $C_{2-8}$ alkynyl, $C_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more $R^3$ and may form a cyclic structure with $R^2$; with the proviso that when Q is —CH=O, Y is not alkynyl;

$R^1$ is selected from —H, $C_{1-8}$ alkyl, $C_{2-8}$ alkenyl, $C_{2-8}$ alkynyl, $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl; or more preferably is selected from —H and $C_{1-4}$ alkyl; or with -A-Y forms a nitrogen containing optionally substituted heterocyclic group where the optional substitution may be $C_{1-8}$ alkyl, $C_{2-8}$ alkenyl, $C_{2-8}$ alkynyl, or $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl;
$R^2$ is selected from —H, $C_{1-8}$ alkyl, $C_{2-8}$ alkenyl, $C_{2-8}$ alkynyl, and $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl, and may form a cyclic structure with Y;
each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein any heterocyclyl may be substituted with one or more $R^4$, and wherein any heteroaryl and any aryl may be substituted with one or more $R^5$;
Z is selected from a single bond, $C_{1-4}$ alkylene, heterocyclylene and $C_{3-6}$ cycloalkylene;
each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —N($R^1$)$_2$, carbamoyl, and —OH;
each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH;
each of $R^6$ and $R^7$ is independently selected from —H, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$; or, alternatively, $R^6$ and $R^7$ may together with the N-atom to which they are attached form an N-heterocyclic ring optionally substituted with one or more independently selected $R^8$;
each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$; wherein any heterocyclyl may be further substituted with one or more $R^4$ as defined above, and wherein any heteroaryl and any aryl may be further substituted with one or more $R^5$ as defined above, and
each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein any heterocyclyl may be substituted with one or more R⁴ as defined above, and wherein any heteroaryl and any aryl may be substituted with one or more R⁵ as defined above;

each of R¹⁰ and R¹¹ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more R⁴ as defined above, and wherein any heteroaryl and any aryl may be substituted with one or more R⁵ as defined above, or, alternatively, R¹⁰ and R¹¹ may together with the N-atom to which they are attached form an N-heterocyclic ring optionally substituted with one or more R⁴ as defined above;

with the proviso that Y is not H when A is —CH₂—;

when Q is —CH═NR¹², R¹² is selected from $C_{1-10}$ alkyl, $C_{2-10}$ alkenyl, $C_{2-10}$ alkynyl, $C_{3-10}$ cycloalkyl, —Z-heterocyclyl, —Z-aryl, —Z-heteroaryl, —Z—NR⁶R⁷, —Z—C(═O)—NR⁶R⁷, —Z—NR⁶—C(═O)—R⁷, —Z—C(═O)—R⁷, —Z—OR⁷, halogen, —Z—SR⁷, —Z—SOR⁷, —Z—SO₂R⁷ and —Z—COOR⁷, which alkyl, alkenyl, alkynyl, cycloalkyl, heterocyclyl, heteroaryl and aryl may optionally be substituted with one or more R³;

when Q is —CH₂NHR¹³, R¹³ is selected from hydrogen, —C(O)R⁷, —C(O)C(O)R⁷, —C(O)C(O)OR⁷, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, and —Z-monocyclic-heteroaryl, which alkyl, alkenyl, alkynyl, cycloalkyl, heterocyclyl, and monocyclic-heteroaryl may optionally be substituted with one or more independently selected R⁸, or is —CR¹⁴R¹⁵—NR⁶R⁷, —CR¹⁴R¹⁵CN, or —CR¹⁴R¹⁵OR⁷, wherein each of R¹⁴ and R¹⁵ is independently selected from —H, $C_{1-8}$ alkyl, $C_{2-8}$ alkenyl, $C_{2-8}$ alkynyl, $C_{3-10}$ cycloalkyl, heterocyclyl, heteroaryl and aryl, and wherein R¹⁴ and R¹⁵ together with the intervening carbon atom may designate a $C_{3-10}$ cycloalkyl or $C_{5-10}$-cycloalkenyl ring, which alkyl, alkenyl, alkynyl, cycloalkyl (ring), cycloalkenyl ring, heterocyclyl, heteroaryl and aryl may optionally be substituted with one or more R³;

when Q is W, W is selected from an 1,3-diaza-$C_{5-7}$-cycloalk-2-yl group which is N-substituted with R¹⁶ and optionally further substituted with one or more R³, and optionally containing one or two oxo groups; a 1,3-thiaza-$C_{5-7}$-cycloalk-2-yl group which is N-substituted with R¹⁶ and optionally further substituted with one or more R³ and optionally containing one or two oxo groups; an 1,3-oxaza-$C_{5-7}$-cycloalk-2-yl group which is N-substituted with R¹⁶ and optionally further substituted with one or more R³, and optionally containing one or two oxo groups, wherein in all three instances two R³'s on the same carbon atom may together form a spiro group;

R¹⁶ is selected from hydrogen, —C(O)R⁷, —C(O)C(O)R⁷, —C(O)C(O)R⁷;

when Q is —CH(OR¹⁷)₂, each R¹⁷ independently is R³, or wherein two R¹⁷ substituents together with the intervening —O—CH(-)—O— may form a heterocyclyl optionally substituted with one or more R³ and containing up to two oxo groups;

or an isomer or a mixture of isomers thereof, or a pharmaceutically acceptable salt, or solvate or prodrug thereof.

The invention includes a compound for use in the treatment of a HDME dependent disease which is of the Formula (I)

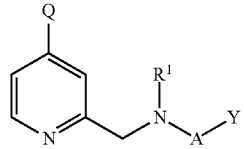

wherein

Q is selected from —CH═NR¹², —W, —CH₂NHR¹³, —CH═O and —CH(OR¹⁷)₂;

A is selected from —CHR²C(O)—, $C_{1-8}$ alkylene, $C_{2-8}$ alkenylene, $C_{2-8}$ alkynylene, $C_{3-10}$ cycloalkylene, heterocyclylene, heteroarylene and arylene, which alkylene, alkenylene, alkynylene, cycloalkylene, heterocyclylene, heteroarylene and arylene may optionally be substituted with one or more R³;

Y is selected from —H, —NR⁶R⁷, —OR⁷, $C_{1-8}$ alkyl, $C_{2-8}$ alkenyl, $C_{2-8}$ alkynyl, $C_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more R³ and may form a cyclic structure with R²;

R¹ is selected from —H, $C_{1-8}$ alkyl, $C_{2-8}$ alkenyl, $C_{2-8}$ alkynyl, $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl; or more preferably is selected from —H and $C_{1-4}$ alkyl; or with -A-Y forms a nitrogen containing optionally substituted heterocyclic group where the optional substitution may be $C_{1-8}$ alkyl, $C_{2-8}$ alkenyl, $C_{2-8}$ alkynyl, or $C_{3-10}$ cycloalkyl, which alkyl, alkenyl, alkynyl and cycloalkyl may be optionally substituted with one or more selected from —OH, aryl, $C_{1-8}$ alkoxy, heteroaryl, aryloxy, heteroaryloxy, F, and $C_{3-6}$ cycloalkyl;

R² is selected from —H, $C_{1-8}$ alkyl, $C_{2-8}$ alkenyl, $C_{2-8}$ alkynyl, and $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl, and may form a cyclic structure with Y;

each R³ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—NR⁶R⁷, —Z—C(═O)—NR⁶R⁷, —Z—NR⁶—C(═O)—R⁷, —Z—C(═O)—R⁷, —Z—OR⁷, halogen, —Z—SR⁷, —Z—SOR⁷, —Z—SO₂R⁷, —Z—SO₂NR⁶R⁷ and —Z—COOR⁷, wherein any heterocyclyl may be substituted with one or more R⁴, and wherein any heteroaryl and any aryl may be substituted with one or more R⁵;

Z is selected from a single bond, $C_{1-4}$ alkylene, heterocyclylene and $C_{3-6}$ cycloalkylene;

each R⁴ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —N(R¹)₂, carbamoyl, and —OH;

each R⁵ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH;

each of R⁶ and R⁷ is independently selected from —H, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected R⁸; or, alternatively, R⁶ and R⁷ may together with the N-atom to which they are attached form an N-heterocyclic ring optionally substituted with one or more independently selected $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—$NR^{10}R^{11}$, —Z—C(=O)—$NR^{10}R^{11}$, —Z—$OR^9$, halogen, —CN, —Z—$SR^9$, —Z—$SOR^9$, —Z—$SO_2R^9$ and —Z—$COOR^9$; wherein any heterocyclyl may be further substituted with one or more $R^4$ as defined above, and wherein any heteroaryl and any aryl may be further substituted with one or more $R^5$ as defined above, and each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein any heterocyclyl may be substituted with one or more $R^4$ as defined above, and wherein any heteroaryl and any aryl may be substituted with one or more $R^5$ as defined above;

each of $R^{10}$ and $R^{11}$ is independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more $R^4$ as defined above, and wherein any heteroaryl and any aryl may be substituted with one or more $R^5$ as defined above, or, alternatively, $R^{10}$ and $R^{11}$ may together with the N-atom to which they are attached form an N-heterocyclic ring optionally substituted with one or more $R^4$ as defined above;

with the proviso that Y is not H when A is —$CH_2$—;

when Q is —CH=$NR^{12}$, $R^{12}$ is selected from $C_{1-10}$ alkyl, $C_{2-10}$ alkenyl, $C_{2-10}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$ and —Z—$COOR^7$, which alkyl, alkenyl, alkynyl, cycloalkyl, heterocyclyl, heteroaryl and aryl may optionally be substituted with one or more $R^3$;

when Q is —$CH_2NHR^{13}$, $R^{13}$ is selected from hydrogen, —C(O)$R^7$, —C(O)C(O)$R^7$, —C(O)C(O)O$R^7$, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$, or is —$CR^{14}R^{15}$—$NR^6R^7$, —$CR^{14}R^{15}$CN, or —$CR^{14}R^{15}OR^7$, wherein each of $R^{14}$ and $R^{15}$ is independently selected from —H, $C_{1-8}$ alkyl, $C_{2-8}$ alkenyl, $C_{2-8}$ alkynyl, $C_{3-10}$ cycloalkyl, heterocyclyl, heteroaryl and aryl, and wherein $R^{14}$ and $R^{15}$ together with the intervening carbon atom may designate a $C_{3-10}$ cycloalkyl or $C_{5-10}$-cycloalkenyl ring, which alkyl, alkenyl, alkynyl, cycloalkyl (ring), cycloalkenyl ring, heterocyclyl, heteroaryl and aryl may optionally be substituted with one or more $R^3$;

when Q is W, W is selected from an 1,3-diaza-$C_{5-7}$-cycloalk-2-yl group which is N-substituted with $R^{16}$ and optionally further substituted with one or more $R^3$, and optionally containing one or two oxo groups; a 1,3-thiaza-$C_{5-7}$-cycloalk-2-yl group which is N-substituted with $R^{16}$ and optionally further substituted with one or more $R^3$ and optionally containing one or two oxo groups; an 1,3-oxaza-$C_{5-7}$-cycloalk-2-yl group which is N-substituted with $R^{16}$ and optionally further substituted with one or more $R^3$, and optionally containing one or two oxo groups, wherein in all three instances two $R^3$'s on the same carbon atom may together form a spiro group;

$R^{16}$ is selected from hydrogen, —C(O)$R^7$, —C(O)C(O)$R^7$, —C(O)C(O)O$R^7$;

when Q is —CH(O$R^{17}$)$_2$, each $R^{17}$ independently is $R^3$, or wherein two $R^{17}$ substituents together with the intervening —O—CH(-)—O— may form a heterocyclyl optionally substituted with one or more $R^3$ and containing up to two oxo groups;

or an isomer or a mixture of isomers thereof, or a pharmaceutically acceptable salt, or solvate or prodrug thereof.

The invention includes the use of a compound for the preparation of a pharmaceutical composition for the treatment of a HDME dependent disease, which compound is of the Formula (I)

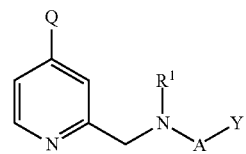

wherein

Q is selected from —CH=$NR^{12}$, —W, —$CH_2NHR^{13}$, —CH=O and —CH(O$R^{17}$)$_2$;

A is selected from —$CHR^2C(O)$—, $C_{1-8}$ alkylene, $C_{2-8}$ alkenylene, $C_{2-8}$ alkynylene, $C_{3-10}$ cycloalkylene, heterocyclylene, heteroarylene and arylene, which alkylene, alkenylene, alkynylene, cycloalkylene, heterocyclylene, heteroarylene and arylene may optionally be substituted with one or more $R^3$;

Y is selected from —H, —$NR^6R^7$, —$OR^7$, $C_{1-8}$ alkyl, $C_{2-8}$ alkenyl, $C_{2-8}$ alkynyl, $C_{3-10}$ cycloalkyl, heterocyclyl, heteroaryl and aryl, which alkyl, alkenyl, alkynyl, cycloalkyl, heterocyclyl, heteroaryl and aryl may optionally be substituted with one or more $R^3$ and may form a cyclic structure with $R^2$;

$R^1$ is selected from —H, $C_{1-8}$ alkyl, $C_{2-8}$ alkenyl, $C_{2-8}$ alkynyl, $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl; or more preferably is selected from —H and $C_{1-4}$ alkyl; or with -A-Y forms a nitrogen containing optionally substituted heterocyclic group where the optional substitution may be $C_{1-8}$ alkyl, $C_{2-8}$ alkenyl, $C_{2-8}$ alkynyl, or $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl;

$R^2$ is selected from —H, $C_{1-8}$ alkyl, $C_{2-8}$ alkenyl, $C_{2-8}$ alkynyl, and $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl, and may form a cyclic structure with Y;

each $R^3$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—$NR^6R^7$, —Z—C(=O)—$NR^6R^7$, —Z—$NR^6$—C(=O)—$R^7$, —Z—C(=O)—$R^7$, —Z—$OR^7$, halogen, —Z—$SR^7$, —Z—$SOR^7$, —Z—$SO_2R^7$, —Z—$SO_2NR^6R^7$ and —Z—$COOR^7$, wherein any heterocyclyl may be substituted with one or more $R^4$, and wherein any heteroaryl and any aryl may be substituted with one or more $R^5$;

Z is selected from a single bond, $C_{1-4}$ alkylene, heterocyclylene and $C_{3-6}$ cycloalkylene;

each $R^4$ is independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —N($R^1$)$_2$, carbamoyl, and —OH;

each $R^5$ is independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH;

each of $R^6$ and $R^7$ is independently selected from —H, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$; or, alternatively, $R^6$ and $R^7$ may together with the N-atom to which they are attached form an N-heterocyclic ring optionally substituted with one or more independently selected $R^8$;

each $R^8$ is independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$; wherein any heterocyclyl may be further substituted with one or more $R^4$ as defined above, and wherein any heteroaryl and any aryl may be further substituted with one or more $R^5$ as defined above, and each $R^9$ is independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein any heterocyclyl may be substituted with one or more $R^4$ as defined above, and wherein any heteroaryl and any aryl may be substituted with one or more $R^5$ as defined above;

each of $R^{10}$ and $R^{11}$ is independently selected from —H, $C_{1-5}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more $R^4$ as defined above, and wherein any heteroaryl and any aryl may be substituted with one or more $R^5$ as defined above, or, alternatively, $R^{10}$ and $R^{11}$ may together with the N-atom to which they are attached form an N-heterocyclic ring optionally substituted with one or more $R^4$ as defined above;

with the proviso that Y is not H when A is —CH$_2$—;

when Q is —CH=NR$^{12}$, $R^{12}$ is selected from $C_{1-10}$ alkyl, $C_{2-10}$ alkenyl, $C_{2-10}$ alkynyl, $C_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$ and —Z—COOR$^7$, which alkyl, alkenyl, alkynyl, cycloalkyl, heterocyclyl, heteroaryl and aryl may optionally be substituted with one or more $R^3$;

When Q is —CH$_2$NHR$^{13}$, $R^{13}$ is selected from hydrogen, —C(O)R$^7$, —C(O)C(O)R$^7$, $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected $R^8$, or is —CR$^{14}$R$^{15}$—NR$^6$R$^7$, —CR$^{14}$R$^{15}$CN, or —CR$^{14}$R$^{15}$OR$^7$, wherein each of $R^{14}$ and $R^{15}$ is independently selected from —H, $C_{1-8}$ alkyl, $C_{2-8}$ alkenyl, $C_{2-8}$ alkynyl, $C_{3-10}$ cycloalkyl, heterocyclyl, heteroaryl and aryl, and wherein $R^{14}$ and $R^{15}$ together with the intervening carbon atom may designate a $C_{3-10}$ cycloalkyl or $C_{5-10}$-cycloalkenyl ring, which alkyl, alkenyl, alkynyl, cycloalkyl (ring), cycloalkenyl ring, heterocyclyl, heteroaryl and aryl may optionally be substituted with one or more $R^3$;

when Q is W, W is selected from an 1,3-diaza-$C_{5-7}$-cycloalk-2-yl group which is N-substituted with $R^{16}$ and optionally further substituted with one or more $R^3$, and optionally containing one or two oxo groups; a 1,3-thiaza-$C_{5-7}$-cycloalk-2-yl group which is N-substituted with $R^{16}$ and optionally further substituted with one or more $R^3$ and optionally containing one or two oxo groups; an 1,3-oxaza-$C_{5-7}$-cycloalk-2-yl group which is N-substituted with $R^{16}$ and optionally further substituted with one or more $R^3$, and optionally containing one or two oxo groups, wherein in all three instances two $R^3$'s on the same carbon atom may together form a spiro group;

$R^{16}$ is selected from hydrogen, —C(O)R$^7$, —C(O)C(O)R$^7$, —C(O)C(O)OR$^7$;

when Q is —CH(OR$^{17}$)$_2$, each $R^{17}$ independently is $R^3$, or wherein two $R^{17}$ substituents together with the intervening —O—CH(-)—O— may form a heterocyclyl optionally substituted with one or more $R^3$ and containing up to two oxo groups;

or an isomer or a mixture of isomers thereof, or a pharmaceutically acceptable salt, or solvate or prodrug thereof.

The invention includes a method of treating a HDME dependent disease in a subject, said method comprises administering to said subject a therapeutically effective amount of at least one compound of Formula (I) as defined in any one of the above paragraphs.

Conditions treatable using compounds or formulations or compositions according to the invention include cancer in the broadest sense, including solid and non-solid tumours. Further details of treatable conditions appear below.

DETAILED DISCLOSURE OF THE INVENTION

The above definitions of the compounds of Formula (I) are referred to herein by the expressions "compounds of Formula (I)" as defined herein, "compound of Formula (I) as defined herein", or simply "compounds of Formula (I)", etc. It should be understood, that such references are intended to encompass not only the above general formula in its stated aspects, but also each and every of the embodiments, etc. discussed above or in the following. It should also be understood, that unless stated to the opposite, such references also encompass isomers, mixtures of isomers, isotopic variants, pharmaceutically acceptable salts, solvates and prodrugs of the compounds of Formula (I).

Without being bound by any particular theory, the current results give reasons to believe that each of the values of Q plays an important role when designing compounds capable of modulating the in vivo activity of histone demethylases (HDMEs), whilst in each case the group Q is transformed in vivo to —COOH. Additionally, it is believed that the substituent combination -A-Y plays a role in establishing affinity for said histone demethylases. Furthermore, it is believed that the pyridine nitrogen and the nitrogen atom of Formula (I) also play a role in the binding of a particular cavity of the histone demethylases where the iron atom lies. It is also believed that the A-Y chain itself, and through its substituents, interacts with the area of the demethylase known to accommodate the lysine chain of the substrate.

A is typically selected from —CHR$^2$C(O)—, $C_{1-8}$ alkylene, $C_{2-8}$ alkenylene, $C_{2-8}$ alkynylene, $C_{3-10}$ cycloalkylene, heterocyclylene, heteroarylene and arylene.

The alkylene, alkenylene, alkynylene, cycloalkylene, heterocyclylene, heteroarylene and arylene as A may optionally be substituted with one or more R$^3$ (see further below).

A may be selected from —CHR$^2$C(O)—, $C_{1-8}$ alkylene, $C_{3-10}$ cycloalkylene, heterocyclylene, heteroarylene and arylene, in particular from —CHR$^2$C(O)—, $C_{1-8}$ alkylene and heterocyclylene, such as —CHR$^2$C(O)—, or $C_{1-8}$ alkylene, or heterocyclylene.

Y is typically selected from —H, —NR$^6$R$^7$, —OR$^7$, $C_{1-8}$ alkyl, $C_{2-8}$ alkenyl, $C_{2-8}$ alkynyl, $C_{3-10}$ cycloalkyl, heterocyclyl, heteroaryl and aryl. R$^6$ and R$^7$ are exemplified further below.

The alkyl, alkenyl, alkynyl, cycloalkyl, heterocyclyl, heteroaryl and aryl as Y may optionally be substituted with one or more R$^3$ (see further below);

In some embodiments, Y is —NR$^6$R$^7$. In one variant type, A is —CHR$^2$C(O)— and Y is —NR$^6$R$^7$. In another variant type, A is $C_{1-8}$ alkyl and Y is —NR$^6$R$^7$. In one scenario within these embodiments and these variants, —NR$^6$R$^7$ represents an N-heterocyclic ring optionally substituted with one or more independently selected R$^8$, preferably substituted with one to two independently selected R$^8$. In another scenario within these embodiments and these variants wherein Y is —NR$^6$R$^7$, one of R$^6$ and R$^7$ represents —H or $C_{1-6}$ alkyl. In still another scenario within these embodiment types and these variants wherein Y is —NR$^6$R$^7$, R$^6$ and R$^7$ are independently selected from $C_{1-8}$ alkyl, $C_{1-4}$ fluoroalkyl, $C_{1-4}$ hydroxyalkyl, $C_{2-8}$ alkenyl, and $C_{2-8}$ alkynyl, e.g. such that R$^6$ and R$^7$ are the same. In still another scenario within these embodiment types and these variants wherein Y is —NR$^6$R$^7$, one of R$^6$ and R$^7$ is selected from heterocyclyl, heteroaryl and aryl.

Y may be —H. In such compounds and in others, A may be selected from $C_{1-8}$ alkylene, $C_{2-8}$ alkenylene, $C_{2-8}$ alkynylene, and $C_{3-10}$ cycloalkylene. In such compounds and in others, A may also be selected from heterocyclyl.

Y may be selected from heterocyclyl, heteroaryl and aryl. In such compounds and others, A may be selected from $C_{1-8}$ alkylene, $C_{2-8}$ alkenylene, $C_{2-8}$ alkynylene, in particular from $C_{1-8}$ alkylene, such as from $C_{1-6}$ alkylene, in particular from $C_{1-4}$ alkylene.

R$^1$ is typically selected from —H and $C_{1-4}$ alkyl (such as methyl, ethyl, propyl and butyl), in particular from —H and methyl.

R$^2$ is typically selected from —H, $C_{1-8}$ alkyl, $C_{2-8}$ alkenyl, $C_{2-8}$ alkynyl, $C_{3-10}$ cycloalkyl, which alkyl, alkenyl, alkynyl and cycloalkyl may be optionally substituted with one or more selected from —OH, aryl, $C_{1-6}$ alkoxy, heteroaryl, aryloxy, heteroaryloxy, F, and $C_{3-6}$ cycloalkyl. In some embodiments, R$^2$ is selected from —H, $C_{1-4}$ alkyl (such as methyl, ethyl, propyl and butyl) and $C_{1-4}$ hydroxyalkyl (such as hydroxymethyl, hydroxyethyl, hydroxypropyl and hydroxybutyl), in particular from —H, methyl and hydroxymethyl.

The R$^3$ (possible substituents to some of the meanings of A and Y) is typically independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$, —Z—SO$_2$NR$^6$R$^7$ and —Z—COOR$^7$, wherein any heterocyclyl may be substituted with one or more R$^4$, and wherein any heteroaryl and any aryl may be substituted with one or more R$^5$.

Z is typically selected from a single bond, $C_{1-4}$ alkylene, heterocyclylene and $C_{3-6}$ cycloalkylene. In one embodiment, Z is selected from $C_{1-4}$ alkylene. In another embodiment, Z is selected from a single bond. It should be understood that the group Z may appear several times in Formula (I) and that such Z's are independently selected.

Each R$^4$ (possible substituents of heterocyclyl) may be independently selected from $C_{1-6}$ alkyl, $C_{1-4}$ fluoroalkyl, $C_{1-4}$ hydroxyalkyl, $C_{1-4}$ alkoxy, $C_{3-10}$ cycloalkyl, —N(R$^1$)$_2$, carbamoyl, and —OH.

Each R$^5$ (possible substituents of heteroaryl and aryl) may be independently selected from $C_{1-6}$ alkyl, $C_{1-4}$ fluoroalkyl, $C_{1-4}$ hydroxyalkyl, $C_{1-4}$ alkoxy, $C_{3-6}$ cycloalkyl, —CN, —F, —Cl, —Br, carbamoyl and —OH.

Each of R$^6$ and R$^7$ (e.g. of the moiety —NR$^6$R$^7$) may be independently selected from —H (in certain aspects), $C_{1-8}$ alkyl, $C_{1-4}$ fluoroalkyl, $C_{1-4}$ perfluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected R$^8$; or, alternatively, R$^6$ and R$^7$ may together with the N-atom to which they are attached form an N-heterocyclic ring optionally substituted with one or more independently selected R$^8$.

Each R$^8$ may be independently selected from $C_{1-6}$ alkyl, $C_{1-4}$ fluoroalkyl, $C_{1-4}$ hydroxyalkyl, $C_{2-6}$ alkenyl, $C_{2-6}$ alkynyl, $C_{3-10}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$, which alkyl, alkenyl, alkynyl, cycloalkyl, heterocyclics, heteroaryl and aryl may optionally be substituted with one or more selected from $C_{1-4}$ alkyl, $C_{1-4}$ fluoroalkyl, $C_{1-4}$ hydroxyalkyl, $C_{3-6}$ cycloalkyl, —Z-heterocyclyl, —Z-heteroaryl, —Z-aryl, —Z—NR$^{10}$R$^{11}$, —Z—C(=O)—NR$^{10}$R$^{11}$, —Z—OR$^9$, halogen, —CN, —Z—SR$^9$, —Z—SOR$^9$, —Z—SO$_2$R$^9$ and —Z—COOR$^9$; wherein any heterocyclyl may be further substituted with one or more R$^4$ as defined above, and wherein any heteroaryl and any aryl may be further substituted with one or more R$^5$ as defined above.

Each R$^9$ may be independently selected from —H, $C_{1-8}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, —Z-heterocyclyl, —Z-aryl, and —Z-heteroaryl, wherein any heterocyclyl may be substituted with one or more R$^4$ as defined above, and wherein any heteroaryl and any aryl may be substituted with one or more R$^5$ as defined above.

Each of R$^{10}$ and R$^{11}$ (of the moiety —NR$^{10}$R$^{11}$) may be independently selected from —H, $C_{1-6}$ alkyl, $C_{1-4}$ fluoroalkyl, $C_{1-4}$ hydroxyalkyl, $C_{2-8}$ alkenyl, $C_{2-8}$ alkynyl, $C_{3-10}$ cycloalkyl, heterocyclyl, heteroaryl, and aryl, wherein any heterocyclyl may be substituted with one or more R$^4$ as defined above, and wherein any heteroaryl and any aryl may be substituted with one or more R$^5$ as defined above, or, alternatively, R$^{10}$ and R$^{11}$ may together with the N-atom to which they are attached form an N-heterocyclic ring optionally substituted with one or more R$^4$ as defined above.

In some embodiments, Q is —CH=N—R$^{12}$. If so, R$^{12}$ may be selected from $C_{1-10}$ alkyl, $C_{2-10}$ alkenyl, $C_{2-10}$ alkynyl, $C_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$ and —Z—COOR$^7$, which alkyl, alkenyl, alkynyl, cycloalkyl, heterocyclyl, heteroaryl and aryl may optionally be substituted with one or more R$^3$. In some embodiments hereof, R$^{12}$ is C$_{1-8}$ alkyl, C$_{1-4}$ fluoroalkyl, C$_{1-4}$ perfluoroalkyl, C$_{2-8}$ alkenyl, C$_{2-8}$ alkynyl, C$_{3-8}$ cycloalkyl, —Z-heterocyclyl, —Z-aryl, —Z-heteroaryl, —Z—NR$^6$R$^7$, and —Z—OR$^7$, wherein —Z— is a single bond or C$_{1-4}$ alkylene, which alkyl, alkenyl, alkynyl, cycloalkyl, heterocyclyl, heteroaryl and aryl may optionally be substituted with one or more R$^3$.

In other embodiments, Q is —W, wherein —W may be an 1,3-azo-C$_{5-7}$-cycloalk-2-yl group which is N-substituted with R$^{16}$ and optionally further substituted with one or more R$^3$. W may be 1,3-diazacyclopent-2-yl (imidazolidin-2-yl), 1,3-diazacyclohex-2-yl (hexahydropyrimidin-2-yl), or 1,3-diazacyclohept-2-yl, for example. The N-substituent may be selected among those defined for R$^{16}$ (see above). W may be further substituted with one or more R$^3$, wherein two R$^3$'s on the same carbon atom may together form a spiro group.

In yet other embodiments, Q is —W, wherein —W may be an 1,3-oxaza-C$_{5-7}$-cycloalk-2-yl group which is N-substituted with R$^{16}$ and optionally further substituted with one or more R$^3$. W may be 1,3-oxazacyclopent-2-yl, 1,3-oxazacyclohex-2-yl, 1,3-oxazacyclohept-2-yl, or 7-oxa-9-azaspiro[4,5]decan-8-yl, for example. The N-substituent may be selected among those defined for R$^{16}$ (see above). W may be further substituted with one or more R$^3$, wherein two R$^3$'s on the same carbon atom may together form a spiro group.

In some embodiments of the above, W may be further substituted with one or more R$^3$, but is typically not further substituted.

R$^{16}$ may be selected from hydrogen, —C(O)R$^7$, —C(O)C(O)R$^7$, and —C(O)C(O)OR$^7$, in particular from hydrogen and —C(O)R$^7$.

In some embodiments Q is —CH$_2$NHR$^{13}$, and R$^{13}$ may be selected from hydrogen, —C(O)R$^7$, —C(O)C(O)R$^7$, —R$^7$ in some aspects), —CR$^{14}$R$^{15}$—NR$^6$R$^7$, —CR$^{14}$R$^{15}$CN, —CR$^{14}$R$^{15}$OR$^7$, wherein each of R$^{14}$ and R$^{15}$ is independently selected from —H, C$_{1-8}$ alkyl, C$_{2-8}$ alkenyl, C$_{2-8}$ alkynyl, C$_{3-10}$ cycloalkyl, heterocyclyl, heteroaryl and aryl, and wherein R$^{14}$ and R$^{15}$ together with the intervening carbon atom may designate a C$_{3-10}$ cycloalkyl or C$_{5-10}$-cycloalkenyl ring, which alkyl, alkenyl, alkynyl, cycloalkyl (ring), cycloalkenyl ring, heterocyclyl, heteroaryl and aryl may optionally be substituted with one or more R$^3$. In some aspects, rather than —R$^7$, R$^{13}$ may be C$_{1-8}$ alkyl, C$_{1-4}$ fluoroalkyl, C$_{1-4}$ perfluoroalkyl, C$_{1-4}$ hydroxyalkyl, C$_{2-8}$ alkenyl, C$_{2-8}$ alkynyl, C$_{3-10}$ cycloalkyl, —Z-heterocyclyl, and —Z-monocyclic-heteroaryl, which alkyl, alkenyl, alkynyl, cycloalkyl, heterocyclyl, and heteroaryl may optionally be substituted with one or more independently selected R$^8$.

In some embodiments Q is —CH(OR$^{17}$)$_2$ and each R$^{17}$ independently may be R$^3$, or the two R$^{17}$ substituents together with the intervening —O—CH(-)—O— may form a heterocyclyl optionally substituted with one or more R$^3$.

It is to be understood that in the Formula (I), Y is not H when A is —CH$_2$—. Generally speaking, it is believed to be advantageous if the moiety -A-Y has a certain "size" with respect to the number of atom (disregarding hydrogen atoms) and/or the molecular weight. Also a limited flexibility of the moiety -A-Y appears to play a certain role.

Hence, it is believed that the moiety -A-Y should preferably consist of at the most 40 heavy atoms, such as at the most 30 heavy atoms, or at the most 25 heavy atoms, or at the most 20 heavy atoms. Preferably, the moiety -A-Y will consist of at least 3, or at least 4, or at least 8 or at least 10 heavy atoms. In some embodiments, the moiety -A-Y preferably consists of 3-40 heavy atoms, such as 4-30 heavy atoms, or 4-25 heavy atoms, or 4-20, or 8-30, or 8-20, or 8-15 heavy atoms. By the term "heavy atom" is meant all atoms in the moiety except the hydrogen atom(s).

Moreover, it is believed that the compounds of Formula (I) should preferably have a molecular weight of at least 130, or at least 150, or at least 180, or at least 250, but not more than 1000, or not more than 800, or not more than 500, or not more than 400 and may be within any range constructable from these preferred upper and lower limits, such as 130-1,000 g/mol, or 150-1,000 g/mol, such as 180-800 g/mol, e.g. 225-600 g/mol or 250-500 g/mol, or 250 to 400.

In some embodiments, and in order to introduce a limited flexibility of the moiety -A-Y, the moiety includes 1-4 rings, i.e. rings derived from cycloalkyl, cycloalkenyl, heterocyclyl, heteroaryl and/or aryl. In some variant, the moiety -A-Y includes 1-3 cyclic moieties selected from monocylic cycloalkyl, monocyclic heterocyclyl, monocylic heteroaryl, dicyclic heteroaryl and monocyclic aryl. Small substituents such as alkyls groups or hydroxyl on alkyl chains also reduce flexibility and favor certain conformations.

It may be preferable that if -A-Y does not include a ring, it includes at least one, for instance from 1 to 3, branches, each of which independently may be of from one heavy atom to six heavy atoms, for instance from one to three heavy atoms, or from one to two heavy atoms. It is preferred that -A-Y should contain at least one hetero-atom, preferably at least one nitrogen atom or at least one oxygen.

DEFINITIONS

The term "alkyl" as used herein refers to a saturated, straight or branched hydrocarbon chain. The hydrocarbon chain preferably contains from one to 8 carbon atoms (C$_{1-8}$-alkyl), more preferred from one to six carbon atoms (C$_{1-5}$-alkyl), in particular from one to four carbon atoms (C$_{1-4}$-alkyl), including methyl, ethyl, propyl, isopropyl, butyl, isobutyl, secondary butyl, tertiary butyl, pentyl, isopentyl, neopentyl, tertiary pentyl, hexyl, isohexyl, heptyl and octyl. In a preferred embodiment "alkyl" represents a C$_{1-4}$-alkyl group, which may in particular include methyl, ethyl, propyl, isopropyl, butyl, isobutyl, secondary butyl, and tertiary butyl. Correspondingly, the term "alkylene" means the corresponding biradical (-alkyl-).

The term "cycloalkyl" as used herein refers to a cyclic alkyl group, preferably containing from three to ten carbon atoms (C$_{3-10}$-cycloalkyl), such as from three to eight carbon atoms (C$_{3-8}$-cycloalkyl), preferably from three to six carbon atoms (C$_{3-5}$-cycloalkyl), including cyclopropyl, cyclobutyl, cyclopentyl, cyclohexyl, cycloheptyl and cyclooctyl. Furthermore, the term "cycloalkyl" as used herein may also include polycyclic groups such as for example bicyclo[2.2.2]octyl, bicyclo[2.2.1]heptanyl, decalinyl and adamantyl. Correspondingly, the term "cycloalkylene" means the corresponding biradical (-cycloalkyl-).

The term "alkenyl" as used herein refers to a straight or branched hydrocarbon chain or cyclic hydrocarbons containing one or more double bonds, including di-enes, tri-enes and poly-enes. Typically, the alkenyl group comprises from two to eight carbon atoms (C$_{2-8}$-alkenyl), such as from two to six carbon atoms (C$_{2-5}$-alkenyl), in particular from two to four carbon atoms (C$_{2-4}$-alkenyl), including at least one double bond. Examples of alkenyl groups include ethenyl; 1- or 2-propenyl; 1-, 2- or 3-butenyl, or 1,3-but-dienyl; 1-, 2-, 3-, 4- or 5-hexenyl, or 1,3-hex-dienyl, or 1,3,5-hex-trienyl; 1-, 2-, 3-, 4-, 5-, 6-, or 7-octenyl, or 1,3-octadienyl, or 1,3,5-octatrienyl, or 1,3,5,7-octatetraenyl, or cyclohexenyl. Correspondingly, the term "alkenylene" means the corresponding biradical (-alkenyl-).

The term "alkynyl" as used herein refers to a straight or branched hydrocarbon chain containing one or more triple bonds, including di-ynes, tri-ynes and poly-ynes. Typically, the alkynyl group comprises of from two to eight carbon atoms ($C_{2-8}$-alkynyl), such as from two to six carbon atoms ($C_{2-5}$-alkynyl), in particular from two to four carbon atoms ($C_{2-4}$-alkynyl), including at least one triple bond. Examples of preferred alkynyl groups include ethynyl; 1- or 2-propynyl; 1-, 2- or 3-butynyl, or 1,3-but-diynyl; 1-, 2-, 3-, 4- or 5-hexynyl, or 1,3-hex-diynyl, or 1,3,5-hex-triynyl; 1-, 2-, 3-, 4-, 5-, 6-, or 7-octynyl, or 1,3-oct-diynyl, or 1,3,5-oct-triynyl, or 1,3,5,7-oct-tetraynyl. Correspondingly, the term "alkynylene" means the corresponding biradical (-alkynyl-).

The terms "halo" and "halogen" as used herein refer to fluoro, chloro, bromo or iodo. Thus a trihalomethyl group represents e.g. a trifluoromethyl group, or a trichloromethyl group. Preferably, the terms "halo" and "halogen" designate fluoro or chloro.

The term "fluoroalkyl" as used herein refers to an alkyl group as defined herein which is substituted one or more times with one or more fluorohalo, preferably perfluorated. The term "perfluoroalkyl" as used herein refers to an alkyl group as defined herein wherein all hydrogen atoms are replaced by fluoro atoms. Preferred fluoroalkyl groups include trifluoromethyl, pentafluoroethyl, etc.

The term "alkoxy" as used herein refers to an "alkyl-O-" group, wherein alkyl is as defined above.

The term "hydroxyalkyl" as used herein refers to an alkyl group (as defined hereinabove), which alkyl group is substituted one or more times with hydroxy. Examples of hydroxyalkyl groups include HO—$CH_2$—, HO—$CH_2$—$CH_2$— and $CH_3$—CH(OH)—.

The term "oxy" as used herein refers to an "—O—" group.
The term "oxo" as used herein refers to an "=O" group.
The term "amine" as used herein refers to primary (R—$NH_2$, R≠H), secondary ($R_2$—NH, $R_2$≠H) and tertiary ($R_3$—N, R≠H) amines. A substituted amine is intended to mean an amine where at least one of the hydrogen atoms has been replaced by the substituent.

The term "carbamoyl" as used herein refers to a "$H_2$N(C=O)—" group.

The term "aryl", as used herein, unless otherwise indicated, includes carbocyclic aromatic ring systems derived from an aromatic hydrocarbon by removal of a hydrogen atom. Aryl furthermore includes bi-, tri- and polycyclic ring systems. Examples of preferred aryl moieties include phenyl, naphthyl, indenyl, indanyl, fluorenyl, biphenyl, indenyl, naphthyl, anthracenyl, phenanthrenyl, pentalenyl, azulenyl, and biphenylenyl. Preferred "aryl" is phenyl, naphthyl or indanyl, in particular phenyl, unless otherwise stated. Any aryl used may be optionally substituted. Correspondingly, the term "arylene" means the corresponding biradical (-aryl-).

The term "heteroaryl", as used herein, refers to aromatic groups containing one or more heteroatoms selected from O, S, and N, preferably from one to four heteroatoms, and more preferably from one to three heteroatoms. Heteroaryl furthermore includes bi-, tri- and polycyclic groups, wherein at least one ring of the group is aromatic, and at least one of the rings contains a heteroatom selected from O, S, and N. Heteroaryl also include ring systems substituted with one or more oxo moieties. Examples of preferred heteroaryl moieties include N-hydroxytetrazolyl, N-hydroxytriazolyl, N-hydroxyimidazolyl, furanyl, triazolyl, pyranyl, thiadiazinyl, benzothiophenyl, dihydro-benzo[b]thiophenyl, xanthenyl, isoindanyl, acridinyl, benzisoxazolyl, quinolinyl, isoquinolinyl, phteridinyl, azepinyl, diazepinyl, imidazolyl, thiazolyl, carbazolyl, pyridinyl, pyridazinyl, pyrimidinyl, pyrazolyl, pyrazinyl, tetrazolyl, furyl, thienyl, isoxazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, azaindolyl, pyrazolinyl, and pyrazolidinyl. Non-limiting examples of partially hydrogenated derivatives are 1,2,3,4-tetrahydronaphthyl, 1,4-dihydronaphthyl, and 1-octalin. Correspondingly, the term "heteroarylene" means the corresponding biradical (-heteroaryl-).

The term "heterocyclyl" as used herein, refers to cyclic non-aromatic groups containing one or more heteroatoms selected from O, S, and N, preferably from one to four heteroatoms, and more preferably from one to three heteroatoms. Heterocyclyl furthermore includes bi-, tri- and polycyclic non-aromatic groups, and at least one of the rings contains a heteroatom selected from O, S, and N. Heterocyclyl also include ring systems substituted with one or more oxo moieties. Examples of heterocyclic groups are oxetane, pyrrolidinyl, pyrrolyl, 3H-pyrrolyl, oxolanyl, furanyl, thiolanyl, thiophenyl, pyrazolyl, pyrazolidinyl, imidazolyl, imidazolidinyl, 3H-pyrazolyl, 1,2-oxazolyl, 1,3-oxazolyl, 1,2-thiazolyl, 1,3-thiazolyl, 1,2,5-oxadiazolyl, piperidinyl, pyridinyl, oxanyl, 2-H-pyranyl, 4-H-pyranyl, thianyl, 2H-thiopyranyl, pyridazinyl, 1,2-diazinanyl, pyrimidinyl, 1,3-diazinanyl, pyrazinyl, piperazinyl, 1,4-dioxinyl, 1,4-dioxanyl, 1,3-diazinanyl, 1,4-oxazinyl, morpholinyl, thiomorpholinyl, 1,4-oxathianyl, benzofuranyl, isobenzofuranyl, indazolyl, benzimidazolyl, quinolinyl, isoquinolinyl, chromayl, isochromanyl, 4H-chromenyl, 1H-isochromenyl, cinnolinyl, quinazolinyl, quinoxalinyl, phthalazinyl, purinyl, naphthyridinyl, pteridinyl, indolizinyl, 1H-pyrrolizinyl, 4H-quinolizinyl and aza-8-bicyclo[3.2.1]octane. Correspondingly, the term "heterocyclylene" means the corresponding biradical (-heterocyclyl-).

The term "N-heterocyclic ring" as used herein, refers to a heterocyclyl or a heteroaryl as defined hereinabove having at least one nitrogen atom, and being bound via a nitrogen atom. Examples of such N-heterocyclic rings are pyrrolidinyl, pyrrolyl, 3H-pyrrolyl, pyrazolyl, pyrazolidinyl, imidazolyl, imidazolidinyl, 3H-pyrazolyl, 1,2-oxazolyl, 1,2-thiazolyl, 1,3-thiazolyl, piperidinyl, pyridinyl, pyridazinyl, pyrazinyl, piperazinyl, morpholinyl, pyridinyl, pyridazinyl, pyrimidinyl, pyrazolyl, pyrazinyl, tetrazolyl, etc.

Isomers

The compounds of Formula (I) may exist as geometric isomers (i.e. cis-trans isomers), optical isomers or stereoisomers, such as diastereomers, as well as tautomers. Accordingly, it should be understood that the definition of compounds of Formula (I) includes each and every individual isomers corresponding to the structural formula: Formula (I), including cis-trans isomers, stereoisomers and tautomers, as well as racemic mixtures of these and pharmaceutically acceptable salts thereof. Hence, the definition of compounds of Formula (I) is also intended to encompass all R- and S-isomers of a chemical structure in any ratio, e.g. with enrichment (i.e. enantiomeric excess or diastereomeric excess) of one of the possible isomers and corresponding smaller ratios of other isomers.

Diastereoisomers, i.e. non-superimposable stereochemical isomers, can be separated by conventional means such as chromatography, distillation, crystallization or sublimation.

The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of Formula (I) with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of Formula (I) can likewise be obtained by utilizing optically active starting materials and/or by utilizing a chiral catalyst. These isomers may be in the form of a free acid, a free base, an ester or a salt. Examples of chiral separation techniques are given in Chiral Separation Techniques, A Practical Approach, $2^{nd}$ ed. by G. Subramanian, Wiley-VCH, 2001.

Pharmaceutically Acceptable Salts

The compound of Formula (I) may be provided in any form suitable for the intended administration, in particular including pharmaceutically acceptable salts, solvates and prodrugs of the compound of Formula (I).

Pharmaceutically acceptable salts refer to salts of the compounds of Formula (I), which are considered to be acceptable for clinical and/or veterinary use. Typical pharmaceutically acceptable salts include those salts prepared by reaction of the compounds of Formula (I) a mineral or organic acid or an organic or inorganic base. Such salts are known as acid addition salts and base addition salts, respectively. It will be recognized that the particular counter-ion or multiple counter-ions forming a part of any salt is not of a critical nature, so long as the salt as a whole is pharmaceutically acceptable and as long as the counter-ion does not contribute undesired qualities to the salt as a whole. These salts may be prepared by methods known to the skilled person. Pharmaceutically acceptable salts are, e.g., those described and discussed in Remington's Pharmaceutical Sciences, 17. Ed. Alfonso R. Gennaro (Ed.), Mack Publishing Company, Easton, Pa., U.S.A., 1985 and more recent editions and in Encyclopedia of Pharmaceutical Technology.

Examples of pharmaceutically acceptable addition salts include acid addition salts formed with inorganic acids e.g. hydrochloric, hydrobromic, sulfuric, nitric, hydroiodic, metaphosphoric, or phosphoric acid; and organic acids e.g. succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic and galacturonic acid; and arylsulfonic, for example benzenesulfonic, p-toluenesulfonic, oxalic, methanesulfonic or naphthalenesulfonic acid; and base addition salts formed with alkali metals and alkaline earth metals and organic bases such as N,N-dibenzylethylenediamine, chloroprocaine, choline, diethanolamine, ethylenediamine, meglumine (N-methylglucamine), lysine and procaine; and internally formed salts.

Solvates

The compound of Formula (I) may be provided in dissoluble or indissoluble forms together with a pharmaceutically acceptable solvent such as water, ethanol, and the like. Dissoluble forms may also include hydrated forms such as the mono-hydrate, the dihydrate, the hemihydrate, the trihydrate, the tetrahydrate, and the like.

Isotopic Variations

Elemental symbols and element names are used herein to include isotopes of the named elements. In particular one, some, or all hydrogens may be deuterium. Radioactive isotopes may be used, for instance to facilitate tracing the fate of the compounds or their metabolic products after administration.

Prodrugs

The compound of Formula (I) may be provided as a prodrug. The term "prodrug" used herein is intended to mean a compound which—upon exposure to certain physiological conditions—will liberate the compound of Formula (I) which then will be able to exhibit the desired biological action. A typical example is a labile carbamate of an amine and a further example would be a trialkylsilyl ether of an alcohol or a trialkylsilyl ester of an acid, each optionally being trimethylsilyl.

Inhibitory Effect

The inventors have surprisingly found that compounds of Formula (I) as defined herein have an inhibitory effect on the activity of one or more HDMEs. In this respect said one or more HDMEs may be any HDME, however preferably the one or more HDMEs are selected from the JmjC (Jumonji) family, more preferably said one or more HDME(s) are HDME of the human JmjC family and even more preferably are HDME belonging to the KDM6, KDM5, KDM4 or KDM2 families. The present invention also relates to a compound of Formula (I) as defined herein in a method for inhibiting HDMEs. The method includes contacting a cell with a compound of Formula (I). In a related embodiment, the method further provides that the compound is present in an amount effective to produce a concentration sufficient to inhibit the demethylation of a histone in the cell.

Thus, preferably in an assay for demethylation of a histone substrate by said HDME, then preferred compounds of Formula (I) are compounds capable of reducing or preferably inhibiting said demethylation by said HDME. Said histone substrate may be any histone, but preferably is histone H3 or a fragment thereof, even more preferred: a fragment comprising K4, K9, K27, or K36 of H3. Preferably, said inhibition is determined as the $IC_{50}$ of said compound of Formula (I) in respect of the said demethylation assay.

Preferred compounds of Formula (I) which have an $IC_{50}$ at or below 1 μM, more preferably less than 300 nM, for example less than 100 nM, such as less than 50 nM in respect of demethylation of any of said histone substrates by any of said HDME. Thus very preferred compounds of Formula (I) which have an $IC_{50}$ at or below 1 μM, more preferably less than 500 nM, for example less than 100 nM, such as less than 50 nM in respect of demethylation of histone H3 methylated at least on one lysine.

In a preferred embodiment $IC_{50}$ is determined as described in Example 2 herein below. Thus, particularly preferred are compounds of Formula (I) which have an $IC_{50}$ at or below 1 μM, more preferably less than 500 nM, for example less than 100 nM, such as less than 50 nM when said $IC_{50}$ is determined as described in and one of the Examples herein below.

Particularly preferred compounds of Formula (I) are compounds that lead to a decreased tumour size and/or decreased number of metastases when tested in a xenograft model (Morton and Houghton, Nature Protocols, 2 (2) 247-250, 2007).

Pharmaceutical Compositions

In one aspect of this invention, there is provided a pharmaceutical composition comprising at, as an active ingredient, at least one compound of Formula (I) as defined herein and optionally one or more pharmaceutically acceptable excipients, diluents and/or carriers. The compounds of Formula (I) may be administered alone or in combination with pharmaceutically acceptable carriers, diluents or excipients, in either single or multiple doses. Suitable pharmaceutically acceptable carriers, diluents and excipients include inert solid diluents or fillers, sterile aqueous solutions and various organic solvents.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 21st Edition, 2000, Lippincott Williams & Wilkins.

The pharmaceutical compositions formed by combining a compound of Formula (I) as defined herein with pharmaceutically acceptable carriers, diluents or excipients can be readily administered in a variety of dosage forms such as tablets, powders, lozenges, syrups, suppositories, injectable solutions and the like. In powders, the carrier is a finely divided solid such as talc or starch which is in a mixture with the finely divided active component. In tablets, the active component is mixed with the carrier having the necessary binding properties in suitable proportions and compacted in the shape and size desired.

The pharmaceutical compositions may be specifically prepared for administration by any suitable route such as the oral and parenteral (including subcutaneous, intramuscular, intrathecal, intravenous and intradermal) route. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be prepared so as to provide controlled release of the active ingredient such as sustained or prolonged release according to methods well known in the art.

For oral administration in the form of a tablet or capsule, a compound of Formula (I) as defined herein may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum, sodium starch glycolate, crospovidone, croscarmellose sodium or the like. Additional excipients for capsules include macrogols or lipids.

For the preparation of solid compositions such as tablets, the active compound of Formula (I) is mixed with one or more excipients, such as the ones described above, and other pharmaceutical diluents such as water to make a solid pre-formulation composition containing a homogenous mixture of a compound of Formula (I). The term "homogenous" is understood to mean that the compound of Formula (I) is dispersed evenly throughout the composition so that the composition may readily be subdivided into equally effective unit dosage forms such as tablets or capsules.

Liquid compositions for either oral or parenteral administration of the compound of Formula (I) include, e.g., aqueous solutions, syrups, elixirs, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrolidone.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. For parenteral administration, solutions containing a compound of Formula (I) in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The oily solutions are suitable for intra-articular, intra-muscular and subcutaneous injection purposes.

The preparation of all these solutions under sterile conditions is readily accomplished by standard pharmaceutical techniques well known to those skilled in the art.

Depot injectable compositions are also contemplated as being within the scope of the present invention.

In addition to the aforementioned ingredients, the compositions of a compound of Formula (I) may include one or more additional ingredients such as diluents, buffers, flavouring agents, colourant, surface active agents, thickeners, preservatives, e.g. methyl hydroxybenzoate (including anti-oxidants), emulsifying agents and the like.

A suitable dosage of the compound of Formula (I) will depend on the age and condition of the patient, the severity of the disease to be treated and other factors well known to the practicing physician. The compound may be administered for example either orally, parenterally or topically according to different dosing schedules, e.g. daily or with intervals, such as weekly intervals. In general a single dose will be in the range from 0.01 to 100 mg/kg body weight, preferably from about 0.05 to 75 mg/kg body weight, more preferably between 0.1 to 50 mg/kg body weight, and most preferably between 0.1 to 25 mg/kg body weight. The compound may be administered as a bolus (i.e. the entire daily dose is administered at once) or in divided doses two or more times a day. Variations based on the aforementioned dosage ranges may be made by a physician of ordinary skill taking into account known considerations such as weight, age, and condition of the person being treated, the severity of the affliction, and the particular route of administration.

The compounds of Formula (I) may also be prepared in a pharmaceutical composition comprising one or more further active substances alone, or in combination with pharmaceutically acceptable carriers, diluents, or excipients in either single or multiple doses. The suitable pharmaceutically acceptable carriers, diluents and excipients are as described herein above, and the one or more further active substances may be any active substances, or preferably an active substance as described in the section "combination treatment" herein below.

Clinical Conditions and Other Uses of Compounds

The compounds according to Formula (I) as defined herein are useful for treatment of a HDME dependent disease, disorder or condition. The treatment may include administering to a mammal, preferably a human, more preferably a human suffering from a HDME dependent disease, a therapeutically effective amount of a compound according to Formula (I) as defined herein.

Said HDME may be any HDME, however preferably the HDME of the present method is selected from the JmjC (Jumonji) family, as described in Cloos et. al., Genes & Development 22, 1115-1140, 2008, which is incorporated herein by reference in its entirety. More preferably said HDME is a HDME of the human JmjC family.

The present invention also relates to a compound of Formula (I) as defined herein for use in the treatment of a HDME dependent disease, such as for the treatment of cancer.

By the term "HDME dependent disease" is meant any disease characterized by elevated HDME expression and/or activity in at least in some instances of the disease, or a disease which is ameliorated by lowering the activity of HDMEs. Thus, the disease to be treated with the inhibitors of HDME, i.e. compounds of Formula (I), may be a proliferative or hyperproliferative disease, which includes benign or malignant tumors, for example a proliferative or hyperproliferative disease selected from the group consisting of a carcinoma of the brain, kidney, liver, adrenal gland, bladder, breast, stomach (for example gastric tumors), ovaries, esophagus, colon, rectum, prostate, pancreas, lung, vagina, thyroid, sarcoma, glioblastomas, multiple myeloma or gastrointestinal cancer, for example, colon carcinoma or colorectal adenoma, or a tumor of the neck and head, an epidermal hyperproliferation, for example, psoriasis, prostate hyperplasia, a neoplasia, including a neoplasia of epithelial character, including mammary carcinoma, and a leukemia.

In one embodiment, compounds of Formula (I) as defined herein are useful in the treatment of one or more cancers. The term "cancer" refers to any cancer caused by the proliferation of neoplastic cells, such as solid tumors, neoplasms, carcinomas, sarcomas, leukemias, lymphomas and the like. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma, (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor, nephroblastoma, lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcfnoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (acute myeloid leukemia, chronic myeloid leukemia, acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

In one embodiment, the compounds of Formula (I) as defined herein are useful in the treatment of one or more cancers selected from the group consisting of: leukemias including acute leukemias and chronic leukemias such as acute lymphocytic leukemia (ALL), Acute myeloid leukemia (AML), chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; mesothelioma, primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain tumors, liver cancer and thyroid cancer.

In another very preferred embodiment, the compound of Formula (I) as defined herein are useful for the treatment of squamous cell carcinomas. Preferably said squamous cell carcinomas are cancers of the carcinoma type of squamous epithelium that may occur in many different organs, including the skin, lips, mouth, esophagus, urinary bladder, prostate, lungs, vagina, and cervix; brain cancer, that is neuroblastoma, glioblastoma and other malignant and benign brain tumors; breast cancer, pancreatic cancer, and multiple myeloma.

In yet another embodiment, the compounds of Formula (I) as defined herein are useful for treatment of brain cancer, tumors of adults such as head and neck cancers (e.g., oral, laryngeal and esophageal), genito urinary cancers (e.g., prostate, bladder, renal, uterine, ovarian, testicular, rectal and colon), and breast cancer.

Other cancer forms for which the compounds of Formula (I) are useful as treatment can be found in Stedman's Medical Dictionary (Lippincott Williams & Wilkins, 28$^{th}$ Ed., 2005), which is incorporated herein by reference in its entirety.

In still another related embodiment, the disease to be treated by compounds of Formula (I) as defined herein is selected from persistent proliferative or hyperproliferative conditions such as angiogenesis, such as psoriasis; Kaposi's sarcoma; restenosis, e.g., stent-induced restenosis; endometriosis; Hodgkin's disease; leukemia; hemangioma; angiofibroma; eye diseases, such as neovascular glaucoma; renal diseases, such as glomerulonephritis; malignant nephrosclerosis; thrombotic microangiopathic syndromes; transplant rejections and glomerulopathy; fibrotic diseases, such as cirrhosis of the liver; mesangial cell-proliferative diseases; injuries of the nerve tissue; and inhibiting the re-occlusion of vessels after balloon catheter treatment, for use in vascular prosthetics or after inserting mechanical devices for holding vessels open, such as, e.g., stents, as immune-suppressants, as an aid in scar-free wound healing, and treating age spots and contact dermatitis.

The compounds of Formula (I) are suitable as active agents in pharmaceutical compositions that are efficacious particularly for treating cellular proliferative or hyperproliferative ailments and/or ailments associated with dysregulated gene expression. Such pharmaceutical compositions have a therapeutically effective amount of the compound of Formula (I) along with other pharmaceutically acceptable excipients, carriers, and diluents and. The phrase, "therapeutically effective amount" as used herein indicates an amount necessary to administer to a host, or to a cell, tissue, or organ of a host, to achieve a therapeutic effect, such as an ameliorating or alternatively a curative effect, for example an anti-tumor effect, e.g. reduction of or preferably inhibition of proliferation of malignant cancer cells, benign tumor cells or other proliferative cells, or of any other HDME dependent disease.

Another aspect of the invention is a pharmaceutical composition comprising a therapeutically effective amount of at least one compound of Formula (I) as defined herein, or a pharmaceutically acceptable salt, solvate or prodrug thereof, in combination with at least one further anti-neoplastic compound, and a pharmaceutically acceptable excipient, carrier or diluent.

Method of Treatment

In a further aspect the present invention relates to a method of treating a diseases in a subject, said method comprises administering to said subject a therapeutically effective amount of at least one compound of Formula (I) as defined herein. The disease may be any disease or disorder as mentioned herein, such as for example mentioned in the section "HDME dependent diseases", and the compound may be administered alone or in a pharmaceutical composition, such as for example mentioned in the section "Pharmaceutical compositions".

Hence, the invention also relates to a compound of Formula (I) as defined herein for use as a medicament.

The term "treating" and "treatment", as used herein, unless otherwise indicated, refers to reversing, alleviating, inhibiting the process of, or preventing the disease, disorder or condition to which such term applies, or one or more symptoms of such disease, disorder or condition and includes the administration of a compound of Formula (I) to prevent the onset of the symptoms or the complications, or alleviating the symptoms or the complications, or eliminating the disease, condition, or disorder. Preferably treatment is curative or ameliorating.

In a preferred embodiment of this aspect of the invention the method is a method of treating a HDME dependent disease in a subject, said method comprises administering to said subject a therapeutically effective amount of a compound of Formula (I) as defined herein to a subject in need of such treatment. The HDME dependent disease may be any HDME dependent disease as described herein above. Preferably the HDME dependent disease is squamous cell carcinomas or any other of the cancer conditions mentioned above.

Hence, the invention also relates to a compound of Formula (I) as defined herein for use in the treatment of a HDME dependent disease, such as for the treatment of cancer.

Further, the invention relates to the use of a compound of Formula (I) as defined herein for the preparation of a pharmaceutical composition for the treatment of a HDME dependent disease.

In one embodiment of the method of treatment of a HDME dependent disease, the compound of Formula (I) as defined herein is administered in combination with one or more further active substances. The active substances may be any active substances, and preferably an active substance as described herein above in the section "combination treatment". More preferably the one or more additional active substances are selected from the group consisting of anti-proliferative or anti-neoplastic agents.

Combination Treatment

A compound of Formula (I) may also be used to advantage in combination with one or more other anti-proliferative or anti-neoplastic agents. Such anti-proliferative agents include, but are not limited to other HDME inhibitors, proteasome inhibitors, including bortezomib (Valcade) and Carfilzomib, aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein tyrosine or serine or threonine kinase activity; compounds targeting/decreasing a lipid kinase activity; compounds targeting/decreasing a carbohydrate kinase activity and further anti-angiogenic compounds; compounds which target, decrease or inhibit the activity of a protein or lipid phosphatase; gonadorelin agonists; anti-androgens; angiostatic steroids; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL(R)); leucovorin; immune stimulating agents, such as BCG, IL-2 or IFN-α, antibodies such as anti-CTLA-4 monoclonal antibody ipilimumab (Yervoy), rituximab or herceptin and cancer vaccines; inhibitors/modulators of mitochondrial activity such as metformin.

A compound of Formula (I) as defined herein may also be used to advantage in combination with known therapeutic processes, e.g., the administration of hormones or tumor cell damaging approaches, especially ionizing radiation.

A compound of Formula (I) as defined herein may also be used as a radiosensitizer, including, for example, the treatment of tumors which exhibit poor sensitivity to radiotherapy.

By the term "combination", is meant either a fixed combination in one dosage unit form, or a kit of parts for the combined administration where a compound of Formula (I) and a combination partner may be administered independently at the same time or separately within time intervals that especially allow that the combination partners show a cooperative, e.g., synergistic, effect, or any combination thereof.

The phrase, "aromatase inhibitor" as used herein relates to a compound which inhibits the estrogen production, i.e., the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g., under the trademark AROMASIN. Formestane can be administered, e.g., in the form as it is marketed, e.g., under the trademark LENTARON. Fadrozole can be administered, e.g., in the form as it is marketed, e.g., under the trademark AFEMA. Anastrozole can be administered, e.g., in the form as it is marketed, e.g., under the trademark ARIMIDEX. Letrozole can be administered, e.g., in the form as it is marketed, e.g., under the trademark FEMARA or FEMAR. Aminoglutethimide can be administered, e.g., in the form as it is marketed, e.g., under the trademark ORIMETEN. A combination of the invention comprising a chemotherapeutic agent which is an aromatase inhibitor is particularly useful for the treatment of hormone receptor positive tumors, e.g., breast tumors.

The term "antiestrogen" as used herein relates to a compound that antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g., under the trademark NOLVADEX. Raloxifene hydrochloride can be administered, e.g., in the form as it is marketed, e.g., under the trademark EVISTA. Fulvestrant can be formulated as disclosed in U.S. Pat. No. 4,659,516 or it can be administered, e.g., in the form as it is marketed, e.g., under the trademark FASLODEX. A combination of the invention comprising a chemotherapeutic agent which is an antiestrogen is particularly useful for the treatment of estrogen receptor positive tumors, e.g., breast tumors.

The term "anti-androgen" as used herein relates to any substance which is capable of inhibiting the biological effects of androgenic hormones and includes, but is not limited to, bicalutamide (CASODEX), which can be formulated, e.g., as disclosed in U.S. Pat. No. 4,636,505.

The phrase, "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g., under the trademark ZOLADEX. Abarelix can be formulated, e.g., as disclosed in U.S. Pat. No. 5,843,901.

The phrase, "topoisomerase I inhibitor" as used herein includes, but is not limited to topotecan, gimatecan, irinotecan, camptothecin and its analogues, 9-nitrocamptothecin and the macromolecular camptothecin conjugate PNU-166148 (compound AI in WO99/17804). Irinotecan can be administered, e.g., in the form as it is marketed, e.g., under the trademark CAMPTOSAR. Topotecan can be administered, e.g., in the form as it is marketed, e.g., under the trademark HYCAMTIN.

The phrase, "topoisomerase II inhibitor" as used herein includes, but is not limited to the anthracyclines such as doxorubicin (including liposomal formulation, e.g., CAELYX), daunorubicin, epirubicin, idarubicin and nemorubicin, the anthraquinones mitoxantrone and losoxantrone, and the podophyllotoxins etoposide and teniposide. Etoposide can be administered, e.g., in the form as it is marketed, e.g., under the trademark ETOPOPHOS. Teniposide can be administered, e.g., in the form as it is marketed, e.g., under the trademark VM 26-BRISTOL. Doxorubicin can be administered, e.g., in the form as it is marketed, e.g., under the trademark ADRIBLASTIN or ADRIAMYCIN. Epirubicin can be administered, e.g., in the form as it is marketed, e.g., under the trademark FARMORUBICIN. Idarubicin can be administered, e.g., in the form as it is marketed, e.g., under the trademark ZAVEDOS. Mitoxantrone can be administered, e.g., in the form as it is marketed, e.g., under the trademark NOVANTRON.

The phrase, "microtubule active agent" relates to microtubule stabilizing, microtubule destabilizing agents and microtublin polymerization inhibitors including, but not limited to taxanes, e.g., paclitaxel and docetaxel, vinca alkaloids, e.g., vinblastine, including vinblastine sulfate, vincristine including vincristine sulfate, and vinorelbine, discodermolides, cochicine and epothilones and derivatives thereof, e.g., epothilone B or D or derivatives thereof. Paclitaxel may be administered e.g., in the fo[pi]n as it is marketed, e.g., TAXOL. Docetaxel can be administered, e.g., in the form as it is marketed, e.g., under the trademark TAXOTERE. Vinblastine sulfate can be administered, e.g., in the form as it is marketed, e.g., under the trademark VINBLASTIN R.P. Vincristine sulfate can be administered, e.g., in the form as it is marketed, e.g., under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Included are Epothilone A and/or B.

The phrase, "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g., under the trademark CYCLOSTIN. Ifosfamide can be administered, e.g., in the form as it is marketed, e.g., under the trademark HOLOXAN.

The phrase, "histone deacetylase inhibitors" or "HDAC inhibitors" relates to compounds which inhibit at least one example of the class of enzymes known as a histone deacetylase, and which compounds generally possess antiproliferative activity. Previously disclosed HDAC inhibitors include compounds disclosed in, e.g., WO 02/22577, including N-hydroxy-3-[4-{[(2-hydroxyethyl)[2-(IH-indol-3-yl)ethyl]-amino]methyl]phenyl]-2E-2-propenamide, N-hydroxy-3-[4-[[[2-(2-methyl-IH-indol-3-yl)-ethylJ-amino]methyl]phenyl]-2E-2-propenamide and pharmaceutically acceptable salts thereof. It further includes Suberoylanilide hydroxamic acid (SAHA). Other publicly disclosed HDAC inhibitors include butyric acid and its derivatives, including sodium phenylbutyrate, thalidomide, trichostatin A and trapoxin.

The term "antineoplastic antimetabolite" includes, but is not limited to, 5-Fluorouracil or 5-FU, capecitabine, gemcitabine, DNA demethylating agents, such as 5-azacytidine and decitabine, methotrexate and edatrexate, and folic acid antagonists such as pemetrexed. Capecitabine can be administered, e.g., in the form as it is marketed, e.g., under the trademark XELODA. Gemcitabine can be administered, e.g., in the form as it is marketed, e.g., under the trademark GEMZAR. Also included is the monoclonal antibody trastuzumab which can be administered, e.g., in the form as it is marketed, e.g., under the trademark HERCEPTIN.

The phrase, "platin compound" as used herein includes, but is not limited to, carboplatin, cis-platin, cisplatinum and oxaliplatin. Carboplatin can be administered, e.g., in the form as it is marketed, e.g., under the trademark CARBOPLAT. Oxaliplatin can be administered, e.g., in the form as it is marketed, e.g., under the trademark ELOXATIN.

The phrase, "compounds targeting/decreasing a protein tyrosine or serine or threonine kinase activity" as used herein includes, but is not limited to, gefinitib, erlotinib, lapatinib, foretinib, cabozantinib, vemurafenib or selumetinib (AZD6244). Gefinitib can be administered, e.g., in the form as it is marketed, e.g., under the trademark IRESSA. Erlotinib can be administered, e.g., in the form as it is marketed, e.g., under the trademark TARCEVA. Lapatinib can be administered, e.g., in the form as it is marketed, e.g., under the trademarks TYKERB and TYVERB. Cabozantinib can be administered, e.g., in the form as it is marketed, e.g., under the trademark COMETRIQ. Vemurafenib can be administered, e.g., in the form as it is marketed, e.g., under the trademark CELBORAF. Foretinib can be formulated, e.g., as disclosed in US 20,120,282,179. Selumetinib (AZD6244) can be formulated, e.g., as disclosed in US 20,080,177,082 and US 20,090,246,274. Other suitable protein kinase inhibitors include without limitation Afatanib (Gilotrif, Boeringer Ingelheim), Axitinib (Inlyta, Pfizer), Bosutinib (Bosulif, Wyeth), Crizotinib (Xalkori, Pfizer), Dabrafenib (Tafinlar, GSK), Dasatinib (Sprycel, Bristol-Myers Squib), Elotinib (Tarceva, OSI), Everolimus (Afinitor, Novartis), Gefitinib (Iressa, Astrazeneca), Ibrutinib (Imbruvica, Pharmacyclics and J&J), Imatanib (Gleevec, Novartis), Nilotinib (Tasigna, Novartis), Pazopanib (Votrient, GlaxoSmithKline), Ponatinib (Iclusig, Ariad), Regorafenib (Stivarga, Bayer), Ruxolitinib (Jakafi, Incyte), Sirolimus (Rapamune, Wyeth), Sorafenib (Nexavar, Bayer), Sunitinib (Sutent, Pfizer), Tofacitinib (Xeljanz, Pfizer), Temsirolimus (Torisel, Wyeth), Trametinib (Mekinist, GSK), Vandetanib (Caprelsa, IPR Pharms) as well as other proposed protein kinase inhibitors that can be found in the literature.

Tumor cell damaging approaches refer to approaches such as ionizing radiation. The phrase, "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See, e.g., Hellman, Principles of Radiation Therapy, Cancer, in Principles and Practice of Oncology, Devita et al., Eds., 4th Edition, Vol. 1, pp. 248-275 (1993).

The phrase, "angiostatic steroids" as used herein refers to agents which block or inhibit angiogenesis, such as, e.g., anecortave, triamcinolone, hydrocortisone, 11-[alpha]-epi-hydrocotisol, cortexolone, 17[alpha]-hydroxyprogesterone, corticosterone, desoxycorticosterone, testosterone, estrone and dexamethasone.

Other chemotherapeutic agents include, but are not limited to, plant alkaloids, hormonal agents and antagonists; biological response modifiers, preferably lymphokines or interferons; antisense oligonucleotides or oligonucleotide derivatives; or miscellaneous agents or agents with other or unknown mechanism of action.

The structure of the active agents identified by code numbers, generic or trade names may be taken from the actual edition of the standard compendium "The Merck Index" or from databases, e.g., Patents International (e.g., IMS World Publications).

The above-mentioned compounds, which can be used in combination with a compound of Formula (I), can be prepared and administered as described in the art such as in the documents cited above.

Furthermore, the compounds of the invention may be used in a method of profiling the functional and structural similarity of histone demethylases comprising taking a panel of at least two histone demethylases and a panel of at least two compounds of formula 1 and determining the extent to which each said compound of formula 1 inhibits the activity of each of said histone demethylases, and generating a similarity index reflecting the degree of similarity between the histone demethylases in respect of their inhibition by said compounds.

Preparation of Compounds of Formula (I): Q is $CH_2NHR^{13}$

Scheme 1

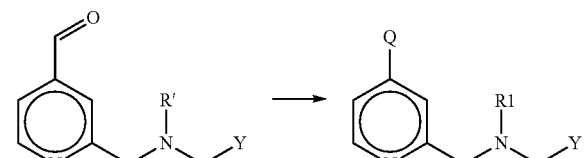

Method A—Reductive Amination

Compounds of Formula (I) may be prepared from 4-formyl pyridines according to Scheme 1, where R' is a suitable protecting group or $R^7$, in one-pot or by a stepwise procedure by mixing with an amine, optionally containing orthogonal protected reactive sites, and a reducing agent such as $NaBH_4$, $NaBH(OAc)_3$, $NaCNBH_3$, or $Et_3SiH$, either at room temperature or by heating for up to several hours by use of a solvent such as an alcohol, DCE, DCM, water, or toluene, optionally adding a catalyst such as an acid or a Lewis acid. Optionally, protecting groups may be removed and a purification method such as silica gel chromatography is employed if needed.

Scheme 2 - Reduction of hydroxylamine to primary amine

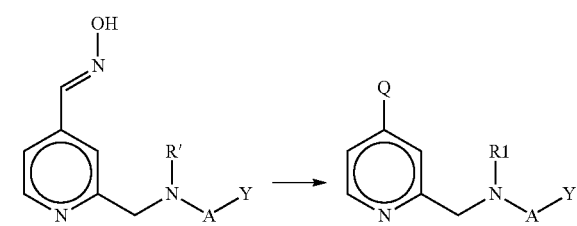

Method B

Compounds of Formula (I) may be prepared from hydroxyl amines, optionally containing orthogonally protected reactive sites, according to Scheme 2, where R' is a suitable protecting group or $R^1$, by use of reducing agents, such as a hydrogen atmosphere over a suitable catalyst, such as palladium on charcoal, in a suitable solvent, such as an alcohol. Optionally, protecting groups may be removed and a purification method such as silica gel chromatography is employed if needed.

Scheme 3—Reductive amination

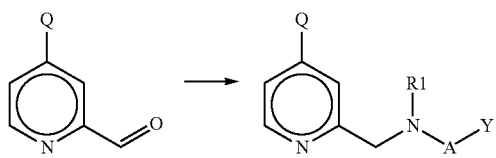

Method C

Compounds of Formula (I) may be prepared from 2-formyl pyridines according to Scheme 3 analogously to Method A.

Scheme 4

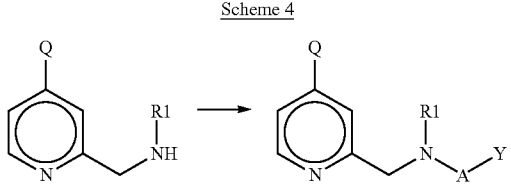

Method D—Buchwald Coupling to Aryls

Compounds of Formula (I) may be prepared according to Scheme 4 using a suitable solvent such as toluene or tetrahydrofuran, a base such as cesium carbonate or potassium t-butoxide, a suitable catalyst such as $Pd_2(dba)_3$, optionally a suitable salt such as lithium chloride and the desired electrophile such as arylbromide or heteroarylbromide. The compounds of Formula I are generated at room temperature or by heating for several hours, such as for 2 to 5 hours. Optionally, protecting groups may be removed and a purification method such as silica gel chromatography is employed if needed.

Method E—Reductive Amination

Compounds of Formula (I) may be prepared from amines according to Scheme 4 according to method A.

Method F—Alkylation/Acylation

The compounds of Formula (I) may be prepared according to scheme 4 by use of a solvent such as DMF or THF, a base such as sodium hydride or cesium carbonate and a suitable electrophilic species such as an epoxide, a heteroaromatic chloride, an aliphatic, allylic or benzylic bromide, chloride or sulfonate, or a carbonyl chloride. Optionally, protecting groups may be removed and a purification method such as silica gel chromatography is employed if needed.

Scheme 5—Reduction of amide

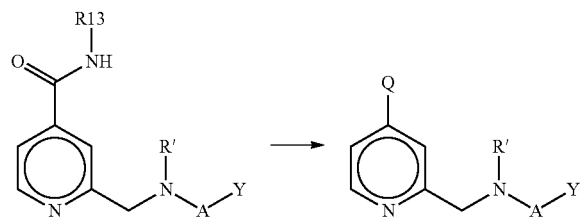

Method G

Compounds of Formula (I) may be prepared from amides, optionally containing orthogonal protected reactive sites, according to Scheme 5, where R' is a suitable protecting group or $R_1$, by use of reducing agents, such as lithium aluminium hydride or borane-complexes, in a suitable solvent, such as an ether or tetrahydrofuran. Optionally, protecting groups may be removed and a purification method such as silica gel chromatography is employed if needed.

Preparation of Compounds of Formula (I): Q is $CH=NR^{12}$

Scheme 6

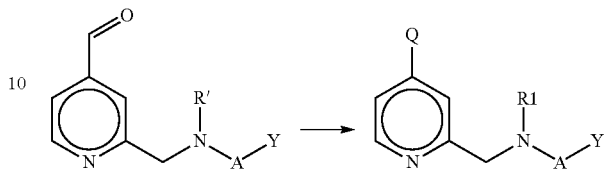

Method H

Compounds of Formula (I) may be prepared from 4-formyl pyridines according to Scheme 6, where R' is a suitable protecting group or R1, by mixing with an amine, optionally containing orthogonally protected reactive sites, either at room temperature or by heating for up to several hours by use of a solvent such as an alcohol, DCE, DCM, water, or toluene, optionally adding a catalyst such as a Lewis acid. Optionally, protecting groups may be removed and a purification method such as silica gel chromatography is employed if needed.

Preparation of Compounds of Formula (I): Q is CH=O

Scheme 7

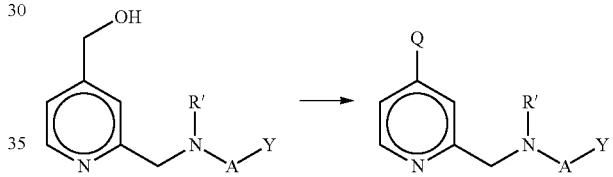

Method I

Compounds of General Formula (I) may be prepared according to Scheme 7, where R' is a suitable protecting group or R1, by a Swern or alternatively a Dess-Martin oxidation of alcohol to aldehyde. Optionally, protecting groups may be removed and a purification method such as silica gel chromatography is employed if needed.

Scheme 8

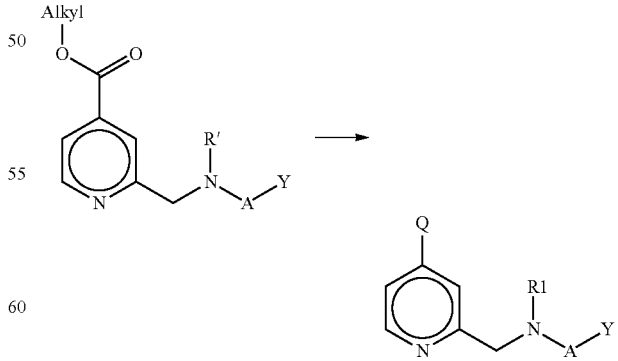

Method J

Compounds of General Formula (I) may be prepared from esters, where R' is a suitable protecting group or R1, optionally containing orthogonal protected reactive sites, according to Scheme 8, by use of reducing agents, such as DIBAL-H, in a suitable solvent, such as toluene. Optionally, protecting groups may be removed and a purification method such as silica gel chromatography is employed if needed.

Scheme 9

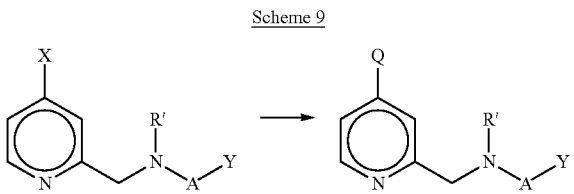

Method K

Compounds of General Formula (I) may prepared at low temperature, e.g. at −78° C., from halides, where R' is a suitable protecting group or R1, optionally containing orthogonal protected reactive sites according to Scheme 9 (X designates a halogen atom) by halogen metal exchange, e.g. by treatment with an alkyl lithium reagent, followed by addition of DMF in a solvent, such as dichloromethane. Optionally, protecting groups may be removed and a purification method such as silica gel chromatography is employed if needed.

Preparation of Compounds of Formula (I): Q is $CH(OR^{17})_2$

Scheme 10

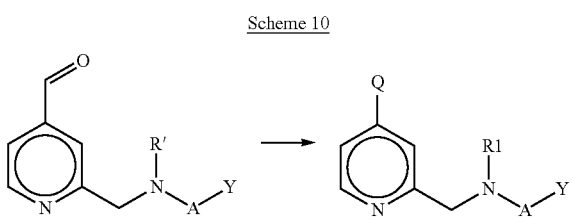

Method L

Compounds of General Formula (I) may prepared from 4-formyl pyridines according to Scheme 10 by stirring in an alcohol in the presence of a Lewis acid or an acid, such as HCL or Pyridinium toluene-4-sulphonate, optionally by reacting with trialkyl orthoformate or in the presence of a drying agent such as an inorganic dry salt, or with azeotropic removal of water, at room temperature or by heating for several hours depending on the method. Optionally, protecting groups may be removed and a purification method such as silica gel chromatography is employed if needed.

Preparation of Compounds of Formula (I): Q is W and $R^{16}$ is H

Method M

Compounds of General Formula (I) may prepared from 4-formyl pyridines according to Scheme 10 by stirring in a diamine, an aminoalcohol or an aminothiol, optionally in the presence of an acid such as HCL or Pyridinium toluene-4-sulphonate, optionally in the presence of a drying agent such as an inorganic dry salt or molecular sieves, or with azeotropic removal of water, at room temperature or by heating for several hours depending on the method. Optionally, protecting groups may be removed and a purification method such as silica gel chromatography is employed if needed.

Preparation of Compounds of Formula (I): Q is W and $R^3$ is not H

Method N

Compounds of General Formula (I) may prepared from the aforementioned compound where Q is W and $R^{16}$ is H, by reacting with a suitably activated acyl group such as an acyl halide or acyl anhydride at room temperature or by heating for several hours is a solvent such as dichloroethane or THF. Optionally, protecting groups may be removed and a purification method such as silica gel chromatography is employed if needed.

Preparation of Intermediates for Compounds of Formula (I)

Scheme 11

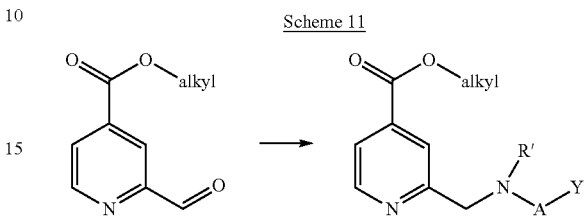

Method AA

Intermediates may be prepared from 2-formyl pyridines according to Scheme 11 analogously to Method A.

Scheme 12

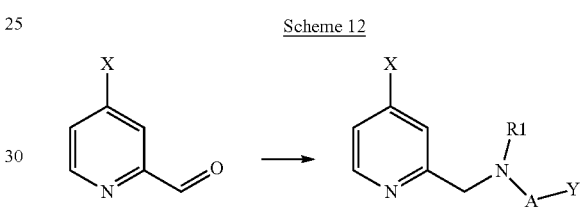

Method AB

Intermediates, where X designates halides or OTf, may be prepared from 2-formyl pyridines according to Scheme 12 analogously to Method A.

Scheme 13

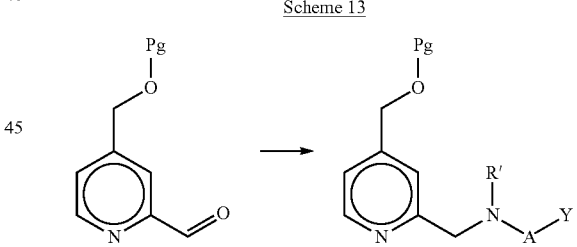

Method AC

Intermediates, where Pg designates a suitable protecting group, such as TBMDS or TIPS, may be prepared from 2-formyl pyridines according to Scheme 13 analogously to Method A.

Scheme 14

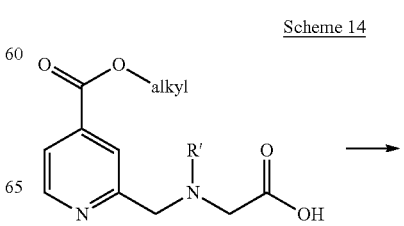

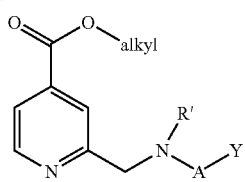

Method AD

Intermediates be prepared according to scheme 14, where R' is a suitable protecting group or $R_1$, by use of a solvent such as DMF or THF, a base such as a hindered tertiary amine, a dehydrating agent such as EDCI or DCC and an amine, and by mixing at or above room temperature for a period up to several hours. Optionally, the said protecting group may be removed, and a purification method such as silica gel chromatography is employed if needed.

Scheme 15

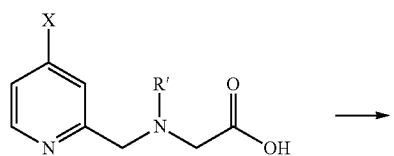 

Method AE

Intermediates may be prepared according to Scheme 15 analogously to Method AD.

Scheme 16

Method AF

Intermediates may be prepared according to Scheme 16 analogously to Method AD.

Scheme 17

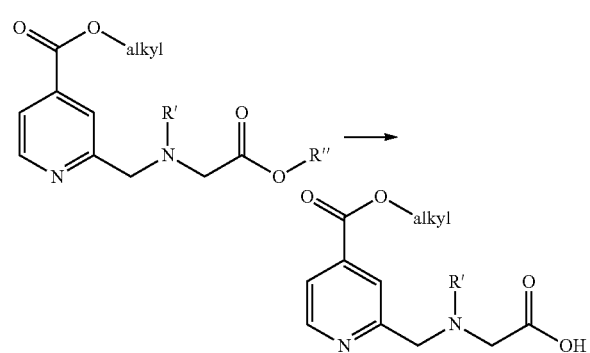

Method AG

Intermediates may be prepared according to scheme 17 from, where R' is a suitable protecting group or $R^1$ and R" is an orthogonal protecting group, which may be selectively removed, such as removal of R": $^t$Bu in presence of R': $CF_3CO$ by treating with trifluoroacetic acid in a solvent such as dichloromethane at room temperature for several hours. A purification method such as silica gel chromatography is employed if needed.

Scheme 18

Method AH

Intermediates may be prepared according to Scheme 18 analogously to Method AG.

Scheme 19

Method AI

Intermediates may be prepared according to Scheme 19 analogously to Method AG.

Scheme 20

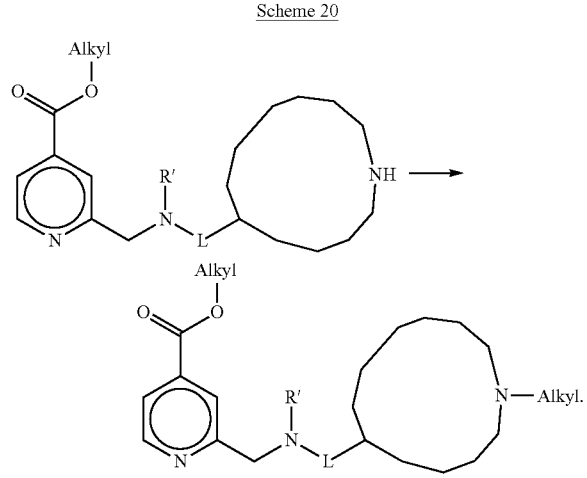

Method AJ

Intermediates may be prepared from aldehydes and intermediates, where L designates a bond or an aliphatic linker, which may comprise an amide bond, attached to an aliphatic heterocycle, according to Scheme 20 analogously to Method A Method AK Intermediates may be prepared according to Scheme 20 analogously to Method F.

Scheme 21

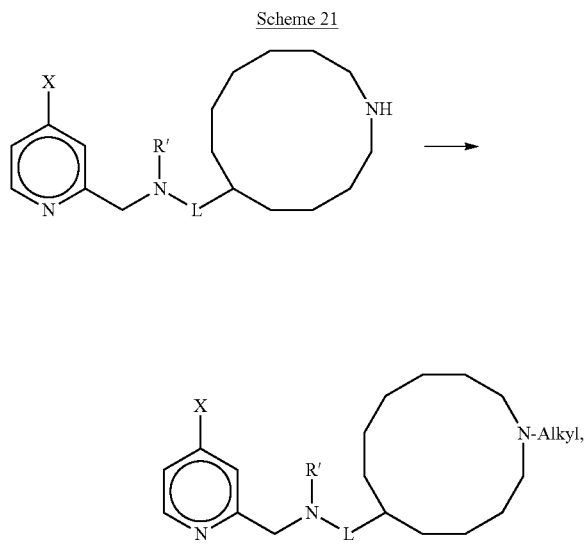

Method AL

Intermediates may be prepared according to Scheme 21 analogously to Method AJ.

Method AM

Intermediates may be prepared according to Scheme 21 analogously to Method F.

Scheme 22

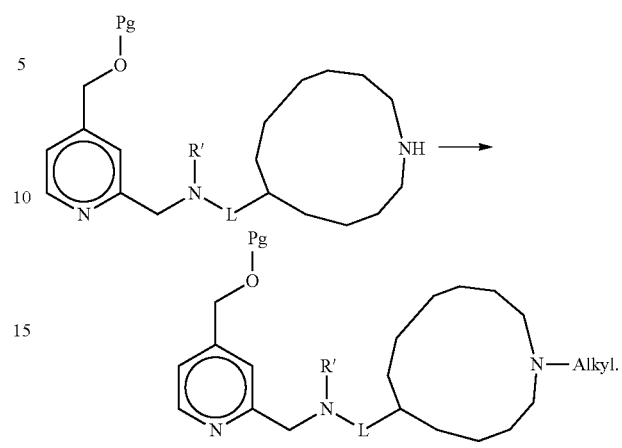

Method AN

Intermediates may be prepared according to Scheme 22 analogously to Method AJ.

Method AO

Intermediates may be prepared according to Scheme 22 analogously to Method F.

Scheme 23

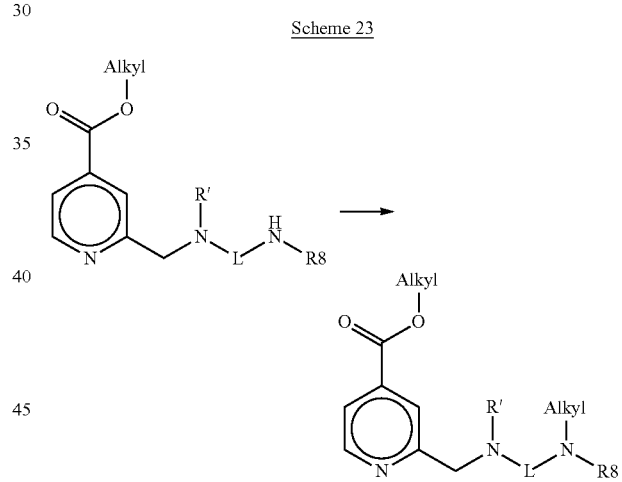

Method AP

Intermediates, where L designates an aliphatic linker, which may comprise an amide bond, may be prepared from aldehydes according to Scheme 23 analogously to Method E.

Method AO

Intermediates may be prepared according to Scheme 23 analogously to Method F.

Scheme 24

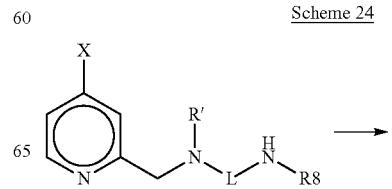

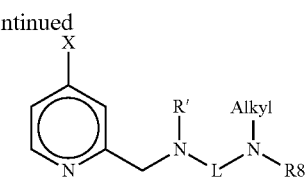

Method AR
Intermediates, where L designates an aliphatic linker, which may comprise an amide bond, may be prepared from aldehydes according to Scheme 24 analogously to Method E.

Method AS
Intermediates may be prepared according to Scheme 24 analogously to Method F.

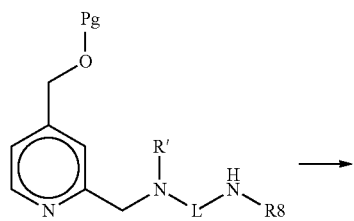

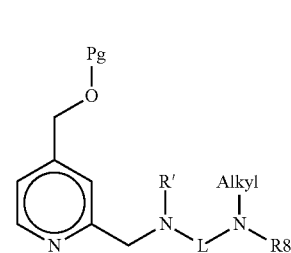

Method AT
Intermediates, where L designates an aliphatic linker, which may comprise an amide bond, may be prepared from aldehydes according to Scheme 25 analogously to Method E.

Method AU
Intermediates may be prepared according to Scheme 25 analogously to Method F.

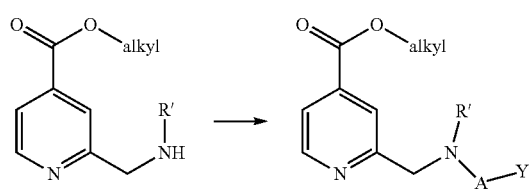

Method AV
Intermediates may be prepared according to Scheme 26 analogously to Method A.

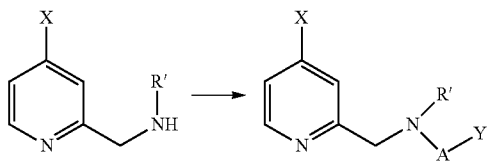

Method AW
Intermediates may be prepared according to Scheme 27 analogously to Method A.

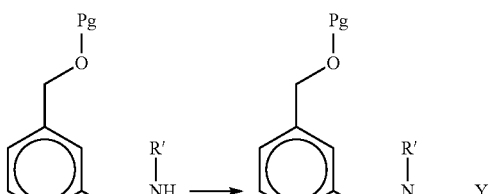

Method AX
Intermediates may be prepared according to Scheme 28 analogously to Method A.

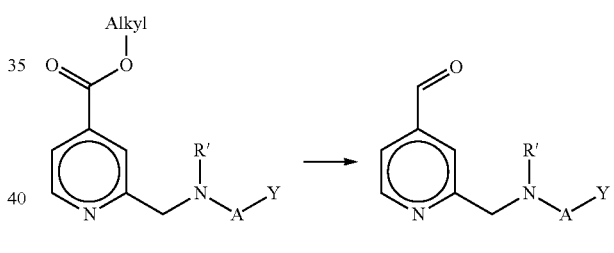

Method AZ
Intermediates may be prepared from esters, optionally containing orthogonal protected reactive sites, according to Scheme 29, by use of reducing agents, such as DIBAL-H, in a suitable solvent, such as toluene. Optionally, protecting groups may be removed and a purification method such as silica gel chromatography is employed if needed.

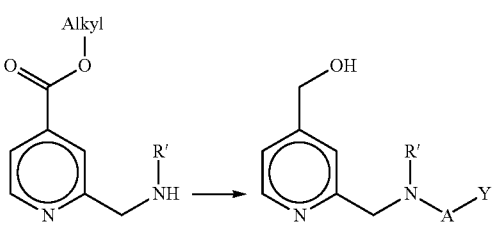

Method BA
Intermediates may be prepared from esters, optionally containing orthogonal protected reactive sites, according to Scheme 30, by use of reducing agents, such as lithium aluminiumhydride or borane-complexes, in a suitable solvent,

Scheme 31

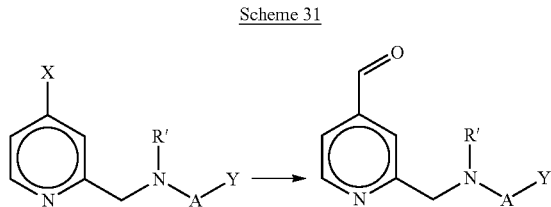

Method BB

Intermediates may be prepared according to Scheme 31 using method K

Method BC

Intermediates may be prepared according to scheme 31 either at room temperature or by heating for several hours by use of a solvent such as toluene or tetrahydrofuran, a base such as cesium carbonate or potassium t-butoxide, a catalyst such as $Pd_2(dba)_3$, optionally a salt such as lithium chloride and the desired nucleophile such as carbon monoxide. A purification method such as silica gel chromatography is employed if needed.

Scheme 32

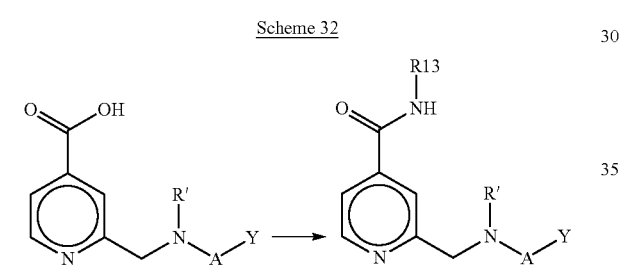

Method BD

Intermediates may be prepared according to scheme 32 analogously to Method AD.

Scheme 33

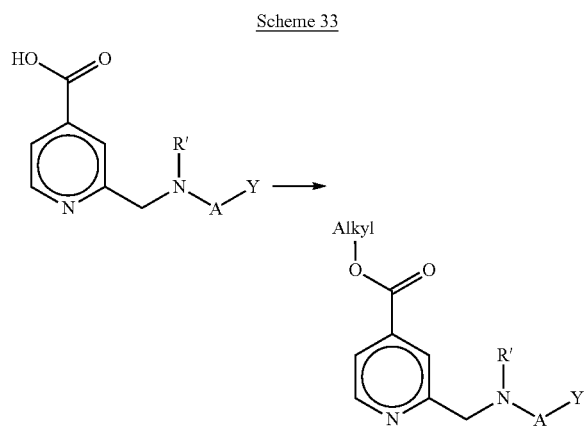

Method BE

Intermediates may be prepared according to Scheme 33 by use of a solvent such as DMF or THF, a base such as cesium carbonate and an electrophile such as an alkyl halide, heteroaromatic halide, alkenyl halide, etc., and by mixing at or above room temperature for several hours. A purification method such as silica gel chromatography or trituration is employed if needed.

Method BF

Intermediates may be prepared according to Scheme 33 by use of acetic catalysis in an alcohol at room temperature or at reflux. A purification method such as silica gel chromatography or trituration is employed if needed.

Scheme 34

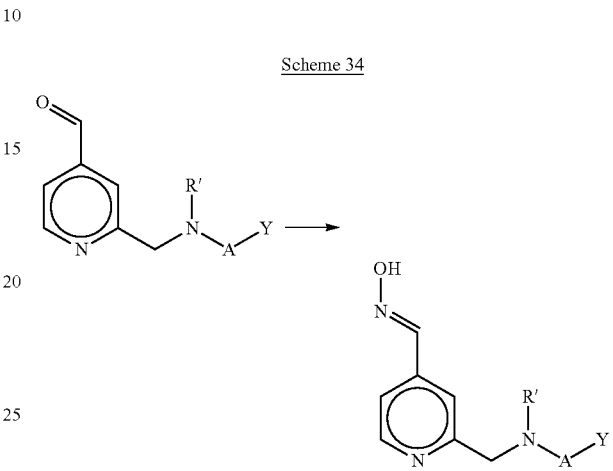

Method BG

Intermediates may be prepared according to scheme 34 from 4-formyl pyridines by reaction with hydroxylamine in a solvent such as an alcohol or water.

Scheme 35

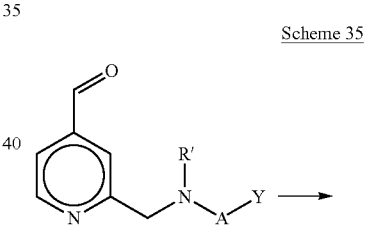

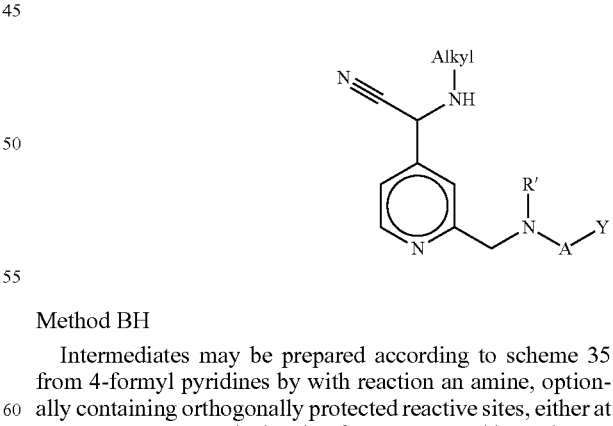

Method BH

Intermediates may be prepared according to scheme 35 from 4-formyl pyridines by with reaction an amine, optionally containing orthogonally protected reactive sites, either at room temperature or by heating for up to several hours by use of a solvent such as an alcohol, DCE, DCM, THF water, or toluene, optionally adding a catalyst such as a Lewis acid. Subsequently reacting with TMSCN in a solvent such as acetonitrile. Optionally, protecting groups may be removed and a purification method such as silica gel chromatography is employed if needed.

Scheme 36

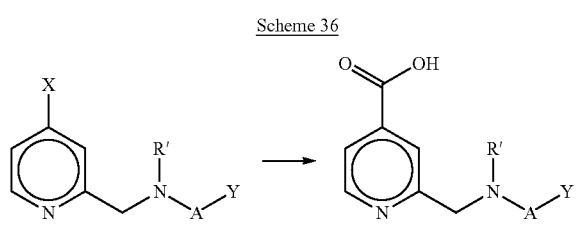

Method BI

Intermediates may be prepared according to Scheme 36 either at room temperature or by heating for several hours by use of a solvent such as wet toluene or tetrahydrofuran, a base such as cesium carbonate or potassium t-butoxide, a catalyst such as Pd$_2$(dba)$_3$, optionally a salt such as lithium chloride and the desired nucleophile such as carbon monoxide. A purification method such as silica gel chromatography is employed if needed.

Scheme 37

Method BJ

Intermediates may be prepared according to Scheme 37 from pyridine 2-carboxylates analogously to Method J.

Scheme 38

Method BK

Intermediates may be prepared according to Scheme 38 from pyridine 2-halides analogously to Method K.

EXAMPLES

Example 1

Preparation of Compounds of the Invention

General Methods and Materials

All chemicals were purchased from Sigma-Aldrich, Alfa Aesar, Matrix, Combiblock, Oakwood, and Chembridge. Anhydrous solvents were Aldrich Sure/Seal™ brand. All reactions were carried out under a dry nitrogen atmosphere using dry solvents. Reactions were monitored by thin-layer chromatography carried out on Sigma-Aldrich 0.25 mm silica gel plates (60 Å, fluorescent indicator). Spots were visualized under UV light (254 nm). Flash column chromatography was performed on Biotage SNAP Flash System, or silica gel 60 (particle size 0.032-0.063 mm) obtained from Silicycle, Inc. Low-resolution ES (electrospray) mass spectra were obtained using a Micromass Quattro Ultima mass spectrometer in the electrospray positive (ES+) or negative (ES−) ion mode. 1H-NMR spectra were recorded on a Bruker AM-300 spectrometer and were calibrated using residual nondeuterated solvent as internal reference. Spectra were processed using Spinworks version 2.5 (developed by Dr. Kirk Marat, Department of Chemistry, University of Manitoba). Preparative HPLC was performed on Waters 2996 with Photodiode Array Detector, Waters 600 Controller, Waters 100 pump, and Waters 717 auto sampler, with UV detection at 254 and 280 nm. Flow rate: 15 mL/minute, run time 30 minutes. Solvents: 0-100% (H$_2$O-MeOH), with and without added TFA (0.1%). Column used was Supelco C18, 25 cm×21.2 mm, particle size 10 micrometer.

Ethyl 2-formylpyridine-4-carboxylate was prepared analogously to Queguiner, G. and Pastour, P. (Comptes Rendus des Séances de l'Académie des Sciences, Série C: Sciences Chimiques (1969), 268(2), 182-5).

Examples of Compounds of Formula (I)

TABLE 1

| Structure | # | Name | May be prepared analogously to Synthetic Route | NMR |
|---|---|---|---|---|
| 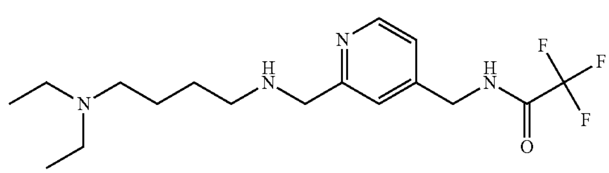 [SMILES: CCN(CC)CCCCNCc1cc(CNC(=O)C(F)(F)F)ccn1] | 1 | N-{[2-({[4-(diethylamino)butyl]amino}methyl)pyridin-4-yl]methyl}-2,2,2-trifluoroacetamide | A | $^1$H NMR (300 MHz, Methanol-d$_4$), δ ppm: 8.57 (d, 1H), 4.53 (s, 2H), 1.94 (s, 6H), 1.25 (t, 6H). |

TABLE 1-continued

| Structure | # | Name | May be prepared analogously to Synthetic Route | NMR |
|---|---|---|---|---|
| 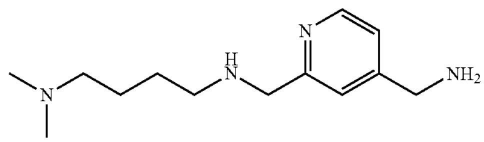 [SMILES: CN(C)CCCCNCc1cc(CN)ccn1] | 2 | [2-({[4-(dimethylamino)butyl]amino}methyl)pyridin-4-yl]methanamine | B | $^1$H-NMR (300 MHz, MeOD), δ ppm: 8.80 (d, 1H), 4.60 (s, 2H), 2.95 (s, 6H), 1.95 (m, 4H). |
| 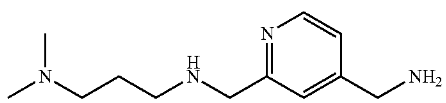 [SMILES: CN(C)CCCNCc1cc(CN)ccn1] | 3 | [2-({[3-(dimethylamino)propyl]amino}methyl)pyridin-4-yl]methanamine | B | $^1$H NMR (300 MHz, Methanol-d$_4$), δ ppm: 8.71 (d, 1H), 4.48 (s, 2H), 2.95 (s, 6H), 2.25 (m, 2H). |
| 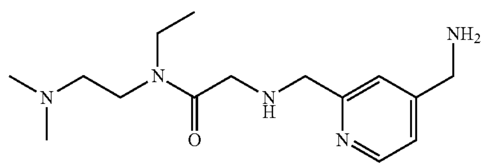 [SMILES: CCN(CCN(C)C)C(=O)CNCc1cc(CN)ccn1] | 4 | 2-({[4-(aminomethyl)pyridin-2-yl]methyl}amino)-N-[2-(dimethylamino)ethyl]-N-ethylacetamide | B | $^1$H NMR (300 MHz, CDCl$_3$), δ ppm: 8.74 (d, 1H), 4.59 (s, 2H), 2.99 (s, 6H), 1.27 (t, 3H). |
| 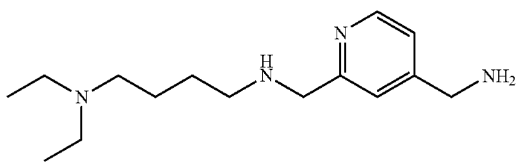 [SMILES: CCN(CC)CCCCNCc1cc(CN)ccn1] | 5 | [2-({[4-(diethylamino)butyl]amino}methyl)pyridin-4-yl]methanamine | B | $^1$H-NMR (300 MHz, MeOD), δ ppm: 8.82 (d, 1H), 4.65 (s, 2H), 3.20 (m, 9H), 1.30 (t, 6H). |
| 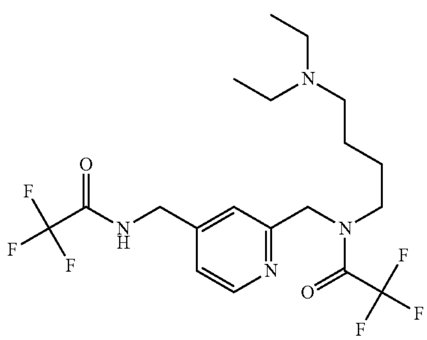 [SMILES: CCN(CC)CCCCN(Cc1cc(CNC(=O)C(F)(F)F)ccn1)C(=O)C(F)(F)F] | 6 | N-[4-(diethylamino)butyl]-2,2,2-trifluoro-N-({4-[(trifluoroacetamido)methyl]pyridin-2-yl}methyl)acetamide | C | $^1$H-NMR (300 MHz, CDCl3), δ ppm: 11.60, 11.45 (d, 1H), 4.70 (d, 2H), 3.10 (m, 4H), 1.50 (t, 6H). |
| 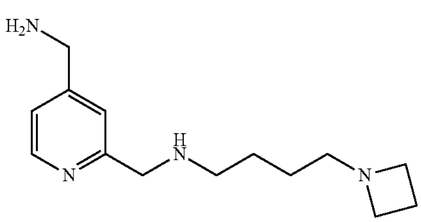 [SMILES: NCc1ccnc(CNCCCCN2CCC2)c1] | 7 | [2-({[4-(azetidin-1-yl)butyl]amino}methyl)pyridin-4-yl]methanamine | D | $^1$H-NMR (300 MHz, CDCl$_3$), δ ppm: 8.70 (d, 1H), 4.40 (s, 2H), 1.80 (m, 4H), 1.20 (m 4H). |
| 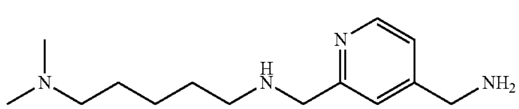 [SMILES: CN(C)CCCCCNCc1cc(CN)ccn1] | 8 | [2-({[5-(dimethylamino)pentyl]amino}methyl)pyridin-4-yl]methanamine | B | $^1$H-NMR (300 MHz, MeOD), δ ppm: 8.88 (d, 1H), 4.70 (s, 2H), 2.85 (s, 6H), 1.85 (m, 4H). |

TABLE 1-continued

| Structure | # | Name | May be prepared analogously to Synthetic Route | NMR |
|---|---|---|---|---|
| 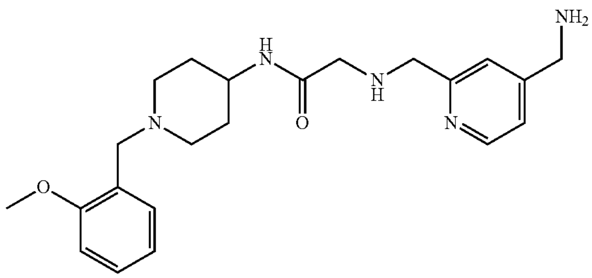 [SMILES: COc1ccccc1CN1CCC(NC(=O)CNCc2cc(CN)ccn2)CC1] | 9 | 2-({[4-(aminomethyl)pyridin-2-yl]methyl}amino)-N-{1-[(2-methoxyphenyl)methyl]piperidin-4-yl}acetamide | B | $^1$H-NMR (300 MHz, Methanol-$d_4$), δ ppm: 8.74 (m, 1H), 7.18-7.10 (m, 2H), 4.45 (d, 2H), 2.25-1.80 (m; 4H). |
| 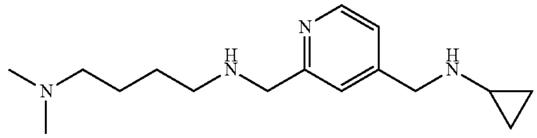 [SMILES: CN(C)CCCCNCc1cc(CNC2CC2)ccn1] | 10 | N-{[2-({[4-(dimethylamino)butyl]amino}methyl)pyridin-4-yl]methyl}cyclopropanamine | E | 1H NMR (300 MHz, CDCl$_3$), δ ppm: 8.42 (d, 1H), 2.20 (s, 6H), 2.15 (m, 1H), 0.5-0.38 (m, 4H). |
| 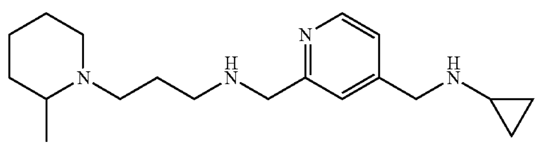 [SMILES: CC1CCCCN1CCCNCc1cc(CNC2CC2)ccn1] | 11 | N-{[2-({[3-(2-methylpiperidin-1-yl)propyl]amino}methyl)pyridin-4-yl]methyl}cyclopropanamine | E | $^1$H-NMR (300 MHz, Methanol-$d_4$), δ ppm: 8.80 (d, 1H), 2.90 (m, 1H), 2.30 (m, 2H), 1.02-0.9 (m, 4H). |
| 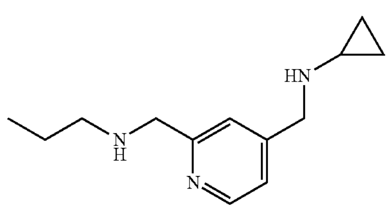 [SMILES: CCCNCc1cc(CNC2CC2)ccn1] | 12 | N-({2-[(propylamino)methyl]pyridin-4-yl}methyl)cyclopropanamine | E | $^1$H NMR (300 MHz, Methanol-$d_4$), δ ppm: 8.70 (d, 1H), 4.40 (s, 2H), 3.06 (m, 1H), 1.03 (t, 3H). |
| 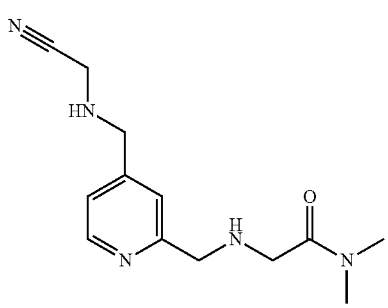 [SMILES: CN(C)C(=O)CNCc1cc(CNCC#N)ccn1] | 13 | 2-{[(4-{[(cyanomethyl)amino]methyl}pyridin-2-yl)methyl]amino}-N,N-dimethylacetamide | F | $^1$H NMR (300 MHz, Methanol-$d_4$), δ ppm: 8.72 (d, 1H), 4.37 (s, 2H), 4.18 (s, 2H), 3.00 (s, 6H). |
| 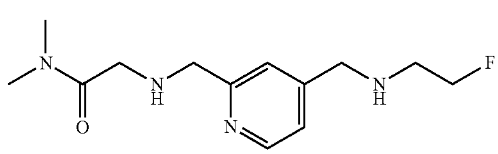 [SMILES: CN(C)C(=O)CNCc1cc(CNCCF)ccn1] | 14 | 2-{[(4-{[(2-fluoroethyl)amino]methyl}pyridin-2-yl)methyl]amino}-N,N-dimethylacetamide | G | $^1$H NMR (300 MHz, Methanol-$d_4$), δ ppm: 8.49 (d, 1H), 4.65 (t, 1H), 3.97 (s, 2H), 2.96 (d, 6H). |
| 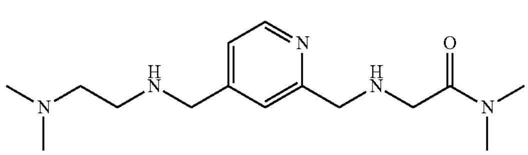 | 15 | 2-({[4-({[2-(dimethylamino)ethyl]amino}methyl)pyridin-2-yl]methyl}amino)-N,N-dimethylacetamide | G | $^1$H NMR (300 MHz, Methanol-$d_4$), δ ppm: 8.44 (d, 1H), 3.90 (s, 2H), 2.96 (s, 6H), 2.25 (s, 6H). |

TABLE 1-continued

| Structure | # | Name | May be prepared analogously to Synthetic Route | NMR |
|---|---|---|---|---|
| 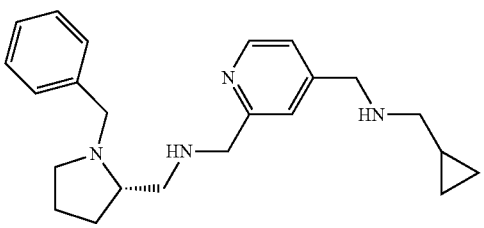 [SMILES: c1ccc(CN2CCC[C@H]2CNCc2cc(CNCC3CC3)ccn2)cc1] | 16 | {[(2S)-1-benzylpyrrolidin-2-yl]methyl}[(4-{[(cyclopropylmethyl)amino]methyl}pyridin-2-yl)methyl]amine | G | $^1$H NMR (300 MHz, Methanol-$d_4$), δ ppm: 8.70 (dd, 1H), 7.59-7.44 (m, 7H), 2.25-2.04 (m, 3H), 1.20-1.08 (m, 1H). |
| 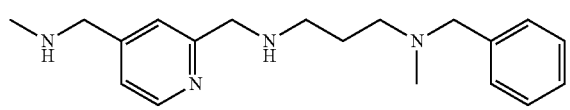 [SMILES: CNCc1ccnc(CNCCCN(C)Cc2ccccc2)c1] | 17 | benzyl(methyl){3-[({4-[(methylamino)methyl]pyridin-2-yl}methyl)amino]propyl}amine | H | $^1$H NMR (300 MHz, CDCl$_3$), δ ppm: 8.8 (d, 1H), 7.8-7.4 (m, 7H), 2.8 (d, 6H), 2.5-2.2 (m, 2H). |
| 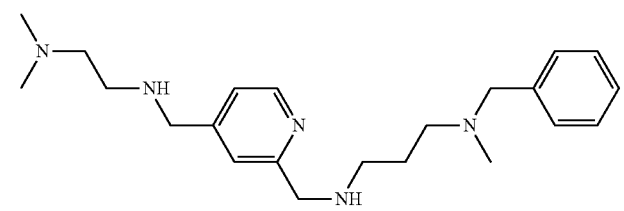 [SMILES: CN(C)CCNCc1ccnc(CNCCCN(C)Cc2ccccc2)c1] | 18 | benzyl[3-({4-({2-(dimethylamino)ethyl]amino}methyl)pyridin-2-yl]methyl}amino)propyl]methylamine | H | $^1$H NMR (300 MHz, Methanol-$d_4$), δ ppm: 8.8 (d, 1H), 7.6-7.4 (m, 5H), 3.05 (s, 6H), 2.8 (s, 3H). |
| 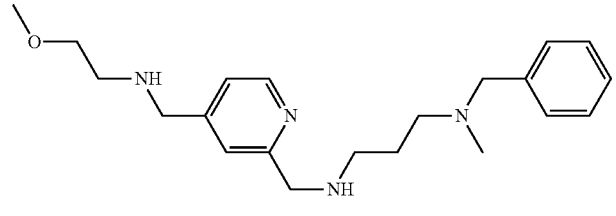 [SMILES: COCCNCc1ccnc(CNCCCN(C)Cc2ccccc2)c1] | 19 | benzyl(3-{[(4-{[(2-methoxyethyl)amino]methyl}pyridin-2-yl)methyl]amino}propyl)methylamine | H | $^1$H NMR (300 MHz, Methanol-$d_4$), δ ppm: 8.9 (d, 1H), 7.6-7.4 (m, 5H), 3.8-3.2 (m, 11H), 2.9 (s, 3H). |
| 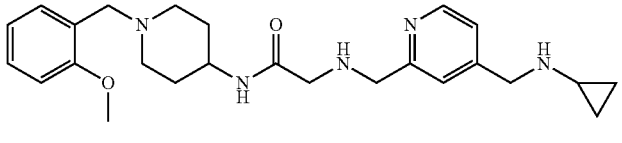 [SMILES: COc1ccccc1CN1CCC(NC(=O)CNCc2cc(CNC3CC3)ccn2)CC1] | 20 | 2-[({4-[(cyclopropylamino)methyl]pyridin-2-yl}methyl)amino]-N-{1-[(2-methoxyphenyl)methyl]piperidin-4-yl}acetamide | I | $^1$H-NMR (300 MHz, Methanol-$d_4$), δ ppm: 8.78 (m, 1H), 7.02 (m, 1H), 2.60 (m, 1H), 0.9-0.8 (m, 4H). |
| 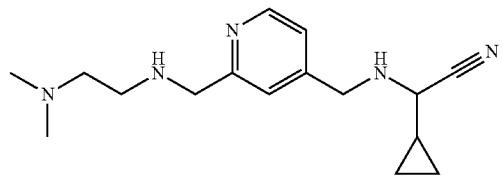 [SMILES: CN(C)CCNCc1cc(CNC(C#N)C2CC2)ccn1] | 21 | 2-cyclopropyl-2-({[2-({[2-(dimethylamino)ethyl]amino}methyl)pyridin-4-yl]methyl}amino)acetonitrile | J | $^1$H NMR (300 MHz, Methanol-$d_4$), δ ppm: 8.68 (d, 1H), 4.50 (s, 2H), 3.00 (s, 6H), 0.61 (m, 2H). |
| 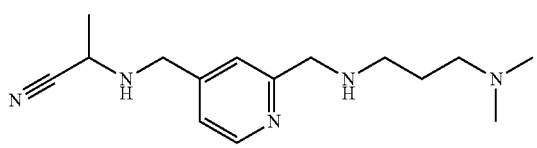 [SMILES: CC(C#N)NCc1ccnc(CNCCCN(C)C)c1] | 22 | 2-({[2-({[3-(dimethylamino)propyl]amino}methyl)pyridin-4-yl]methyl}amino)propanenitrile | J | $^1$H NMR (300 MHz, Methanol-$d_4$), δ ppm: 8.61 (d, 1H), 4.43 (s, 2H), 2.94 (s, 6H), 1.54 (d, 3H). |

TABLE 1-continued

| Structure | # | Name | May be prepared analogously to Synthetic Route | NMR |
|---|---|---|---|---|
| 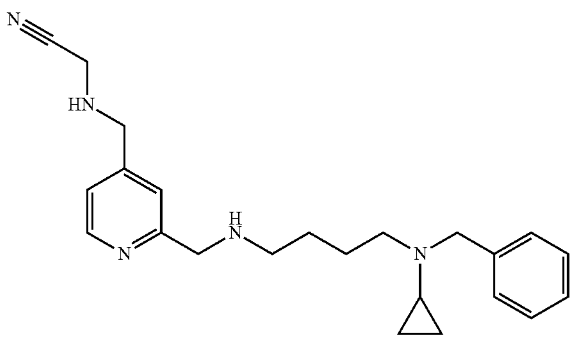 [SMILES: N#CCNCc1ccnc(CNCCCCN(Cc2ccccc2)C2CC2)c1] | 23 | 2-[({2-[({4-[benzyl (cyclopropyl)amino] butyl}amino)methyl] pyridin-4-yl}methyl) amino]acetonitrile | K | $^1$H-NMR (300 MHz, CDCl$_3$), δ ppm: 8.45 (d, 1H), 7.20-7.00 (m, 7H), 1.40 (m, 12H) 0.40 (m, 4H), ppm. |
| 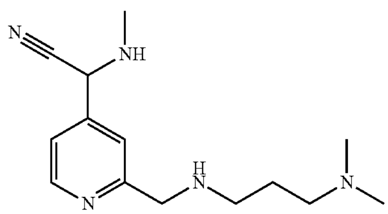 [SMILES: CNC(C#N)c1ccnc(CNCCCN(C)C)c1] | 24 | 2-[2-({[3-(dimethyl-amino)propyl]amino} methyl)pyridin-4-yl]-2-(methylamino) acetonitrile | J | $^1$H NMR (300 MHz, Methanol-d$_4$), δ ppm: 8.83 (d, 1H), 4.54 (s, 3H), 2.93 (s, 6H), 2.25 (m, 2H). |
| 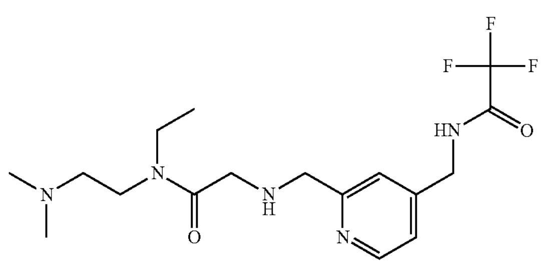 [SMILES: CCN(CCN(C)C)C(=O)CNCc1cc(CNC(=O)C(F)(F)F)ccn1] | 25 | N-[(2-{[({[2-(dimethylamino)ethyl] (ethyl)carbamoyl} methyl)amino]methyl} pyridin-4-yl)methyl]-2,2,2-trifluoroacetamide | L | $^1$H NMR (300 MHz, Methanol-d$_4$), δ 8.61 (d, 1H), 7.35 (d, 1H), 4.53 (s, 2H), 4.46 (s, 2H), 4.23 (s, 2H), 3.82 (t, 2H), 2.98 (s, 6H), 1.24 (t, 3H). |
| 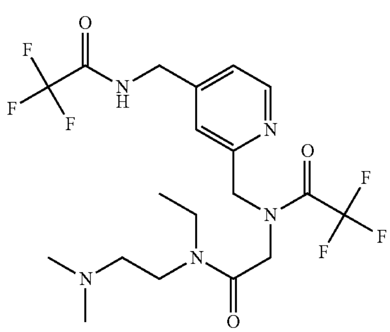 [SMILES: CCN(CCN(C)C)C(=O)CN(Cc1cc(CNC(=O)C(F)(F)F)ccn1)C(=O)C(F)(F)F] | 26 | N-[(2-{[N-({[2-(dimethylamino)ethyl] (ethyl)carbamoyl} methyl)-2,2,2-trifluoroacetamido] methyl}pyridin-4-yl)methyl]-2,2,2-trifluoroacetamide | C | $^1$H-NMR (300 MHz, CDCl$_3$), δ ppm 8.50 (m, 1H), 7.88 (m, 1H), 7.21 (m, 2H), 4.53 (m, 6H), 3.33 (m 4H), 2.44 (m, 2H), 2.23 (m, 6H), 1.14 (m, 3H). |
| 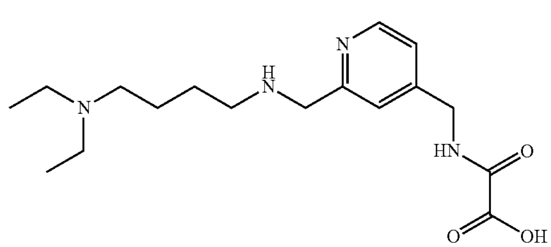 [SMILES: CCN(CC)CCCCNCc1cc(CNC(=O)C(=O)O)ccn1] | 27 | ({2-({[4-(diethyl-amino)butyl]amino} methyl)pyridin-4-yl]methyl}carbamoyl) formic acid | M | $^1$H NMR (300 MHz, Methanol-d$_4$), δ ppm: 8.40 (d, 1H), 4.45 (s, 2H), 2.70-2.40 (m, 8H), 1.00 (m, 6H). |

TABLE 1-continued

| Structure | # | Name | May be prepared analogously to Synthetic Route | NMR |
|---|---|---|---|---|
| 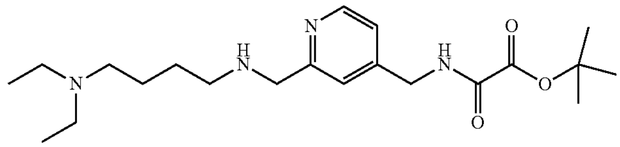 [SMILES: CCN(CC)CCCCNCc1cc(CNC(=O)C(=O)OC(C)(C)C)ccn1] | 28 | tert-butyl ({[2-({[4-(diethylamino)butyl]amino}methyl)pyridin-4-yl]methyl} carbamoyl)formate | M | $^1$H-NMR (300 MHz, CDCl$_3$), δ ppm: 8.50 (m, 1H), 4.50 (m, 2H), 1.65-1.50 (m, 13H), 1.20 (m, 6H). |
| 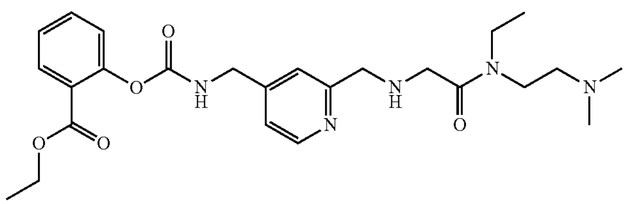 [SMILES: CCOC(=O)c1ccccc1OC(=O)NCc1ccnc(CNCC(=O)N(CC)CCN(C)C)c1] | 29 | ethyl 2-({[(2-{[({[2-(dimethylamino)ethyl](ethyl)carbamoyl}methyl)amino]methyl}pyridin-4-yl)methyl]carbamoyl}oxy)benzoate | L | $^1$H-NMR (300 MHz, CDCl$_3$), δ ppm: 8.50 (m, 1H), 7.20 (m, 4H), 4.50 (m, 2H), 4.40 (q, 2H), 250 (s, 6H), 1.38 (t, 3H). |
| 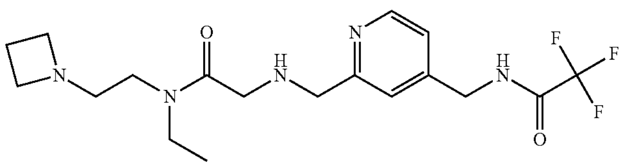 [SMILES: CCN(CCN1CCC1)C(=O)CNCc1cc(CNC(=O)C(F)(F)F)ccn1] | 30 | N-[(2-{[({[2-(azetidin-1-yl)ethyl](ethyl)carbamoyl}methyl)amino]methyl}pyridin-4-yl)methyl]-2,2,2-trifluoroacetamide | A | $^1$H NMR (300 MHz, Methanol-d$_4$), δ 8.50 (d, 1H), 7.40 (m, 2H), 4.50 (s, 2H), 4.40 (s, 2H), 4.20 (m, 2H), 3.50 (m, 2H), 3.30 (m, 2H) 2.40 (m, 2H), 1.10 (t, 3H) |
| 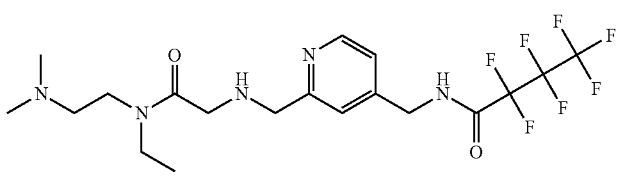 [SMILES: CCN(CCN(C)C)C(=O)CNCc1cc(CNC(=O)C(F)(F)C(F)(F)C(F)(F)F)ccn1] | 31 | N-[(2-{[({[2-(dimethylamino)ethyl](ethyl)carbamoyl}methyl)amino]methyl}pyridin-4-yl)methyl]-2,2,3,3,4,4,4-heptafluorobutanamide | L | $^1$H NMR (300 MHz, Methanol-d$_4$), δ ppm: 8.70, (d, 1H), 4.51 (s, 2H), 2.98 (s, 6H), 1.22 (m, 3H). |
| 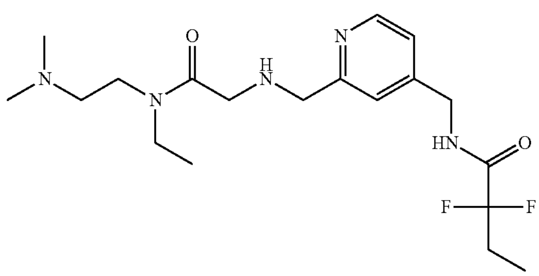 [SMILES: CCN(CCN(C)C)C(=O)CNCc1cc(CNC(=O)C(F)(F)CC)ccn1] | 32 | N-[(2-{[({[2-(dimethylamino)ethyl](ethyl)carbamoyl}methyl)amino]methyl}pyridin-4-yl)methyl]-2,2-difluorobutanamide | L | $^1$H NMR (300 MHz, Methanol-d$_4$), δ 8.60 (d, 1H), 7.39 (s, 1H), 7.36 (d, 1H), 4.48 (m, 4H), 4.24 (s, 2H), 3.82 (t, 2H), 3.38 (m, 4H), 2.98 (s, 6H), 2.32 (m, 2H), 1.24 (t, 3H), 1.02 (t, 3H). |
| 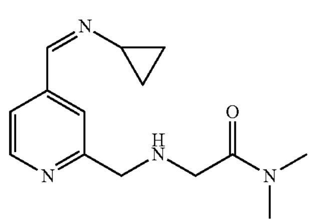 [SMILES: CN(C)C(=O)CNCc1cc(/C=N\C2CC2)ccn1] | 33 | 2-[({4-[(N-cyclopropylcarboximidoyl]pyridin-2-yl}methyl)amino]-N,N-dimethylacetamide | N | $^1$H NMR (300 MHz, CDCl$_3$), δ ppm: 8.55 (d, 1H), 8.52 (s, 1H), 3.17 (m, 1H), 2.96 (d, 6H). |
| 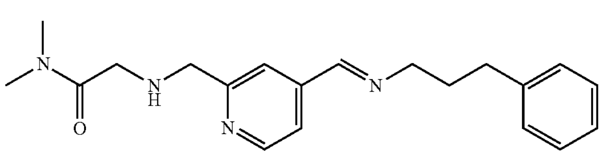 [SMILES: CN(C)C(=O)CNCc1cc(/C=N/CCCc2ccccc2)ccn1] | 34 | N,N-dimethyl-2-[({4-[[(3-phenylpropyl)imino]methyl]pyridin-2-yl}methyl)amino]acetamide | N | $^1$H NMR (300 MHz, CDCl$_3$), δ ppm: 8.62 (d, 1H), 8.26 (s, 1H), 7.25 (m, 5H), 2.96 (d, 6H). |

TABLE 1-continued

| Structure | # | Name | May be prepared analogously to Synthetic Route | NMR |
|---|---|---|---|---|
| 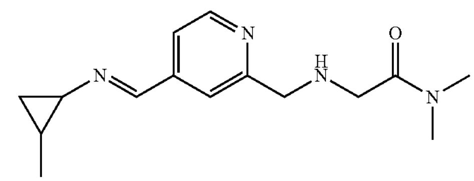 [SMILES: CC1CC1/N=C/c1ccnc(CNCC(=O)N(C)C)c1] | 35 | N,N-dimethyl-2-[({4-[N-(2-methyl-cyclopropyl)carbox-imidoyl]pyridin-2-yl}methyl)amino]acetamide | O | $^1$H NMR (300 MHz, CDCl$_3$), δ ppm: 8.57 (d, 1H), 8.36 (s, 1H), 2.96 (d, 6H), 0.81 (m, 1H). |
| 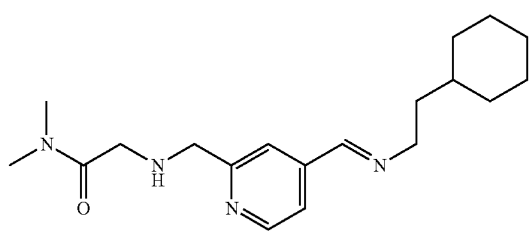 [SMILES: CN(C)C(=O)CNCc1cc(/C=N/CCC2CCCCC2)ccn1] | 36 | 2-[({4-[[(2-cyclo-hexylethyl)imino]methyl]pyridin-2-yl}methyl)amino]-N,N-dimethylacetamide | O | $^1$H NMR (300 MHz, CDCl$_3$), δ ppm: 8.61 (d, 1H), 8.26 (s, 1H), 2.95 (d, 6H), 1.78-0.88 (m, 13H). |
| 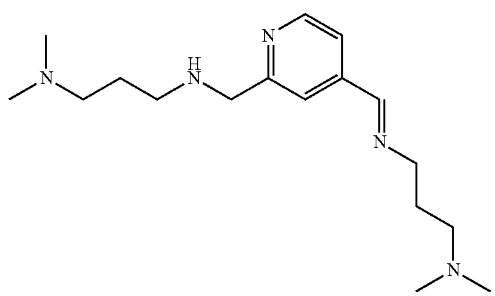 | 37 | [3-(dimethyl-amino)propyl]({4-[{[3-(dimethylamino)propyl]imino}methyl]pyridin-2-yl}methyl)amine | N | $^1$H NMR (300 MHz, CDCl$_3$), δ ppm: 8.59 (dd, 1H), 8.24 (s, 1H), 2.20 (s, 6H), 2.19 (s, 6H). |
| 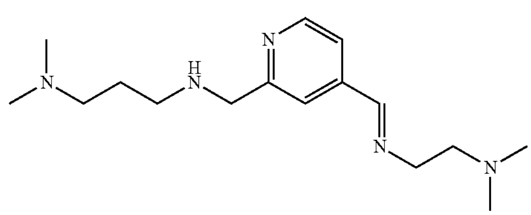 | 38 | ({4-[{[2-(dimethyl-amino)ethyl]imino}methyl]pyridin-2-yl}methyl)[3-(dimethyl-amino)propyl]amine | N | $^1$H NMR (300 MHz, CDCl$_3$), δ ppm: 8.60 (d,1H), 8.28 (s, 1H), 2.30 (s, 6H), 2.25 (s, 6H). |
| 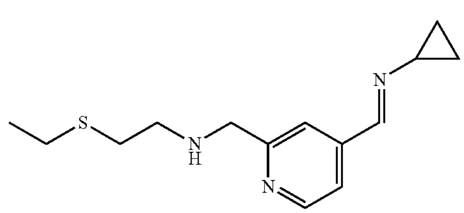 [SMILES: CCSCCNCc1cc(/C=N/C2CC2)ccn1] | 39 | N-{[2-({[2-(ethyl-sulfanyl)ethyl]amino}methyl)pyridin-4-yl]methylidene}cyclo-propanamine | P | $^1$H-NMR (300 MHz, CDCl$_3$), δ ppm: 8.5 (d, 1H), 8.4 (s, 1H), 1.2 (t, 3H), 1.0 (m, 4H). |
| 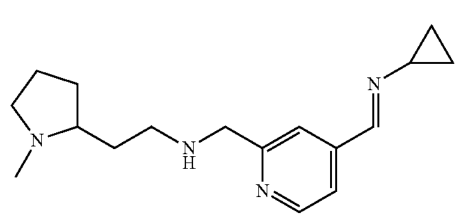 [SMILES: CN1CCCC1CCNCc1cc(/C=N/C2CC2)ccn1] | 40 | N-{[2-({[2-(1-methylpyrrolidin-2-yl)ethyl]amino}methyl)pyridin-4-yl]methylidene}cyclopropanamine | P | $^1$H-NMR (300 MHz, CDCl$_3$), δ ppm: 8.5 (d, 1H), 8.4 (s, 1H), 2.8 (s, 3H), 1.0 (m, 4H). |

TABLE 1-continued

| Structure | # | Name | May be prepared analogously to Synthetic Route | NMR |
|---|---|---|---|---|
| 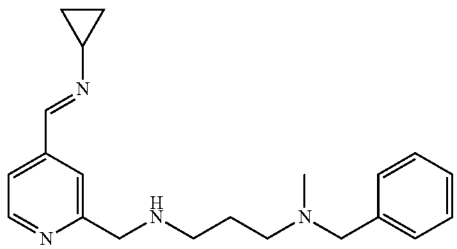 [SMILES: CN(CCCNCc1cc(/C=N/C2CC2)ccn1)Cc1ccccc1] | 41 | N-({2-[({3-[benzyl (methyl)amino]propyl} amino)methyl]pyridin-4-yl}methylidene) cyclopropanamine | Q | ¹H NMR (300 MHz, CDCl3), ppm: 8.55 (d, 1H), 8.50 (s, 1H), 7.28-7.22 (m, 5H), 1.04-0.97 (m, 4H). |
| 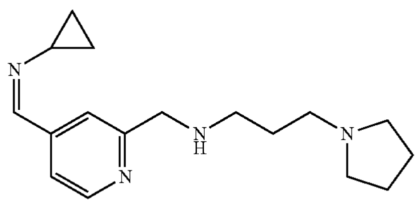 [SMILES: C(=N/C1CC1)/c1ccnc(CNCCCN2CCCC2)c1] | 42 | N-{[2-({[3-(pyrrolidin-1-yl)propyl]amino}methyl) pyridin-4-yl]methylidene}cyclo-propanamine | P | ¹H-NMR (300 MHz, Methanol-d₄), δ ppm: 8.58 (m, 1H), 8.40 (s, 1H), 2.78-2.60 (m, 6H), 1.90-1.75 (m, 6H). |
| 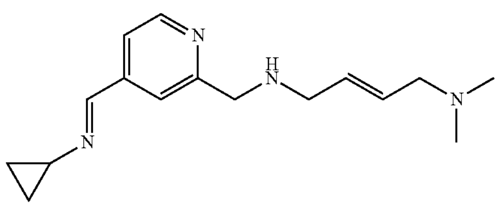 [SMILES: CN(C)C/C=C/CNCc1cc(/C=N/C2CC2)ccn1] | 43 | N-{[2-({[(2E)-4-(dimethylamino)but-2-en-1-yl]amino}methyl)pyridin-4-yl]methylidene}cyclo-propanamine | R | ¹H NMR (300 MHz, CDCl₃), δ ppm: 8.59 (d, 1H), 8.41 (s, 1H), 2.23 (s, 6H), 0.94 (m, 4H). |
| 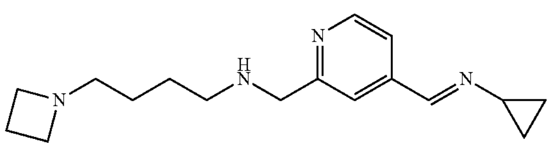 [SMILES: C(=N\C1CC1)/c1ccnc(CNCCCCN2CCC2)c1] | 44 | N-{[2-({[4-(azetidin-1-yl)butyl]amino}methyl) pyridin-4-yl]methylidene}cyclo-propanamine | S | ¹H-NMR (300 MHz, CDCl₃), ), δ ppm: 8.50 (d, 1H), 8.40 (s, 1H), 1.50 (m 6H), 1.00 (m, 4H). |
| 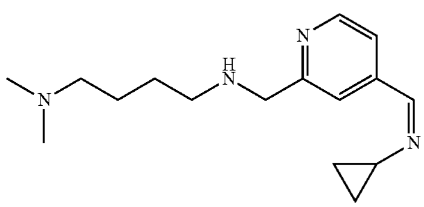 [SMILES: CN(C)CCCCNCc1cc(/C=N\C2CC2)ccn1] | 45 | N-{[2-({[4-(dimethyl-amino)butyl]amino} methyl)pyridin-4-yl] methylidene}cyclo-propanamine | T | ¹H-NMR (300 MHz, CDCl3), ), δ ppm: 8.50 (s, 1H), 8.30 (s, 1H), 2.20 (s, 6H), 1.00 (m, 4H) |
| 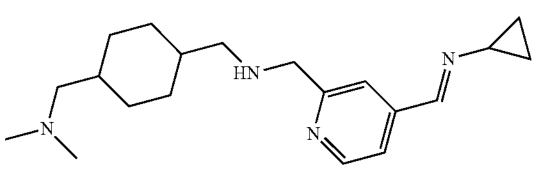 [SMILES: CN(C)CC1CCC(CNCc2cc(/C=N/C3CC3)ccn2)CC1] | 46 | N-[(2-{[({4-[(dimethylamino)methyl] cyclohexyl}methyl) amino]methyl}pyridin-4-yl)methylidene]cyclo-propanamine | N | ¹H NMR (300 MHz, CDCl₃), δ ppm: 8.57 (d, 1H), 8.41 (s, 1H), 2.20 (s, 6H), 0.98 (m, 8H). |
| 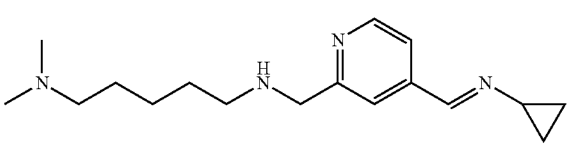 [SMILES: CN(C)CCCCCNCc1cc(/C=N/C2CC2)ccn1] | 47 | N-{[2-({[5-(dimethylamino)pentyl] amino}methyl)pyridin-4-yl]methylidene}cyclo-propanamine | U | ¹H-NMR (300 MHz, CDCl3), ), δ ppm: 8.50 (d, 1H), 8.40 (s, 1H), 2.15 (s, 6H), 1.50-1.30 (m, 6H). |

TABLE 1-continued

| Structure | # | Name | May be prepared analogously to Synthetic Route | NMR |
|---|---|---|---|---|
| 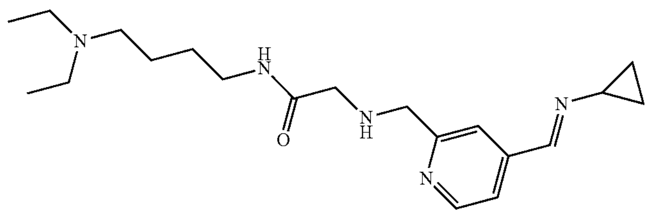 [SMILES: CCN(CC)CCCCNC(=O)CNCc1cc(/C=N/C2CC2)ccn1] | 48 | 2-[({4-[N-cyclopropylcarboximidoyl]pyridin-2-yl}methyl)amino]-N-[4-(diethylamino)butyl]acetamide | V | $^1$H NMR (300 MHz, CDCl$_3$), δ ppm: 8.61 (d, 1H), 8.41 (s, 1H), 1.09 (t, 6H), 1.03 (m, 4H). |
| 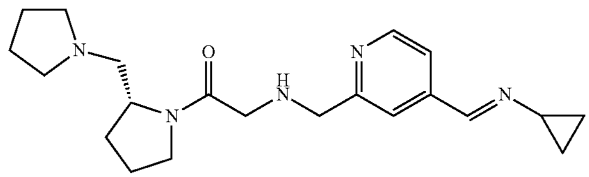 [SMILES: O=C(CNCc1cc(/C=N/C2CC2)ccn1)N1CCC[C@@H]1CN1CCCC1] | 49 | 2-[({4-[N-cyclopropylcarboximidoyl]pyridin-2-yl}methyl)amino]-1-[(2R)-2-(pyrrolidin-1-ylmethyl)pyrrolidin-1-yl]ethan-1-one | V | $^1$H NMR (300 MHz, CDCl$_3$), δ ppm: 8.57 (d, 1H), 8.41 (s, 1H), 1.81-1.69 (m, 4H), 1.07 (m, 4H). |
| 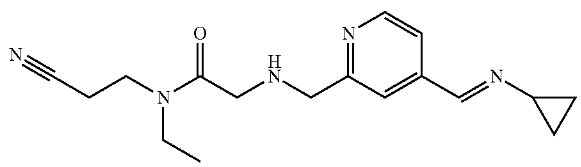 [SMILES: CCN(CCC#N)C(=O)CNCc1cc(/C=N/C2CC2)ccn1] | 50 | N-(2-cyanoethyl)-2-[({4-[N-cyclopropylcarboximidoyl]pyridin-2-yl}methyl)amino]-N-ethylacetamide | V | $^1$H NMR (300 MHz, CDCl$_3$), δ ppm: 8.56 (d, 1H), 8.40 (s, 1H), 1.17 (t, 3H), 1.04-0.95 (m, 4H). |
| 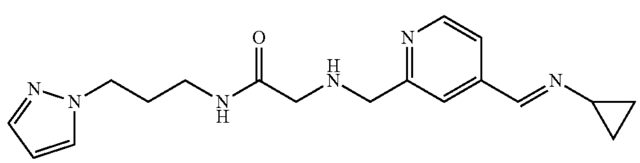 [SMILES: O=C(CNCc1cc(/C=N/C2CC2)ccn1)NCCCn1cccn1] | 51 | 2-[({4-[N-cyclopropylcarboximidoyl]pyridin-2-yl}methyl)amino]-N-[(1-ethylpyrrolidin-2-yl)methyl]acetamide | V | $^1$H-NMR (300 MHz, CDCl3), ), δ ppm: 8.50 (d, 1H), 8.40 (s, 1H), 1.70 (s, 1H), 1.10 (m, 6H). |
| 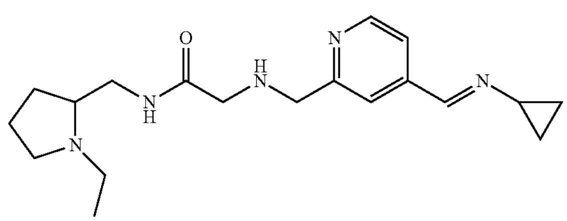 [SMILES: CCN1CCCC1CNC(=O)CNCc1cc(/C=N/C2CC2)ccn1] | 52 | 2-[({4-[N-cyclopropylcarboximidoyl]pyridin-2-yl}methyl)amino]-N-methyl-N-[3-(1H-pyrazol-1-yl)propyl]acetamide | V | $^1$H NMR (300 MHz, CDCl$_3$), δ ppm: 8.57 (d, 1H), 8.41 (s, 1H), 6.22 (m, 1H), 1.01 (m, 4H). |
| 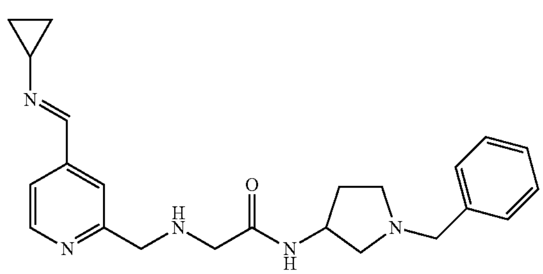 [SMILES: O=C(CNCc1cc(/C=N/C2CC2)ccn1)NC1CCN(Cc2ccccc2)C1] | 53 | N-(1-benzyl-pyrrolidin-3-yl)-2-[({4-[N-cyclopropyl-carboximidoyl]pyridin-2-yl}methyl)amino]acetamide | V | $^1$H-NMR (300 MHz, CDCl3), ), δ ppm: 8.50 (d, 1H), 8.35 (s, 1H), 7.20 (m, 6H), 1.60 (m, 1H). |
| 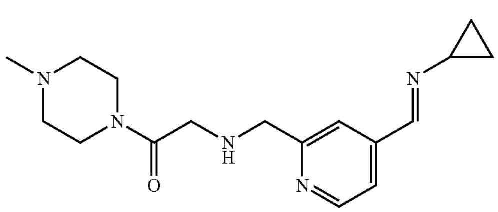 [SMILES: CN1CCN(C(=O)CNCc2cc(/C=N/C3CC3)ccn2)CC1] | 54 | 2-[({4-[N-cyclopropylcarboximidoyl]pyridin-2-yl}methyl)amino]-1-(4-methylpiperazin-1-yl)ethan-1-one | V | $^1$H NMR (300 MHz, CDCl$_3$), δ ppm: 8.56 (d, 1H), 8.39 (s, 1H), 2.29 (s, 3H), 0.99 (m, 4H). |

| Structure | # | Name | May be prepared analogously to Synthetic Route | NMR |
|---|---|---|---|---|
| 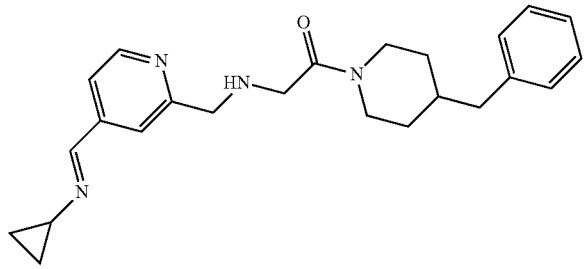 [SMILES: O=C(CNCc1cc(/C=N/C2CC2)ccn1)N1CCC(Cc2ccccc2)CC1] | 55 | 1-(4-benzylpiperidin-1-yl)-2-[({4-[N-cyclopropylcarboximidoyl]pyridin-2-yl}methyl)amino]ethan-1-one | V | $^1$H NMR (300 MHz, CDCl$_3$), δ ppm: 8.59 (d, 1H), 8.42 (s, 1H), 7.32-7.12 (m, 5H), 0.99 (m, 4H). |
| 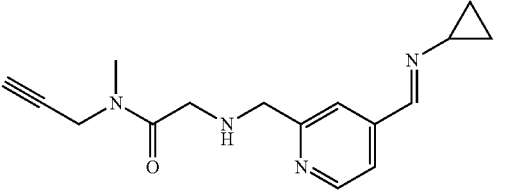 [SMILES: C#CCN(C)C(=O)CNCc1cc(/C=N/C2CC2)ccn1] | 56 | 2-[({4-[N-cyclopropylcarboximidoyl]pyridin-2-yl}methyl)amino]-N-methyl-N-(prop-2-yn-1-yl)acetamide | V | $^1$H NMR (300 MHz, CDCl$_3$), δ ppm: 8.58 (d, 1H), 8.42 (s, 1H), 3.01 (m, 3H), 1.02 (m, 4H). |
| 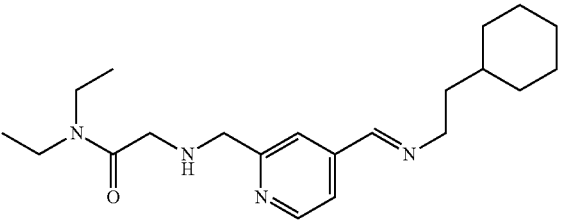 [SMILES: CCN(CC)C(=O)CNCc1cc(/C=N/CCC2CCCCC2)ccn1] | 57 | 2-[({4-[[(2-cyclohexylethyl)imino]methyl]pyridin-2-yl}methyl)amino]-N,N-diethylacetamide | V | $^1$H-NMR (300 MHz, CDCl$_3$), δ ppm: 8.6 (d, 1H), 8.3 (s, 1H), 1.6 (m, 6H), 1.4-1.1 (m, 11H) |
| 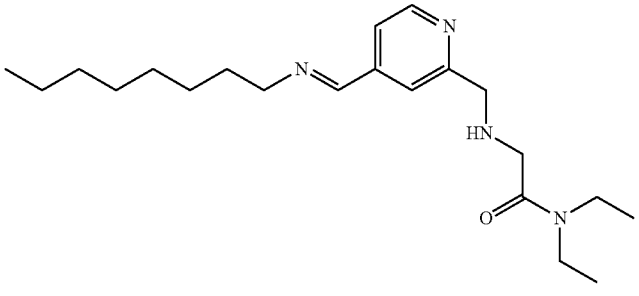 [SMILES: CCCCCCCC/N=C/c1ccnc(CNCC(=O)N(CC)CC)c1] | 58 | N,N-diethyl-2-[({4-[(octylimino)methyl]pyridin-2-yl}methyl)amino]acetamide | V | $^1$H-NMR (300 MHz, CDCl$_3$), δ ppm: 8.6 (d, 1H), 8.2 (s, 1H), 1.4 (m, 10H), 0.9 (t, 3H) |
| 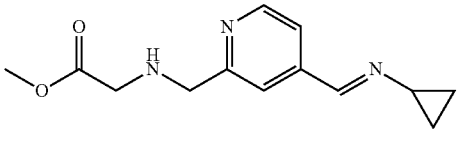 [SMILES: COC(=O)CNCc1cc(/C=N/C2CC2)ccn1] | 59 | methyl 2-[({4-[N-cyclopropylcarboximidoyl]pyridin-2-yl}methyl)amino]acetate | P | $^1$H-NMR (300 MHz, CDCl$_3$), δ ppm: 8.6 (d, 1H), 8.3 (s, 1H), 3.7 (s, 3H), 3.1 (m, 1H) |
| 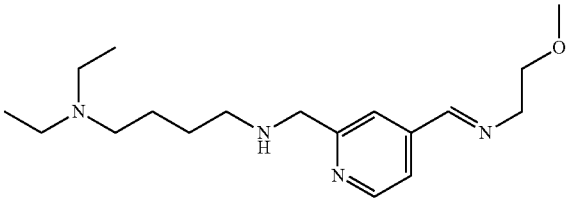 [SMILES: CCN(CC)CCCCNCc1cc(/C=N/CCOC)ccn1] | 60 | [4-(diethylamino)butyl]({4-[[(2-methoxyethyl)imino]methyl]pyridin-2-yl}methyl)amine | X | $^1$H NMR (300 MHz, CDCl$_3$), δ ppm: 8.61 (d, 1H), 8.29 (s, 1H), 2.51 (q, 4H), 1.01 (t, 6H). |

TABLE 1-continued

| Structure | # | Name | May be prepared analogously to Synthetic Route | NMR |
|---|---|---|---|---|
| 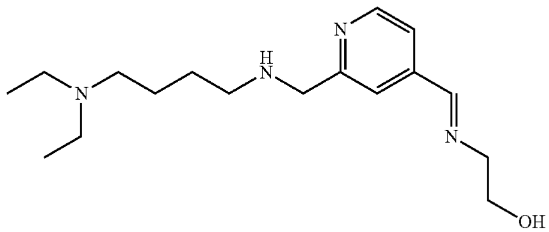 [SMILES: CCN(CC)CCCCNCc1cc(/C=N/CCO)ccn1] | 61 | 2-[{[2-({[4-(diethyl-amino)butyl]amino}methyl)pyridin-4-yl]methylidene}amino]ethan-1-ol | N | $^1$H-NMR (300 MHz, CDCl$_3$), δ ppm: 8.6 (d, 1H), 8.3 (s, 1H), 1.5 (m, 4H), 1.0 (t, 6H) |
| 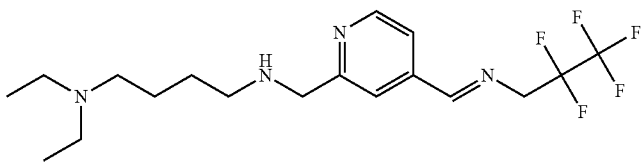 [SMILES: CCN(CC)CCCCNCc1cc(/C=N/CC(F)(F)C(F)(F)F)ccn1] | 62 | {[2-({[4-(diethyl-amino)butyl]amino}methyl)pyridin-4-yl]methylidene}(2,2,3,3,3-penta-fluoropropyl)amine | N | $^1$H-NMR (300 MHz, CDCl3), δ ppm: 8.53 (d, 1H), 8.30 (s, 1H), 1.90 (m, 4H), 1.30 (t, 6H). |
| 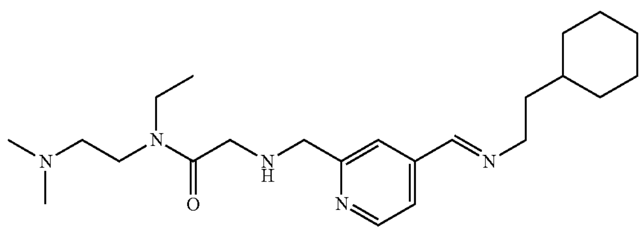 [SMILES: CCN(CCN(C)C)C(=O)CNCc1cc(/C=N/CCC2CCCCC2)ccn1] | 63 | 2-[({4-[[(2-cyclo-hexylethyl)imino]methyl]pyridin-2-yl}methyl)amino]-N-[2-(dimethyl-amino)ethyl]-N-ethylacetamide | X | $^1$H NMR (300 MHz, CDCl$_3$), δ ppm: 8.56 (d, 1H), 8.22 (s, 1H), 1.76-1.51 (m, 7H), 1.22-1.07 (m, 6H) |
| 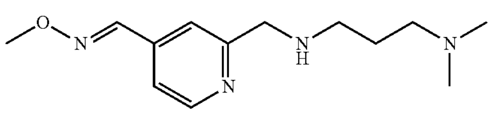 | 64 | [3-(dimethyl-amino)propyl]({4-[(methoxyimino)methyl]pyridin-2-yl}methyl)amine | N | $^1$H NMR (300 MHz, Methanol-d$_4$), δ ppm: 8.66 (d, 1H), 8.15 (s, 1H), 4.01 (s, 3H), 2.93 (s, 6H). |
| 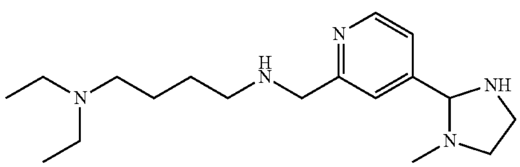 [SMILES: CCN(CC)CCCCNCc1cc(C2NCCN2C)ccn1] | 65 | [4-(diethyl-amino)butyl]({[4-(1-methylimidazolidin-2-yl)pyridin-2-yl]methyl})amine | N | $^1$H-NMR (300 MHz, CDCl$_3$), δ ppm: 8.5 (d, 1H), 7.4 (s, 1H), 2.3 (s, 3H), 1.0 (t, 6H) |
| 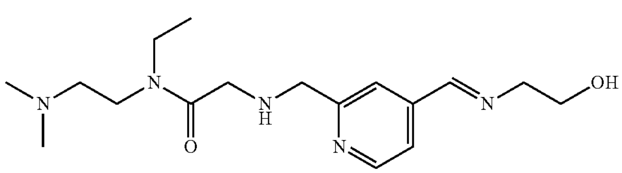 [SMILES: CCN(CCN(C)C)C(=O)CNCc1cc(/C=N/CCO)ccn1] | 66 | N-[2-(dimethyl-amino)ethyl]-N-ethyl-2-[({4-[([(2-hydroxyethyl)imino]methyl]pyridin-2-yl}methyl)amino]acetamide | X | 1H NMR (300 MHz, CDCl3): δ ppm 8.54 (d, 1H), 3.93 (s, 2H), 3.43 (s, 2H), 3.40-3.32 (m, 2H), 3.25-3.17 (m, 2H), , 2.21 and 2.16 (two singlets, 6H, rotamers). |
| 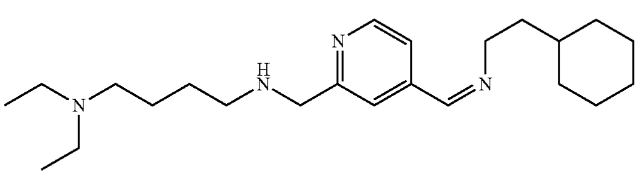 [SMILES: CCN(CC)CCCCNCc1cc(/C=N\CCC2CCCCC2)ccn1] | 67 | (2-cyclohexyl-ethyl)({[2-({[4-(diethylamino)butyl]amino}methyl)pyridin-4-yl]methylidene})amine | X | 1H NMR (300 MHz, CDCl3) δ ppm 8.56 (d, 1H), , 3.93 (s, 2H), , 2.65 (q, 4H), 2.56 (t, 2H), 1.05 (t, 6H). |
| 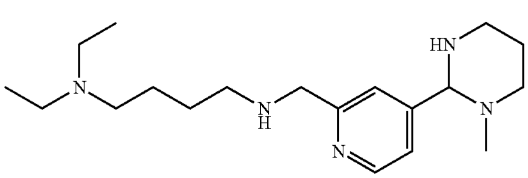 [SMILES: CCN(CC)CCCCNCc1cc(C2NCCCN2C)ccn1] | 68 | [4-(diethyl-amino)butyl]({[4-(1-methyl-1,3-diazinan-2-yl)pyridin-2-yl]methyl})amine | N | 1H NMR (300 MHz, chloroform-d): δ ppm 8.49 (d, 1H), 3.87 (s, 2H), 3.68 (s, 1H), 3.51 (q, 4H), 2.36 (m, 4H), 1.93 (s, 3H), 0.99 (t, 6H). |

TABLE 1-continued

| Structure | # | Name | May be prepared analogously to Synthetic Route | NMR |
|---|---|---|---|---|
| 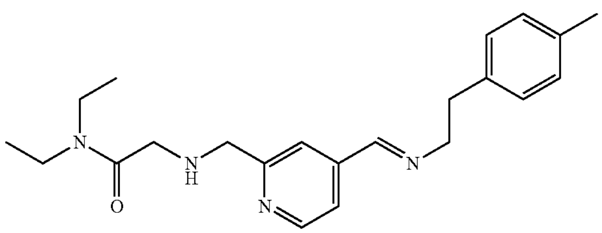 [SMILES: CCN(CC)C(=O)CNCc1cc(/C=N/CCc2ccc(C)cc2)ccn1] | 69 | N,N-diethyl-2-[({4-[{[2-(4-methyl-phenyl)ethyl]imino}methyl]pyridin-2-yl}methyl)amino]acetamide | O | 1H NMR (300 MHz, CDCl3), δ ppm: 8.6 (d, 1H), 8.1 (s, 1H), 4.1 (s, 2H), 3.8 (m, 2H), 3.6 (s, 2H), 1.1 (m, 6H). |
| 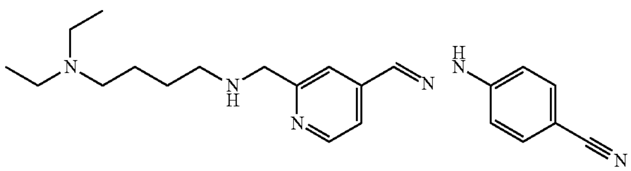 | 70 | 4-[2-{[2-({[4-(diethylamino)butyl]amino}methyl)pyridin-4-yl]methylidene}hydrazin-1-yl]benzonitrile | N | 1H NMR (300 MHz, chloroform-d): δ ppm 8.63 (d, 1H), 7.88 (s, 1H), 7.82 (s, 1H), 4.46 (s, 2H), 3.32 (m, 4H), 1.34 (t, 6H). |
| 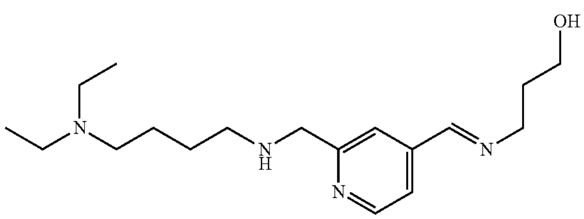 [SMILES: CCN(CC)CCCCNCc1cc(/C=N/CCCO)ccn1] | 71 | 3-[{[2-({[4-(diethylamino)butyl]amino}methyl)pyridin-4-yl]methylidene}amino]propan-1-ol | X | 1H NMR (300 MHz, chloroform-d): δ ppm 8.61 (d, 1H), 7.88 (s, 1H), , 2.67 (m, 2H), 2.51 (q, 4H), 1.00 (t, 6H). |
| 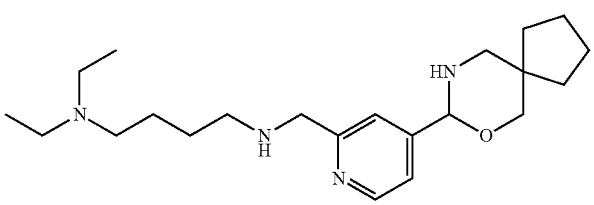 [SMILES: CCN(CC)CCCCNCc1cc(C2NCC3(CCCC3)CO2)ccn1] | 72 | [4-(diethyl-amino)butyl][(4-{7-oxa-9-azaspiro[4.5]decan-8-yl}pyridin-2-yl)methyl]amine | X | 1H NMR (300 MHz, chloroform-d): δ ppm 8.53 (d, 1H), 7.44 (s, 1H), 5.08 (s, 1H), 2.53 (q, 4H), 1.57 (m, 8H), 1.02 (t, 6H). |
| 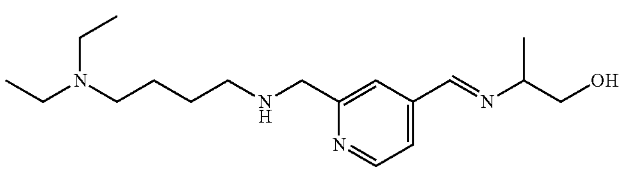 [SMILES: CCN(CC)CCCCNCc1cc(/C=N/C(C)CO)ccn1] | 73 | 2-[{[2-({[4-(diethylamino)butyl]amino}methyl)pyridin-4-yl]methylidene}amino]propan-1-ol | X | 1H NMR (300 MHz, chloroform-d): δ ppm 8.60 (d, 1H), 8.32 (s, 1H), 3.94 (s, 2H), , 2.51 (q, 4H), 1.24 (d, 3H), 1.02 (t, 6H). |
| 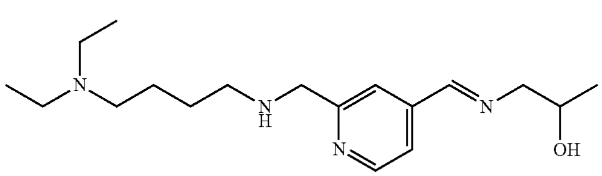 [SMILES: CCN(CC)CCCCNCc1cc(/C=N/CC(C)O)ccn1] | 74 | 1-[{[2-({[4-(diethylamino)butyl]amino}methyl)pyridin-4-yl]methylidene}amino]propan-2-ol | X | 1H NMR (300 MHz, chloroform-d): δ ppm 8.62 (d, 1H), 8.30 (s, 1H), 4.11 (m, 1H), 3.95 (s, 2H), 2.52 (q, 4H), 1.01 (t, 6H). |
| 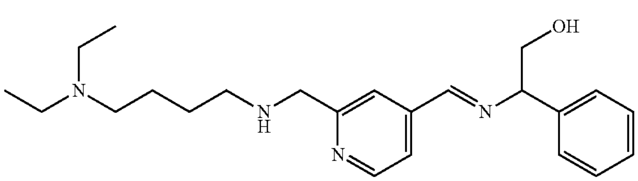 [SMILES: CCN(CC)CCCCNCc1cc(/C=N/C(CO)c2ccccc2)ccn1] | 75 | 2-[{[2-({[4-(diethylamino)butyl]amino}methyl)pyridin-4-yl]methylidene}amino]-2-phenylethan-1-ol | X | 1H NMR (300 MHz, chloroform-d): δ ppm 8.57 (d, 1H), 8.36 (s, 1H), 7.37 (m, 6H), 4.51 (m, 1H), 2.51 (q, 4H), 1.00 (t, 6H). |

TABLE 1-continued

| Structure | # | Name | May be prepared analogously to Synthetic Route | NMR |
|---|---|---|---|---|
| 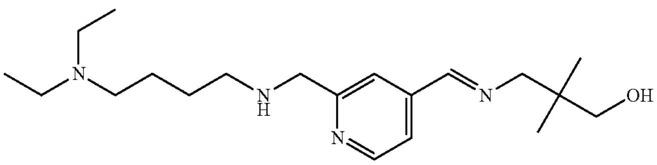 [SMILES: CCN(CC)CCCCNCc1cc(/C=N/CC(C)(C)CO)ccn1] | 76 | 3-[{[2-({[4-(diethylamino)butyl]amino}methyl)pyridin-4-yl]methylidene}amino]-2,2-dimethyl-propan-1-ol | X | 1H NMR (300 MHz, chloroform-d): δ ppm 8.54 (d, 1H), 7.45 (s, 1h), 3.91 (s, 2H), 2.52 (q, 4H), 1.00 (t, 6H), 0.96 (s, 6H). |
| 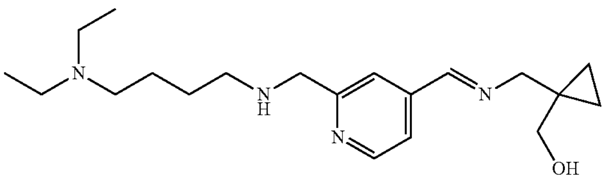 [SMILES: CCN(CC)CCCCNCc1cc(/C=N/CC2(CO)CC2)ccn1] | 77 | (l-{[{[2-({[4-(diethylamino)butyl]amino}methyl)pyridin-4-yl]methylidene}amino]methyl}cyclopropyl)methanol | X | 1H NMR (300 MHz, chloroform-d): δ ppm 8.64 (d, 1H), 8.19 (s, 1H), 3.94 (s, 2H), 2.53 (q, 4H), 1.02 (t, 6H), 0.52 (m, 4H). |
| 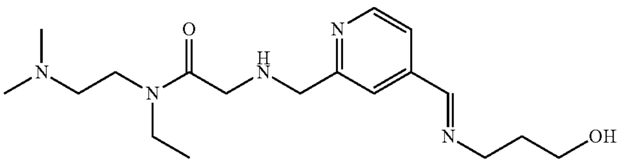 [SMILES: CCN(CCN(C)C)C(=O)CNCc1cc(/C=N/CCCO)ccn1] | 78 | N-[2-(dimethylamino)ethyl]-N-ethyl-2-[({4-[[(3-hydroxypropyl)imino]methyl]pyridin-2-yl}methyl)amino]acetamide | X | 1H NMR (300 MHz, chloroform-d): δ: 8.6 (m, 1H), 8.2 (s, 1H), 3.5 (m, 2H), 2.3 (s, 3H), 2.2 (s, 3H), 1.1 (m, 3H). |
| 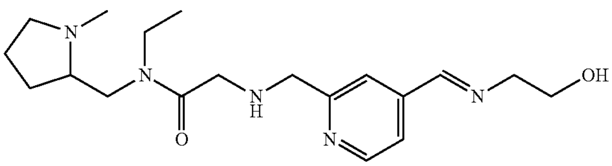 [SMILES: CCN(CC1CCCN1C)C(=O)CNCc1cc(/C=N/CCO)ccn1] | 79 | N-ethyl-2-[({4-[[(2-hydroxyethyl)imino]methyl]pyridin-2-yl}methyl)amino]-N-[(1-methyl-pyrrolidin-2-yl)methyl]acetamide | X | 1H NMR (300 MHz, CDCl3): δ ppm 8.59 (d, 1H), 8.31 (s, 1H), 3.98 (s, 2H), , 2.44 (m, 1H), 2.37 and 2.28 (two singlets, 3H), , 1.16-1.10 (m, 3H). |
| 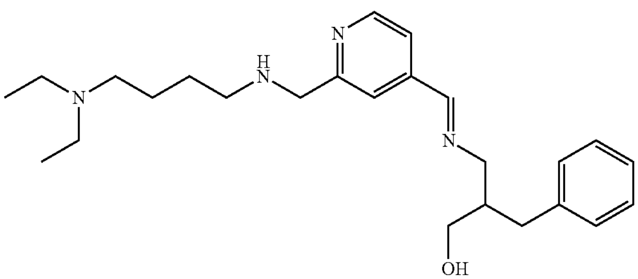 [SMILES: CCN(CC)CCCCNCc1cc(/C=N/CC(CO)Cc2ccccc2)ccn1] | 80 | 2-{[{[2-({[4-(diethylamino)butyl]amino}methyl)pyridin-4-yl]methylidene}amino]methyl}-3-phenylpropan-1-ol | X | 1H NMR (300 MHz, chloroform-d): δ ppm 8.51 (d, 1H), 7.44 (s, 1H), 7.24 (m, 6H), 3.94 (s, 2H), 3.70 (m, 2H), 2.72 (m, 2H), 2.61 (q, 4H), 2.49 (m, 4H), 1.57 (m, 4H), 1.06 (t, 6H). |
| 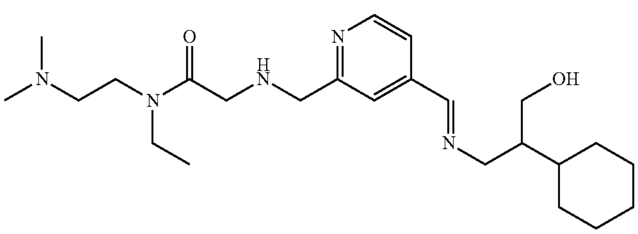 [SMILES: CCN(CCN(C)C)C(=O)CNCc1cc(/C=N/CC(CO)C2CCCCC2)ccn1] | 81 | 2-[({4-[[(2-cyclohexyl-3-hydroxypropyl)imino]methyl]pyridin-2-yl}methyl)amino]-N-[2-(dimethylamino)ethyl]-N-ethylacetamide | X | 1H NMR (300 MHz, chloroform-d): δ ppm: 8.6 (m, 1H), 8.2 (s, 1H), 4.0-3.8 (m, 4H), 2.3 (s, 3H), 2.2 (s, 3H), 1.8-1.6 (m, 12H), 1.1 (m, 3H). |
| 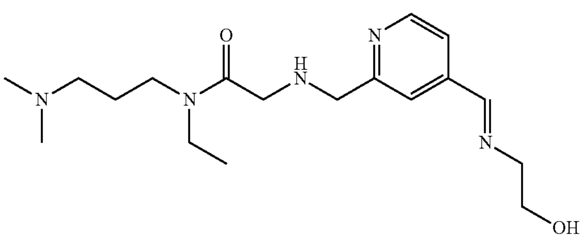 [SMILES: CCN(CCCN(C)C)C(=O)CNCc1cc(/C=N/CCO)ccn1] | 82 | N-[3-(dimethylamino)propyl]-N-ethyl-2-[({4-[[(2-hydroxyethyl)imino]methyl]pyridin-2-yl}methyl)amino]acetamide | X | 1H NMR (300 MHz, CDCl3): δ ppm 8.55 (d, 1H), 8.27 (s, 1H), 3.95 (s, 2H), , 2.18 and 2.13 (two singlets, 6H), 1.13-1.07 (m, 3H). |

TABLE 1-continued

| Structure | # | Name | May be prepared analogously to Synthetic Route | NMR |
|---|---|---|---|---|
| 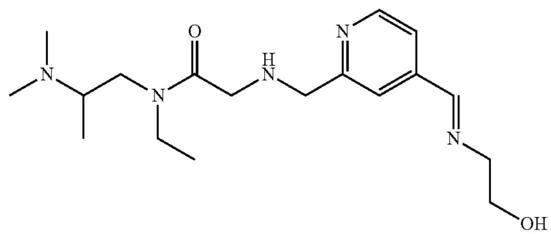 [SMILES: CCN(CC(C)N(C)C)C(=O)CNCc1cc(/C=N/CCO)ccn1] | 83 | N-[2-(dimethyl-amino)propyl]-N-ethyl-2-[({4-[[(2-hydroxyethyl)imino]methyl]pyridin-2-yl}methyl)amino]acetamide | O | 1H NMR (300 MHz, CDCl3): δ ppm 8.59 (d, 1H), 8.31 (s, 1H), 3.98 (s, 2H), 3.43 (s, 2H), 3.43 (m, 1H), , 2.25 and 2.19 (two singlets, 6H), 0.91 (d, 3H). |
| 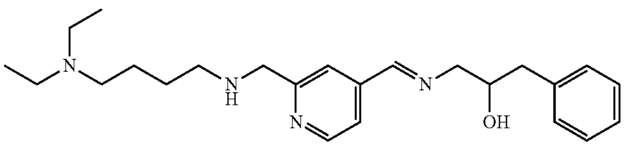 [SMILES: CCN(CC)CCCCNCc1cc(/C=N/CC(O)Cc2ccccc2)ccn1] | 84 | 1-[{[2-({[4-(diethyl-amino)butyl]amino}methyl)pyridin-4-yl]methylidene}amino]-3-phenyl-propan-2-ol | N | 1H NMR (300 MHz, chloroform-d): δ ppm 8.63 (d, 1H), 8.31 (s, 1H), 7.27 (m, 5H), 4.19 (m, 1H), 3.96 (s, 2H), 2.51 (q, 4H), 1.01 (t, 6H). |
| 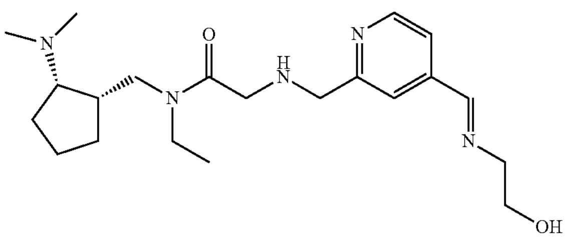 [SMILES: CCN(C[C@@H]1CCC[C@@H]1N(C)C)C(=O)CNCc1cc(/C=N/CCO)ccn1] | 85 | N-{[(1S,2S)-2-(dimethylamino)cyclo-pentyl]methyl}-N-ethyl-2-[({4-[[(2-hydroxyethyl)imino]methyl]pyridin-2-yl}methyl)amino]acetamide | N | 1H NMR (300 MHz, CDCl3): δ ppm 8.55 (d, 1H), 8.27 (s, 1H), 3.96 (s, 2H), 2.38 (m, 1H), 2.23 and 2.16 (two singlets, 6H), 1.65-1.41 (m, 5H), 1.12-1.07 (m, 3H). |
| 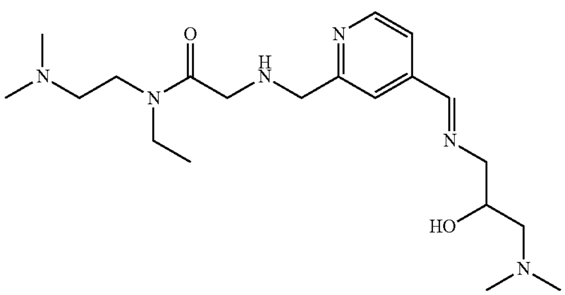 | 86 | 2-[({4-[{[3-(dimethylamino)-2-hydroxypropyl]imino}methyl]pyridin-2-yl}methyl)amino]-N-[2-(dimethyl-amino)ethyl]-N-ethylacetamide | N | 1H NMR (300 MHz, chloroform-d): δ ppm: 8.6 (d, 1H), 8.2 (s, 1H), 4.0-3.8 (m, 4H), 3.3 (m, 6H), 2.3-2.1 (m, 12H), 1.1 (m, 3H). |
| 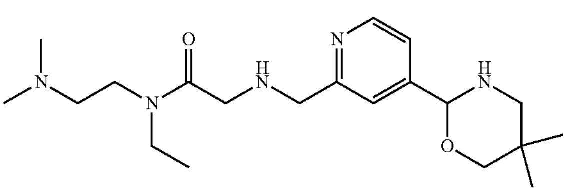 | 87 | 2-({[4-(5,5-dimethyl-1,3-oxazinan-2-yl)pyridin-2-yl]methyl}amino)-N-[2-(dimethyl-amino)ethyl]-N-ethylacetamide | N | NMR (300 MHz, chloroform-d): δ ppm 8.50 (m, 1H), 5.00 (s, 1H), 4.00 (s, 2H), 2.20 (d, 6H), 1.10 (m, 6H). |
| 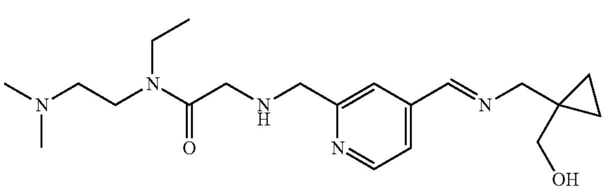 [SMILES: CCN(CCN(C)C)C(=O)CNCc1cc(/C=N/CC2(CO)CC2)ccn1] | 88 | N-[2-(dimethyl-amino)ethyl]-N-ethyl-2-[({4-[({[1-(hydroxymethyl)cyclo-propyl]methyl}imino)methyl]pyridin-2-yl}methyl)amino]acetamide | N | 1H NMR (300 MHz, CD3OD), δ ppm: 8.9 (d, 1H), 7.7 (s, 1H), 7.6 (d, 1H), 5.9 (s, 1H), 4.6 (s, 2H), 4.3, 2H), 3.8 (m, 2H), 3.5 (s, 2H), 3.3 (m, 8H), 1.2 (m, 3H), 0.9 (m, 3H), 0.6 (m, 2H), 0.4 (m, 2H). |

TABLE 1-continued

| Structure | # | Name | May be prepared analogously to Synthetic Route | NMR |
|---|---|---|---|---|
| 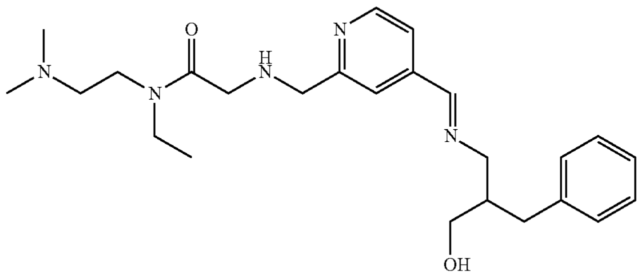 [SMILES: CCN(CCN(C)C)C(=O)CNCc1cc(/C=N/CC(CO)Cc2ccccc2)ccn1] | 89 | 2-[({4-[[(2-benzyl-3-hydroxypropyl)imino]methyl]pyridin-2-yl}methyl)amino]-N-[2-(dimethylamino)ethyl]-N-ethylacetamide | N | 1H-NMR (300 MHz, CD₃OD), δ 8.75 (d, 1H), 7.70 (s, 1H), 7.60 (d, 1H), 7.30 (m, 5H), 5.70 (s, 1H), 4.50 (s, 2H), 4.25 (m, 2H), 3.80 (m, 3H), 3.00 (s, 6H), 2.60 (m, 4H), 1.20 (t, 3H) |
| 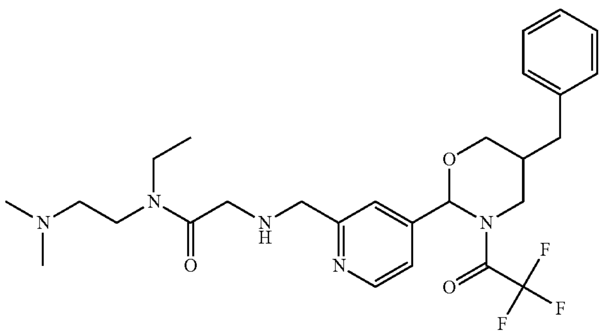 [SMILES: CCN(CCN(C)C)C(=O)CNCc1cc(C2OCC(Cc3ccccc3)CN2C(=O)C(F)(F)F)ccn1] | 90 | 2-[({4-[5-benzyl-3-(trifluoroacetyl)-1,3-oxazinan-2-yl]pyridin-2-yl}methyl)amino]-N-[2-(dimethylamino)ethyl]-N-ethylacetamide | Y | 1H-NMR (300 MHz, CD₃OD), δ 8.70 (d, 1H), 7.40 (m, 2H), 7.25 (m, 5H), 4.50 (s, 1H), 4.20 (m, 4H), 3.80 (m, 3H), 3.05 (s, 6H), 2.60 (m, 4H), 1.20 (t, 3H). |
| 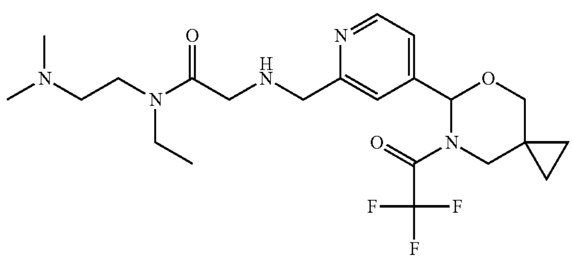 [SMILES: CCN(CCN(C)C)C(=O)CNCc1cc(C2OCC3(CC3)CN2C(=O)C(F)(F)F)ccn1] | 91 | N-[2-(dimethylamino)ethyl]-N-ethyl-2-[({4-[7-(trifluoroacetyl)-5-oxa-7-azaspiro[2.5]octan-6-yl]pyridin-2-yl}methyl)amino]acetamide | Y | 1H-NMR (300 MHz, CD₃OD), δ ppm: 8.8 (d, 1H), 7.5 (m, 2H), 6.7 (m, 1H), 4.5 (s, 2H), 4.2 (s, 2H), 3.7 (t, 2H), 3.4 (m, 6H), 3.0 (m, 8H), 1.2 (m, 3H), 0.6 (m, 2H), 0.4 (m, 2H). |
| 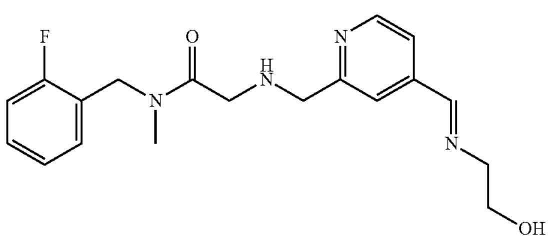 [SMILES: CN(Cc1ccccc1F)C(=O)CNCc1cc(/C=N/CCO)ccn1] | 92 | N-[(2-fluorophenyl)methyl]-2-[({4-[[(2-hydroxyethyl)imino]methyl]pyridin-2-yl}methyl)amino]-N-methylacetamide | O | 1H-NMR (300 MHz, CD₃OD), δ 8.55 (d, 1H), 7.55 (s, 1H), 7.50 (s, 1H 7.30 (m, 3H), 7.10 (m, 3H), 5.50 (s, 1H), 4.70 (s, 2H), 4.50 (s, 2H), 3.30 (s, 2H), 3.00 (m, 6H), 2.60 (m, 4H). |
| 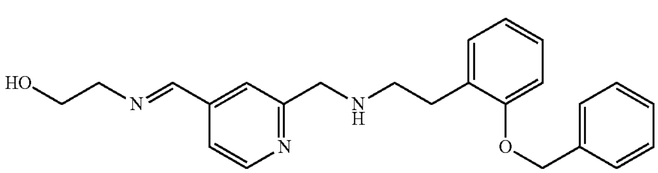 [SMILES: OCC/N=C/c1ccnc(CNCCc2ccccc2OCc2ccccc2)c1] | 93 | 2-[({2-[({2-[2-(benzyloxy)phenyl]ethyl}amino)methyl]pyridin-4-yl}methylidene)amino]ethan-1-ol | N | NMR (300 MHz, chloroform-d): δ ppm 8.60 (m, 1H), 8.20 (s, 1H), 6.90 (m, 3H), 5.10 (s, 2H), 2.96 (m, 4H). |
| 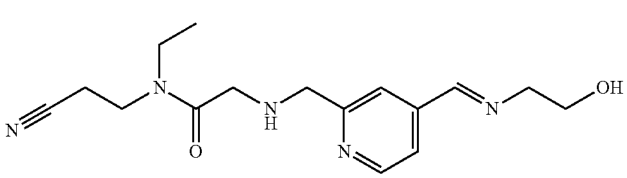 [SMILES: CCN(CCC#N)C(=O)CNCc1cc(/C=N/CCO)ccn1] | 94 | N-(2-cyanoethyl)-N-ethyl-2-[({4-[[(2-hydroxyethyl)imino]methyl]pyridin-2-yl}methyl)amino]acetamide | O | 1H NMR (300 MHz, chloroform-d): δ ppm 8.58 (d, 1H), 8.29 (s, 1H), 7.65 (s, 1H), 7.44 (d, 1H), 3.97 (s, 2H), 3.91 (m, 2H), 3.78 (m, 2H), 3.55 (t, 2H), 3.50 (s, 2H), 3.36 (q, 2H), 2.68 (m, |

TABLE 1-continued

| Structure | # | Name | May be prepared analogously to Synthetic Route | NMR |
|---|---|---|---|---|
| | | | | 4H), 1.17 (t, 3H). |
| 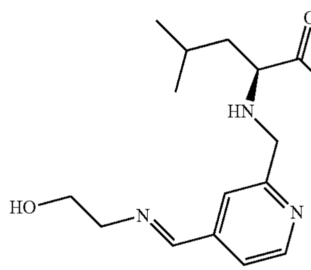 | 95 | (2S)-2-[({4-[[(2-hydroxyethyl)imino]methyl]pyridin-2-yl}methyl)amino]-4-methyl-1-(piperidin-1-yl)pentan-1-one | O | 1H NMR (300 MHz, chloroform-d): δ ppm: 8.7 (s, 1H), 8.3 (s, 1H), 7.7 (s, 1H), 7.5 (d, 1H), 4.1-3.3 (m, 1H), 1.7-1.4 (m, 8H), 0.9 (d, 6H). |
| 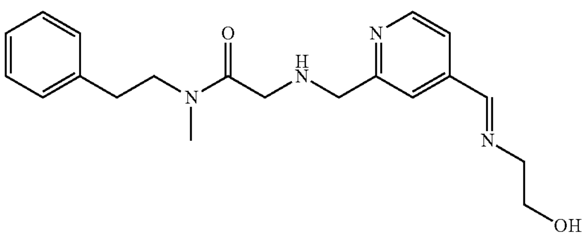 [SMILES: CN(CCc1ccccc1)C(=O)CNCc1cc(/C=N/CCO)ccn1] | 96 | 2-[{4-[(((2-hydroxy-ethyl)imino]methyl]pyridin-2-yl}methyl)amino]-N-methyl-N-(2-phenylethyl)acetamide | O | 1H NMR (300 MHz, chloroform-d): δ ppm: 8.6 (d, 1H), 8.3 (s, 1H), 7.6 (d, 1H), 7.4 (s, 1H), 7.3-7.1 (m, 5H), 4.0-3.8 (m, 11H), 2.1 (m, 1H), 3.4 (m, 2H), 3.0 (s, 2H), 2.9 (m, 5H). |
| 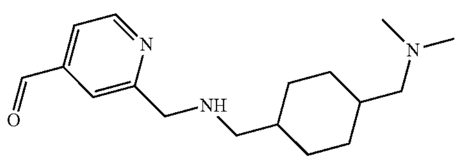 [SMILES: CN(C)CC1CCC(CNCc2cc(C=O)ccn2)CC1] | 97 | 2-{[({4-[(dimethylamino)methyl]cyclohexyl}methyl)amino]methyl}pyridine-4-carbaldehyde | Z | 1H NMR (300 MHz, Methanol-d4), δ ppm: 8.89 (d, 1H), 8.26 (s, 1H), 2.91 (s, 6H), 1.95 (m, 6H). |
| 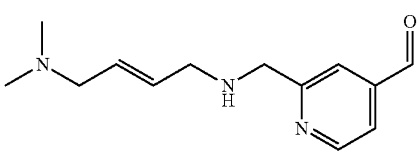 [SMILES: CN(C)C/C=C/CNCc1cc(C=O)ccn1] | 98 | 2-({[(2E)-4-(dimethylamino)but-2-en-1-yl]amino}methyl)pyridine-4-carbaldehyde | Z | 1H NMR (300 MHz, Methanol-d4), δ ppm: 8.91 (d, 1H), 6.25 (m, 2H), 5.75 (s, 1H), 2.93 (s, 6H). |
| 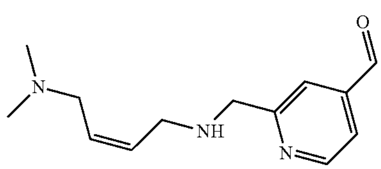 [SMILES: CN(C)C/C=C\CNCc1cc(C=O)ccn1] | 99 | 2-({[(2Z)-4-(dimethylamino)but-2-en-1-yl]amino}methyl)pyridine-4-carbaldehyde | AA | 1H-NMR (300 MHz, Methanol-d4), δ ppm: 8.8 (d, 1H), 6.2 (m, 2H), 4.6 (s, 2H), 2.9 (s, 6H) |
| 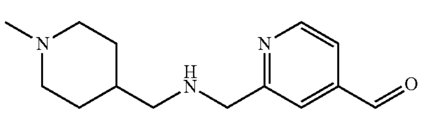 [SMILES: CN1CCC(CNCc2cc(C=O)ccn2)CC1] | 100 | 2-({[(1-methyl-piperidin-4-yl)methyl]amino}methyl)pyridine-4-carbaldehyde | Z | 1H NMR (300 MHz, Methanol-d4), δ ppm: 8.97 (d, 1H), 5.79 (s, 1H), 2.89 (s, 3H), 1.69 (m, 2H) |
| 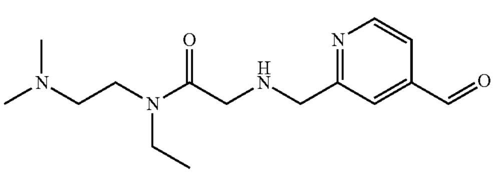 [SMILES: CCN(CCN(C)C)C(=O)CNCc1cc(C=O)ccn1] | 101 | N-[2-(dimethylamino)ethyl]-N-ethyl-2-{[(4-formylpyridin-2-yl)methyl]amino}acetamide | AA | 1H NMR (300 MHz, CD3OD), δ ppm: 8.94 (d, 1H), 8.42 (s, 1H), 2.99 (s, 6H), 1.29 (t, 3H). |

TABLE 1-continued

| # | Name | May be prepared analogously to Synthetic Route | NMR |
|---|------|---|-----|
| 102 | 2-[({2-oxo-2-[(2R)-2-(pyrrolidin-1-ylmethyl)pyrrolidin-1-yl]ethyl}amino)methyl]pyridine-4-carbaldehyde | AB | 1H NMR (300 MHz, CD3OD), δ ppm: 8.91 (m, 1H), 8.36 (s, 1H), 2.27-2.00 (m, 7H), 1.85 (m, 1H) |
| 103 | 2-({[2-(4-methylpiperazin-1-yl)-2-oxoethyl]amino}methyl)pyridine-4-carbaldehyde | AB | 1H NMR (300 MHz, Methanol-d4), δ ppm: 8.89 (d, 1H), 5.74 (s, 1H), 4.51 (m, 4H), 2.97 (s, 3H). |
| 104 | N-[(1-ethylpyrrolidin-2-yl)methyl]-2-{[(4-formylpyridin-2-yl)methyl]amino}acetamide | AB | 1H-NMR (300 MHz, MeOD), δ ppm: 8.50 (d, 1H), 7.50 (s, 1H), 2.10 (m, 2H), 1.40 (t, 3H) |
| 105 | N,N-diethyl-2-{[(4-formylpyridin-2-yl)methyl]amino}acetamide | AB | 1H-NMR (300 MHz, MeOD), δ ppm: 8.90 (d, 1H), 8.40 (s, 1H), 3.20 (q, 2H), 1.20 (t, 3H) |
| 106 | 2-({[2-(4-benzylpiperidin-1-yl)-2-oxoethyl]amino}methyl)pyridine-4-carbaldehyde | AB | 1H NMR (300 MHz, Methanol-d4), δ ppm: 8.95 (d, 1H), 7.22 (m, 5H), 5.79 (s, 1H), 1.86 (m, 1H). |
| 107 | 2-({[4-(diethylamino)butyl]amino}methyl)pyridine-4-carbaldehyde | Z | 1H-NMR (300 MHz, MeOD), δ ppm: δ 8.90 (d, 1H), 8.48 (s, 2H), 1.90 (m, 4H), 1.40 (t 6H) |
| 108 | 2-({[4-(dimethylamino)butyl]amino}methyl)pyridine-4-carbaldehyde | Z | 1H-NMR (300 MHz, MeOD), δ ppm: 8.85 (d, 1H), 8.30 (s, 1H), 2.90 (s, 6H), 1.90 (m, 4H) |

TABLE 1-continued

| Structure | # | Name | May be prepared analogously to Synthetic Route | NMR |
|---|---|---|---|---|
| 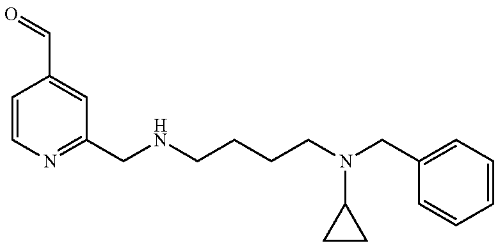 [SMILES: O=Cc1ccnc(CNCCCCN(Cc2ccccc2)C2CC2)c1] | 109 | 2-[({4-[benzyl(cyclopropyl)amino]butyl}amino)methyl]pyridine-4-carbaldehyde | AC | 1H-NMR (300 MHz, CDCl3), δ ppm: 8.90 (d, 1H), 8.40 (s, 1H), 7.50 (m, 5H), 0.90 (m, 4H) |
| 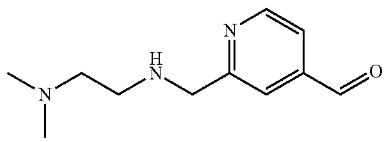 | 110 | 2-({[2-(dimethylamino)ethyl]amino}methyl)pyridine-4-carbaldehyde | Z | 1H NMR (300 MHz, Methanol-d4), δ ppm: 8.94 (d, 1H), 5.76 (s, 1H), 3.76 (m, 4H), 3.05 (m, 6H) |
| 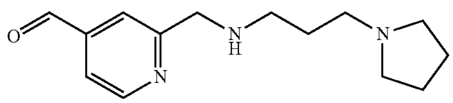 [SMILES: O=Cc1ccnc(CNCCCN2CCCC2)c1] | 111 | 2-({[3-(pyrrolidin-1-yl)propyl]amino}methyl)pyridine-4-carbaldehyde | Z | 1H-NMR (300 MHz, Methanol-d4), δ ppm: 8.80 (s, 1H), 5.70 (s, 1H), 4.10-3.40 (m, 6H), 2.98-2.40 (m, 2H). |
| 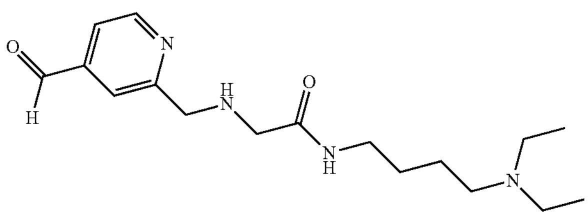 [SMILES: CCN(CC)CCCCNC(=O)CNCc1cc(C=O)ccn1] | 112 | N-[4-(diethylamino)butyl]-2-{[(4-formylpyridin-2-yl)methyl]amino}acetamide | AB | 1H NMR (300 MHz, Methanol-d4), δ ppm: 8.84 (d, 0.5H), 5.71 (s, 1H), 1.61 (m, 2H), 1.35 (m, 6H). |
| 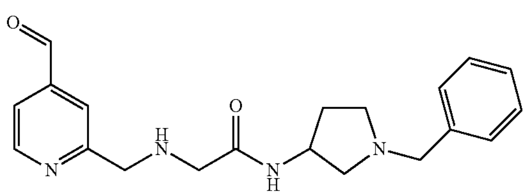 [SMILES: O=Cc1ccnc(CNCC(=O)NC2CCN(Cc3ccccc3)C2)c1] | 113 | N-(1-benzylpyrrolidin-3-yl)-2-{[(4-formylpyridin-2-yl)methyl]amino}acetamide | AB | 1H-NMR (300 MHz, MeOD), δ ppm: 8.90 (m, 2H), 8.30 (m, 1H), 7.40 (m, 5H), 2.00 (m, 2H) |
| 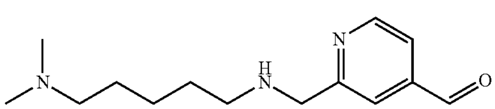 [SMILES: CN(C)CCCCCNCc1cc(C=O)ccn1] | 114 | 2-({[5-(dimethylamino)pentyl]amino}methyl)pyridine-4-carbaldehyde | Z | 1H-NMR (300 MHz, MeOD), δ ppm: 8.80 (d, 1H), 8.20 (s, 1H), 2.90 (s, 6H), 1.80 (m, 4H) |
| 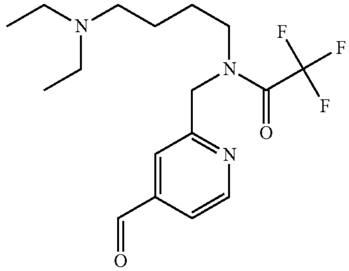 [SMILES: CCN(CC)CCCCN(Cc1cc(C=O)ccn1)C(=O)C(F)(F)F] | 115 | N-[4-(diethylamino)butyl]-2,2,2-trifluoro-N-[(4-formylpyridin-2-yl)methyl]acetamide | AD | 1H NMR (300 MHz, CDCl3), δ ppm: 10.09 (d, 1H), 8.83 (dd, 1H), 1.76 (m, 4H), 1.33 (m, 6H) |

TABLE 1-continued

| Structure | # | Name | May be prepared analogously to Synthetic Route | NMR |
|---|---|---|---|---|
| 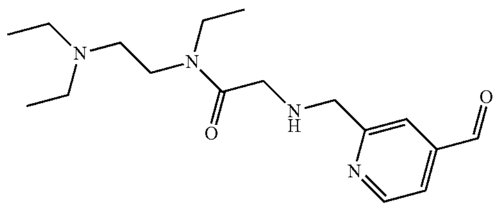 [SMILES: CCN(CC)CCN(CC)C(=O)CNCc1cc(C=O)ccn1] | 116 | N-[2-(diethylamino)ethyl]-N-ethyl-2-{[(4-formylpyridin-2-yl)methyl]amino}acetamide | AA | 1H NMR (300 MHz, CD₃OD): δ ppm 8.87 (d, 1H), 8.19 (s, 1H), 8.00 (dd, 1H), 5.73 (s, 1H), 4.74 (s, 2H), 4.39 (s, 2H), 3.83 (t, 2H), 3.49-3.28 (m, 8H), 1.38 (t, 6H), 1.29 (t, 3H). |
| 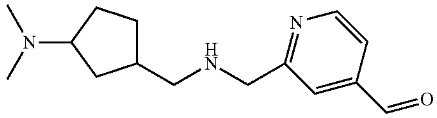 [SMILES: CN(C)C1CCC(CNCc2cc(C=O)ccn2)C1] | 117 | 2-[({[3-(dimethylamino)cyclopentyl]methyl}amino)methyl]pyridine-4-carbaldehyde | Z | 1H-NMR (300 MHz, CDCl₃), δ ppm: 8.90 (s, 1H), 5.80 (s, 1H), 2.80 (s, 6H), 2.50-2.00 (m, 6H). |
| 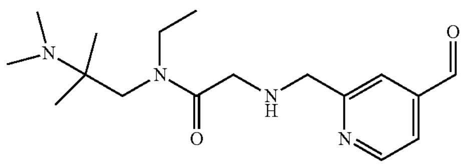 [SMILES: CCN(CC(C)(C)N(C)C)C(=O)CNCc1cc(C=O)ccn1] | 118 | N-[2-(dimethylamino)-2-methylpropyl]-N-ethyl-2-{[(4-formylpyridin-2-yl)methyl]amino}acetamide | AA | 1H NMR (300 MHz, DMSO-d₆) δ 10.1 (s, 1H), 8.91 (d, 1H), 4.49 (s, 2H), 4.24 (s, 2H), 2.72 (s, 6H), 1.34 (s, 6H), 1.12 (t, 3H). |
| 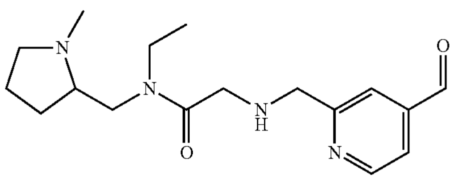 [SMILES: CCN(CC1CCCN1C)C(=O)CNCc1cc(C=O)ccn1] | 119 | N-ethyl-2-{[(4-formylpyridin-2-yl)methyl]amino}-N-[(1-methylpyrrolidin-2-yl)methyl]acetamide | AA | 1H NMR (300 MHz, CD₃OD): δ ppm 8.26 (s, 1H), 4.77 (s, 2H), 4.45 (s, 2H), 3.21 (m, 1H), 3.03 (s, 3H), 2.20-2.07 (m, 2H), 1.29 (t, 3H). |
| 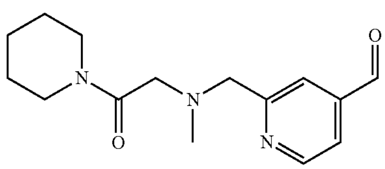 [SMILES: CN(CC(=O)N1CCCCC1)Cc1cc(C=O)ccn1] | 120 | 2-({methyl[2-oxo-2-(piperidin-1-yl)ethyl]amino}methyl)pyridine-4-carbaldehyde | Z | 1H-NMR (300 MHz, CDCl₃): δ 10.08 (s, 1H), 8.78 (d, 1H), 7.92 (s, 1H), 7.58 (d, 1H). |

N-{[2-({[4-(diethylamino)butyl]amino}methyl)pyridin-4-yl]methyl}-2,2,2-trifluoroacetamide (#1)

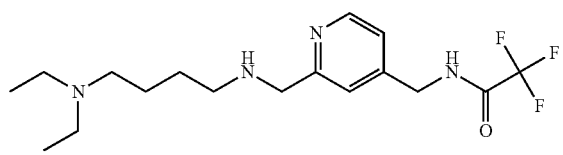 [SMILES: CCN(CC)CCCCNCc1cc(CNC(=O)C(F)(F)F)ccn1]

Synthetic Route A

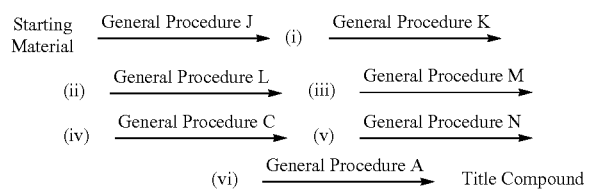

General Procedure A (Reductive Amination)

A solution of aldehyde (2,2,2-trifluoro-N-[(2-formylpyridin-4-yl)methyl]acetamide) and amine ((4-aminobutyl)diethylamine) (1.3 equiv.) in 1,2-dichloroethane was stirred for 2 h at room temperature, before NaBH(AcO)₃ (2 eq) was added. The mixture was stirred overnight at room temperature. The solvents were removed in vacuo and the residue was purified by preparative TLC (40% MeOH in DCM). The title product was isolated as colorless oil as the acetate salt. ¹H NMR (300 MHz, CD₃OD) δ ppm: 8.57 (d, 1H), 7.38 (s, 1H), 7.29 (d, 1H), 4.53 (s, 2H), 4.13 (s, 2H), 3.13 (q, 4H), 3.04 (t, 2H), 2.91 (t, 2H), 1.94 (s, 6H), 1.77 (m, 4H), 1.25 (t, 6H). ES-MS: 361 [M+H].

[2-({[4-(diethylamino)butyl]amino}methyl)pyridin-4-yl]methanamine (#5)

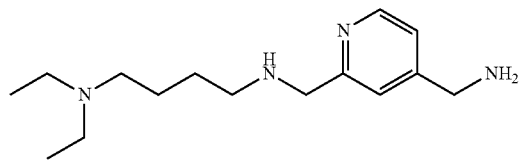 [SMILES: CCN(CC)CCCCNCc1cc(CN)ccn1]

Synthetic Route B

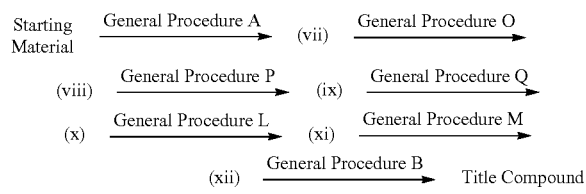

General Procedure B (Amines from Tert-Butyl Carbamates)

Concentrated hydrochloric acid was added dropwise to the tert-butyl carbamate (tert-butyl N-{[4-(aminomethyl)pyridin-2-yl]methyl}-N-[4-(diethylamino)butyl]carbamate (1)) at 0° C. The resulting solution was reduced to dryness in vacuo to yield the title product as colorless solid as the hydrochloric acid salt. $^1$H-NMR (300 MHz, MeOD): δ 8.82 (d, 1H), 8.05 (s, 1H), 7.80 (d, 1H), 4.65 (s, 2H), 4.05 (s, 2H), 3.20 (m, 9H), 1.85 (m, 4H), 1.30 (t, 6H) ppm. ES-MS: 265 [M+H$^+$].

N-[4-(diethylamino)butyl]-2,2,2-trifluoro-N-({4-[(trifluoroacetamido)methyl]pyridin-2-yl}methyl)acetamide (#6)

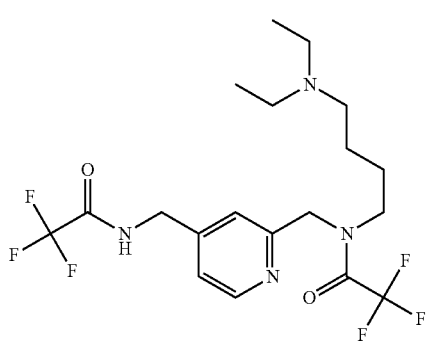 [SMILES: CCN(CC)CCCCN(Cc1cc(CNC(=O)C(F)(F)F)ccn1)C(=O)C(F)(F)F]

Synthetic Route C

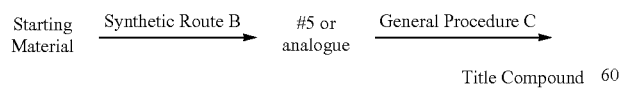

General Procedure C (Formation of Trifluoroacetamide or Trifluoroacetate)

Trifluoroacetic anhydride (2.2 equiv.) was added dropwise to a solution of the amine ([2-({[4-(diethylamino)butyl]amino}methyl)pyridin-4-yl]methanamine) (1 equiv.) and DIPEA (2.5 equiv.) in anhydrous DCM at 0° C. The mixture was allowed to warm to room temperature and stirred for 12 hours. Quenched with sat. NaHCO$_3$ (aq.). Aqueous work up gave the title compound. $^1$H-NMR (300 MHz, CDCl3): δ 11.60, 11.45 (d, 1H), 9.10, 8.70 (d, 1H), 8.45, 8.40 (s, 1H), 7.20, 7.10 (d, 1H), 4.70 (d, 2H), 4.50 (t, 2H), 3.10 (m, 4H), 1.50 (t, 6H) ppm. ES-MS: 457 [M+1].

[2-({[4-(azetidin-1-yl)butyl]amino}methyl)pyridin-4-yl]methanamine (#7)

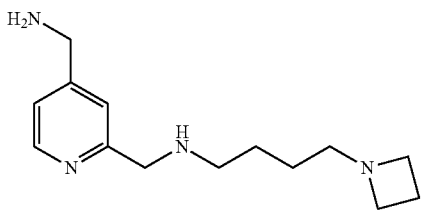 [SMILES: NCc1ccnc(CNCCCCN2CCC2)c1]

Synthetic Route D

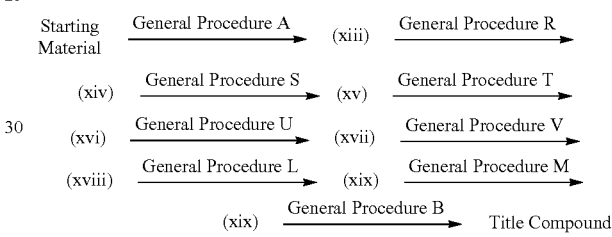

General Procedure B from tert-butyl N-{[4-(aminomethyl)pyridin-2-yl]methyl}-N-[4-(azetidin-1-yl)butyl]carbamate yielded the hydrochloric acid salt of the title product as colorless solid. $^1$H-NMR (300 MHz, CDCl$_3$): δ 8.70 (d, 1H), 7.60 (s, 1H), 7.40 (d, 1H), 4.40 (s, 2H), 4.20 (s, 2H), 3.20 (s, 4H), 2.20 (m, 2H), 1.80 (m, 4H), 1.20 (m 4H) ppm. ES-MS: 249 [M+1].

N-{[2-({[4-(dimethylamino)butyl]amino}methyl)pyridin-4-yl]methyl}cyclopropanamine (#10)

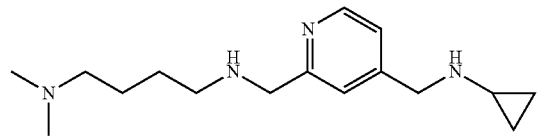 [SMILES: CN(C)CCCCNCc1cc(CNC2CC2)ccn1]

Synthetic Route E

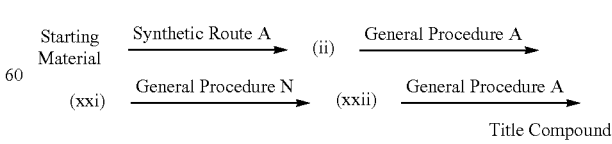

By General Procedure A from (4-[(cyclopropylamino)methyl]pyridine-2-carbaldehyde and (4-aminobutyl)dimethylamine) (1.0 equiv.). Purification by column chromatography (CH2Cl2/MeOH/NH4OH, 90:10:1) yielded the title compound as a colorless glue. ¹H NMR (300 MHz, CDCl₃): δ 8.42 (d, 1H), 7.22 (S, 1H), 6.95 (m, 1H), 3.70 (s, 2H), 3.65 (s, 2H), 2.65 (m, 2H), 2.25 (m, 2H), 2.20 (s, 6H), 2.15 (m, 1H), 2.10-2.00 (m, 4H), 1.62-1.52 (m, 2H), 0.5-0.38 (m, 4H).

2-{[(4-{[(cyanomethyl)amino]methyl}pyridin-2-yl)methyl]amino}-N,N-dimethylacetamide (#13)

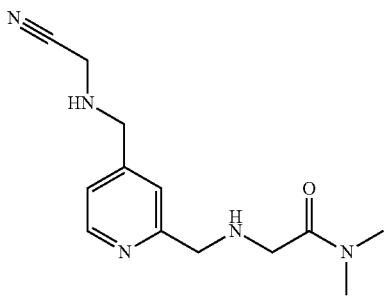 [SMILES: CN(C)C(=O)CNCc1cc(CNCC#N)ccn1]

Synthetic Route F

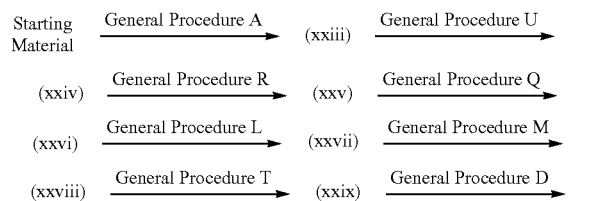

General Procedure D (Acids from Tert-Butyl Esters or Amines from Tert-Butyl Carbamates)

Trifluoroacetic acid (100 equiv.) was added to a solution of the tert-butyl carbamate (or tert-butyl ester) (tert-butyl N-[(4-{[(cyanomethyl)amino]methyl}pyridin-2-yl)methyl]-N-[(dimethylcarbamoyl)methyl]carbamate) (1 equiv.) in DCM at 0° C. The mixture was stirred at room temperature for 3 h. Evaporated to dryness to give the title product as trifluoroacetic acid salt. ¹H NMR (300 MHz, methanol-d₄): δ ppm 8.72 (d, 1H), 7.57 (s, 1H), 7.53 (d, 1H), 4.37 (s, 2H), 4.36 (s, 2H), 4.29 (s, 2H), 4.18 (s, 2H), 3.00 (s, 6H). ES-MS: 262 [M+1].

2-({[4-({[2-(dimethylamino)ethyl]amino}methyl)pyridin-2-yl]methyl}amino)-N,N-dimethylacetamide (#15)

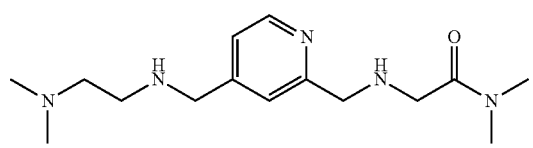

Synthetic Route G

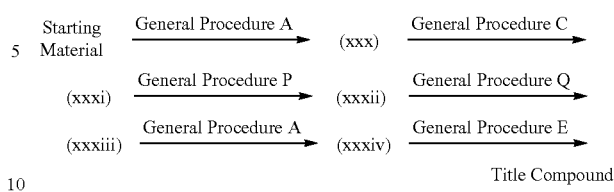

General Procedure E (Hydrolysis of Trifluoroacetamide)

KOH (1.0 M in H₂O, 2.0 equiv.) was added to a solution of the trifluoroacetamide (N-{[4-({[2-(Dimethylamino)ethyl]amino}methyl)pyridin-2-yl]methyl}-N-[(dimethylcarbamoyl)methyl]-2,2,2-trifluoroacetamide) MeOH/H₂O (1:1 vol). Stirred at 60° C. for about 1.0 h. Evaporated to dryness. Aqueous work up gave the title product as oil. ¹H NMR (300 MHz, methanol-d₄): δ ppm 8.44 (d, ¹H), 7.47 (s, 1H), 7.32 (d, 1H), 3.90 (s, 2H), 3.83 (s, 2H), 3.50 (s, 2H), 2.96 (d, 6H), 2.71 (t, 2H), 2.49 (t, 2H), 2.25 (s, 6H). ES-MS: 294 [M+1].

Benzyl(methyl){3-[({4-[(methylamino)methyl]pyridin-2-yl}methyl)amino]propyl}amine (#17)

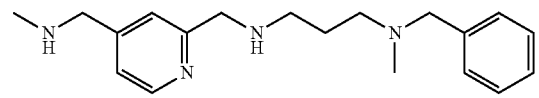 [SMILES: CNCc1ccnc(CNCCCN(C)Cc2ccccc2)c1]

Synthetic Route H

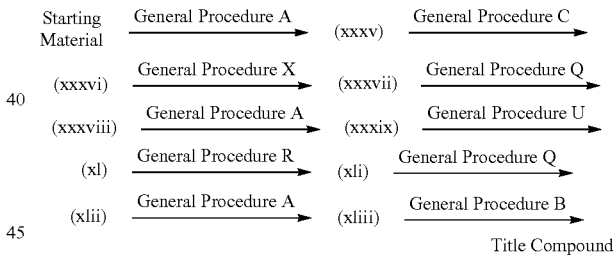

General Procedure B from tert-butyl N-{3-[benzyl(methyl)amino]propyl}-N-({4-[(methylamino)methyl]pyridin-2-yl}methyl)carbamate gave the hydrochloric acid salt of title compound. ¹H NMR (300 MHz, CDCl₃), δ ppm: 8.8 (d, 1H), 8.0-7.4 (m, 7H), 4.6-4.2 (m, 6H), 3.9 (s, 2H), 3.5-3.2 (m, 4H), 3.0-2.7 (m, 4H), 2.4-2.2 (m, 2H), 1.2-0.9 (m, 4H).

2-[({4-[(cyclopropylamino)methyl]pyridin-2-yl}methyl)amino]-N-{1-[(2-ethoxyphenyl)methyl]-piperidin-4-yl}acetamide (#20)

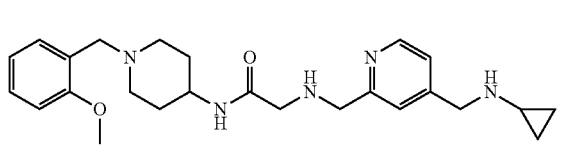 [SMILES: COc1ccccc1CN1CCC(NC(=O)CNCc2cc(CNC3CC3)ccn2)CC1]

Synthetic Route I

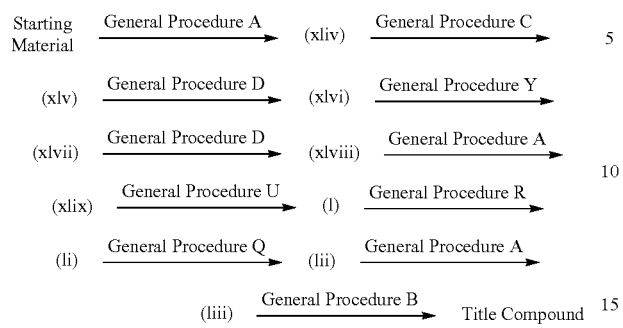

By General procedure B from tert-butyl N-({4-[(cyclopropylamino)methyl]pyridin-2-yl}methyl)-N-[({1-[(2-methoxyphenyl)methyl]piperidin-4-yl}carbamoyl)methyl]carbamate to give the title product as colorless sticky gum. $^1$H-NMR (300 MHz, CD$_3$OD): δ 8.78 (m, 1H), 7.90 (d, 1H), 7.80 (m, 1H), 7.45 (m, 2H), 7.10 (m, 1H), 7.02 (m, 1H), 4.58 & 4.50 (2s, 2H, rotamer), 4.40 & 4.30 (2S, 2H; rotamer), 4.10 (m, 1H), 3.90 (m, 5H), 3.60-3.65 (m, 2H), 3.20 (m, 2H), 2.60 (m, 1H), 2.18 (m, 2H), 1.82 (m, 2H), 0.9-0.8 (m, 4H).

2-[2-({[3-(dimethylamino)propyl]amino}methyl)pyridin-4-yl]-2-(methylamino)acetonitrile (#24)

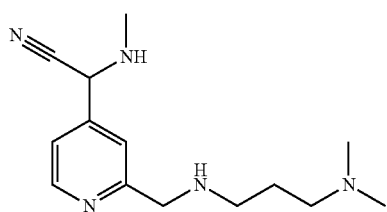 [SMILES: CNC(C#N)c1ccnc(CNCCCN(C)C)c1]

Synthetic Route 3

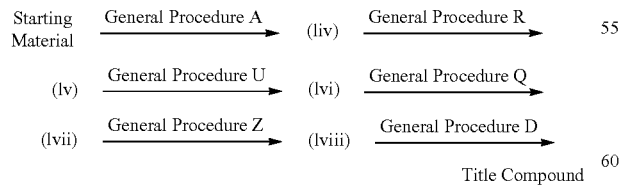

By General procedure D from tert-butyl N-({4-[cyano(methylamino)methyl]pyridin-2-yl}methyl)-N-[3-(dimethylamino)propyl]carbamate. Evaporation gave the title product as trifluoroacetic acid salt. $^1$H NMR (300 MHz, CD$_3$OD) δ ppm: 8.83 (d, 1H), 7.75 (s, 1H), 7.68 (dd, 1H), 4.54 (s, 3H), 3.27 (m, 4H), 2.93 (s, 6H), 2.83 (s, 3H), 2.25 (m, 2H). ES-MS: 262 [M+1].

2-[({2-[({4-[benzyl(cyclopropyl)amino]butyl}amino)methyl]pyridin-4-yl}methyl)amino]acetonitrile (#23)

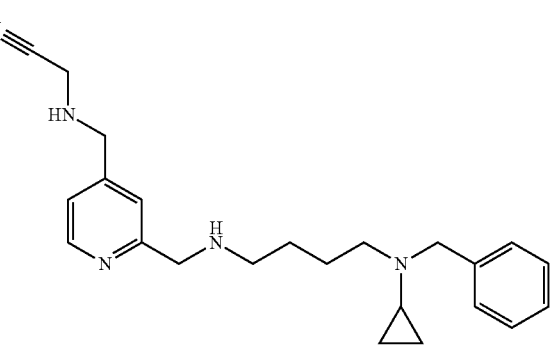

Synthetic Route K

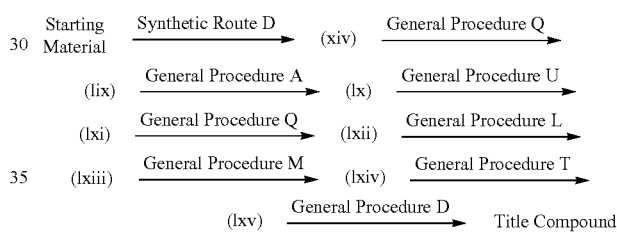

By General procedure D from tert-butyl N-{4-[benzyl(cyclopropyl)amino]butyl}-N-[(4-{[(cyanomethyl)amino]methyl}pyridin-2-yl)methyl]carbamate. Purification by prep TLC (10% MeOH, 1% NH$_4$OH in DCM) gave the title compound as colorless viscous oil. $^1$H-NMR (300 MHz, CDCl$_3$): δ 8.45 (d, 1H), 7.20-7.00 (m, 7H), 4.50 (m, 2H), 3.90 (s, 2H), 3.70 (s, 2H), 3.00 (m, 2H), 2.50 (m, 2H), 1.80 (m, 4H), 1.40 (m, 12H) 0.40 (m, 4H), ppm. ES-MS: 378 [M+1].

N-[(2-{[({[2-(Dimethylamino)ethyl](ethyl)carbamoyl}methyl)amino]methyl}pyridin-4-yl)methyl]-2,2-difluorobutanamide (#32)

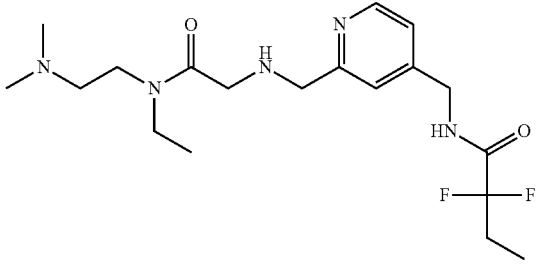 [SMILES: CCN(CCN(C)C)C(=O)CNCc1cc(CNC(=O)C(F)(F)CC)ccn1]

Synthetic Route L

Starting Material —Synthetic Route B→ Analogue of (xii) —General Procedure Y (Or General Procedure C)→ (lxvi) —General Procedure D→ Title Compound By General procedure D from tert-butyl N-({4-[(2,2-difluorobutanamido)methyl]pyridin-2-yl}methyl)-N-({[2-(dimethylamino)ethyl](ethyl)carbamoyl}methyl)carbamate to get the title compound as it's trifluoroacetic acid salt as colorless oil. $^1$H NMR (300 MHz, CD$_3$OD) δ 8.60 (d, 1H), 7.39 (s, 1H), 7.36 (d, 1H), 4.48 (m, 4H), 4.24 (s, 2H), 3.82 (t, 2H), 3.38 (m, 4H), 2.98 (s, 6H), 2.32 (m, 2H), 1.24 (t, 3H), 1.02 (t, 3H). ES-MS: 400.61 [M+1]

{2-({[4-(diethylamino)butyl]amino}methyl)pyridin-4-yl]methyl}carbamoyl)formic acid (#27

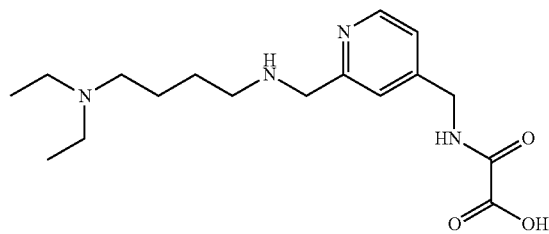 [SMILES: CCN(CC)CCCCNCc1cc(CNC(=O)C(=O)O)ccn1]

Synthetic Route M

Starting Material —Synthetic Route C→ (lxvii) —#6 or analogue / General Procedure E→ —General Procedure AA→ Title Compound By General Procedure E from tert-butyl ({[2-({N-[4-(diethylamino)butyl]-2,2,2-trifluoroacetamido}methyl)pyridin-4-yl]methyl}carbamoyl)formate. Concurrent hydrolysis of the tert-butyl ester and the trifluoroacetamide gave the title product as a yellow sticky gum. $^1$H NMR (300 MHz, methanol-d): δ ppm 8.40 (d, 1H), 7.38 (s, 1H), 7.20 (d, 1H), 4.45 (s, 2H), 3.80 (s, 2H), 2.70-2.40 (m, 8H), 1.60-1.42 (m, 4H), 1.00 (m, 6H). ES-MS: 337.58 [M+1]

2-[({4-[(N-cyclopropylcarboximidoyl]pyridin-2-yl}methyl)amino]-N,N-dimethylacetamide (#33)

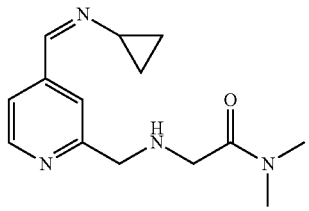 [SMILES: CN(C)C(=O)CNCc1cc(/C=N\C2CC2)ccn1]

Synthetic Route N

Starting Material —Synthetic Route F→ (xxvii) —General Procedure F→ (lxviii) —General Procedure D→ Title Compound General Procedure D from tert-butyl-N-({4-[(E)-N-cyclopropylcarboximidoyl]pyridin-2-yl}methyl)-N-[(dimethylcarbamoyl)methyl]carbamate) gave the title product as it's trifluoroacetic acid salt as yellow oil. $^1$H NMR (300 MHz, chloroform-d): δ ppm 8.55 (d, 1H), 8.52 (s, 1H), 7.73 (s, 1H), 7.56 (d, 1H), 3.96 (s, 2H), 3.55 (s, 2H), 3.17 (m, 1H), 2.96 (d, 6H), 1.00 (m, 4H). ES-MS: 261 [M+1].

N,N-dimethyl-2-[({4-[N-(2-methylcyclopropyl)carboximidoyl]pyridin-2-yl}methyl)amino]acetamide (#35)

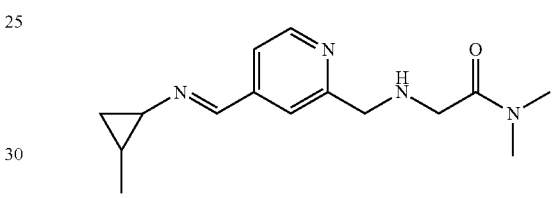

Synthetic Route O

Starting Material —Synthetic Route F→ (xxiv) —General Procedure C→ (lxix) —General Procedure Q→ (lxx) —General Procedure F→ (lxxi) —General Procedure E→ Title Compound General Procedure E from N-[(dimethylcarbamoyl)methyl]-2,2,2-trifluoro-N-({4-[N-(2-methylcyclopropyl)carboximidoyl]pyridin-2-yl}methyl)acetamide gave the title product as yellow oil. $^1$H NMR (300 MHz, chloroform-d): δ ppm 8.57 (d, 1H), 8.36 (s, 1H), 7.64 (s, 1H), 7.42 (d, 1H), 4.99 (s, 2H), 3.46 (s, 2H), 2.96 (d, 6H), 2.77 (m, 1H), 1.29 (m, 2H), 1.15 (d, 3H), 0.81 (m, 1H). ES-MS: 275 [M+1].

N-{2-({[2-(ethylsulfanyl)ethyl]amino}methyl)pyridin-4-yl]methylidene}cyclopropanamine (#39)

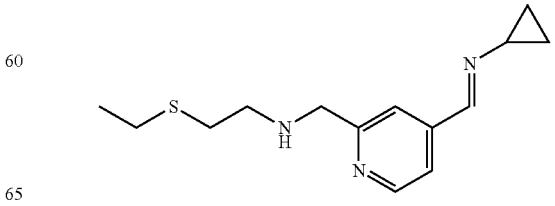

Synthetic Route P

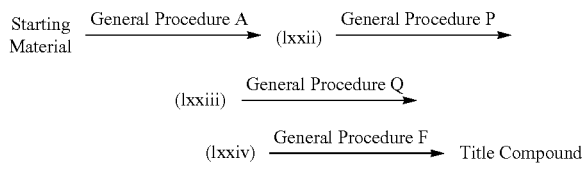

General Procedure F (Formation of Imine)

Amine (cyclopropylamine) (10 equiv.) was added to a solution of aldehyde (2-({[2-(methylsulfanyl)ethyl] amino}methyl)pyridine-4-carbaldehyde) (1 equiv.) in DCE. Stirred at room temperature overnight. Evaporated to dryness. Purification by preparative TLC (DCM/MeOH/NH$_4$OH (95/5/1)) gave the title product as pale yellow oil. $^1$H-NMR (300 MHz, CDCl$_3$): δ 8.5 (d, 1H), 8.4 (s, 1H), 7.6 (s, 1H), 7.4 (d, 1H), 3.9 (s, 2H), 3.0 (s, 1H), 2.8 (m, 2H), 2.7 (m, 2H) 2.5 (m, 2H), 1.2 (t, 3H), 1.0 (m, 4H).

N-({2-[({3-[benzyl(methyl)amino]propyl}amino) methyl]pyridin-4-yl}methylidene)cyclopropanamine (#41)

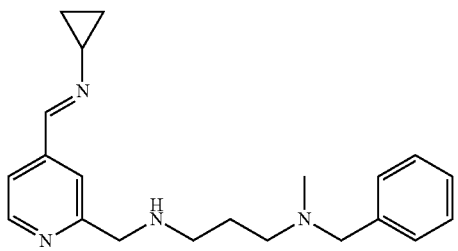 [SMILES: CN(CCCNCc1cc(/C=N/C2CC2)ccn1)Cc1ccccc1]

Synthetic Route Q

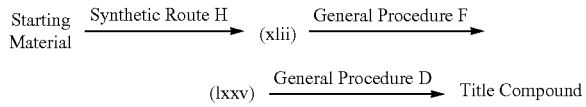

General Procedure D from tert-butyl N-{3-[benzyl(methyl)amino]propyl}-N-({4-[(N-cyclopropylcarboximidoyl] pyridin-2-yl}methyl)carbamate. Evaporated to dryness to give the title product as trifluoroacetic acid salt without further purification. $^1$H NMR (300 MHz, CDCl$_3$), δ ppm: 8.55 (d, 1H), 8.50 (s, 1H), 7.69 (s, 1H), 7.56 (dd, 1H), 7.28-7.22 (m, 5H), 3.89 (s, 2H), 3.50 (s, 2H), 3.20-3.13 (m, 1H), 2.65 (t, 2H), 2.45 (t, 2H), 2.11 (s, 3H), 1.82-1.73 (m, 2H), 1.04-0.97 (m, 4H).

N-({2-[({3-[benzyl(methyl)amino]propyl}amino) methyl]pyridin-4-yl}methylidene)cyclopropanamine (#43)

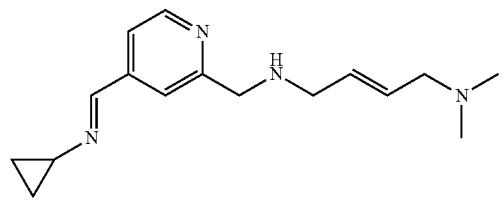 [SMILES: CN(C)C/C=C/CNCc1cc(/C=N/C2CC2)ccn1]

Synthetic Route R

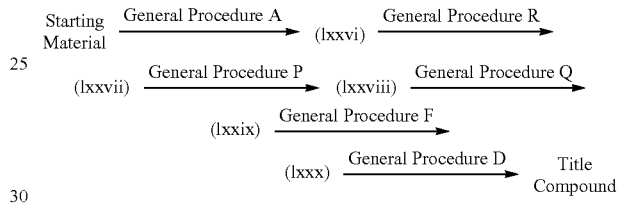

By General Procedure D from tert-butyl N-({4-[N-cyclopropylcarboximidoyl]pyridin-2-yl}methyl)-N-[(2E)-4-(dimethylamino)but-2-en-1-yl]carbamate. Purified by preparative TLC with 1% NH$_4$OH and 10% MeOH in DCM to give title product as light yellow oil. $^1$H NMR (300 MHz, chloroform-d): δ ppm 8.59 (d, 1H), 8.41 (s, 1H), 7.55 (s, 1H), 7.42 (d, 1H), 5.71 (m, 2H), 3.93 (s, 2H), 3.31 (d, 2H), 3.08 (m, 1H), 2.92 (d, 2H), 2.23 (s, 6H), 0.94 (m, 4H). ES-MS: 273 [M+1].

N-{[2-({[4-(azetidin-1-yl)butyl]amino}methyl)pyridin-4-yl]methylidene}cyclopropanamine (#44)

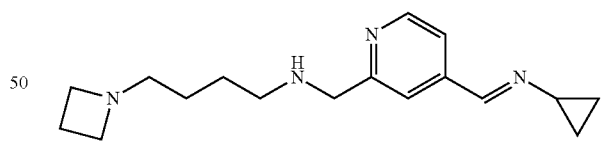

Synthetic Route S

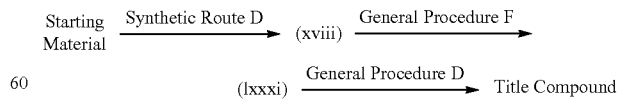

General Procedure D from tert-butyl N-[4-(azetidin-1-yl) butyl]-N-({4-[N-cyclopropylcarboximidoyl]pyridin-2-yl}methyl)carbamate. Evaporation gave the title product as it trifluoroacetic acid salt without further purification. $^1$H-NMR (300 MHz, CDCl$_3$): δ 8.50 (d, 1H), 8.40 (s, 1H), 7.50 (s, 1H), 7.40 (d, 1H), 3.90 (s, 2H), 3.00 (m, 1H), 2.70 (m, 2H), 2.50 (m, 4H), 1.80 (m, 2H), 1.50 (m 6H), 1.00 (m, 4H) ppm. ES-MS: 287 [M+1].

N-{[2-({[4-(dimethylamino)butyl]amino}methyl)pyridin-4-yl]methylidene}cyclopropanamine (#45)

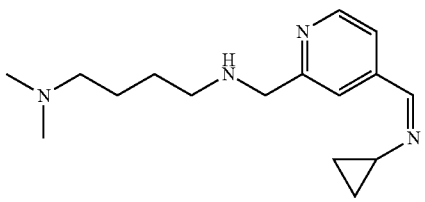 [SMILES: CN(C)CCCCNCc1cc(/C=N\C2CC2)ccn1]

Synthetic Route T

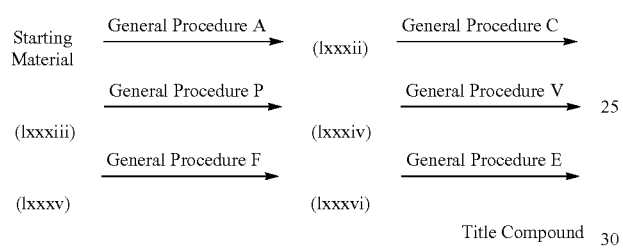

By General Procedure E from N-({4-[N-cyclopropylcarboximidoyl]pyridin-2-yl}methyl)-N-[4-(dimethylamino)butyl]-2,2,2-trifluoroacetamide. Evaporated to and the residue was neutralized with cyclopropylamine. 1M KOH solution was added and work-up gave the title product as colorless viscous oil without further purification. $^{1}$H-NMR (300 MHz, CDCl$_{3}$): δ 8.50 (s, 1H), 8.30 (s, 1H), 7.50 (s, 1H), 7.30 (d, 1H), 3.90 (s, 2H), 2.70 (m, 2H), 2.25 (m, 2H), 2.20 (s, 6H), 1.50 (m, 4H), 1.00 (m, 4H), ppm.

N-{[2-({[5-(dimethylamino)pentyl]amino}methyl)pyridin-4-yl]methylidene}cyclopropanamine (#47)

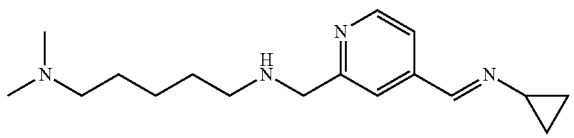 [SMILES: CN(C)CCCCCNCc1cc(/C=N/C2CC2)ccn1]

Synthetic Route U

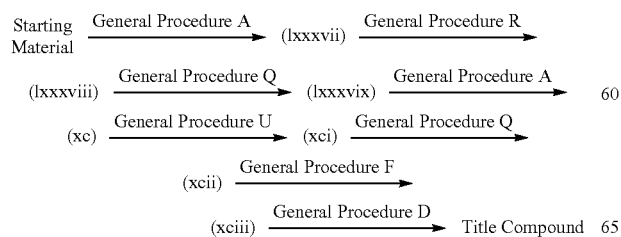

By General Procedure D from tert-butyl N-({4-[N-cyclopropylcarboximidoyl]pyridin-2-yl}methyl)-N-[5-(dimethylamino)pentyl]carbamate. Evaporated to and the residue was neutralized with cyclopropylamine. 1M KOH solution was added and work-up gave the title product as colorless viscous oil without further purification. $^{1}$H-NMR (300 MHz, CDCl3): δ 8.50 (d, 1H), 8.40 (s, 1H), 7.50 (s, 1H), 7.40 (d, 1H), 3.90 (s, 2H), 3.00 (m, 1H), 2.60 (m, 2H), 2.20 (m, 2H), 2.15 (s, 6H), 1.50-1.30 (m, 6H), 0.88 (m, 4H) ppm. ES-MS: 289 [M+1].

2-[({4-[N-cyclopropylcarboximidoyl]pyridin-2-yl}methyl)amino]-N-[4-(diethylamino)butyl]acetamide (#48)

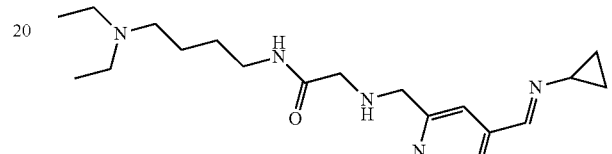

Synthetic Route V

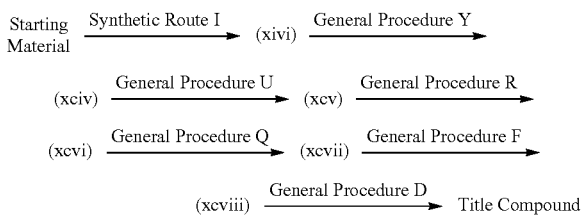

By General Procedure D from tert-butyl-N-({4-[(E)-N-cyclopropylcarboximidoyl]pyridin-2-yl}methyl)-N-({[4-(diethylamino)butyl]carbamoyl}methyl)carbamate. Purified by preparative TLC (10% MeOH and 1% NH$_4$OH in DCM) to give title product as yellow oil. $^{1}$H NMR (300 MHz, chloroform-d): δ ppm 8.61 (d, 1H), 8.41 (s, 1H), 7.57 (t, 1H), 7.50 (s, 1H), 7.41 (d, 1H), 3.90 (s, 2H), 3.32 (s, 2H), 3.29 (m, 2H), 3.09 (m, 1H), 2.67 (q, 4H), 2.60 (m, 2H), 1.56 (m, 4H), 1.09 (t, 6H), 1.03 (m, 4H). ES-MS: 360 [M+1].

2-[({4-[[(2-cyclohexylethyl)imino]methyl]pyridin-2-yl}methyl)amino]-N-[2-(dimethylamino)ethyl]-N-ethylacetamide (#63)

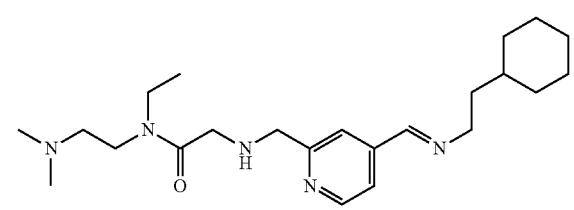 [SMILES: CCN(CCN(C)C)C(=O)CNCc1cc(/C=N/CCC2CCCCC2)ccn1]

Synthetic Route X

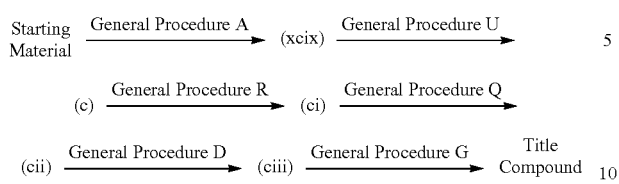

General Procedure G (Formation of Imine)

To a stirred solution of aldehyde (N-[2-(dimethylamino)ethyl]-N-ethyl-2-{[(4-formylpyridin-2-yl)methyl]amino}acetamide) (1 equiv.) in 1,2-DCE and $H_2O$ were added amine (2-cyclohexylethylamine) (1.01 equiv.) and $Na_2CO_3$ (2 equiv.) at room temperature and stirred for 3 hours. Evaporated to dryness. Suspended in DCM, filtered and evaporated to give the title compound as brown oil. $^1H$ NMR (300 MHz, chloroform-d): δ ppm 8.56 (d, 1H), 8.22 (s, 1H), 7.63 (s, 1H), 7.45 (dd, 1H), 3.96 (s, 2H), 3.63 (t, 2H), 3.45 (s, 2H), 3.45-3.34 (m, 2H), 3.27-3.19 (m, 2H), 2.43-2.33 (m, 2H), 2.23 and 2.17 (2 singlets, 6H), 1.76-1.51 (m, 7H), 1.38-1.25 (m, 1H), 1.22-1.07 (m, 6H), 0.98-0.89 (m, 2H). ESI-MS (m/z): 402 [M+1].

2-[({4-[5-benzyl-3-(trifluoroacetyl)-1,3-oxazinan-2-yl]pyridin-2-yl}methyl)amino]-N-[2-(dimethylamino)ethyl]-N-ethylacetamide (#90)

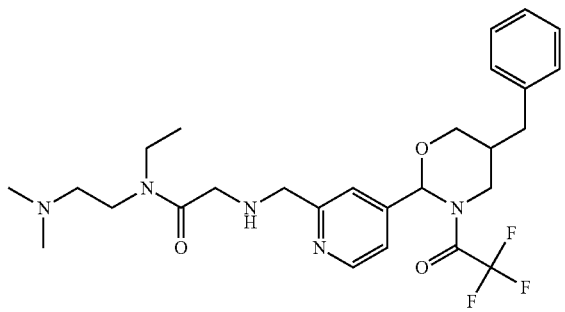 [SMILES: CCN(CCN(C)C)C(=O)CNCc1cc(C2OCC(Cc3ccccc3)CN2C(=O)C(F)(F)F)ccn1]

Synthetic Route Y

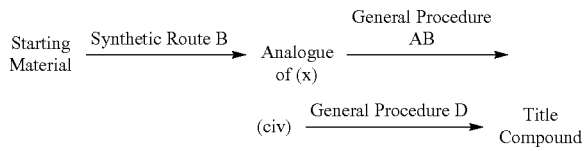

By General Procedure D from tert-butyl N-({4-[5-benzyl-3-(trifluoroacetyl)-1,3-oxazinan-2-yl]pyridin-2-yl}methyl)-N-({[2-(dimethylamino)ethyl](ethyl)carbamoyl}methyl)carbamate without any purification gave the trifluoroacetic acid salt of the title product as yellow oil $^1H$-NMR (300 MHz, CD3OD): δ 8.70 (d, 1H), 7.40 (m, 2H), 7.25 (m, 5H), 4.50 (s, 1H), 4.20 (m, 4H), 3.80 (m, 3H), 3.05 (s, 6H), 2.60 (m, 4H), 1.20 (t, 3H). ES-MS: 536 [M+1]

2-{[({4-[(dimethylamino)methyl]cyclohexyl}methyl)amino]methyl}pyridine-4-carbaldehyde (#97)

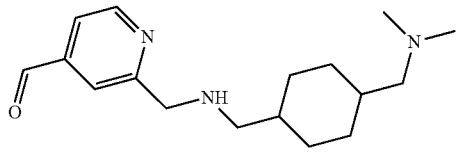 [SMILES: CN(C)CC1CCC(CNCc2cc(C=O)ccn2)CC1]

Synthetic Route Z

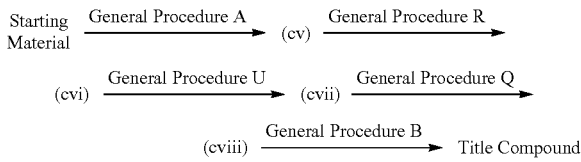

By General Procedure B from tert-butyl N-({4-[(dimethylamino)methyl]cyclohexyl}methyl)-N-[(4-formylpyridin-2-yl)methyl]carbamate to yield the title product as colorless solid as the hydrochloric acid salt. $^1H$ NMR (300 MHz, methanol-$d_4$): δ ppm 8.89 (d, 1H), 8.26 (s, 1H), 8.05 (d, 1H), 5.73 (s, 1H), 4.66 (s, 2H), 3.12 (d, 2H), 3.04 (d, 2H), 2.91 (s, 6H), 1.95 (m, 6H), 1.20 (m, 4H). ES-MS: 290 [M+1].

2-({[(2Z)-4-(dimethylamino)but-2-en-1-yl]amino}methyl)pyridine-4-carbaldehyde (#99)

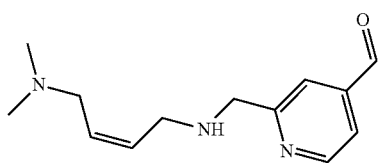 [SMILES: CN(C)C/C=C\CNCc1cc(C=O)ccn1]

Synthetic Route AA

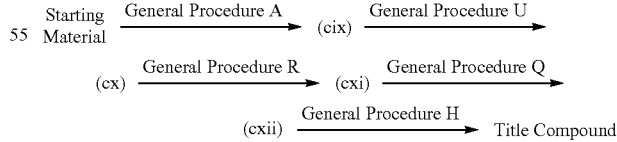

General Procedure H (Amines from Tert Butyl Carbamates)

HCl in dioxane (4M) was added to a solution of tert butyl carbamate ((Z)-tert-butyl 4-(dimethylamino)but-2-enyl((4-formylpyridin-2-yl)methyl)carbamate)) in DCM. The mixture was stirred at room temperature for 1 hour. Evaporated to give the title compound. 1H NMR (300 MHz, MeOH-$d_4$: (δ

8.8 (d, 1H), 8.0 (s, 1H), 7.7 (d, 1H), 6.2 (m, 2H), 4.5 (m, 2H), 4.1 (m, 2H), 2.9 (s, 6H), 2.2 (s, 6H).

2-[({2-Oxo-2-[(2R)-2-(pyrrolidin-1-ylmethyl)pyrrolidin-1-yl]ethyl}amino)methyl]pyridine-4-carbaldehyde (#102)

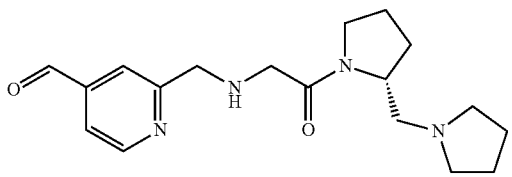 [SMILES: O=Cc1ccnc(CNCC(=O)N2CCC[C@@H]2CN2CCCC2)c1]

Synthetic Route AB

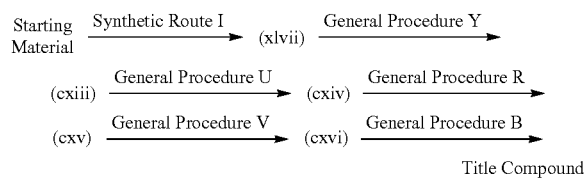

By General Procedure B from tert-butyl N-[(4-formylpyridin-2-yl)methyl]-N-{2-oxo-2-[(2R)-2-(pyrrolidin-1-ylmethyl)pyrrolidin-1-yl]ethyl}carbamate. Evaporation gave the title product as brown solid. $^1$H NMR (300 MHz, CD$_3$OD), δ ppm: 8.91 (m, 1H), 8.36 (s, 1H), 8.12 (m, 1H), 5.77 (s, 1H), 4.85-4.75 (m, 2H), 4.56 (m, 1H), 4.38-4.23 (m, 2H), 4.14 (m, 1H), 3.84 (m, 1H), 3.64-3.44 (m, 3H), 3.30-3.19 (m, 2H), 3.11 (m, 1H), 2.27-2.00 (m, 7H), 1.85 (m, 1H).

2-[({4-[Benzyl(cyclopropyl)amino]butyl}amino)methyl]pyridine-4-carbaldehyde (#109)

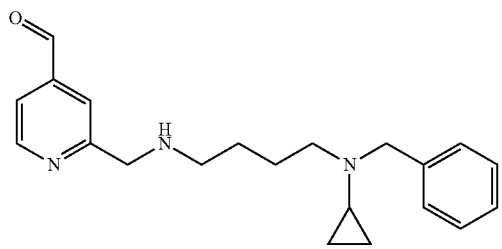 [SMILES: O=Cc1ccnc(CNCCCCN(Cc2ccccc2)C2CC2)c1]

Synthetic Route AC

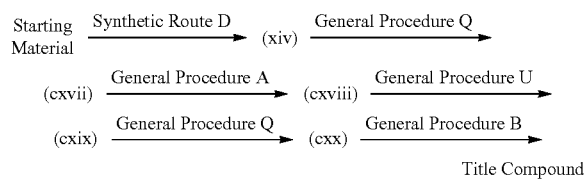

By General Procedure B from tert-butyl N-{4-[benzyl(cyclopropyl)amino]butyl}-N-[(4-formylpyridin-2-yl)methyl] carbamate. Evaporation gave the title product as yellow oil. $^1$H-NMR (300 MHz, MeOD): δ 8.90 (d, 1H), 8.40 (s, 1H), 8.10 (d, 1H), 7.50 (m, 5H), 5.70 (s, 1H), 4.70 (m, 2H), 4.50 (m, 2H), 2.80 (m, 2H), 2.00 (m, 5H), 0.90 (m, 4H) ppm.

N-[4-(diethylamino)butyl]-2,2,2-trifluoro-N-[(4-formylpyridin-2-yl)methyl]acetamide (#115)

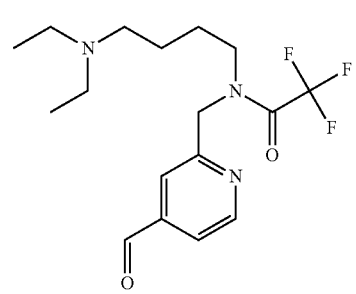 [SMILES: CCN(CC)CCCCN(Cc1cc(C=O)ccn1)C(=O)C(F)(F)F]

Synthetic Route AD

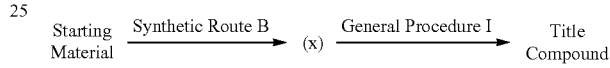

General Procedure I (Trifluoroacetamides from Tert-Butyl Carbamates)

Concentrated H$_2$SO$_4$ (2 drops) was added to the tert butyl carbamate (tert-butyl N-[4-(diethylamino)butyl]-N-[(4-formylpyridin-2-yl)methyl]carbamate) (1 equiv.) in trifluoroacetic anhydride at 0° C. The mixture was stirred for 2 h at 0° C. Solid NaHCO$_3$ was added. Diluted with DCM before evaporating to dryness. Purification by preparative TLC (10% MeOH in DCM) gave the title compound as yellow oil. $^1$H NMR (300 MHz, CDCl$_3$), δ ppm: 10.09 (d, 1H), 8.83 (dd, 1H), 7.68 (m, 2H), 4.85 (d, 2H), 3.53 (m, 2H), 3.10 (m, 6H), 1.76 (m, 4H), 1.33 (m, 6H). ES-MS: 360 [M+1].

Intermediates

Ethyl 2-(dimethoxymethyl)pyridine-4-carboxylate (i)

General Procedure J (Formation of Methyl Acetal)

Pyridinium toluene-4-sulphonate (0.1 equiv.) was added to a solution of aldehyde (ethyl 2-formylpyridine-4-carboxylate) (1.0 equiv.) and trimethyl orthoformate (6.5 equiv.) in methanol. Heated at 60° C. overnight. Aqueous work up (EtOAc/NaHCO$_3$) gave the title compound as oil. $^1$H NMR (300 MHz, CDCl$_3$), δ ppm: 8.77 (dd, 1H), 8.09 (s, 1H), 7.82 (dd, 1H), 5.44 (s, 1H), 4.41 (q, 2H), 3.42 (s, 6H), 1.41 (t, 3H).

2-(Dimethoxymethyl)pyridine-4-carbaldehyde (ii)

General Procedure K (Reduction of Ester to Aldehyde)

DIBAL-H (1.5 equiv., 1.0 M in toluene) was added slowly to a solution of the ester (Ethyl 2-(dimethoxymethyl)pyridine-4-carboxylate) (1.0 equiv.) in toluene at −78° C. Stirring continued for 1.5 h before the reaction was quenched by dropwise addition of sat. NH$_4$Cl. Allowed to warm to room temperature. EtOAc and a satd. solution of sodium potassium tartrate (excess) were added and stirring was continued overnight. Aqueous work up gave the title product, which was used without further purification. $^1$H NMR (300 MHz, CDCl$_3$), δ ppm: 10.10 (s, 1H), 8.86 (d, 1H), 7.97 (s, 1H), 7.68 (dd, 1H), 5.46 (s, 1H), 3.42 (s, 6H).

N-{[2-(dimethoxymethyl)pyridin-4-yl]methylidene}hydroxylamine (iii)

General Procedure L (Formation of Hydroxylamine)

Aldehyde (2-(dimethoxymethyl)pyridine-4-carbaldehyde) (1.0 equiv.) was dissolved in a mixture of ethanol and water (3:1) and hydroxylamine hydrochloride (1.5 equiv.) was added followed by addition of Na$_2$CO$_3$ (1.7 equiv.) The suspension was stirred at room temperature for three hours after that solvent was removed in vacuum. EtOH was added to the residue, filtered and washed with EtOH. The combined filtrates were evaporated. Triturated with H$_2$O and filtered to give the title product as colorless solid, which was used without further purification. $^1$H NMR (300 MHz, CDCl$_3$), δ ppm: 9.95 (s, 1H), 8.65 (d, 1H), 8.14 (s, 1H), 7.74 (s, 1H), 7.50 (d, 1H), 5.45 (s, 1H), 3.43 (s, 6H).

[2-(dimethoxymethyl)pyridin-4-yl]methanamine (iv)

General Procedure M (Hydrogenation to Form Amines)

A solution of hydroxyl amine (N-{[2-(dimethoxymethyl)pyridin-4-yl]methylidene}hydroxylamine) (1.0 equiv.) in MeOH over 10 Pd/C (0.2 equiv. w/w) was charged with H$_2$ (45 psi). The reaction was followed by TLC. Filtered and evaporated to give the title compound. $^1$H NMR (300 MHz, CDCl$_3$), δ ppm: 8.54 (dd, 1H), 7.50 (s, 1H), 7.22 (dt, 1H), 5.35 (s, 1H), 3.91 (s, 2H), 3.40 (s, 6H).

N-{[2-(dimethoxymethyl)pyridin-4-yl]methyl}-2,2,2-trifluoroacetamide (v)

By General Procedure C from 2-(dimethoxymethyl)pyridin-4-yl)methanamine. Evaporated to give the title compound. $^1$H-NMR (300 MHz, CDCl3): δ 8.6 (d, 1H), 7.4 (s, 1H), 7.2 (d, 1H), 5.4 (s, 2H), 4.6 (d, 2H), 3.4 (s, 6H). ES-MS: 277 [M+1] and 321 [M+23]

2,2,2-trifluoro-N-[(2-formylpyridin-4-yl)methyl]acetamide (vi)

General Procedure N (Hydrolysis of Acetal)

Concentrated hydrochloric acid (3.5 eq) was added to a solution the acetal (N-{[2-(dimethoxymethyl)pyridin-4-yl]methyl}-2,2,2-trifluoroacetamide) (1 equiv.) in THF. The mixture was stirred for 2 h at 60° C. Solid NaHCO$_3$ (5 eq) was added at 0° C. and the suspension was filtered to remove the solids, which were washed with dichloromethane. The combined filtrates were evaporated to dryness and the residual was purified by column chromatography (0-20% MeOH/DCM) to yield the title product. $^1$H NMR (300 MHz, CDCl$_3$) δ ppm: 10.05 (s, 1H), 8.77 (d, 1H), 7.86 (m, 1H), 7.47 (dd, 1H), 7.44 (bs, 1H), 4.65 (d, 2H). ES-MS: 233 [M+H].

[(4-{[(tert-butyldimethylsilyl)oxy]methyl}pyridin-2-yl)methyl][4-(diethylamino)butyl]amine (vii)

By General Procedure A from 4-{[(tert-butyldimethylsilyl)oxy]methyl}pyridine-2-carbaldehyde and 4-(diethylamino)butyl]amine. Purification by column chromatography (5% MeOH/DCM) gave the target compound as greenish oil. $^1$H-NMR (300 MHz, CDCl$_3$): δ 8.46 (d, 1H), 7.20 (s, 2H), 7.10 (d, 1H), 4.70 (s, 2H), 3.90 (s, 2H), 2.50 (m, 8H), 1.50 (m, 4H), 1.00 (t, 6H, 0.9 (s, 9H, 0.05 (s, 6H) ppm.

tert-butyl N-[(4-{[(tert-butyldimethylsilyl)oxy]methyl}pyridin-2-yl)methyl]-N-[4-(diethylamino)butyl]carbamate (viii)

General Procedure O (Boc Protection)

Di-tert-butyl dicarbonate (1.2 equiv.) was added to a solution of the amine ([(4-{[(tert-butyldimethylsilyl)oxy]methyl}pyridin-2-yl)methyl][4-(diethylamino)butyl]amine) (1.0 equiv.) and triethylamine (1.3 equiv.) in anhydrous DCM at 0° C. The reaction mixture was stirred at room temperature for 12 hours. Na$_2$CO$_3$ was added and the mixture was stirred for 30 min. Evaporated to dryness and the residual was extracted with DCM. Evaporation of the extract gave the title compound, which was used without any further purification.

Tert-butyl N-[4-(diethylamino)butyl]-N-{[4-(hydroxymethyl)pyridin-2-yl]methyl}carbamate (ix)

General Procedure P (Removal of Silyl Alcohol Protecting Group)

TBAF (2 equiv.) was added at room temperature to a solution of the silyl ether (tert-butyl N-[(4-{[(tert-butyldimethylsilyl)oxy]methyl}pyridin-2-yl)methyl]-N-[4-(diethylamino)butyl]carbamate) (1 equiv.) in THF and the reaction mixture was stirred overnight. Sat. NaHCO$_3$ (aq) was added. Stirred for 30 min, before work-up with DCM. Purification by column chromatography (DCM, MEOH and NH$_4$ (aq.)) gave the title product as colorless oil. $^1$H-NMR (300 MHz, CDCl$_3$): δ 8.40 (d, 1H), 7.00 (m, 2H), 4.60 (s, 2H), 4.40 (m, 2H), 3.20 (m, 2H), 2.40 (m, 6H), 1.40 (m, 9H), 1.00 (t, 6H) ppm.

Tert-butyl N-[4-(diethylamino)butyl]-N-[(4-formylpyridin-2-yl)methyl]carbamate (x)

General Procedure Q (Swern Oxidation)

DMSO (4 equiv.) in anhydrous DCM was cooled to −78° C. and oxalyl chloride (2 equiv.) was added drop-by-drop and stirred for 30 min at −78° C. The alcohol (tert-butyl N-[4-(diethylamino)butyl]-N-{[4-(hydroxymethyl)pyridin-2-yl]methyl}carbamate) (1.0 equiv.) was dissolved in DCM and added slowly at the same temperature and the reaction mixture was stirred for one hour. Triethylamine (5.0 equiv.) was added and reaction mixture was stirred overnight in the same cooling bath. Quenched with water, and worked up by extraction with DCM. Purification by column chromatography using ethyl acetate/hexane 20-50% yielded the title product. $^1$H-NMR (300 MHz, CDCl$_3$): δ 10.05 (s, 1H), 8.80 (d, 1H), 7.50 (m, 2H), 4.50 (d, 2H), 3.30 (d, 2H), 2.50 (m, 6H), 1.4-1.5 (br d, 16H) 1.00 (t, 6H) ppm. ES-MS: 364 [M+1].

tert-butyl N-[4-(diethylamino)butyl]-N-({4-[(hydroxyimino)methyl]pyridin-2-yl}methyl)carbamate (xi)

By General Procedure L from tert-butyl N-[4-(diethylamino)butyl]-N-[(4-formylpyridin-2-yl)methyl]carbamate. Evaporated to dryness. The residue was suspended in dichloromethane, filtered, and the filtrate was evaporated to give the crude title product, which was used without further purification. $^1$H-NMR (300 MHz, CDCl$_3$): δ 8.40 (d, 1H), 8.00 (s, 1H), 7.39 (m, 2H), 4.45 (m, 2H), 3.35 (m, 2H), 2.60 (m, 8H), 1.60-1.20 (m, 18H) ppm.

tert-butyl N-{[4-(aminomethyl)pyridin-2-yl]methyl}-N-[4-(diethylamino)butyl]carbamate (xii)

By General Procedure M from tert-butyl N-[4-(diethylamino)butyl]-N-({4-[(hydroxyimino)methyl]-pyridin-2-yl}methyl)carbamate to give the title product which was used without further purification.

Ethyl 2-[(4-hydroxybutyl)carbamoyl]pyridine-4-carboxylate (xiii)

By General Procedure A from ethyl 2-formylpyridine-4-carboxylate and 4-aminobutan-1-ol. Purification by column chromatography (5% MeOH/DCM) gave the target compound as greenish oil. $^1$H-NMR (300 MHz, CDCl$_3$): δ 8.60 (d, 1H), 7.80 (s, 1H), 7.70 (d, 1H), 4.40 (q, 2H), 4.05 (s, 1H), 3.60 (m, 2H), 2.80 (m, 2H), 1.70 (m, 4H), 1.40 (t, 3H) ppm.

Ethyl 2-({[(tert-butoxy)carbonyl](4-hydroxybutyl)amino}carbonyl)pyridine-4-carboxylate (xiv)

General Procedure R (Boc Protection of Amine)

Aqueous solution NaHCO$_3$ (5.0 equiv.) was added to a solution of the amine (ethyl 2-[(4-hydroxybutyl)carbamoyl] pyridine-4-carboxylate) (1.0 equiv.) in THF. Stirred for 5 min, before a solution of di-tert-butyl dicarbonate (1.2 equiv.) in THF was added. The reaction mixture was stirred over night at room temperature. Evaporated to dryness and extracted with ethyl acetate to give the title product as a white solid. $^1$H-NMR (300 MHz, CDCl$_3$): δ 8.60 (d, 1H), 7.80 (s, 1H), 7.70 (d, 1H), 4.50 (m, 2H), 4.40 (q, 2H), 3.60 (m, 2H), 3.30 (m, 2H), 1.70-1.35 (m, 17H) ppm.

Ethyl 2-{[(4-bromobutyl)[(tert-butoxy)carbonyl] amino]carbonyl}pyridine-4-carboxylate (xv)

General Procedure S (Alcohol to Bromide)

CBr$_4$ (1.1 equiv.) was added to a cold (0° C.) solution of alcohol (ethyl 2-({[(tert-butoxy)carbonyl](4-hydroxybutyl) amino}carbonyl)pyridine-4-carboxylate) (1 equiv.) and PPh$_3$ ((1.1 equivalent). Stirred for 20 min and then allowed to warm to room temperature over 3-4 hour. Aqueous work up and purification by column chromatography using (DCM:MeOH (95:5)) gave the title product as white solid. $^1$H-NMR (300 MHz, CDCl$_3$): δ 8.50 (d, 1H), 7.80 (s, 1H), 7.60 (d, 1H), 4.50 (m, 2H), 4.40 (q, 2H), 3.60 (m, 2H), 3.30 (m, 2H), 1.80 (m 2H), 1.60 (m, 2H), 130 (m, 12H) ppm. ES-MS: 415 [M+1].

Ethyl 2-({[4-(azetidin-1-yl)butyl][(tert-butoxy)carbonyl]amino}carbonyl)pyridine-4-carboxylate (xvi)

General Procedure T (Nucleophilic Substitution with Amine)

The amine (azetidine hydrochloride) (5.0 equiv.) and subsequently DIPEA (6.0 equiv.) was added to a solution of the bromide (ethyl 2-{[(4-bromobutyl)[(tert-butoxy)carbonyl] amino]carbonyl}pyridine-4-carboxylate) (1 equiv.) in acetonitrile. Stirred at 60° C. for 12 hours. Evaporated to dryness and purified by column chromatography (DCM/MeOH (95: 5)) to give the title product as colorless oil. $^1$H-NMR (300 MHz, CDCl$_3$): δ 8.58 (d, 1H), 7.70 (s, 1H), 7.60 (d, 1H), 4.40 (m, 2H), 4.30 (q, 2H), 3.60 (m, 2H), 3.30 (m, 2H), 3.00 (m, 4H), 1.60 (m 4H), 1.40 (m, 12H) ppm. ES-MS: 392 [M+1].

Tert-butyl N-[4-(azetidin-1-yl)butyl]-N-[4-(hydroxymethyl)pyridine-2-carbonyl]carbamate (xvii)

General Procedure U (Reduction of Ester to Alcohol)

NaBH$_4$ (2.0 equiv.) was added at room temperature to a solution of ester (ethyl 2-({[4-(azetidin-1-yl)butyl][(tert-butoxy)carbonyl]amino}carbonyl)pyridine-4-carboxylate) (1.0 equiv.) in EtOH. Stirred at room temperature for 10 min and then reflux for 3 hours. Cooled to room temperature and sat. NH$_4$Cl solution was added. Evaporated to dryness and extracted with DCM. Purification by column chromatography (DCM, MeOH and HN$_4$OH (aq.) (85:10:5) gave the title product as viscous oil. $^1$H-NMR (300 MHz, CDCl$_3$): δ 8.40 (d, 1H), 7.35 (s, 1H), 7.00 (d, 1H), 4.60 (s, 2H), 4.50 (m, 2H), 3.25 (m, 6H), 3.20 (m, 2H), 2.00 (m, 2H), 1.40 (m 14H) ppm.

Tert-butyl N-[4-(azetidin-1-yl)butyl]-N-(4-formylpyridine-2-carbonyl)carbamate (xviii)

General Procedure V (Dess-Martin Oxidation)

1,1,1-Triacetoxy-1,1-dihydro-1,2-benziodoxol-3(1H)-one (1.1 equiv.) was added at 0° C. to a solution of alcohol (tert-butyl N-[4-(azetidin-1-yl)butyl]-N-[4-(hydroxymethyl) pyridine-2-carbonyl]carbamate) in anhydrous DCM. Stirred for 10 min. and then allowed to warm to room temperature and stirred for two to three hours. KOH solution (1M) was added and extraction with DCM gave the title product as light yellow oil. $^1$H-NMR (300 MHz, CDCl$_3$): δ δ 10.0 (s, 1H), 8.70 (d, 1H), 7.55 (s, 1H), 7.50 (d, 1H), 4.50 (m, 2H), 3.20 (m, 2H), 2.50 (m, 4H), 1.80 (m, 2H), 1.40 (m 15H) ppm.

Tert-butyl N-[4-(azetidin-1-yl)butyl]-N-{4-[((hydroxyimino)methyl]pyridine-2-carbonyl}carbamate (xix)

General Procedure L from tert-butyl N-[4-(azetidin-1-yl) butyl]-N-(4-formylpyridine-2-carbonyl)carbamate gave the title product which was used without further purification. $^1$H-NMR (300 MHz, CDCl$_3$): δ 8.40 (d, 1H), 8.00 (s, 1H), 7.30 (s, 1H), 7.25 (d, 1H), 4.40 (m, 2H), 3.20 (m, 4H), 2.00 (m, 2H), 1.60-1.20 (m 20H) ppm.

Tert-butyl N-[4-(aminomethyl)pyridine-2-carbonyl]-N-[4-(azetidin-1-yl)butyl]carbamate (xx)

General Procedure M from tert-butyl N-[4-(azetidin-1-yl) butyl]-N-{4-[((hydroxyimino)methyl]pyridine-2-carbonyl}carbamate gave the title product as colorless oil, which was used without further purification.

N-{[2-(dimethoxymethyl)pyridin-4-yl]methyl}cyclopropanamine (xxi)

By General Procedure A from 2-(dimethoxymethyl)pyridine-4-carbaldehyde, cyclopropylamine, and acetic acid (1 equiv.). Purification by column chromatography (CH$_2$Cl$_2$/MeOH, 97:3) gave the title compound as a colorless oil. $^1$H NMR (300 MHz, CDCl$_3$): δ 8.55 (d, 1H), 7.50 (S, 1H), 7.22 (m, 1H), 5.40 (s, 1H), 3.90 (s, 2H), 3.40 (s, 6H), 2.18 (m, 1H), 0.5 (m, 4H).

4-[(cyclopropylamino)methyl]pyridine-2-carbaldehyde (xxii)

By General Procedure N from N-{[2-(dimethoxymethyl)pyridin-4-yl]methyl}cyclopropanamine. Used without further purification. $^1$H-NMR (300 MHz, CDCl$_3$): δ 10.02 (s, 1H), 8.70 (d, 1H), 7.98 (s, 2H), 7.50 (m, 1H), 3.98 (s, 2H), 2.25 (m, 1H), 0.50-0.40 (m, 4H).

Ethyl 2-({[(dimethylcarbamoyl)methyl]amino}methyl)pyridine-4-carboxylate (xxiii)

By General Procedure A from Ethyl 2-formylpyridine-4-carboxylate, N,N-dimethylglycineamide hydrochloride, and triethylamine. Purification by column chromatography with a gradient of 0-10% MeOH in DCM gave the title product as yellow oil. $^1$H NMR (300 MHz, chloroform-d): δ ppm 8.69 (s, 1H), 7.94 (s, 1H), 7.72 (d, 1H), 4.40 (q, 2H), 4.03 (s, 2H), 3.48 (s, 2H), 2.95 (d, 6H), 1.40 (t, 3H).

2-({[4-(Hydroxymethyl)pyridin-2-yl]methyl}amino)-N,N-dimethylacetamide (xxiv)

By General Procedure U from ethyl 2-({[(dimethylcarbamoyl)methyl]amino}methyl)pyridine-4-carboxylate. Purification by column chromatography (10% MeOH and 1% NH$_4$OH in DCM) gave the title product as light yellow oil. $^1$H NMR (300 MHz, chloroform-d): δ ppm 8.44 (d, 1H), 7.47 (s, 1H), 7.30 (d, 1H), 4.67 (s, 2H), 3.93 (s, 2H), 3.53 (s, 2H), 2.96 (d, 6H).

Tert-Butyl N-[(dimethylcarbamoyl)methyl]-N-{[4-(hydroxymethyl)pyridin-2-yl]methyl}carbamate (xxv)

General Procedure R from 2-({[4-(Hydroxymethyl)pyridin-2-yl]methyl}amino)-N,N-dimethylacetamide. Purification by column chromatography (10% MeOH and 1% NH$_4$OH in DCM) gave the title product as light yellow oil. $^1$H NMR (300 MHz, chloroform-d): δ ppm 8.46 (m, 1H), 7.36 (m, 1H), 7.19 (m, 1H), 4.72 (m, 2H), 4.60 (m, 2H), 4.11 (m, 2H), 2.95 (m, 6H), 1.43 (m, 9H).

Tert-Butyl N-[(dimethylcarbamoyl)methyl]-N-[(4-formylpyridin-2-yl)methyl]carbamate (xxvi)

General Procedure Q from tert-butyl N-[(dimethylcarbamoyl)methyl]-N-{[4-(hydroxymethyl)pyridin-2-yl]methyl}carbamate. The title product was isolated after extractions as yellow sticky oil and used without further purification. $^1$H NMR (300 MHz, chloroform-d): δ ppm 10.09 (m, 1H), 8.79 (m, 1H), 7.80 (m, 1H), 7.60 (m, 1H), 4.72 (m, 2H), 4.18 (m, 2H), 2.97 (m, 6H), 1.43 (m, 9H).

tert-Butyl N-[(dimethylcarbamoyl)methyl]-N-({4-[(1E)-(hydroxyimino)methyl]pyridin-2-yl}methyl)carbamate (xxvii)

General Procedure L from tert-Butyl N-[(dimethylcarbamoyl)methyl]-N-[(4-formylpyridin-2-yl)methyl]carbamate. The title product was isolated after extraction as light yellow oil and used without further purification. $^1$H NMR (300 MHz, methanol-d$_4$): δ ppm 8.47 (m, 1H), 8.10 (d, 1H), 7.61 (d, $^1$H), 7.46 (m, 1H), 4.58 (m, 2H), 4.20 (m, 2H), 2.98 (m, 6H), 1.40 (m, 9H).

Tert-Butyl N-{[4-(aminomethyl)pyridin-2-yl]methyl}-N-[(dimethylcarbamoyl)methyl]carbamate (xxviii)

General Procedure M from tert-Butyl N-{[4-(aminomethyl)pyridin-2-yl]methyl}-N-[(dimethylcarbamoyl)methyl]carbamate. Purification by column chromatography (0-15% MeOH in DCM) gave the product as light yellow oil. $^1$H NMR (300 MHz, chloroform-d): δ ppm 8.38 (m, 1H), 7.26 (m, 1H), 7.10 (m, 1H), 4.55 (m, 2H), 4.05 (m, 2H), 3.84 (m, 2H), 2.89 (m, 6H), 1.36 (m, 9H).

Tert-Butyl N-[(4-{[(cyanomethyl)amino]methyl}pyridin-2-yl)methyl]-N-[(dimethylcarbamoyl)methyl]carbamate (xxix)

General Procedure T from tert-butyl N-{[4-(aminomethyl)pyridin-2-yl]methyl}-N-[(dimethylcarbamoyl)methyl]carbamate (1.0 equiv.), DIPEA (2.0 equiv.) and bromoacetonitrile (1.1 equiv.). Purification by preparative TLC (10% MeOH and 1% NH$_4$OH in DCM) gave the title product as light yellow oil. $^1$H NMR (300 MHz, methanol-d$_4$): δ ppm 8.42 (d, 1H), 7.46 (s, 1H), 7.33 (s, 1H), 4.58 (m, 2H), 4.19 (m, 2H), 3.93 (s, 2H), 3.65 (s, 2H), 2.98 (m, 6H), 1.42 (m, 9H).

2-{[(4-{[(tert-Butyldimethylsilyl)oxy]methyl}pyridin-2-yl)methyl]amino}-N,N-dimethylacetamide (xxx)

By General Procedure A from N,N-dimethylglycineamide hydrochloride, triethylamine, and 4-{[(tert-butyldimethylsilyl)oxy]methyl}pyridine-2-carbaldehyde. Purification by column chromatography (0-10% MeOH in DCM) gave the title product as yellow oil. $^1$H NMR (300 MHz, chloroform-d): δ ppm 8.49 (d, 1H), 7.32 (s, 1H), 7.17 (d, 1H), 4.74 (s, 2H), 3.97 (s, 2H), 3.47 (s, 2H), 2.95 (d, 6H), 0.95 (s, 9H), 0.11 (s, 6H).

N-[(4-{[(tert-Butyldimethylsilyl)oxy]methyl}pyridin-2-yl)methyl]-N-[(dimethylcarbamoyl)methyl]-2,2,2-trifluoroacetamide (xxxi)

By General Procedure C from 2-{[(4-{[(tert-butyldimethylsilyl)oxy]methyl}pyridin-2-yl)methyl]amino}-N,N-dimethylacetamide. Evaporation gave the product as yellow oil, which was used without further purification. $^1$H NMR (300 MHz, chloroform-d): δ ppm 8.50 (m, 1H), 7.25 (m, 2H), 4.80 (m, 4H), 4.33 (m, 2H), 2.99 (m, 6H), 0.96 (s, 9H), 0.13 (s, 6H).

N-[(Dimethylcarbamoyl)methyl]-2,2,2-trifluoro-N-{[4-(hydroxymethyl)pyridin-2-yl]methyl}acetamide (xxxii)

By General Procedure P from N-[(4-{[(tert-butyldimethylsilyl)oxy]methyl}pyridin-2-yl)methyl]-N-[(dimethylcarbamoyl)methyl]-2,2,2-trifluoroacetamide. Purification by column chromatography (0-10% MeOH in DCM) gave the title product as yellow oil. $^1$H NMR (300 MHz, chloroform-d): δ ppm 8.45 (m, 1H), 7.26 (m, 2H), 4.74 (m, 4H), 4.33 (m, 2H), 3.88 (s(br), 1H), 2.92 (m, 6H).

N-[(Dimethylcarbamoyl)methyl]-2,2,2-trifluoro-N-[(4-formylpyridin-2-yl)methyl]acetamide (xxxiii)

By General Procedure Q from N-[(dimethylcarbamoyl)methyl]-2,2,2-trifluoro-N-{[4-hydroxymethyl)pyridin-2-yl]methyl}acetamide. Purification by column chromatography (30-60% EtOAc in DCM) gave the title product as yellow oil. $^1$H NMR (300 MHz, chloroform-d): δ ppm 10.01 (d, 1H), 8.74 (m, 1H), 7.63 (m, 2H), 4.82 (m, 2H), 4.29 (m, 2H), 2.90 (m, 6H).

N-[(Dimethylcarbamoyl)methyl]-2,2,2-trifluoro-N-[(4-formylpyridin-2-yl)methyl]acetamide (xxxiv)

By General Procedure A from N-[(dimethylcarbamoyl)methyl]-2,2,2-trifluoro-N-[(4-formylpyridin-2-yl)methyl]acetamide and N,N-dimethylethylenediamine. Purification by preparative TLC (10% MeOH, 1% NH$_4$OH in DCM) gave the title product as colorless oil. $^1$H NMR (300 MHz, chloroform-d): δ ppm 8.48 (m, 1H), 7.29 (m, 2H), 4.80 (m, 2H), 4.37 (m, 2H), 3.84 (m, 2H), 2.98 (m, 6H), 2.71 (t, 2H), 2.49 (t, 2H), 2.26 (m, 6H). ES-MS: 390 [M+1].

Ethyl 2-{[(3-hydroxypropyl)amino]methyl}pyridine-4-carboxylate (xxxv)

By General Procedure A from ethyl 2-formylpyridine-4-carboxylate and 3-aminopropan-1-ol. Purification by column chromatography (0-5% MeOH in DCM) gave the title compound. $^1$H NMR (300 MHz, CDCl$_3$), δ ppm: 8.72 (d, 1H), 7.98 (s, 1H), 7.75 (d, 1H), 4.45 (q, 2H), 3.95 (s, 2H), 3.70 (t, 2H), 2.80 (t, 2H), 1.75 (m, 2H), 1.40 (t, 3H).

Ethyl 2-[(2,2,2-trifluoro-N-{3-[(trifluoroacetyl)oxy]propyl}acetamido)methyl]pyridine-4-carboxylate (xxxvi)

By General Procedure C from ethyl 2-{[(3-hydroxypropyl)amino]methyl}pyridine-4-carboxylate (1 equiv.), DIPEA (7.0 equiv.), and trifluoroacetic anhydride (5.0 equiv.). The title product was isolated after extractions and used without further purification. $^1$H-NMR (300 MHz, CDCl$_3$), (rotamers): δ 8.74 (dd, 0.5H), 8.70 (dd, 0.5H), 7.85 (s, 0.5H), 7.83-7.78 (m, 1H), 7.74 (s, 0.5H), 4.81 (s, 1H), 4.77 (s, 1H), 4.47-4.35 (m, 4H), 3.70 (t, 1H), 3.58 (t, 1H), 2.23-2.13 (m, 1H), 2.10-2.01 (m, 1H), 1.42 (td, 3H).

Ethyl 2-{[2,2,2-trifluoro-N-(3-hydroxypropyl)acetamido]methyl}pyridine-4-carboxylate (xxxvii)

General Procedure X (Ester Hydrolysis)

1M LiOH (aq, 1.0 equiv) was added to a solution of ester (ethyl 2-[(2,2,2-trifluoro-N-{3-[(trifluoroacetyl)oxy]propyl}acetamido)methyl]pyridine-4-carboxylate) (1.0 equiv.) in THF-MeOH—H$_2$O (1:1:1). Stirred at room temperature, while following the reaction by TLC. Evaporated to dryness and purified by flash chromatography using MeOH:DCM (10:90) to yield the title compound. $^1$H NMR (300 MHz, CDCl$_3$), (rotamers) δ ppm: 8.74 (two d, 1H), 7.80 (m, 2H), 4.85 (s, 2H), 4.45 (m, 2H), 3.65 (m, 4H), 1.90 (m, 2H), 1.45 (m, 3H).

Ethyl 2-{[2,2,2-trifluoro-N-(3-oxopropyl)acetamido]methyl}pyridine-4-carboxylate (xxxviii)

By General Procedure Q from ethyl 2-{[2,2,2-trifluoro-N-(3-hydroxypropyl)acetamido]methyl}pyridine-4-carboxylate to give the title product. $^1$H NMR (300 MHz, CDCl$_3$), (rotamers) δ ppm: 9.80 (two singlets, 1H), 8.70 (two doublets, 1H), 7.80 (m, 2H), 4.90/4.75 (two singlets, 2H), 4.45 (m, 2H), 3.95/3.75 (m, 2H), 2.90 (two t, 2H), 1.45 (m, 3H).

Ethyl 2-[(N-{3-[benzyl(methyl)amino]propyl}-2,2,2-trifluoroacetamido)methyl]pyridine-4-carboxylate (xxxix)

By General Procedure A from ethyl 2-{[2,2,2-trifluoro-N-(3-oxopropyl)acetamido]methyl}pyridine-4-carboxylate and benzyl(methyl)amine to give the title product. $^1$H NMR (300 MHz, CDCl3), (rotamers) δ ppm: 8.7 (dd, 1H), 7.90-7.75 (m, 2H), 7.4-7.2 (m, 5H), 4.8 (d, 2H), 4.4 (q, 2H), 4.0 (q, 2H), 3.7-3.4 (m, 2H), 2.8-2.5 (m, 2H), 2.0-1.8 (m, 7H), 1.4 (t, 3H).

{2-[({3-[Benzyl(methyl)amino]propyl}amino)methyl]pyridin-4-yl}methanol (xl)

By General Procedure U from ethyl 2-[(N-{3-[benzyl(methyl)amino]propyl}-2,2,2-trifluoroacetamido)methyl]pyridine-4-carboxylate using 5.0 equiv. of NaBH$_4$. Purification by column chromatography gave the title product. $^1$H NMR (300 MHz, CDCl3) δ ppm: 8.5 (dd, 1H), 7.80 (s, 1H), 7.6-7.3 (m, 1H), 4.6 (s, 2H), 4.3 (s, 2H), 3.6-3.2 (m, 4H), 2.8 (s, 3H), 2.2-2.0 (m, 2H), 1.7-1.3 (m, 3H).

Tert-butyl N-{3-[benzyl(methyl)amino]propyl}-N-{[4-(hydroxymethyl)pyridin-2-yl]methyl}carbamate (xli)

By General Procedure R from, {2-[({3-[benzyl(methyl)amino]propyl}amino)methyl]pyridin-4-yl}methanol to give the title product. $^1$H NMR (300 MHz, CDCl3), (rotamers) δ ppm: 8.6 (d, 1H), 7.4-7.1 (m, 8H), 4.8 (s, 2H), 4.6-4.4 (m, 2H), 3.4-3.2 (m, 2H), 2.5-2.2 (m, 2H), 2.1 (s, 3H), 1.9-1.3 (m, 11H).

Tert-butyl N-{3-[benzyl(methyl)amino]propyl}-N-[(4-formylpyridin-2-yl)methyl]carbamate (xlii)

General Procedure Q from tert-butyl N-{3-[benzyl(methyl)amino]propyl}-N-{[4-(hydroxymethyl)pyridin-2-yl]methyl}carbamate. $^1$H NMR (300 MHz, CDCl3), (rotamers) δ ppm: 10.0 (s, 1H), 8.8 (d, 1H), 7.7-7.1 (m, 7H), 4.8-4.6 (m, 2H), 3.6-3.2 (m, 4H), 2.5-2.3 (m, 2H), 2.2 (s, 3H), 1.9-1.3 (m, 11H).

Tert-butyl N-{3-[benzyl(methyl)amino]propyl}-N-({4-[(cyclopropylamino)methyl]pyridin-2-yl}methyl)carbamate (xliii)

By General Procedure A from tert-butyl N-{3-[benzyl(methyl)amino]propyl}-N-[(4-formylpyridin-2-yl)methyl]carbamate and cyclopropanamine. Purification by column chromatography using DCM:MeOH:NH$_4$OH (8:2:1) gave the title compound. $^1$H NMR (300 MHz, CDCl$_3$), (rotamers) δ ppm: 8.4 (d, 1H), 7.4-7.2 (m, 7H), 4.5 (s, 2H), 3.9 (s, 2H), 3.7-3.2 (m, 4H), 2.6-1.7 (m, 8H), 1.4 (d, 9H), 0.6-01.3 (m, 4H).

Ethyl 2-({[2-(tert-butoxy)-2-oxoethyl]amino}methyl)pyridine-4-carboxylate (xliv)

Prepared by General Procedure A from ethyl 2-formylpyridine-4-carboxylate and tert-butyl 2-aminoacetate. Title compound isolated as yellow oil by column chromatography (EtOAc/hexanes). $^1$H-NMR (300 MHz, MeOH-d$_4$): δ 8.7 (d, 1H), 7.8 (s, 1H), 7.7 (d, 1H), 4.4 (s, 2H), 4.3 (q, 2), 3.8 (s, 2H), 3.3 (s, 2H), 1.4 (s, (H), 1.3 (t, 3H). ES-MS: 295 [M+1].

Ethyl 2-({N-[2-(tert-butoxy)-2-oxoethyl]-2,2,2-trifluoroacetamido}methyl)pyridine-4-carboxylate (xlv)

By General Procedure C from ethyl 2-({[2-(tert-butoxy)-2-oxoethyl]amino}methyl)pyridine-4-carboxylate in anhydrous DCM. Aqueous work up gave the title compound, which was used without further purification. $^1$H-NMR (300 MHz, CDCl$_3$), (rotamers): δ 8.7 (dd, 1H), 7.8 (ss, 1H), 7.7 (dd, 1H), 4.8 (ss, 2H), 4.3 (q, 2), 4.2 (ss, 2H), 1.4 (s, 9H), 1.3 (t, 3H).

2-(N-{[4-(ethoxycarbonyl)pyridin-2-yl]methyl}-2,2,2-trifluoroacetamido)acetic acid (xlvi)

By General Procedure D from ethyl 2-({N-[2-(tert-butoxy)-2-oxoethyl]-2,2,2-trifluoroacetamido}methyl)pyridine-4-carboxylate. Evaporation gave the title compound, which was used without further purification. $^1$H-NMR (300 MHz, CD$_3$OD): δ 8.75 (m, 1H), 7.8 8.00 (m, 2H), 5.45, 4.99 (2s, 2H; rotamer), 4.20-4.40 (m, 4H), 1.40 (t, 3H).

Ethyl 2-({N-[({1-[(tert-butoxy)carbonyl]piperidin-4-yl}carbamoyl)methyl]-2,2,2-trifluoroacetamido}methyl)pyridine-4-carboxylate (xlvii)

General Procedure Y (Amide Formation)

An amine (tert-butyl 4-aminopiperidine-1-carboxylate) (2 equiv.) was added to a solution of an acid (2-(N-{[4-(ethoxycarbonyl)pyridin-2-yl]methyl}-2,2,2-trifluoroacetamido)acetic acid) (1 equiv.) in DMF. Cooled to 0° C. before EDC HCl (1.5 equivalent) and ethyl(hydroxyl iminocyanoaectate (oxyma; 1.5 equivalent) were added. The reaction mixture was allowed to warm slowly to room temperature and stirred overnight. Aqueous work up and purification by column chromatography gave the title compound as brown foam. $^1$H-NMR (300 MHz, CDCl$_3$): δ 8.70 & 8.60 (2d, 1H; rotamer), 7.80 (m, 2H), 4.90 & 4.78 (2s, 2H, rotamer), 4.42 (q, 2H), 4.30 & 4.10 (2s, 2H), 4.10 (m, 1H), 2.80 (m, 2H) 2.0 (m, 2H), 1.48 (s, 9H), 1.40 (t, 3H).

Ethyl 2-[(2,2,2-trifluoro-N-{[(piperidin-4-yl)carbamoyl]methyl}acetamido)methyl]pyridine-4-carboxylate (xlviii)

Prepared by General Procedure D from ethyl 2-({N-[({1-[(tert-butoxy)carbonyl]piperidin-4-yl}carbamoyl)methyl]-2,2,2-trifluoroacetamido}methyl)pyridine-4-carboxylate. Purification by column chromatography (MeOH/DCM and 1% NH4OH) gave the title compound as a brown foam. $^1$H-NMR (300 MHz, CD$_3$OD): δ 8.75 (m, 1H), 7.90 (m, 2H), 5.00 & 4.90 (2s, 2H, rotamer), 4.42 (q, 2H), 4.32 & 4.12 (2s, 2H; rotamer), 3.95 (m, 1H), 3.40 (m, 2H) 3.10 (m, 2H), 2.10 (m, 2H), 1.80 (m, 2H), 1.38 (t, 3H).

Ethyl 2-({2,2,2-trifluoro-N-[({1-[(2-methoxyphenyl)methyl]piperidin-4-yl}carbamoyl)methyl]acetamido}methyl)pyridine-4-carboxylate (xlix)

Prepared by General Procedure A from 2-methoxybenzaldehyde and ethyl 2-[(2,2,2-trifluoro-N-{[(piperidin-4-yl)carbamoyl]methyl}acetamido)methyl]pyridine-4-carboxylate. $^1$H-NMR (300 MHz, CDCl$_3$): δ 8.75 & 8.71 (2d, 1H; rotamer), 7.91-7.78 (m, 2H), 7.36 (m, 1H), 7.25 (m, 1H), 7.99-7.86 (m, 2H), 4.95 & 4.72 (2s, 2H, rotamer), 4.45 (q, 2H), 4.30 & 4.08 (2s, 2H; rotamer), 3.83 (m, 4H), 3.60 (m, 2H) 2.95 (m, 2H), 2.22 (m, 2H), 1.90 (m, 2H), 1.60 (m, 2H), 1.40 (t, 3H).

2-({[4-(hydroxymethyl)pyridin-2-yl]methyl}amino)-N-{1-[(2-methoxyphenyl)methyl]piperidin-4-yl}acetamide (l)

By General Procedure U from ethyl 2-({2,2,2-trifluoro-N-[({1-[(2-methoxyphenyl)methyl]piperidin-4-yl}carbamoyl)methyl]acetamido}methyl)pyridine-4-carboxylate using 5 equiv. of NaBH$_4$. Purification by column chromatography using 1% MeOH/DCM to 28% MeOH/DCM/1% NH$_4$OH as elutent to get the product as an off white solid. $^1$H-NMR (300 MHz, CDCl$_3$): δ 8.42 (d, 1H), 7.42 (d, 1H), 7.35 (d, 1H), 7.25 (m, 2H), 7.15 (m, 1H), 6.99-6.85 (m, 2H), 4.65 (s, 2H), 3.80 (m, 4H), 3.60 (s, 2H), 3.45 (s, 2H), 3.25 (s, 2H), 2.90 (m, 2H), 2.22 (m, 2H), 1.90 (m, 2H), 1.60 (m, 2H).

tert-butyl N-{[4-(hydroxymethyl)pyridin-2-yl]methyl}-N-[({1-[(2-methoxyphenyl)methyl]piperidin-4-yl}carbamoyl)methyl]carbamate (li)

By General Procedure R from 2-({[4-(hydroxymethyl)pyridin-2-yl]methyl}amino)-N-{1-[(2-methoxyphenyl)methyl]piperidin-4-yl}acetamide to get the title compound as a white foam. $^1$H-NMR (300 MHz, CDCl$_3$): δ 9.80 (d, 1H), 8.70 (d, 1H), 7.50-7.40 (m, 2H), 7.25 (m, 2H), 7.10-6.80 (m, 2H), 4.70 (s, 2H), 4.50 (d, 2H), 4.12 (d, 2H), 3.98 (m, 3H), 3.85 (s, 3H), 3.35 (d, 2H), 2.80-2.50 (m, 2H), 2.10-1.80 (m, 4H), 1.40, 1.20 (ss, 9H).

tert-butyl N-[(4-formylpyridin-2-yl)methyl]-N-[({1-[(2-methoxyphenyl)methyl]piperidin-4-yl}carbamoyl)methyl]carbamate (lip By General Procedure Q from tert-butyl N-{[4-(hydroxymethyl)pyridin-2-yl]methyl}-N-[({1-[(2-methoxyphenyl)methyl]piperidin-4-yl}carbamoyl)methyl]carbamate to get the title compound as a light yellow foam. $^1$H-NMR (300 MHz, CDCl$_3$): δ 10.00 (s, 1H), 9.00-8.20 (m, 2H), 7.76 (2d, 1H; rotamer), 7.40 (m, 1H), 7.30 (m, 1H), 7.00-6.80 (m, 2H), 4.52 (m, 2H), 4.42 (q, 2H), 4.20 & 4.00 (2s, 2H; rotamer), 3.90 (m, 4H), 3.55 (s, 2H) 3.00 (m, 2H), 2.22 (m, 2H), 2.00 (m, 2H), 1.80-1.50 (m, 4H), 1.40, 1.20 (2s, 9H; rotamer).

tert-butyl N-({4-[(cyclopropylamino)methyl]pyridin-2-yl}methyl)-N-[({1-[(2-methoxyphenyl)methyl]piperidin-4-yl}carbamoyl)methyl]carbamate (liii)

By General Procedure A from tert-butyl N-[(4-formylpyridin-2-yl)methyl]-N-[({1-[(2-methoxyphenyl)methyl]piperidin-4-yl}carbamoyl)methyl]carbamate and cyclopropylamine. Purification by column chromatography (CH2Cl2/MeOH/NH$_4$OH, 90:10:1) gave the title compound as a colorless glue. $^1$H NMR (300 MHz, CDCl$_3$): δ 9.40 (br s, 1H), 8.62 (2S, 1H; rotamer), 8.40 (s, 1H), 7.50-7.40 (m, 2H), 7.38 (m, 1H), 7.20 (m, 1H), 7.00-6.80 (m, 2H), 4.58 & 4.48 (2S, 2H; rotamer), 4.00-3.60 (m, 8H), 3.18-2.99 (m, 4H), 2.40-2.20 (m, 2H), 1.80 (m, 2H), 1.70 (m, 2H), 1.40 & 1.20 (2S, 9H; rotamer), 1.00 (m, 4H).

Ethyl 2-({[3-(dimethylamino)propyl]amino}methyl)pyridine-4-carboxylate (liv)

By General Procedure A from Ethyl 2-formylpyridine-4-carboxylate and (3-aminopropyl)dimethylamine to get the title compound as dark-orange oil. $^1$H NMR (300 MHz, CDCl$_3$): δ 8.53 (dd, 1H), 7.70 (s, 1H), 7.56 (dd, 1H), 4.24 (q, 2H), 3.86 (s, 2H), 2.60 (t, 2H), 2.26 (t, 2H), 2.10 (s, 6H), 1.58 (t, 2H), 1.24 (t, 3H). ES-MS: 266 [M+1].

Ethyl 2-({[(tert-butoxy)carbonyl][3-(dimethylamino) propyl]amino}methyl)pyridine-4-carboxylate (lv)

General Procedure R from Ethyl 2-({[3-(dimethylamino) propyl]amino}methyl)pyridine-4-carboxylate. Purification by column chromatography (0-20% MeOH/DCM) gave the title product. $^1$H NMR (300 MHz, CDCl$_3$) δ ppm: 8.68 (dd, 1H), 7.79 (s, 1H), 7.73 (d, 1H), 4.62 (d, 2H), 4.41 (q, 2H), 3.34 (m, 2H), 2.26 (m, 2H), 2.19 (s, 6H), 1.72 (m, 2H), 1.47 (m, 12H). ES-MS: 366 [M+1].

Tert-butyl N-[3-(dimethylamino)propyl]-N-{[4-(hydroxymethyl)pyridin-2-yl]methyl}carbamate (lvi)

By General Procedure U from Ethyl 2-({[(tert-butoxy)carbonyl][3-(dimethylamino)propyl]-amino}methyl)pyridine-4-carboxylate. Purification by column chromatography (0-30% MeOH/DCM) gave the title product. $^1$H NMR (300 MHz, CDCl$_3$) δ ppm: 8.34 (d, 1H), 7.15 (s, 1H), 7.10 (d, 1H), 5.18 (bs, 1H), 4.58 (s, 2H), 4.46 (d, 2H), 3.22 (m, 2H), 2.19 (m, 2H), 2.10 (s, 6H), 1.61 (m, 2H), 1.36 (d, 9H). ES-MS: 324 [M+1]

Tert-butyl N-[3-(dimethylamino)propyl]-N-[(4-formylpyridin-2-yl)methyl]carbamate (lvii)

General Procedure Q from tert-butyl N-[3-(dimethylamino)propyl]-N-{[4-(hydroxymethyl)pyridin-2-yl] methyl}carbamate. Purification by column chromatography (0-20% MeOH/DCM) gave the title product. $^1$H NMR (300 MHz, CDCl$_3$) δ ppm: 10.00 (s, 1H), 8.72 (d, 1H), 7.57 (s, 1H), 7.52 (m, 1H), 4.59 (d, 2H), 3.28 (m, 2H), 2.20 (m, 2H), 2.12 (s, 6H), 1.66 (m, 2H), 1.38 (d, 9H). ES-MS: 322 [M+1].

Tert-butyl N-({4-[cyano(methylamino)methyl]pyridin-2-yl}methyl)-N-[3-(dimethylamino)propyl]carbamate (lviii)

General Procedure Z (Formation of Amino Alkyl Nitriles)

A solution of aldehyde (tert-butyl N-[3-(dimethylamino) propyl]-N-[(4-formylpyridin-2-yl)methyl]carbamate) (1 equiv.) and amine (methylamine) (2 equiv.) in anhydrous THF was stirred overnight at room temperature. Evaporated to dryness and re-dissolved in anhydrous acetonitrile, before TMSCN (1.1 equiv.) was added. The mixture was stirred overnight at room temperature. Aqueous work-up and purification by preparative TLC (3% TEA in 20% MeOH/DCM) gave the title product. $^1$H NMR (300 MHz, CDCl$_3$) δ ppm: 8.58 (d, 1H), 7.45 (s, 1H), 7.38 (d, 1H), 4.81 (s, 1H), 4.58 (m, 2H), 3.35 (m, 4H), 2.57 (s, 3H), 2.30 (m, 4H), 1.78 (m, 2H), 1.46 (d, 9H). ES-MS: 362 [M+1].

Ethyl 2-({[(tert-butoxy)carbonyl](4-oxobutyl)amino}methyl)pyridine-4-carboxylate (lix)

By General Procedure Q from ethyl 2-({[(tert-butoxy)carbonyl](4-hydroxybutyl)amino}methyl)-pyridine-4-carboxylate. Purified by column chromatography (ethyl acetate/hexane 20-40%) to give the title product. $^1$H-NMR (300 MHz, CDCl$_3$): δ 9.70 (s, 1H), 8.60 (d, 1H), 7.70 (s, 1H), 7.60 (d, 1H), 4.55 (d, 2H), 4.40 (q, 2H), 3.40 (m, 2H), 2.480 (m, 2H), 1.85 (m, 2H), 1.50-1.20 (m, 12H) ppm.

Ethyl 2-[({4-[benzyl(cyclopropyl)amino]butyl}[(tert-butoxy)carbonyl]amino)methyl]pyridine-4-carboxylate (lx)

By General Procedure A from ethyl 2-({[(tert-butoxy)carbonyl](4-oxobutyl)amino}methyl)pyridine-4-carboxylate and N-benzylcyclopropanamine. Purification by column chromatography (5% MeOH/DCM) gave the title compound as colorless oil. $^1$H-NMR (300 MHz, CDCl$_3$): δ 8.60 (d, 1H), 7.70 (s, 1H), 7.60 (d, 1H), 7.10 (m, 5H), 4.50 (d, 2H), 4.40 (q, 2H), 3.50 (m, 2H), 3.15 (m, 2H), 2.50 (m, 2H), 1.60 (m, 1H), 1.45 (m, 16H), 0.4 (m, 4H) ppm.

Tert-butyl N-{4-[benzyl(cyclopropyl)amino]butyl}-N-{[4-(hydroxymethyl)pyridin-2-yl] methyl}carbamate (lxi)

By General Procedure U from ethyl 2-[({4-[benzyl(cyclopropyl)amino]butyl}[(tert-butoxy)carbonyl]amino)methyl] pyridine-4-carboxylate. Purification by column chromatography (DCM, MeOH and HN$_4$OH (85; 10:5)) gave the title product as viscous oil. $^1$H-NMR (300 MHz, CDCl$_3$): δ 8.45 (d, 1H), 7.20 (m, 6H), 7.00 (d, 1H), 4.70 (m, 2H), 4.50 (m, 2H), 3.60 (m, 2H), 3.10 (m, 2H), 2.40 (m, 2H), 1.55 (m, 2H), 1.40 (m, 13H) ppm.

Tert-butyl N-{4-[benzyl(cyclopropyl)amino]butyl}-N-[(4-formylpyridin-2-yl)methyl]carbamate (lxii)

By General Procedure Q from tert-butyl N-{4-[benzyl(cyclopropyl)amino]butyl}-N-{[4-(hydroxymethyl)pyridin-2-yl]methyl}carbamate. Purification by column chromatography (ethyl acetate/hexane 20-50%) gave the title product. $^1$H-NMR (300 MHz, CDCl$_3$): δ 10.0 (s, 1H), 8.70 (d, 1H), 7.50 (m, 2H), 7.20 (m, 5H), 4.50 (m, 2H), 3.80 (m, 2H), 3.15 (m, 2H), 2.50 (m, 2H), 1.60 (m, 2H), 1.45 (m, 12H), 0.40 (m, 4H) ppm.

Tert-butyl N-{4-[benzyl(cyclopropyl)amino]butyl}-N-({4-[(1E)-(hydroxyimino)methyl]pyridin-2-yl}methyl)carbamate (lxiii)

By General Procedure L from tert-butyl N-{4-[benzyl(cyclopropyl)amino]butyl}-N-[(4-formylpyridin-2-yl)methyl] carbamate. Evaporation gave the title product, which was used without further purification. $^1$H-NMR (300 MHz, CDCl$_3$): δ 8.45 (d, 1H), 8.00 (s, 1H), 7.20-7.00 (m, 7H), 4.50 (m, 2H), 3.70 (s, 2H), 3.20 (m, 2H), 2.50 (m, 2H), 1.60-1.20 (m, 14H), 0.40 (m, 4H) ppm.

Tert-butyl N-{[4-(aminomethyl)pyridin-2-yl]methyl}-N-{4-[benzyl(cyclopropyl)amino] butyl}carbamate (lxiv)

By General Procedure M from tert-butyl N-{4-[benzyl(cyclopropyl)amino]butyl}-N-({4-[(1E)-(hydroxyimino)methyl]pyridin-2-yl}methyl)carbamate. Purification by column chromatography (DCM, MeOH and HN$_4$OH (85; 10:5)) gave the title product as colorless oil. $^1$H-NMR (300 MHz, CDCl$_3$): δ 8.45 (d, 1H), 7.20-7.00 (m, 7H), 4.50 (m, 2H), 3.90 (s, 2H), 3.70 (s, 2H), 3.00 (m, 2H), 2.50 (m, 2H), 1.80 (m, 4H), 1.40 (m, 12H) 0.40 (m, 4H), ppm.

Tert-butyl N-{4-[benzyl(cyclopropyl)amino]butyl}-N-[(4-{[(cyanomethyl)amino]methyl}pyridin-2-yl)methyl]carbamate (lxv)

By General Procedure T from tert-butyl N-{[4-(aminomethyl)pyridin-2-yl]methyl}-N-{4-[benzyl(cyclopropyl)amino]butyl}carbamate (1 equiv.) and bromoacetonitrile (1.1 equiv.), using 2 equiv. DIPEA. Aqueous work up gave the title product, which was used without further purification.

Tert-butyl N-({4-[(2,2-difluorobutanamido)methyl]pyridin-2-yl}methyl)-N-({[2-(dimethylamino)ethyl](ethyl)carbamoyl}methyl)carbamate (lxvi)

By General Procedure Y from tert-butyl N-{[4-(aminomethyl)pyridin-2-yl]methyl}-N-({[2-(dimethylamino)ethyl](ethyl)carbamoyl}methyl)carbamate (prepared by synthetic route B (analogously to intermediate xii)) and 2,2-difluorobutanoic acid to get the title compound as colorless oil. $^1$H NMR (300 MHz, CDCl3) δ 8.48 (m, 1H), 7.27 (m, 1H), 7.07 (m, 2H), 4.55 (m, 4H), 4.10 (m, 2H), 3.33 (m, 5H), 2.26 (m, 14H), 1.43 (m, 9H), 1.13 (m, 9H).

Tert-butyl ({[2-({N-[4-(diethylamino)butyl]-2,2,2-trifluoroacetamido}methyl)pyridin-4-yl]methyl}carbamoyl)formate (lxvii)

General Procedure AA (Amide from Acid Chloride)

The acid chloride (tert-Butyl 2-chloro-2-oxoacetate (2 equiv.) was added dropwise to a solution of the amine or trifluoroacetamide (N-[4-(diethylamino)butyl]-2,2,2-trifluoro-N-({4-[(trifluoroacetamido)methyl]pyridin-2-yl}methyl)acetamide) and DIPEA in anhydrous DCM at 0° C. The mixture was allowed to warm to room temperature and stirred for 12 hours. Quenched with sat. NHaHCO$_3$ (aq.). Aqueous work up (in case of reaction from acetamide: basic workup (NaOH 1N)) product as yellow oil. $^1$H NMR (300 MHz, chloroform-d): δ ppm 8.50 (m, 1H), 7.35 (br s, 1H), 7.10-6.90 (m, 2H), 4.70 (m, 2H), 4.50 (m, 2H), 3.55-3.30 (m, 2H), 2.58-2.40 (m, 6H), 1.70-1.25 (m, 4H), 1.00 (m, 6H). ES-MS: 489.54 [M+1].

tert-Butyl N-({4-[(N-cyclopropylcarboximidoyl]pyridin-2-yl}methyl)-N-[(dimethylcarbamoyl)methyl]carbamate (lxviii)

By General Procedure F from tert-butyl N-[(dimethylcarbamoyl)methyl]-N-[(4-formylpyridin-2-yl)methyl]carbamate (1.0 equiv.) and cyclopropylamine (1.2 equiv.). Evaporated to give the title product as yellow oil. $^1$H NMR (300 MHz, chloroform-d): δ ppm 8.55 (d, 1H), 8.52 (s, 1H), 7.73 (s, 1H), 7.56 (d, 1H), 3.96 (s, 2H), 3.55 (s, 2H), 3.17 (m, 1H), 2.96 (d, 6H), 1.00 (m, 4H). ES-MS: 261 [M+1].

N-[(Dimethylcarbamoyl)methyl]-2,2,2-trifluoro-N-{[4-(hydroxymethyl)pyridin-2-yl]methyl}acetamide (lxix)

General Procedure C from 2-({[4-(hydroxymethyl)pyridin-2-yl]methyl}amino)-N,N-dimethylacetamide gave the title product as yellow oil. $^1$H NMR (300 MHz, chloroform-d): δ ppm 8.45 (m, 1H), 7.26 (m, 2H), 4.74 (m, 4H), 4.33 (m, 2H), 3.88 (s(br), 1H), 2.92 (m, 6H).

N-[(Dimethylcarbamoyl)methyl]-2,2,2-trifluoro-N-[(4-formylpyridin-2-yl)methyl]acetamide (lxx)

By General Procedure Q from N-[(dimethylcarbamoyl)methyl]-2,2,2-trifluoro-N-{[4-(hydroxymethyl)pyridin-2-yl]methyl}acetamide. Purification by column chromatography (EtOAc 30-60% in DCM) gave the title product as yellow sticky oil. $^1$H NMR (300 MHz, chloroform-d): δ ppm 10.01 (d, 1H), 8.74 (m, 1H), 7.63 (m, 2H), 4.82 (m, 2H), 4.29 (m, 2H), 2.90 (m, 6H).

N-[(Dimethylcarbamoyl)methyl]-2,2,2-trifluoro-N-({4-[(N-(2-methylcyclopropyl)carboximidoyl]pyridin-2-yl}methyl)acetamide (lxxi)

By General Procedure F from N-[(dimethylcarbamoyl)methyl]-2,2,2-trifluoro-N-[(4-formylpyridin-2-yl)methyl]acetamide (1.0 equiv.) and 2-methylcyclopropan-1-amine (1.2 equiv.). Evaporation gave the title product as oil. Used without further purification. $^1$H NMR (300 MHz, chloroform-d): δ ppm 8.56 (m, 1H), 8.37 (m, 1H), 7.52 (m, 2H), 4.84 (m, 2H), 4.36 (m, 2H), 2.99 (m, 6H), 2.78 (m, 1H), 1.43 (m, 1H), 1.25 (m, 1H), 1.15 (m, 3H), 0.83 (m, 1H).

[(4-{[(tert-butyldimethylsilyl)oxy]methyl}pyridin-2-yl)methyl][2-(methylsulfanyl)ethyl]amine (lxxii)

By General Procedure A from 4-{[(tert-butyldimethylsilyl)oxy]methyl}pyridine-2-carbaldehyde and 2-(methylsulfanyl)ethan-1-amine. Purification by column chromatography (DCM/MeOH/NH$_4$OH (90:10:1)) gave the title compound as yellow oil. $^1$H NMR (300 MHz, Methanol-d$_4$): δ 8.4 (d, 1H), 7.3 (s, 1H), 7.1 (d, 1H), 4.7 (s, 2H), 3.9 (s, 2H), 2.7 (t, 2H), 2.6 (t, 2H), 2.58 (q, 2H), 1.2 (t, 3H), 0.9 (s, 9H).

[2-({[2-(methylsulfanyl)ethyl]amino}methyl)pyridin-4-yl]methanol (lxxiii)

General Procedure P from [(4-{[(tert-butyldimethylsilyl)oxy]methyl}pyridin-2-yl)methyl][2-(methylsulfanyl)ethyl]amine gave the title compound as yellow oil. $^1$H NMR (300 MHz, CDCl$_3$): δ 8.4 (d, 1H), 7.3 (s, 1H), 7.1 (d, 1H), 4.7 (s, 2H), 3.8 (s, 2H), 2.7 (t, 2H), 2.6 (t, 2H), 2.5 (q, 2H), 1.2 (t, 3H).

2-({[2-(methylsulfanyl)ethyl]amino}methyl)pyridine-4-carbaldehyde (lxxiv)

By General Procedure Q from [2-({[2-(methylsulfanyl)ethyl]amino}methyl)pyridin-4-yl]methanol. The title compound was isolated after evaporation and used without further purification.

tert-Butyl N-{3-[benzyl(methyl)amino]propyl}-N-({4-[(N-cyclopropylcarboximidoyl]pyridin-2-yl}methyl)carbamate (lxxv)

General Procedure F from tert-butyl N-{3-[benzyl(methyl)amino]propyl}-N-[(4-formylpyridin-2-yl)methyl]carbamate (1.0 equiv.) and cyclopropanamine (2 equiv.). Purified by column chromatography (0-5% MeOH in DCM) to give the title compound.

[(4-{[(tert-Butyldimethylsilyl)oxy]methyl}pyridin-2-yl)methyl][(2E)-4-(dimethylamino)but-2-en-1-yl]amine (lxxvi)

By General Procedure A from 4-{[(tert-butyldimethylsilyl)oxy]methyl}pyridine-2-carbaldehyde (1.0 equiv.), [(2E)-4-aminobut-2-en-1-yl]dimethylamine hydrochloride (1.0 equiv.), and triethylamine (1.0 equiv.). Purification by column chromatography (0-10% MeOH in DCM) gave the title product as yellow oil. $^1$H NMR (300 MHz, chloroform-d): δ ppm 8.45 (d, 1H), 7.20 (s, 1H), 7.11 (d, 1H), 5.67 (m, 2H), 4.68 (s, 2H), 3.85 (s, 2H), 2.89 (s, 2H), 2.19 (s, 6H), 0.89 (m, 9H), 0.07 (m, 6H).

tert-Butyl N-[(4-{[(tert-butyldimethylsilyl)oxy]methyl}pyridin-2-yl)methyl]-N-[(2E)-4-(dimethylamino)but-2-en-1-yl]carbamate (lxxvii)

By General Procedure R from [(4-{[(tert-butyldimethylsilyl)oxy]methyl}pyridin-2-yl)methyl][(2E)-4-(dimethylamino)but-2-en-1-yl]amine. Purification by column chromatography (10% MeOH and 1% NH$_4$OH in DCM) gave the title product as light yellow oil. $^1$H NMR (300 MHz, chloroform-d): δ ppm 8.41 (m, 1H), 7.12 (m, 2H), 5.55 (m, 2H), 4.68 (s, 2H), 4.49 (m, 2H), 3.83 (m, 2H), 2.85 (m, 2H), 2.15 (s, 6H), 1.40 (m, 9H), 0.91 (s, 9H), 0.07 (s, 6H).

tert-Butyl N-[(2E)-4-(dimethylamino)but-2-en-1-yl]-N-{[4-(hydroxymethyl)pyridin-2-yl]methyl}carbamate (lxxviii)

By General Procedure P from tert-butyl N-[(4-{[(tert-butyldimethylsilyl)oxy]methyl}pyridin-2-yl)methyl]-N-[(2E)-4-(dimethylamino)but-2-en-1-yl]carbamate. Purification by column chromatography (10% MeOH and 1% NH$_4$OH in DCM) gave the title product as light yellow oil. $^1$H NMR (300 MHz, chloroform-d): δ ppm 8.36 (d, 1H), 7.23 (s, 1H), 7.12 (s, 1H), 5.50 (m, 2H), 4.61 (s, 2H), 4.48 (m, 2H), 3.82 (m, 2H), 2.80 (d, 2H), 2.09 (s, 6H), 1.39 (m, 9H).

tert-Butyl N-[(2E)-4-(dimethylamino)but-2-en-1-yl]-N-[(4-formylpyridin-2-yl)methyl]carbamate (lxxix)

By General Procedure Q from tert-butyl N-[(2E)-4-(dimethylamino)but-2-en-1-yl]-N-{[4-(hydroxymethyl)pyridin-2-yl]methyl}carbamate. Evaporation gave the title product as yellow sticky oil. Used without further purification. $^1$H NMR (300 MHz, chloroform-d): δ ppm 10.07 (d, 1H), 8.79 (m, 1H), 7.61 (m, 2H), 5.61 (m, 2H), 4.61 (m, 2H), 3.95 (m, 2H), 2.90 (m, 2H), 2.20 (s, 6H), 1.45 (m, 9H).

tert-Butyl N-({4-[N-cyclopropylcarboximidoyl]pyridin-2-yl}methyl)-N-[(2E)-4-(dimethylamino)but-2-en-1-yl]carbamate (lxxx)

By General Procedure F from tert-butyl N-[(2E)-4-(dimethylamino)but-2-en-1-yl]-N-[(4-formylpyridin-2-yl)methyl]carbamate (1. Equiv.) and cyclopropanamine (1.2 equiv.). Evaporation gave the title product as oil. Used without further purification. $^1$H NMR (300 MHz, chloroform-d): δ ppm 8.53 (d, 1H), 8.38 (s, 1H), 7.43 (m, 2H), 5.61 (m, 2H), 4.51 (m, 2H), 3.89 (m, 2H), 3.06 (m, 1H), 2.94 (m, 2H), 2.24 (s, 6H), 1.44 (m, 9H), 0.99 (m, 4H).

tert-Butyl N-[4-(azetidin-1-yl)butyl]-N-({4-[(N-cyclopropylcarboximidoyl]pyridin-2-yl}methyl)carbamate (lxxxi)

General Procedure F from tert-butyl N-[4-(azetidin-1-yl)butyl]-N-(4-formylpyridine-2-carbonyl)carbamate (1.0 equiv.) and cyclopropylamine (5 equiv.). Evaporation gave the title product, which was used without further purification. $^1$H-NMR (300 MHz, CDCl$_3$): δ 8.50 (d, 1H), 8.35 (s, 1H), 7.50 (s, 1H), 7.40 (d, 1H), 4.50 (m, 2H), 3.20 (m, 2H), 3.00 (m, 2H), 2.90 (m, 2H), 2.10 (m, 2H), 1.70 (m, 2H), 1.45 (m, 15H), 1.00 (m, 4H) ppm.

[(4-{[(tert-Butyldimethylsilyl)oxy]methyl}pyridin-2-yl)methyl][4-(dimethylamino)butyl]amine (lxxxii)

By General Procedure A from 4-{[(tert-butyldimethylsilyl)oxy]methyl}pyridine-2-carbaldehyde and (4-aminobutyl)dimethylamine. Purification by column chromatography (DCM/MeOH (95:5)) gave the title compound as greenish oil. $^1$H-NMR (300 MHz, CDCl$_3$): δ 8.48 (d, 1H), 7.25 (s, 2H), 7.10 (d, 1H), 4.70 (s, 2H), 3.90 (s, 2H), 2.60 (m, 2H), 2.30 (m, 2H), 2.20 (s, 6H), 1.50 (m, 4H), 1.00 (s, 9H, 0.9 (s, 9H), 0.1 (s, 6H) ppm.

N-[(4-{[(tert-Butyldimethylsilyl)oxy]methyl}pyridin-2-yl)methyl]-N-[4-(dimethylamino)butyl]-2,2,2-trifluoroacetamide (lxxxiii)

By General Procedure C from [(4-{[(tert-butyldimethylsilyl)oxy]methyl}pyridin-2-yl)methyl][4-(dimethylamino)butyl]amine. Evaporation gave the title compounds, which was used without further purification.

N-[4-(Dimethylamino)butyl]-2,2,2-trifluoro-N-{[4-(hydroxymethyl)pyridin-2-yl]methyl}acetamide (lxxxiv)

By General Procedure P from N-[(4-{[(tert-butyldimethylsilyl)oxy]methyl}pyridin-2-yl)methyl]-N-[4-(dimethylamino)butyl]-2,2,2-trifluoroacetamide. Purification by column chromatography (DCM/MeOH (90:10)) gave the title compound as greenish oil. $^1$H-NMR (300 MHz, CDCl$_3$): δ 8.40 (m, 1H), 7.30 (m, 1H), 7.20 (m, 1H), 4.70 (m, 4H), 3.45 (m, 2H), 2.20 (m, 6H), 2.00 (s, 2H), 1.50 (m 4H) ppm.

N-[4-(Dimethylamino)butyl]-2,2,2-trifluoro-N-[(4-formylpyridin-2-yl)methyl]acetamide (lxxxv)

By General Procedure V from N-[4-(dimethylamino)butyl]-2,2,2-trifluoro-N-{[4-(hydroxymethyl)pyridin-2-yl]methyl}acetamide. Aqueous work up gave the title compound as light yellow oil. $^1$H-NMR (300 MHz, CDCl3): δ 10.0 (s, 1H), 8.80 (d, 1H), 7.55 (s, 2H), 4.80 (m, 2H), 3.50 (m, 2H), 2.25 (m, 2H), 2.20 (s, 6H), 1.70 (m, 2H), 1.50 (m, 2H) ppm.

N-({4-[(N-Cyclopropylcarboximidoyl]pyridin-2-yl}methyl)-N-[4-(dimethylamino)butyl]-2,2,2-trifluoroacetamide (lxxxvi)

By General Procedure F from N-[4-(dimethylamino)butyl]-2,2,2-trifluoro-N-[(4-formylpyridin-2-yl)methyl]acetamide (1.0 equiv.) and cyclopropylamine (5 equiv.). Evaporation gave the title product, which was used without further purification. $^1$H-NMR (300 MHz, CDCl$_3$): δ 8.65, 8.50 (d, 1H), 8.45, 8.40 (s, 1H), 7.45 (m, 2H), 4.70 (m, 2H), 3.00 (m, 2H), 2.75 (m, 1H), 2.55 (s, 6H), 1.80 (m, 1H), 1.50 (m, 5H), 1.00 (m, 4H) ppm.

Ethyl 2-{[(5-hydroxypentyl)amino]methyl}pyridine-4-carboxylate (lxxxvii)

Prepared by General Procedure A from ethyl 2-formylpyridine-4-carboxylate (1.0 equiv.) and 5-aminopentan-1-ol (1.2 equiv.). Purification by column chromatography (DCM/MeOH (85:15) gave the title compound as greenish oil. $^1$H-NMR (300 MHz, CDCl$_3$): δ 8.60 (d, 1H), 7.80 (s, 1H), 7.00 (d, 1H), 4.30 (q, 2H), 3.90 (s, 2H), 3.50 (t 2H), 3.10 (s, 2H), 2.60 (m, 2H), 1.50 (m, 4H), 1.30 (t, 3H) ppm.

Ethyl 2-({[(tert-butoxy)carbonyl](5-hydroxypentyl) amino}methyl)pyridine-4-carboxylate (lxxxviii)

Prepared by General Procedure R from ethyl 2-{[(5-hydroxypentyl)amino]methyl}pyridine-4-carboxylate. Evaporation gave the title product as white solid. Used without further purification. $^1$H-NMR (300 MHz, CDCl$_3$): δ 8.60 (d, 1H), 7.75 (s, 1H), 7.60 (d, 1H), 4.50 (m, 2H), 4.30 (q, 2H), 3.50 (t 2H), 3.20 (m, 2H), 2.20 (m, 1H), 1.60-1.20 (m, 18H) ppm.

Ethyl 2-({[(tert-butoxy)carbonyl](5-oxopentyl) amino}methyl)pyridine-4-carboxylate (lxxxix)

Prepared by General Procedure Q from Ethyl 2-({[(tert-butoxy)carbonyl](5-hydroxypentyl)amino}methyl)pyridine-4-carboxylate. Purification by column chromatography (EtOAc/hexane 20-50%) gave the title product. $^1$H-NMR (300 MHz, CDCl$_3$): δ 9.70 (s, 1H), 8.60 (d, 1H), 7.75 (s, 1H), 7.60 (d, 1H), 4.50 (m, 2H), 4.40 (q, 2H), 3.20 (m, 2H), 2.45 (m, 2H), 1.70-1.30 (m, 17H) ppm.

Ethyl 2-({[(tert-butoxy)carbonyl][5-(dimethylamino) pentyl]amino}methyl)pyridine-4-carboxylate (xc)

Prepared by General Procedure A from ethyl 2-({[(tert-butoxy)carbonyl](5-oxopentyl)amino}methyl)pyridine-4-carboxylate (1.0 equiv.), dimethylamine hydrochloride (1.2 equiv.), and triethylamine (1.3 equiv.). Purification by column chromatography (MeOH/DCM (5:95)) gave the title compound as colorless oil. $^1$H-NMR (300 MHz, CDCl3): δ 8.50 (d, 1H), 7.60 (s, 1H), 7.50 (d, 1H), 4.50 (d, 2H), 4.20 (q, 2H), 3.05 (m, 2H), 2.01 (s, 6H), 1.50-1.05 (m, 20H) ppm.

tert-Butyl N-[5-(dimethylamino)pentyl]-N-{[4-(hydroxymethyl)pyridin-2-yl]methyl}carbamate (xci)

Prepared by General Procedure U from ethyl 2-({[(tert-butoxy)carbonyl][5-(dimethylamino)pentyl]amino}methyl) pyridine-4-carboxylate. Purification by column chromatography (NH$_4$OH MeOH/DCM (5:10:85)) gave the title compound as colorless viscous oil. $^1$H-NMR (300 MHz, CDCl3): δ 8.40 (d, 1H), 7.20 (s, 1H), 7.10 (d, 1H), 4.65 (s, 2H), 4.40 (m, 2H), 3.20 (m, 2H), 2.20 (m, 2H), 2.10 (s, 6H), 1.50-1.20 (m, 15H) ppm.

tert-Butyl N-[5-(dimethylamino)pentyl]-N-[(4-formylpyridin-2-yl)methyl]carbamate (xcii)

Prepared by General Procedure Q tert-butyl N-[5-(dimethylamino)pentyl]-N-{[4-(hydroxymethyl)pyridin-2-yl] methyl}carbamate. $^1$H-NMR (300 MHz, CDCl3): δ 10.05 (s, 1H), 8.70 (d, 1H), 7.50 (m, 2H), 4.50 (m, 2H), 3.20 (m, 2H), 2.40 (s, 6H), 1.60-1.00 (m, 15H) ppm.

tert-Butyl N-({4-[N-cyclopropylcarboximidoyl]pyridin-2-yl}methyl)-N-[5-(dimethylamino)pentyl]carbamate (xciii)

Prepared by General Procedure F from tert-butyl N-[5-(dimethylamino)pentyl]-N-[(4-formylpyridin-2-yl)methyl] carbamate (1 equiv.) and cyclorpropylamine (5 equiv.). Evaporation gave the title product, which was used without further purification. $^1$H-NMR (300 MHz, CDCl$_3$): δ δ 8.50 (d, 1H), 8.40 (s, 1H), 7.45 (m, 2H), 4.45 (m, 2H), 3.10 (m, 4H), 2.75 (m, 2H), 2.60 (s, 6H), 1.80 (m, 1H), 1.45 (m, 13H), 0.95 (m, 4H) ppm.

Ethyl 2-{[N-({[4-(diethylamino)butyl] carbamoyl}methyl)-2,2,2-trifluoroacetamido] methyl}pyridine-4-carboxylate (xciv)

By General procedure Y from (4-aminobutyl)diethylamine and 2-(N-{[4-(ethoxycarbonyl)pyridin-2-yl]methyl}-2,2,2-trifluoroacetamido)acetic acid. Purification by column chromatography gave the title compound as oil. $^1$H NMR (300 MHz, chloroform-d): δ ppm 9.09 (t, 1H), 8.67 (m, 1H), 7.83 (m, 2H), 4.85 (m, 2H), 4.42 (q, 2H), 4.17 (m, 2H), 3.26 (m, 2H), 2.46 (m, 6H), 1.52 (m, 4H), 1.40 (t, 3H), 0.97 (m, 6H).

N-[4-(Diethylamino)butyl]-2-({[4-(hydroxymethyl) pyridin-2-yl]methyl}amino)acetamide (xcv)

Prepared by General Procedure U from ethyl 2-{[N-({[4-(diethylamino)butyl]carbamoyl}methyl)-2,2,2-trifluoroacetamido]methyl}pyridine-4-carboxylate, using 5 equivalents of NaBH$_4$. Purification by column chromatography with (10% MeOH and 1% NH$_4$OH in DCM) gave the title product as light yellow oil. $^1$H NMR (300 MHz, methanol-d$_4$): δ ppm 8.45 (d, 1H), 7.47 (s, 1H), 7.31 (d, 1H), 4.68 (s, 2H), 3.88 (s, 2H), 3.28 (m, 4H), 2.59 (q, 4H), 2.51 (m, 2H), 1.52 (m, 4H), 1.05 (t, 6H).

tert-Butyl N-({[4-(diethylamino)butyl] carbamoyl}methyl)-N-{[4-(hydroxymethyl)pyridin-2-yl]methyl}carbamate (xcvi)

Prepared by General Procedure R from N-[4-(diethylamino)butyl]-2-({[4-(hydroxymethyl)pyridin-2-yl] methyl}amino)acetamide. Purification by column chromatography with (0-20% MeOH in DCM) gave the title product as light yellow oil. $^1$H NMR (300 MHz, chloroform-d): δ ppm 8.55 (s, 1H), 8.47 (m, 1H), 7.38 (s, 1H), 7.33 (m, 1H), 4.69 (s, 2H), 4.61 (m, 2H), 3.99 (m, 2H), 3.58 (t, 0.5H), 3.22 (m, 1H), 2.97 (m, 5H), 2.25 (t, 0.5H), 1.82 (m, 1H), 1.64 (m, 4H), 1.36 (m, 9H), 1.22 (m, 6H).

tert-Butyl N-({[4-(diethylamino)butyl] carbamoyl}methyl)-N-[(4-formylpyridin-2-yl)methyl]carbamate (xcvii)

Prepared by General Procedure Q from tert-butyl N-({[4-(diethylamino)butyl]carbamoyl}methyl)-N-{[4-(hydroxymethyl)pyridin-2-yl]methyl}carbamate. Evaporated to give the title product as a yellow oil, which was used without further purification. $^1$H NMR (300 MHz, chloroform-d): δ ppm 11.8 (m, 0.5H), 10.1 (s, 1H), 9.17 (m, 0.5H), 8.80 (m, 1H), 7.68 (m, 2H), 4.67 (m, 2H), 4.05 (m, 2H), 3.36 (m, 2H), 3.05 (m, 6H), 1.91 (m, 2H), 1.66 (m, 2H), 1.38 (m, 9H), 1.17 (m, 6H).

tert-Butyl N-({4-[N-cyclopropylcarboximidoyl]pyridin-2-yl}methyl)-N-({[4-(diethylamino)butyl] carbamoyl}methyl)carbamate (xcviii)

Prepared by General Procedure F from tert-butyl N-({[4-(diethylamino)butyl]carbamoyl}methyl)-N-[(4-formylpyridin-2-yl)methyl]carbamate and cyclopropyl amine. Evaporated to give the title product as yellow oil, which was used without further purification. $^1$H NMR (300 MHz, chloroform-d): δ ppm 9.60 (t, 1H), 8.51 (m, 1H), 8.39 (s, 1H), 7.46 (m, 2H), 4.53 (m, 2H), 3.97 (m, 2H), 3.48 (m, 1H), 3.32 (m, 2H), 2.94 (m, 6H), 1.80 (m, 2H), 1.61 (m, 1H), 1.33 (m, 9H), 1.08 (m, 6H).

Ethyl 2-{[({[2-(dimethylamino)ethyl](ethyl) carbamoyl}methyl)amino]methyl}pyridine-4-carboxylate (xcix)

By General Procedure A from ethyl 2-formylpyridine-4-carboxylate and 2-amino-N-[2-(dimethylamino)ethyl]-N-ethylacetamide. $^1$H NMR (300 MHz, CDCl$_3$), δ ppm: 3.47-3.32 (m, 4H), 3.27-3.20 (m, 2H), 2.44-2.35 (m, 2H), 2.22 (s, 6H), 1.53 (s, 2H), 1.15-1.06 (m, 3H).

N-[2-(dimethylamino)ethyl]-N-ethyl-2-({[4-(hydroxymethyl)pyridin-2-yl]methyl}amino)acetamide (c)

By General Procedure U from ethyl 2-{[({[2-(dimethylamino)ethyl](ethyl)carbamoyl}methyl)amino]methyl}pyridine-4-carboxylate. $^1$H NMR (300 MHz, CDCl$_3$), δ ppm: 8.45 (d, 1H), 7.39 and 7.36 (2 singlets, 1H), 7.14 (d, 1H), 4.67 (s, 2H), 3.94 (s, 2H), 3.54-3.47 (m, 4H), 3.32-3.24 (m, 2H), 2.60-2.40 (m, 2H), 2.37 and 2.24 (2 singlets, 6H), 1.18-1.10 (m, 3H).

tert-Butyl N-({[2-(dimethylamino)ethyl](ethyl) carbamoyl}methyl)-N-{[4-(hydroxymethyl)pyridin-2-yl]methyl}carbamate (ci)

By General Procedure R from N-[2-(dimethylamino)ethyl]-N-ethyl-2-({[4-(hydroxymethyl)pyridin-2-yl]methyl}amino)acetamide. $^1$H NMR (300 MHz, CDCl$_3$), δ ppm: 8.49 (d, 1H), 7.37 and 7.32 (2 singlets, 1H), 7.19 (d, 1H), 4.73 (s, 2H), 4.67 and 4.63 (2 singlets, 2H), 4.20 and 4.07 (2 singlets, 2H), 3.48-3.22 (m, 4H), 2.49-2.39 (m, 2H), 2.27 and 2.23 (2 singlets, 6H), 1.46 and 1.41 (2 singlets, 9H), 1.21-1.09 (m, 3H).

tert-butyl N-({[2-(dimethylamino)ethyl](ethyl) carbamoyl}methyl)-N-[(4-formylpyridin-2-yl)methyl]carbamate (cii)

By General Procedure Q from tert-buty-N-({[2-(dimethylamino)ethyl](ethyl)carbamoyl}methyl)-N-{[4-(hydroxymethyl)pyridin-2-yl]methyl}carbamate. $^1$H NMR (300 MHz, CDCl$_3$), δ ppm: 10.07 and 10.06 (2 singlets, 1H), 8.78 and 8.75 (2 doublets, 1H), 7.80 and 7.74 (2 doublets, 1H), 7.58 and 7.57 (2 singlets, 1H), 4.75 and 4.70 (2 singlets, 2H), 4.24 and 4.09 (2 singlets, 2H), 3.54-3.21 (m, 4H), 2.60-2.39 (m, 2H), 2.37, 2.33 and 2.22 (3 singlets, 6H), 1.44 and 1.36 (2 singlets, 9H), 1.23-1.08 (m, 3H).

N-[2-(dimethylamino)ethyl]-N-ethyl-2-{[(4-formylpyridin-2-yl)methyl]amino}acetamide (ciii)

By General Procedure D from tert-butyl-N-({[2-(dimethylamino)ethyl](ethyl)carbamoyl}methyl)-N-[(4-formylpyridin-2-yl)methyl]carbamate. $^1$H NMR (300 MHz, CD$_3$OD), δ ppm: 8.94 (d, 1H), 8.42 (s, 1H), 8.17 (dd, 1H), 5.79 (s, 1H), 4.85 (s, 2H), 4.44 (s, 2H), 3.86 (t, 2H), 3.49-3.41 (m, 4H), 2.99 (s, 6H), 1.29 (t, 3H).

Tert-butyl N-({4-[5-benzyl-3-(trifluoroacetyl)-1,3-oxazinan-2-yl]pyridin-2-yl}methyl)-N-({[2-(dimethylamino)ethyl](ethyl)carbamoyl}methyl)carbamate (civ)

General Procedure AB (Preparation of N-acyl-1,3-oxazinanes)

Optionally substituted 3-aminopropanol (3-amino-2-phenylpropan-1-ol) (1.1 eq) was added to a stirred solution of aldehyde (tert-butyl N-({[2 (dimethylamino)ethyl](ethyl) carbamoyl}methyl)-N-[(4-formylpyridin-2-yl)methyl]carbamate) (1.0 eq) in toluene. Stirred at room temperature for 2 h. Anhydride (trifluoroacetic anhydride) (1.5 equiv.) was added dropwise to the solution followed by 5 equivalent of DIPEA. The mixture was heated at 80° C. for two hours. Aqueous work up and purification by HPLC (0.1% TFA solution/MeOH) gave the title product. $^1$H-NMR (300 MHz, CD$_3$OD): δ 8.50 (d, 1H), 7.45 (m, 1H), 7.25 (m, 6H), 4.60 (s, 2H), 4.30 (m, 2H), 3.70 (m, 3H), 2.90 (s, 6H), 1.50 (s, 9H), 1.30 (t, 3H) ppm. ES-MS: 636 [M+1]

Ethyl 2-{[({4-[(dimethylamino)methyl] cyclohexyl}methyl)amino]methyl}pyridine-4-carboxylate (cv)

By General Procedure A from ethyl 2-formylpyridine-4-carboxylate and {4-[(dimethylamino)methyl] cyclohexyl}methanamine. Aqueous work up gave the title compound as a yellow oil. Used without further purification. $^1$H NMR (300 MHz, chloroform-d): δ ppm 8.41 (d, 1H), 8.04 (s, 1H), 7.49 (d, 1H), 4.04 (q, 2H), 3.39 (s, 2H), 2.46 (m, 4H), 2.38 (d, 6H), 1.60 (m, 4H), 1.34 (t, 3H), 1.03 (m, 2H), 0.68 (m, 4H).

Ethyl 2-({[(tert-butoxy)carbonyl]({4-[(dimethylamino)methyl]cyclohexyl}methyl)amino}-methyl) pyridine-4-carboxylate (cvi)

By General Procedure R from ethyl 2-{[({4-[(dimethylamino)methyl]cyclohexyl}methyl)amino]methyl}pyridine-4-carboxylate. Purification by column chromatography (0-10% MeOH in DCM) gave the title product as light yellow oil. $^1$H NMR (300 MHz, chloroform-d): δ ppm 8.62 (m, 1H), 7.71 (m, 2H), 4.56 (m, 2H), 4.36 (m, 2H), 3.11 (m, 2H), 2.17 (s, 6H), 2.05 (m, 2H), 1.74 (m, 4H), 1.40 (m, 14H), 0.85 (m, 4H).

tert-Butyl N-({4-[(dimethylamino)methyl] cyclohexyl}methyl)-N-{[4-(hydroxymethyl)pyridin-2-yl]methyl}carbamate (cvii)

By General Procedure U from ethyl 2-({[(tert-butoxy)carbonyl]({4-[(dimethylamino)methyl]cyclohexyl}methyl) amino}methyl)pyridine-4-carboxylate) (1.0 equiv.) in EtOH. Stirred at reflux for 2 hours. Cooled to room temperature and sat. NH$_4$Cl solution was added. Evaporated to dryness. Purification by column chromatography (DCM, MeOH (10%) and HN$_4$OH (1%)) gave the title product as light yellow oil. $^1$H NMR (300 MHz, chloroform-d): δ ppm 8.41 (d, 1H), 7.17 (m, 2H), 4.65 (s, 2H), 4.50 (d, 2H), 3.10 (m, 2H), 2.17 (s, 6H), 2.07 (d, 2H), 1.74 (m, 4H), 1.41 (m, 11H), 0.87 (m, 4H).

tert-Butyl N-({4-[(dimethylamino)methyl] cyclohexyl}methyl)-N-[(4-formylpyridin-2-yl)methyl]carbamate (cviii)

General Procedure Q from tert-butyl N-({4-[(dimethylamino)methyl]-cyclohexyl}methyl)-N-{[4-(hydroxymethyl)pyridin-2-yl]methyl}carbamate gave the title product as yellow sticky oil without further purification. $^1$H NMR (300 MHz, chloroform-d): δ ppm 10.07 (s, 1H), 8.79 (m, 1H), 7.61 (m, 2H), 4.63 (d, 2H), 3.18 (m, 2H), 2.22 (s, 6H), 2.10 (d, 2H), 1.79 (m, 4H), 1.45 (m, 11H), 0.91 (m, 4H).

Ethyl 2-({[(2Z)-4-(dimethylamino)but-2-en-1-yl] amino}methyl)pyridine-4-carboxylate (cix)

By General Procedure A from ethyl 2-formylpyridine-4-carboxylate, (Z)—N1,N1-dimethylbut-2-ene-1,4-diamine.

Purification by column chromatography (DCM/MeOH/NH₄OH, 90:10:1) gave the title compound as yellow viscous oil. ¹H NMR (300 MHz, CDCl₃): δ 8.8 (d, 1H), 7.8 (s, 1H), 7.7 (d, 1H), 5.7 (m, 2H), 4.34 (q, 2H), 4.0 (s, 2H), 3.4 (d, 2H), 2.9 (d, 2H), 2.2 (s, 6H), 1.32 (t, 3H).

[2-({[(2Z)-4-(Dimethylamino)but-2-en-1-yl]amino}methyl)pyridin-4-yl]methanol (cx)

By General Procedure U from ethyl 2-({[(2Z)-4-(dimethylamino)but-2-en-1-yl]amino}methyl)pyridine-4-carboxylate. Purification by column chromatography (DCM/MeOH/NH₄OH, 85:15:1 gave the title compound as yellow viscous oil. ¹H NMR (300 MHz, CDCl₃): δ 8.5 (d, 1H), 7.2 (s, 1H), 7.1 (d, 1H), 5.8 (m, 2H), 5.4 (s, 2H), 3.9 (s, 2H), 3.4 (d, 2H), 2.9 (d, 2H), 2.2 (s, 6H).

tert-Butyl N-[(2Z)-4-(dimethylamino)but-2-en-1-yl]-N-{[4-(hydroxymethyl)pyridin-2-yl]methyl}carbamate (cxi)

By General Procedure R from [2-({[(2Z)-4-(dimethylamino)but-2-en-1-yl]amino}methyl)pyridin-4-yl]methanol. Evaporation gave the title compound as a colorless glue, which was used without further purification. ¹H NMR (300 MHz, CDCl₃): δ 8.5 (d, 1H), 7.2 (s, 1H), 7.1 (d, 1H), 5.8 (m, 2H), 4.6 (s, 2H), 4.4 (s, 2H), 3.9 (s, 2H), 2.9 (d, 2H), 2.2 (s, 6H), 1.3 (s, 9H).

tert-Butyl N-[(2Z)-4-(dimethylamino)but-2-en-1-yl]-N-[(4-formylpyridin-2-yl)methyl]carbamate (cxii)

By General Procedure Q from tert-butyl-N-[(2Z)-4-(dimethylamino)but-2-en-1-yl]-N-{[4-(hydroxymethyl)pyridin-2-yl]methyl}carbamate. ¹H NMR (300 MHz, CDCl₃), (rotamers): δ 10.1 (s, 1H), 8.8 (d, 1H), 7.5 (m, 2H), 5.8 (m, 2H), 4.6 (s, 2H), 3.9 (s, 2H), 2.9 (d, 2H), 2.2 (s, 6H), 1.3 (s, 9H).

Ethyl 2-[(2,2,2-trifluoro-N-{2-oxo-2-[(2R)-2-(pyrrolidin-1-ylmethyl)pyrrolidin-1-yl]ethyl}acetamido)methyl]pyridine-4-carboxylate (cxiii)

General Procedure Y from (2R)-2-(pyrrolidin-1-ylmethyl)pyrrolidine and 2-(N-{[4-(ethoxycarbonyl)pyridin-2-yl]methyl}-2,2,2-trifluoroacetamido)acetic acid gave the title product as yellow oil, which was used without further purification.

2-({[4-(Hydroxymethyl)pyridin-2-yl]methyl}amino)-1-[(2R)-2-(pyrrolidin-1-ylmethyl)pyrrolidin-1-yl]ethan-1-one (cxiv)

Prepared by General Procedure U from ethyl 2-[(2,2,2-trifluoro-N-{2-oxo-2-[(2R)-2-(pyrrolidin-1-ylmethyl)pyrrolidin-1-yl]ethyl}acetamido)methyl]pyridine-4-carboxylate, using 5 equiv. of NaBH₄. The residue was purified by column chromatography on silica gel using NH₄OH (2%)+MeOH (20%) in CH₂Cl₂ to give the title as yellow oil. ¹H NMR (300 MHz, CD₃OD), δ ppm: 8.44 (d, 1H), 7.49 (s, 1H), 7.31 (d, 1H), 4.90 (s, 2H), 4.69 (s, 2H), 4.24 (m, 1H), 3.93 (s, 2H), 3.50-3.36 (m, 3H), 2.67-2.42 (m, 6H), 2.06-1.89 (m, 4H), 1.84-1.72 (s, 4H). ESI-MS (m/z): 333 [M+1].

tert-Butyl N-{[4-(hydroxymethyl)pyridin-2-yl]methyl}-N-{2-oxo-2-[(2R)-2-(pyrrolidin-1-ylmethyl)pyrrolidin-1-yl]ethyl}carbamate (cxv)

Prepared by General Procedure R from 2-({[4-(hydroxymethyl)pyridin-2-yl]methyl}amino)-1-[(2R)-2-(pyrrolidin-1-ylmethyl)pyrrolidin-1-yl]ethan-1-one. Purified by column chromatography on silica gel using NH₄OH (1.5%)+MeOH (15%) in CH₂Cl₂ to give the title compound as brown oil. ¹H NMR (300 MHz, CDCl₃), δ ppm: 8.44 (d, 1H), 7.35 and 7.31 (2 singlets, 1H), 7.18 (d, 1H), 4.71 and 4.68 (2 singlets, 2H), 4.61 (s, 2H), 4.29 (m, 1H), 4.08 and 4.07 (2 singlets, 2H), 3.95 (m, 1H), 3.48-3.01 (m, 7H), 2.87 (m, 1H), 2.35 (m, 1H), 2.07-1.93 (m, 7H), 1.43 and 1.41 (2 singlets, 9H). ESI-MS: 433 [M+1].

tert-Butyl N-[(4-formylpyridin-2-yl)methyl]-N-{2-oxo-2-[(2R)-2-(pyrrolidin-1-ylmethyl)pyrrolidin-1-yl]ethyl}carbamate (cxvi)

General Procedure V from 2-({[4-(hydroxymethyl)pyridin-2-yl]methyl}amino)-1-[(2R)-2-(pyrrolidin-1-ylmethyl)pyrrolidin-1-yl]ethan-1-one gave the title compound as yellow oil. ¹H NMR (300 MHz, CDCl₃), δ ppm: 10.09 (s, 1H), 8.78 (m, 1H), 7.81 (m, 1H), 7.60 (m, 1H), 4.87-4.51 (m, 2H), 4.42-3.87 (m, 2H), 3.66-3.17 (m, 3H), 2.80-2.38 (m, 6H), 2.17-1.74 (m, 8H), 1.46 and 1.39 (2 singlets, 9H).

Ethyl 2-({[(tert-butoxy)carbonyl](4-oxobutyl)amino}methyl)pyridine-4-carboxylate (cxvii)

By General Procedure Q from ethyl 2-({[(tert-butoxy)carbonyl](4-hydroxybutyl)amino}methyl)-pyridine-4-carboxylate. Purified by column chromatography (ethyl acetate/hexane 20-40%) to give the title product. ¹H-NMR (300 MHz, CDCl₃): δ 9.70 (s, 1H), 8.60 (d, 1H), 7.70 (s, 1H), 7.60 (d, 1H), 4.55 (d, 2H), 4.40 (q, 2H), 3.40 (m, 2H), 2.480 (m, 2H), 1.85 (m, 2H), 1.50-1.20 (m, 12H) ppm.

Ethyl 2-[({4-[benzyl(cyclopropyl)amino]butyl}[(tert-butoxy)carbonyl]amino)methyl]pyridine-4-carboxylate (cxviii)

By General Procedure A from ethyl 2-({[(tert-butoxy)carbonyl](4-oxobutyl)amino}methyl)pyridine-4-carboxylate and N-benzylcyclopropanamine. Purification by column chromatography (5% MeOH/DCM) gave the title compound as colorless oil. ¹H-NMR (300 MHz, CDCl₃): δ 8.60 (d, 1H), 7.70 (s, 1H), 7.60 (d, 1H), 7.10 (m, 5H), 4.50 (d, 2H), 4.40 (q, 2H), 3.50 (m, 2H), 3.15 (m, 2H), 2.50 (m, 2H), 1.60 (m, 1H), 1.45 (m, 16H), 0.4 (m, 4H) ppm.

tert-Butyl N-{4-[benzyl(cyclopropyl)amino]butyl}-N-{[4-(hydroxymethyl)pyridin-2-yl]methyl}carbamate (cxix)

By General Procedure U from ethyl 2-[({4-[benzyl(cyclopropyl)amino]butyl}[(tert-butoxy)carbonyl]amino)methyl]pyridine-4-carboxylate. Purification by column chromatography (DCM, MeOH and HN₄OH (85; 10:5)) gave the title product as viscous oil. ¹H-NMR (300 MHz, CDCl₃): δ 8.45 (d, 1H), 7.20 (m, 6H), 7.00 (d, 1H), 4.70 (m, 2H), 4.50 (m, 2H), 3.60 (m, 2H), 3.10 (m, 2H), 2.40 (m, 2H), 1.55 (m, 2H), 1.40 (m, 13H) ppm.

tert-Butyl N-{4-[benzyl(cyclopropyl)amino]butyl}-N-[(4-formylpyridin-2-yl)methyl]carbamate (cxx)

By General Procedure Q from tert-butyl N-{4-[benzyl(cyclopropyl)amino]butyl}-N-{[4-(hydroxymethyl)pyridin-2-yl]methyl}carbamate. Purification by column chromatography (ethyl acetate/hexane 20-50%) gave the title product. ¹H-NMR (300 MHz, CDCl₃): δ 10.0 (s, 1H), 8.70 (d, 1H), 7.50 (m, 2H), 7.20 (m, 5H), 4.50 (m, 2H), 3.80 (m, 2H), 3.15 (m, 2H), 2.50 (m, 2H), 1.60 (m, 2H), 1.45 (m, 12H), 0.40 (m, 4H) ppm.

Reagents

Methyl 4-{[(tert-butyldimethylsilyl)oxy]methyl}pyridine-2-carboxylate

General Procedure AC (Formation of Silyl Ether)

Tert-butyldimethylsilyl chloride (1.2 equiv) was added to a solution of alcohol (4-(hydroxymethyl)pyridine-2-carboxylate) (1.equiv.), triethylamine (2.30 equiv.) and 4-dimethylaminopyridine (0.10 equiv.) in dichloromethane at 0° C., Stirred at room temperature overnight. Aqueous work up and purification by flash chromatography (Hexane-EtOAc, 5-25%) gave the title compound as colorless oil. $^1$H-NMR (300 MHz, CD$_3$OD): δ 8.60 (d, 1H), 8.15 (s, 1H), 7.60 (d, 1H), 4.88 (s, 2H), 3.97 (s, 3H), 0.98 (s, 9H), 0.15 (s, 6H).

4-{[(tert-butyldimethylsilyl)oxy]methyl}pyridine-2-carbaldehyde

By General Procedure K from methyl 4-{[(tert-butyldimethylsilyl)oxy]methyl}pyridine-2-carboxylate (1 equiv.). Aqueous work up gave the title compound, which was used without further purification. $^1$H-NMR (300 MHz, CDCl$_3$): δ 10.11 (s, 1H), 8.75 (d, 1H), 7.92 (s, 1H), 7.54 (d, 1H), 7.27 (s, 1H), 4.83 (s, 2H), 0.98 (s, 9H), 0.15 (s, 6H).

Ethyl 2-[(chlorocarbonyl)oxy]benzoate

General Procedure AD (Acid Chloride from Carboxylic Acid)

The carboxylic acid (Ethyl 2-hydroxybenzoate) (1 eq) in toluene was cooled to 0° C., N, N-dimethyl amine (1 eq) was added, phosgene (1 eq) was added dropwise and stirred at same temperature for 2 h. The solid was filtered off and the filtrate was concentrated and used as reagent without further purification.

2-amino-(N-[2-(dimethylamino)ethyl]-N-ethyl)acetamide

By General Procedure Y from 2-{[(tert-butoxy)carbonyl]amino}acetic acid and [2-(dimethylamino)ethyl](ethyl)amine. The product was treated with concentrated hydrochloric acid to get the title compound as hydrochloric acid salt. $^1$H NMR (300 MHz, CDCl$_3$), δ ppm: 3.47-3.32 (m, 4H), 3.27-3.20 (m, 2H), 2.44-2.35 (m, 2H), 2.22 (s, 6H), 1.53 (s, 2H), 1.15-1.06 (m, 3H).

Tert-butyl 2-[(1EH)-(ethylimino)methyl]pyrrolidine-1-carboxylate

By General Procedure G from tert-Butyl 2-formylpyrrolidine-1-carboxylate and ethylamine. Used without further purification Ethyl[(1-methylpyrrolidin-2-yl)methyl]amine General Procedure AE (Amines from Amides)

LAH was added to a solution of tert-butyl 2-[(1E)-(ethylimino)methyl]pyrrolidine-1-carboxylate in THF and refluxed for 6 hr. Aqueous work up. NaBH$_4$ and AcOH were added to a methanolic solution of the resulting intermediate. Aqueous work up gave the title compound as yellow oil. $^1$H NMR (300 MHz, CDCl3): δ ppm 3.05 (m, 1H), 2.77 (dd, 1H), 2.68 (q, 2H), 2.55 (m, 1H), 2.35 (s, 3H), 2.26-2.15 (m, 2H), 1.94 (m, 1H), 1.81-1.57 (m, 5H), 1.12 (t, 3H).

syn-2-(dimethylamino)-N-ethylcyclopentane-1-carboxamide

General Procedure Y from Ethyl[(1-methylpyrrolidin-2-yl)methyl]amine and ethylamine gave the product as yellow oil. $^1$H NMR (300 MHz, CDCl3): δ ppm 3.10 (q, 2H), 3.07-2.98 (m, 2H), 2.75 (s, 6H), 2.10-1.81 (m, 6H), 1.10 (t, 3H). ESI-MS (m/z): 185 [M+1].

syn-2-[(ethylamino)methyl]-N,N-dimethylcyclopentan-1-amine

General Procedure AE from syn-2-(dimethylamino)-N-ethylcyclopentane-1-carboxamide gave the title compound as yellow oil $^1$H NMR (300 MHz, CDCl3): δ ppm 2.76 (dd, 1H), 2.71-2.57 (m, 2H), 2.34 (m, 1H), 2.23 (m, 1H), 2.22 (s, 6H), 2.16 (m, 1H), 1.84-1.69 (m, 2H), 1.68-1.56 (m, 3H), 1.51-1.42 (m, 1H), 1.11 (t, 3H).

[2-(Dimethylamino)-2-methylpropyl](ethyl)amine

Prepared by General Procedure A from 2-(dimethylamino)-2-methylpropanal and ethylamine to get the title compound as colorless oil. $^1$H NMR (300 MHz, CDCl$_3$) δ 2.63 (q, 2H), 2.50 (s, 2H), 2.19 (s, 6H), 1.11 (t, 3H), 1.01 (s, 6H).

3-(aminomethyl)-N,N-dimethylcyclopentan-1-amine

General procedure M from 3-(dimethylamino)cyclopentane-1-carbonitrile to get the title product. $^1$H-NMR (300 MHz, CDCl$_3$), δ ppm: 2.8 (m, 2H), 2.5 (m, 1H), 2.6 (m, 1H), 2.2 (s, 3H), 2.1 (s, 3H).

Example 2

Histone Lysine Demethylase AlphaLISA Assays for IC50 Value Determination

This example demonstrates the ability of compounds of the invention to inhibit the activity in vitro of tested enzymes.

Assays are performed analogously to the protocol described by PerkinElmer (Roy et al. PerkinElmer Technical Note: AlphaLISA #12, April 2011)

General Method

Enzymes are dissolved in enzyme buffer and incubated for 10 min before being added to 3% DMSO solutions of compounds in enzyme buffer. Incubated for another 10 minutes, before substrate solution is added and the reaction mixture is incubated at room temperature. 10 µL acceptor beads, suspended in Epigenetic Buffer (Perkin Elmer AL008) from stock, are added and the suspension is incubated in the dark at room temperature, before a suspension of streptavidin donor beads (Perkin Elmer 6760002) in Epigenetic Buffer is added. After incubation at room temperature in the dark the plates are read.

Enzymes:

| Protein name | Vendor/source | Sequence | Expression organism |
|---|---|---|---|
| KDM2B (FBXL10) | BPS, Bioscience, US | 1-650 | Bac |
| KDM3B (JMJD1B) | BRIC | 842-1761 | Bac |
| KDM4A (JMJD2A) | BPS, Bioscience, US | 1-350 | E. coli |
| KDM4B (JMJD2B) | BPS | 2-500 | Bac |
| KDM4C (JMJD2C) | BRIC, Denmark | 1-349 | E. coli |
| KDM5C (JARID1C) | BPS | 2-1560 | Bac |
| KDM5B (PLU-1) | BRIC | 1-809 | E. coli |
| KDM6A (UTX) | BRIC | 919-1401 | E. coli |
| KDM6B (JMJD3) | BPS | 1043-end | Bac |
| KDM7 (PHF8) | BRIC | 1-1322 | Bac |
| KDM3A (JMJD1A) | BPS, Bioscience, US | 2-end | Bac |

Substrates:
BK9M3: Biotin-ARTKQTAR(KMe$_3$)STGGKAPRKQ-NH$_2$ (Caslo, Denmark) SEQ ID NO.: 1
BK9M2: Biotin-ARTKQTAR(KMe$_2$)STGGKAPRKQ-NH$_2$ (AnaSpec 64359) SEQ ID NO.: 2
BK9M1: Biotin-ARTKQTAR(KMe$_1$)STGGKAPRKQ-NH$_2$ (AnaSpec 64358) SEQ ID NO.: 3
H3K4M3B: H-ART(Kme3)QTARKSTGGKAPRKQLA-NH-Biotin (Caslo, Denmark) SEQ ID NO.: 4
BK27M3: Biotin-ATKAAR(Kme3)SAPATGGVKKPHRY-NH2 (Caslo, Denmark) SEQ ID NO.: 5
BH3K36M2: RKAAPATGGVK(Me2)KPHRYRPGTVK-(BIOTIN) (Anaspec) SEQ ID NO.: 6
Enzyme Buffer: 50 mM Hepes (pH 7.4 or 8.0), 0.003% Tween-20, 0.1% BSA; 5 μM (NH$_4$)$_2$Fe(SO$_4$)$_2$
Buffer A: 50 mM Hepes (pH 7.4 or 8.0), 0.003% Tween-20, 0.1% BSA
Substrate Solution: Substrate, 25 μM L-Asc, and 10 μM α-KG in Buffer A.

| | HDME INHIBITION | | | | | | | | | | |
|---|---|---|---|---|---|---|---|---|---|---|---|
| Compound Name | Compound # | KDM4C | KDM2B | KDM5C | KDM3A | KDM3B | KDM4A | KDM4B | KDM6B | PHF8 | KDM6A | KDM5B |
| N-[2-({[4-(diethylamino)butyl]amino}methyl)pyridin-4-yl]methyl]-2,2,2-trifluoroacetamide | 1 | + | + | ++ | + | + | ++ | +++ | + | ++ | + | ++ |
| [2-({[4-(dimethylamino)butyl]amino}methyl)pyridin-4-yl]methanamine | 2 | + | + | | + | | + | + | + | + | + | + |
| [2-({[3-(dimethylamino)propyl]amino}methyl)pyridin-4-yl]methanamine | 3 | + | + | +++ | + | + | +++ | +++ | + | ++ | + | ++ |
| 2-({[4-(aminomethyl)pyridin-2-yl]methyl}amino)-N-[2-(dimethylamino)ethyl]-N-ethylacetamide | 4 | ++ | + | +++ | | + | ++ | +++ | + | ++ | + | +++ |
| [2-({[4-(diethylamino)butyl]amino}methyl)pyridin-4-yl]methanamine | 5 | + | + | | + | + | + | + | + | + | + | + |
| N-[4-(diethylamino)butyl]-2,2,2-trifluoro-N-{4-[(trifluoroacetamido)methyl]pyridin-2-yl]methyl)acetamide | 6 | + | + | + | + | + | ++ | +++ | + | ++ | + | + |
| 2-({[4-(azetidin-1-yl)butyl]amino}methyl)pyridin-4-yl]methanamine | 7 | + | + | | + | + | + | + | + | + | + | ++ |
| [2-({[5-(dimethylamino)pentyl]amino}methyl)pyridin-4-yl]methanamine | 8 | + | + | +++ | + | + | + | +++ | + | + | + | +++ |
| 2-({[4-(aminomethyl)pyridin-2-yl]methyl}amino)-N-{1-[2-methoxyphenyl]methyl}piperidin-4-yl}acetamide | 9 | + | + | +++ | | + | + | + | + | + | + | ++ |
| N-[2-({[4-(dimethylamino)butyl]amino}methyl)pyridin-4-yl]methyl]cyclopropanamine | 10 | + | + | | + | + | + | + | + | + | + | + |
| N-[2-({[3-(2-methylpiperidin-1-yl)propyl]amino}methyl)pyridin-4-yl]methyl]cyclopropanamine | 11 | + | + | ++ | + | + | + | + | + | + | + | ++ |
| N-(2-{(propylamino)methyl]pyridin-4-yl}methyl)cyclopropanamine | 12 | ++ | + | + | + | ++ | + | ++ | + | ++ | + | ++ |
| 2-[({4-[(cyanomethyl)amino]methyl}pyridin-2-yl)methyl]amino]-N,N-dimethylacetamide | 13 | + | + | + | + | + | + | + | + | + | + | ++ |
| N-{[4-({[(2-fluoroethyl)amino]methyl}pyridin-2-yl)methyl]amino}-N,N-dimethylacetamide | 14 | ++ | + | ++ | + | + | ++ | ++ | + | + | + | ++ |
| 2-({[4-({[2-(dimethylamino)ethyl]amino}methyl)pyridin-2-yl]methyl}amino)-N,N-dimethylacetamide | 15 | ++ | + | ++ | + | + | ++ | ++ | + | + | + | +++ |
| N-2-({[3-(2-methylpyrrolidin-2-yl)methyl][(2S)-1-benzylpyrrolidin-2-yl)methyl][(cyclopropyl)methyl]amine | 16 | + | + | ++ | + | ++ | + | + | + | ++ | + | ++ |
| benzyl(methyl){3-[(4-{(methylamino)methyl]pyridin-2-yl}methyl)amino]propyl}amine | 17 | ++ | + | +++ | + | + | ++ | ++ | ++ | + | + | +++ |
| benzyl{3-({[4-({[2-(dimethylamino)ethyl]amino}methyl)pyridin-2-yl]methyl}amino)propyl}methylamine | 18 | + | + | | + | + | + | + | + | + | + | ++ |
| benzyl(3-{[(4-{[(2-methoxyethyl)amino]methyl}pyridin-2-yl)methyl]amino}propyl)methylamine | 19 | + | + | + | + | + | +++ | + | + | + | + | ++ |
| 2-[(4-{(cyclopropyl)amino]methyl]pyridin-2-yl}methyl)amino]-N-{1-[(2-methoxyphenyl)methyl]piperidin-4-yl}acetamide | 20 | ++ | + | +++ | + | + | +++ | +++ | + | +++ | + | +++ |
| 2-cyclopropyl-2-({[2-({[2-(dimethylamino)ethyl]amino}methyl)pyridin-4-yl]methyl}amino)acetonitrile | 21 | + | + | + | + | + | + | + | + | + | + | + |
| 2-({[3-(dimethylamino)propyl]amino}methyl)pyridin-4-yl]methyl]aminopropanenitrile | 22 | + | + | +++ | + | + | ++ | + | + | + | + | ++ |
| 2-({2-[({4-[benzyl(cyclopropyl)amino]butyl]amino}methyl)pyridin-4-yl]methyl}amino)acetonitrile | 23 | ++ | + | +++ | + | + | +++ | +++ | + | +++ | + | +++ |
| 2-[(2-{[3-(dimethylamino)propyl]amino}methyl)pyridin-4-yl]methyl](ethyl)carbamoyl]methylamino}acetonitrile | 24 | + | + | ++ | + | + | ++ | + | + | + | + | ++ |
| N-{[2-({[2-(dimethylamino)ethyl](ethyl)carbamoyl]methyl)ami- | 25 | + | + | + | + | + | + | + | + | + | + | ++ |

-continued

| | | | | | HDME INHIBITION | | | | | | |
|---|---|---|---|---|---|---|---|---|---|---|---|
| Compound # | Compound Name | KDM4C | KDM2B | KDM5C | KDM3A | KDM3B | KDM4A | KDM4B | KDM6B | PHF8 | KDM6A | KDM5B |
| 26 | no]methyl}pyridin-4-yl)methyl]-2,2,2-trifluoroacetamide | + | | | | | | | | | | + |
| 27 | N-[(2-{[N-({[2-(dimethylamino)ethyl][(ethyl)carbamoyl]}methyl)-2,2,2-trifluoroacetamido]methyl}pyridin-4-yl)methyl]-2,2,2-trifluoroacetamide | + | + | | | | | | | + | + | +++ |
| 28 | ({[2-({[4-(diethylamino)butyl]amino}methyl)pyridin-4-yl]methyl}carbamoyl)formic acid | + | | | | | | | | | | ++ |
| 29 | tert-butyl ({[2-({[4-(diethylamino)butyl]amino}methyl)pyridin-4-yl]methyl}carbamoyl)formate | + | | | | | | | | | | ++ |
| 30 | ethyl 2-({[(2-{[(dimethylamino)ethyl](ethyl)carbamoyl]methyl}amino)methyl]pyridin-4-yl)methyl]carbamoyl}oxy)benzoate | + | + | | | | | | | | + | ++ |
| 31 | N-[(2-{[([2-(azetidin-1-yl)ethyl](ethyl)carbamoyl}methyl)amino]methyl}pyridin-4-yl)methyl]-2,2,2-trifluoroacetamide | + | + | | | | | | | | + | ++ |
| 32 | N-[(2-{[([2-(dimethylamino)ethyl](ethyl)carbamoyl]methyl)amino]methyl}pyridin-4-yl)methyl]-2,2,3,3,4,4,4-heptafluorobutanamide | + | + | | | | | | | | | +++ |
| 33 | N-[(2-{[([2-(dimethylamino)ethyl](ethyl)carbamoyl]methyl)amino]methyl}pyridin-4-yl)methyl]-2,2-difluorobutanamide | +++ | ++ | +++ | + | + | +++ | + | + | + | + | +++ |
| 34 | 2-({4-[N-cyclopropyl(carboximidoyl)]pyridin-2-yl]methyl}amino)-N,N-dimethylacetamide | ++ | + | +++ | + | + | + | +++ | + | + | + | +++ |
| 35 | N,N-dimethyl-2-[(4-{[(3-phenylpropyl)imino]methyl}pyridin-2-yl)methyl]amino]acetamide | ++ | ++ | +++ | + | + | +++ | +++ | + | +++ | + | ++ |
| 36 | N,N-dimethyl-2-[(4-[N-(2-methylcyclopropyl)carboximidoyl]pyridin-2-yl)methyl]amino]acetamide | ++ | + | +++ | + | + | ++ | +++ | + | ++ | + | +++ |
| 37 | 2-[(4-{[(2-cyclohexylethyl)imino]methyl}pyridin-2-yl)methyl]amino-N,N-dimethylacetamide | + | + | +++ | + | + | + | ++ | + | + | + | +++ |
| 38 | [3-(dimethylamino)propyl]{(4-[{[3-(dimethylamino)propyl]imino}methyl]pyridin-2-yl}methyl)amine | ++ | + | +++ | + | + | ++ | + | + | + | + | +++ |
| 39 | ({4-[[[2-(dimethylamino)ethyl]imino]methyl]pyridin-2-yl}methyl)[3-(dimethylamino)propyl]amine | ++ | ++ | +++ | + | + | + | +++ | + | +++ | + | ++ |
| 40 | N-{[2-({[2-(ethylsulfanyl)ethyl]amino}methyl)pyridin-4-yl]methylidene}cyclopropanamine | + | + | +++ | | | + | ++ | ++ | + | + | +++ |
| 41 | N-{[2-({[2-(1-methylpyrrolidin-2-yl)ethyl]amino}methyl)pyridin-4-yl]methylidene}cyclopropanamine | ++ | + | | | | +++ | +++ | + | +++ | + | +++ |
| 42 | N-{[2-({[3-benzyl(methyl)amino]propyl}amino)methyl]pyridin-4-yl]methylidene}cyclopropanamine | + | + | +++ | | | + | +++ | + | + | + | +++ |
| 43 | N-{[2-({[3-(pyrrolidin-1-yl)propyl]amino}methyl)pyridin-4-yl]methylidene}cyclopropanamine | +++ | + | +++ | | | ++ | +++ | + | ++ | + | +++ |
| 44 | N-{[2-({[(2E)-4-(dimethylamino)but-2-en-1-yl]amino}methyl)pyridin-4-yl]methylidene}cyclopropanamine | +++ | + | +++ | | | + | +++ | + | + | + | +++ |
| 45 | N-{[2-({[4-(azetidin-1-yl)butyl]amino}methyl)pyridin-4-yl]methylidene}cyclopropanamine | + | + | +++ | | | + | + | + | + | + | +++ |
| 46 | N-{[2-({[4-(dimethylamino)butyl](methyl)amino}methyl)pyridin-4-yl]methylidene}cyclopropanamine | + | + | +++ | | | ++ | ++ | + | + | + | ++ |
| 47 | N-{[2-({[4-(dimethylamino)butyl]amino}methyl)pyridin-4-yl]methylidene}cyclohexyl)methyl]amino]pyridin-4-yl)methylidene}cyclopropanamine | ++ | + | +++ | | | ++ | ++ | + | + | + | +++ |
| 48 | 2-[({4-[N-cyclopropyl(carboximidoyl)]pyridin-2-yl}methyl)amino]-N-[4-(diethylamino)butyl]acetamide | ++ | + | +++ | + | + | +++ | +++ | + | +++ | + | +++ |

-continued

| | | | | | HDME INHIBITION | | | | | | | |
|---|---|---|---|---|---|---|---|---|---|---|---|---|
| Compound Name | Compound # | KDM4C | KDM2B | KDM5C | KDM3A | KDM3B | KDM4A | KDM4B | KDM6B | PHF8 | KDM6A | KDM5B |
| 2-[({4-[N-cyclopropylcarboximidoyl]pyridin-2-yl}methyl)amino]-1-[(2R)-2-(pyrrolidin-1-yl)methyl]pyrrolidin-1-yl]ethan-1-one | 49 | ++ | + | +++ | + | + | +++ | +++ | + | ++ | + | +++ |
| N-(2-cyanoethyl)-2-[({4-[N-cyclopropylcarboximidoyl]pyridin-2-yl}methyl)amino]-N-ethylacetamide | 50 | ++ | ++ | +++ | + | + | +++ | +++ | + | +++ | + | +++ |
| 2-[({4-[N-cyclopropylcarboximidoyl]pyridin-2-yl}methyl)amino]-N-(1-ethylpyrrolidin-2-yl)methyl]acetamide | 51 | + | + | +++ | + | + | ++ | +++ | + | ++ | + | +++ |
| 2-[({4-[N-cyclopropylcarboximidoyl]pyridin-2-yl}methyl)amino]-N-methyl-N-[3-(1H-pyrazol-1-yl)propyl]acetamide | 52 | ++ | ++ | +++ | + | + | ++ | +++ | + | | + | +++ |
| N-(1-benzylpyrrolidin-3-yl)-2-[({4-[N-cyclopropylcarboximidoyl]pyridin-2-yl}methyl)amino]acetamide | 53 | ++ | ++ | +++ | ++ | ++ | +++ | +++ | ++ | +++ | + | +++ |
| 2-[({4-[N-cyclopropylcarboximidoyl]pyridin-2-yl}methyl)amino]-1-(4-methylpiperazin-1-yl)ethan-1-one | 54 | ++ | + | +++ | + | + | ++ | ++ | + | + | + | +++ |
| 1-(4-benzylpiperidin-1-yl)-2-[({4-[N-cyclopropylcarboximidoyl]pyridin-2-yl}methyl)amino]ethan-1-one | 55 | ++ | + | ++ | + | + | ++ | +++ | + | ++ | + | ++ |
| 2-[({4-[N-cyclopropylcarboximidoyl]pyridin-2-yl}methyl)amino]-N-methyl-N-(prop-2-yn-1-yl)acetamide | 56 | + | + | +++ | + | + | ++ | ++ | + | + | + | ++ |
| 2-[({4-[[(2-cyclohexylethyl)imino]methyl]pyridin-2-yl}methyl)amino]-N,N-diethylacetamide | 57 | ++ | ++ | +++ | + | + | ++ | +++ | + | + | + | +++ |
| N,N-diethyl-2-[({4-[N-(octylimino)methyl]pyridin-2-yl}methyl)amino]acetamide | 58 | ++ | ++ | +++ | + | + | ++ | + | ++ | ++ | + | +++ |
| methyl 2-[({4-[N-cyclopropylcarboximidoyl]pyridin-2-yl}methyl)amino]acetate | 59 | ++ | + | +++ | + | + | ++ | +++ | + | + | + | +++ |
| [4-(diethylamino)butyl]({4-[[(2-methoxyethyl)imino]methyl]pyridin-2-yl})amine | 60 | + | + | +++ | + | + | + | +++ | + | ++ | + | +++ |
| 2-[{2-({[4-(diethylamino)butyl]amino}methyl)pyridin-4-yl]methylidene}amino]ethan-1-ol | 61 | ++ | + | +++ | + | + | +++ | +++ | + | + | + | +++ |
| {2-({[4-(diethylamino)butyl]amino}methyl)pyridin-4-yl]methylidene}(2,2,3,3,3-pentafluoropropyl)amine | 62 | + | + | +++ | + | + | + | ++ | + | + | + | +++ |
| 2-[({4-[[(2-cyclohexylethyl)imino]methyl]pyridin-2-yl}methyl)amino]-N-[2-(dimethylamino)ethyl]-N-ethylacetamide | 63 | +++ | ++ | +++ | + | + | + | ++ | + | + | + | +++ |
| [3-(dimethylamino)propyl]({4-[(methoxyimino)methyl]pyridin-2-yl})methyl]amine | 64 | + | + | + | + | + | ++ | +++ | + | + | + | +++ |
| [4-(diethylamino)butyl]({[4-(1-methylimidazolidin-2-yl)pyridin-2-yl]methyl})amine | 65 | ++ | + | +++ | + | + | + | + | ++ | ++ | + | +++ |
| N-[2-(dimethylamino)ethyl]-N-ethyl-2-[({4-[((2-hydroxyethyl)imino]methyl]pyridin-2-yl}methyl)amino]acetamide | 66 | +++ | + | +++ | + | + | +++ | +++ | + | ++ | + | +++ |
| (2-cyclohexylethyl)({2-({[4-(diethylamino)butyl]amino}methyl)pyridin-4-yl]methylidene})amine | 67 | ++ | + | +++ | + | + | + | + | + | + | + | +++ |
| 2-({[4-(diethylamino)butyl]({[4-(1-methyl-1,3-diazinan-2-yl)pyridin-2-yl]methyl})amine | 68 | ++ | | | | | | | | | + | +++ |
| N,N-diethyl-2-[({4-[[2-(4-methylphenyl)ethyl]imino}methyl]pyridin-2-yl}methyl)amino]acetamide | 69 | ++ | + | | | | | | | | + | +++ |
| 4-[2-[{[4-(diethylamino)butyl]amino}methyl]pyridin-4-yl]methylidene]hydrazin-1-yl]benzonitrile | 70 | + | | | | | | | | | + | ++ |
| 3-[({[4-(diethylamino)butyl]amino}methyl)pyridin-4-yl]methylidene}amino]propan-1-ol | 71 | + | | | | | | | | | + | +++ |
| [4-(diethylamino)butyl]({[4-{7-oxa-9-azaspiro[4.5]decan-8-yl}pyridin-2-yl]methyl})amine | 72 | + | | | | | | | | | + | ++ |
| 2-[{[2-({[4-(diethylamino)butyl]amino}methyl)pyridin-4-yl]methyl})amine | 73 | + | | | | | | | | | + | +++ |

-continued

| Compound # | Compound Name | HDME INHIBITION | | | | | | | | | | |
|---|---|---|---|---|---|---|---|---|---|---|---|---|
| | | KDM4C | KDM2B | KDM5C | KDM3A | KDM3B | KDM4A | KDM4B | KDM6B | PHF8 | KDM6A | KDM5B |
| 74 | 1-[[2-({[4-(diethylamino)butyl]amino}methyl)pyridin-4-yl]methylidene]amino]propan-1-ol | | | | | | | | | | | ++ |
| 75 | 1-[{2-({[4-(diethylamino)butyl]amino}methyl)pyridin-4-yl]methylidene}amino]propan-2-ol | + | | | | | | | | | | ++ |
| 76 | 2-[{2-({[4-(diethylamino)butyl]amino}methyl)pyridin-4-yl]methylidene}amino]-2-phenylethan-1-ol | + | + | | | | | | | | | ++ |
| 77 | 3-[{[2-({[4-(diethylamino)butyl]amino}methyl)pyridin-4-yl]methylidene}amino]-2,2-dimethylpropan-1-ol | + | + | | | | | | | | | ++ |
| 78 | (1-{[{2-({[4-(diethylamino)butyl]amino}methyl)pyridin-4-yl]methylidene}amino]methyl}cyclopropyl)methanol | ++ | + | | | | | | | | | +++ |
| 79 | N-[2-(dimethylamino)ethyl]-N-ethyl-2-[({4-[[(3-hydroxypropyl)imino]methyl]pyridin-2-yl}methyl)amino]acetamide | ++ | + | | | | | | | | | +++ |
| 80 | N-ethyl-2-[({4-[[(2-hydroxyethyl)imino]methyl]pyridin-2-yl}methyl)amino]-N-(1-methylpyrrolidin-2-yl)methyl]acetamide | +++ | ++ | | | | | | | | | +++ |
| 81 | 2-[{[2-({[4-(diethylamino)butyl]amino}methyl)pyridin-4-yl]methylidene}amino]-3-phenylpropan-1-ol | ++ | + | | | | | | | | | +++ |
| 82 | 2-({4-[[(2-cyclohexyl-3-hydroxypropyl)imino]methyl]pyridin-2-yl}methyl)amino]-N-[2-(dimethylamino)ethyl]-N-ethylacetamide | + | + | | | | | | | | | + |
| 83 | N-[3-(dimethylamino)propyl]-N-ethyl-2-[({4-[[(2-hydroxyethyl)imino]methyl]pyridin-2-yl}methyl)amino]acetamide | ++ | + | | | | | | | | | +++ |
| 84 | N-[2-(dimethylamino)ethyl]-N-ethyl-2-[({4-[[(2-hydroxyethyl)imino]methyl]pyridin-2-yl}methyl)amino]acetamide | + | + | | | | | | | | | ++ |
| 85 | 1-[{2-({[4-(diethylamino)butyl]amino}methyl)pyridin-4-yl]methylidene}amino]-3-phenylpropan-2-ol | +++ | + | | | | | | | | | +++ |
| 86 | N-[(1S,2S)-2-(dimethylamino)cyclo-pentyl]methyl]-N-ethyl-2-E({4-[[(2-hydroxyethyl)imino]methyl]pyridin-2-yl}methyl)amino]acetamide | | + | | | | | | | | + | +++ |
| 87 | 2-[({4-[[(3-dimethylamino)-2-hydroxypropyl)imino]methyl]pyridin-2-yl}methyl)amino]-N-[2-(dimethylamino)ethyl]-N-ethylacetamide | ++ | + | | | | | | | | + | +++ |
| 88 | 2-({4-[(5,5-dimethyl-1,3-oxazinan-2-yl)pyridin-2-yl]methyl}amino)-N-[2-(dimethylamino)ethyl]-N-ethylacetamide | ++ | + | | | | | | | + | + | +++ |
| 89 | 2-({4-[[(2-benzyl-3-hydroxypropyl)imino]methyl]pyridin-2-yl}methyl)amino]-N-[2-(dimethylamino)ethyl]-N-ethylacetamide | ++ | + | | | | | | | + | + | +++ |
| 90 | 2-({4-[5-benzyl-3-(trifluoroacetyl)-1,3-oxazinan-2-yl]pyridin-2-yl}methyl)amino]-N-[2-(dimethylamino)ethyl]-N-ethylacetamide | ++ | + | | | | | | | + | + | +++ |
| 91 | N-[2-(dimethylamino)ethyl]-N-ethyl-2-[({4-[7-(trifluoroacetyl)-5-oxa-7-azaspiro[2.5]octan-6-yl]pyridin-2-yl}methyl)amino]acetamide | + | + | | | | | | | + | + | +++ |
| 92 | 2-[({4-[[(2-fluorophenyl)methyl]-2-[({4-[[(2-hydroxyethyl)imino]methyl]pyridin-2-yl}methyl)amino]-N-methylacetamide | ++ | + | | | | | | | + | + | ++ |
| 93 | 2-[({2-[[(2-(benzyloxy)phenyl]ethyl}amino)methyl]pyridin-4-yl]methylidene}amino]ethan-1-ol | + | + | | | | | | | + | + | + |
| 94 | N-(2-cyanoethyl)-N-ethyl-2-[({4-[[(2-hydroxyethyl)imino]methyl]pyridin-2-yl}methyl)amino]acetamide | ++ | ++ | | | | | | | ++ | + | +++ |
| 95 | (2S)-2-[({4-[[(2-hydroxyethyl)imino]methyl]pyridin-2-yl}methyl]amino]-4-methyl-1-(piperidin-1-yl)pentan-1-one | + | + | | | | | | | | + | + |
| 97 | 2-[{({4-[[(dimethylamino)methyl]cyclohexyl}methyl)amino]methyl}pyridine-4-carbaldehyde | + | + | | + | | + | | | | + | ++ |

-continued

| | | | | HDME INHIBITION | | | | | | | | |
|---|---|---|---|---|---|---|---|---|---|---|---|---|
| Compound Name | Compound # | KDM4C | KDM2B | KDM5C | KDM3A | KDM3B | KDM4A | KDM4B | KDM6B | PHF8 | KDM6A | KDM5B |
| 2-({[(2E)-4-(dimethylamino)but-2-en-1-yl]amino}methyl)pyridine-4-carbaldehyde | 98 | ++ | + | +++ | + | + | + | + | + | + | + | +++ |
| 2-({[(2Z)-4-(dimethylamino)but-2-en-1-yl]amino}methyl)pyridine-4-carbaldehyde | 99 | + | + | +++ | + | + | + | + | + | + | + | +++ |
| 2-({[(1-methylpiperidin-4-yl)methyl]amino}methyl)pyridine-4-carbaldehyde | 100 | + | + | +++ | + | + | +++ | +++ | + | + | + | +++ |
| N-[2-(dimethylamino)ethyl]-N-ethyl-2-{[(4-formylpyridin-2-yl)methyl]amino}acetamide | 101 | +++ | + | +++ | + | + | + | ++ | + | ++ | + | +++ |
| 2-[(2-oxo-2-(2R)-2-(pyrrolidin-1-ylmethyl)pyrrolidin-1-yl]ethyl}amino)methyl]pyridine-4-carbaldehyde | 102 | +++ | + | +++ | + | + | + | ++ | + | + | + | ++ |
| 2-({[2-(4-methylpiperazin-1-yl)-2-oxoethyl]amino}methyl)pyridine-4-carbaldehyde | 103 | + | + | +++ | + | + | + | + | + | + | + | ++ |
| N-[(1-ethylpyrrolidin-2-yl)methyl]-2-{[(4-formylpyridin-2-yl)methyl]amino}acetamide | 104 | ++ | + | +++ | + | + | + | +++ | + | ++ | + | +++ |
| N,N-diethyl-2-{[(4-formylpyridin-2-yl)methyl]amino}acetamide | 105 | + | + |  | + | + | + | +++ | + | + | + | ++ |
| 2-({[2-(4-benzylpiperidin-1-yl)-2-oxoethyl]amino}methyl)pyridine-4-carbaldehyde | 106 | ++ | + | + | + | + | ++ | +++ | + | ++ | + | +++ |
| 2-({[4-(diethylamino)butyl]amino}methyl)pyridine-4-carbaldehyde | 107 | + | + | +++ | + | + | + | +++ | + | + | + | +++ |
| 2-({[4-(dimethylamino)butyl]amino}methyl)pyridine-4-carbaldehyde | 108 | + | + | +++ | + | + | + | +++ | + | + | + | ++ |
| 2-({[4-[benzyl(cyclopropyl)amino]butyl}amino]methyl)pyridine-4-carbaldehyde | 109 | ++ | + | +++ | + | + | + | +++ | + | + | + | +++ |
| 2-({[2-(dimethylamino)ethyl]amino}methyl)pyridine-4-carbaldehyde | 110 | + | + | +++ | + | + | ++ |  | + | + | + | ++ |
| 2-({[3-(pyrrolidin-1-yl)propyl]amino}methyl)pyridine-4-carbaldehyde | 111 | + | + | +++ | + | + | + | ++ | + | + | + | +++ |
| N-[4-(diethylamino)butyl]-2-{[(4-formylpyridin-2-yl)methyl]amino}acetamide | 112 | ++ | + | +++ | + | + | +++ | +++ | + | +++ | + |  |
| N-(1-benzylpyrrolidin-3-yl)-2-{[(4-formylpyridin-2-yl)methyl]amino}acetamide | 113 | ++ |  | ++ | + | + | ++ | +++ | + | + | + | +++ |
| 2-({[5-(dimethylamino)pentyl]amino}methyl)pyridine-4-carbaldehyde | 114 | ++ | + | +++ | + | + | + | ++ | + | + | + | +++ |
| N-[4-(diethylamino)butyl]-2,2,2-trifluoro-N-[(4-formylpyridin-2-yl)methyl]acetamide | 115 | + |  | +++ | + | + | ++ |  | + | ++ | + | + |
| N-[2-(diethylamino)ethyl]-N-ethyl-2-{[(4-formylpyridin-2-yl)methyl]amino}acetamide | 116 | +++ |  |  |  |  |  |  | + |  | + | +++ |
| 2-{[[3-(dimethylamino)cyclopentyl]methyl]amino}methyl)pyridine-4-carbaldehyde | 117 | ++ |  |  |  |  |  |  |  |  | + | +++ |
| N-[2-(dimethylamino)-2-methylpropyl]-N-ethyl-2-{[(4-formylpyridin-2-yl)methyl]amino}acetamide | 118 | +++ | + |  |  |  |  |  | ++ | ++ | + | +++ |
| N-ethyl-2-{[(4-formylpyridin-2-yl)methyl]amino}-N-[(1-methylpyrrolidin-2-yl)methyl]acetamide | 119 | + |  |  |  |  |  |  |  |  | + | +++ |
| 2-({methyl[2-oxo-2-(piperidin-1-yl)ethyl]amino}methyl)pyridine-4-carbaldehyde | 120 | + | + |  |  |  |  |  |  | ++ | + | + |

(a) +++: IC$_{50}$ < 250 nM; ++: 250 nM ≤ IC$_{50}$ ≤ 2500 nM; +: IC$_{50}$ > 2500 nM

Example 3

Cell Assays for IC50 Value Determination

Histone Lysine Demethylase Immunofluorescence Assays for IC50 value Determination, non-transfected cells This example demonstrates the ability of compounds of the invention to inhibit demethylation of a specific histone lysine mark in a human osteosarcoma cancer cell line.

General Method

U2OS cells were harvested and seeded into multi well plates into media containing compound. The media used was DMEM containing 5% FBS and pen/strep. 20 hours after incubation of cells with compounds, the cells were washed once in PBS, harvested by fixation with formaldehyde 4% aqueous solution, and washed in PBS. Subsequently, the cells were permeabilized in PBS with 0.2% Triton X-100. Blocking was performed in PBS with 0.2% Triton X-100 and 5% FBS. The cells were incubated with αH3K4me3 primary antibody (Cell Signaling, #9751S) in blocking solution over night at 4° C. After incubation with primary antibody, the cells were washed with PBS, incubated with secondary antibody (Alexa fluor 594 goat anti rabbit IgG, Invitrogen, A11012) and Hoechst, (Sigma, 33342) in blocking solution, and washed again with PBS. Finally, PBS was added and high throughput imaging and analysis were performed by an IN Cell Analyzer 1000 (GE Healthcare). The IC50 values were based on an average measure of the staining of the H3K4me3 mark in cells.

| Compound Name | Compound # | IC50 |
|---|---|---|
| N-{[2-({[4-(diethylamino)butyl]amino}methyl)pyridin-4-yl]methyl}-2,2,2-trifluoroacetamide | 1 | +++ |
| [2-({[3-(dimethylamino)propyl]amino}methyl)pyridin-4-yl]methanamine | 3 | +++ |
| 2-({[4-(aminomethyl)pyridin-2-yl]methyl}amino)-N-[2-(dimethylamino)ethyl]-N-ethylacetamide | 4 | +++ |
| N-[4-(diethylamino)butyl]-2,2,2-trifluoro-N-({4-[(trifluoroacetamido)methyl]pyridin-2-yl}methyl)acetamide | 6 | +++ |
| [2-({[4-(azetidin-1-yl)butyl]amino}methyl)pyridin-4-yl]methanamine | 7 | +++ |
| 2-({[4-(aminomethyl)pyridin-2-yl]methyl}amino)-N-{1-[(2-methoxyphenyl)methyl]piperidin-4-yl}acetamide | 9 | ++ |
| 2-{[(4-{[(cyanomethyl)amino]methyl}pyridin-2-yl)methyl]amino}-N,N-dimethylacetamide | 13 | ++ |
| 2-[({4-[(cyclopropylamino)methyl]pyridin-2-yl}methyl)amino]-N-{1-[(2-methoxyphenyl)methyl]piperidin-4-yl}acetamide | 20 | ++ |
| 2-({[2-({[3-(dimethylamino)propyl]amino}methyl)pyridin-4-yl]methyl}amino)propanenitrile | 22 | +++ |
| 2-[({2-[({4-[benzyl(cyclopropyl)amino]butyl}amino)methyl]pyridin-4-yl}methyl)amino]acetonitrile | 23 | +++ |
| 2-[2-({[3-(dimethylamino)propyl]amino}methyl)pyridin-4-yl]-2-(methylamino)acetonitrile | 24 | +++ |
| N-[(2-{[({[2-(dimethylamino)ethyl](ethyl)carbamoyl}methyl)amino]methyl}pyridin-4-yl)methyl]-2,2,2-trifluoroacetamide | 25 | +++ |
| ({[2-({[4-(diethylamino)butyl]amino}methyl)pyridin-4-yl]methyl}carbamoyl)formic acid | 27 | +++ |
| tert-butyl ({[2-({[4-(diethylamino)butyl]amino}methyl)pyridin-4-yl]methyl}carbamoyl)formate | 28 | ++ |
| N-[(2-{[({[2-(azetidin-1-yl)ethyl](ethyl)carbamoyl}methyl)amino]methyl}pyridin-4-yl)methyl]-2,2,2-trifluoroacetamide | 30 | +++ |
| N-[(2-{[({[2-(dimethylamino)ethyl](ethyl)carbamoyl}methyl)amino]methyl}pyridin-4-yl)methyl]-2,2-difluorobutanamide | 32 | + |
| 2-[({4-[(N-cyclopropylcarboximidoyl]pyridin-2-yl}methyl)amino]-N,N-dimethylacetamide | 33 | ++ |
| 2-[({4-[[(2-cyclohexylethyl)imino]methyl]pyridin-2-yl}methyl)amino]-N,N-dimethylacetamide | 36 | +++ |
| ({4-[{[2-(dimethylamino)ethyl]imino}methyl]pyridin-2-yl}methyl)[3-(dimethylamino)propyl]amine | 38 | +++ |
| N-{[2-({[2-(1-methylpyrrolidin-2-yl)ethyl]amino}methyl)pyridin-4-yl]methylidene}cyclopropanamine | 40 | +++ |
| N-{[2-({[(2E)-4-(dimethylamino)but-2-en-1-yl]amino}methyl)pyridin-4-yl]methylidene}cyclopropanamine | 43 | +++ |
| N-{[2-({[4-(azetidin-1-yl)butyl]amino}methyl)pyridin-4-yl]methylidene}cyclopropanamine | 44 | +++ |
| N-[(2-{[({4-[(dimethylamino)methyl]cyclohexyl}methyl)amino]methyl}pyridin-4-yl)methylidene]cyclopropanamine | 46 | +++ |
| 2-[({4-[[(2-cyclohexylethyl)imino]methyl]pyridin-2-yl}methyl)amino]-N,N-diethylacetamide | 57 | ++ |

-continued

| Compound Name | Compound # | IC50 |
|---|---|---|
| N,N-diethyl-2-[({4-[(octylimino)methyl]pyridin-2-yl}methyl)amino]acetamide | 58 | + |
| 2-[{[2-({[4-(diethylamino)butyl]amino}methyl)pyridin-4-yl]methylidene}amino]ethan-1-ol | 61 | +++ |
| {[2-({[4-(diethylamino)butyl]amino}methyl)pyridin-4-yl]methylidene}(2,2,3,3,3-pentafluoropropyl)amine | 62 | +++ |
| [3-(dimethylamino)propyl]({4-[(methoxyimino)methyl]pyridin-2-yl}methyl)amine | 64 | ++ |
| (2-cyclohexylethyl)({[2-({[4-(diethylamino)butyl]amino}methyl)pyridin-4-yl]methylidene})amine | 67 | +++ |
| [4-(diethylamino)butyl]({[4-(1-methyl-1,3-diazinan-2-yl)pyridin-2-yl]methyl})amine | 68 | +++ |
| 4-[2-{[2-({[4-(diethylamino)butyl]amino}methyl)pyridin-4-yl]methylidene}hydrazin-1-yl]benzonitrile | 70 | ++ |
| 1-[{[2-({[4-(diethylamino)butyl]amino}methyl)pyridin-4-yl]methylidene}amino]propan-2-ol | 74 | +++ |
| (1-{[{[2-({[4-(diethylamino)butyl]amino}methyl)pyridin-4-yl]methylidene}amino]methyl}cyclopropyl)methanol | 77 | +++ |
| N-ethyl-2-[({4-[[(2-hydroxyethyl)imino]methyl]pyridin-2-yl}methyl)amino]-N-[(1-methylpyrrolidin-2-yl)methyl]acetamide | 79 | +++ |
| N-[3-(dimethylamino)propyl]-N-ethyl-2-[({4-[[(2-hydroxyethyl)imino]methyl]pyridin-2-yl}methyl)amino]acetamide | 82 | +++ |
| N-[2-(dimethylamino)propyl]-N-ethyl-2-[({4-[[(2-hydroxyethyl)imino]methyl]pyridin-2-yl}methyl)amino]acetamide | 83 | +++ |
| N-{[(1S,2S)-2-(dimethylamino)cyclopentyl]methyl}-N-ethyl-2-[({4-[[(2-hydroxyethyl)imino]methyl]pyridin-2-yl}methyl)amino]acetamide | 85 | +++ |
| N-[2-(dimethylamino)ethyl]-N-ethyl-2-[({4-[({[1-(hydroxymethyl)cyclopropyl]methyl}imino)methyl]pyridin-2-yl}methyl)amino]acetamide | 88 | +++ |
| 2-[({4-[5-benzyl-3-(trifluoroacetyl)-1,3-oxazinan-2-yl]pyridin-2-yl}methyl)amino]-N-[2-(dimethylamino)ethyl]-N-ethylacetamide | 90 | +++ |
| N-[2-(dimethylamino)ethyl]-N-ethyl-2-[({4-[7-(trifluoroacetyl)-5-oxa-7-azaspiro[2.5]octan-6-yl]pyridin-2-yl}methyl)amino]acetamide | 91 | +++ |
| 2-{[({4-[(dimethylamino)methyl]cyclohexyl}methyl)amino]methyl}pyridine-4-carbaldehyde | 97 | +++ |
| 2-({[(2Z)-4-(dimethylamino)but-2-en-1-yl]amino}methyl)pyridine-4-carbaldehyde | 99 | ++ |
| 2-({[(1-methylpiperidin-4-yl)methyl]amino}methyl)pyridine-4-carbaldehyde | 100 | +++ |
| N-[2-(dimethylamino)ethyl]-N-ethyl-2-{[(4-formylpyridin-2-yl)methyl]amino}acetamide | 101 | +++ |
| 2-({[4-(diethylamino)butyl]amino}methyl)pyridine-4-carbaldehyde | 107 | +++ |
| 2-({[3-(pyrrolidin-1-yl)propyl]amino}methyl)pyridine-4-carbaldehyde | 111 | +++ |
| N-[4-(diethylamino)butyl]-2,2,2-trifluoro-N-[(4-formylpyridin-2-yl)methyl]acetamide | 115 | +++ |
| N-[2-(diethylamino)ethyl]-N-ethyl-2-{[(4-formylpyridin-2-yl)methyl]amino}acetamide | 116 | +++ |
| N-[2-(dimethylamino)-2-methylpropyl]-N-ethyl-2-{[(4-formylpyridin-2-yl)methyl]amino}acetamide | 118 | +++ |
| N-ethyl-2-{[(4-formylpyridin-2-yl)methyl]amino}-N-[(1-methylpyrrolidin-2-yl)methyl]acetamide | 119 | +++ |

(a) +++: $IC_{50}$ < 250 nM; ++: 250 nM ≤ $IC_{50}$ ≤ 2500 nM; +: $IC_{50}$ > 2500 nM

Example 4

Histone Lysine Demethylase Immunofluorescence Assays for IC50 Value Determination This example demonstrates the ability of the compounds of the invention to inhibit specific histone lysine demethylases expressed in a human osteosarcoma cell line.

General Method

U2OS cells were seeded 24 hours before transfection. Transfection was performed with Fugene HD transfection reagent as recommended by the manufacturer. 6 hours after transfection, the cells were harvested and seeded into multi well plates into media containing compound. The media used was DMEM containing 10% FBS and pen/strep. 20 hours after incubation of cells with compounds, the cells were washed in PBS, harvested by fixation with formaldehyde 4% aqueous solution, and washed in PBS. Subsequently, the cells were permeabilized in PBS with 0.2% Triton X-100 for. Blocking was performed in PBS with 0.2% Triton X-100 and 5% FBS. The cells were incubated with primary antibodies in blocking solution over night at 4° C. The primary antibodies used in the assays were HA.11 (Covance, MMS-101P) and the antibody detecting the mark specified in the table below. After incubation with primary antibodies, the cells were washed with PBS, incubated with secondary antibodies (Alexa fluor 594 goat anti rabbit IgG, Invitrogen, A11012; Alexa flour 488 donkey anti mouse IgG, Invitrogen, A21202) and Hoechst, (Sigma, 33342) in blocking solution, and washed again with PBS. Finally, PBS was added and high throughput imaging and analysis were performed by an IN Cell Analyzer 1000 (GE Healthcare). The robot software analyzed individual cells and divided these into HA+ (transfected cells) and HA− (non-transfected cells). The IC50 values were based on an average measure of the staining of the mark specified in the table below in the transfected cells.

| Construct name | Vendor/source | Sequence | Mark detected | Primary antibody used for detection of mark | mRNA NCBI ID |
|---|---|---|---|---|---|
| pCMVHA KDM2A | Kazusa | Full length | H3K36me2 | Milipore 7369-1 | NM_012308 |
| pCMVHA KDM4A | BRIC | Full length | H3K9me3 | Abeam Ab8898 | NM_015061 |
| pCMVHA KDM4C | BRIC | Full length | H3K9me3 | Abeam Ab8898 | NM_014663 |
| pCMVHA KDM5B | BRIC | Fragment (a.a. 1-752) | H3K4me2 | Millipore 07-030 | NM_006618 |
| pCMVHA KDM6B | BRIC | Fragment (a.a. 1026-1682) | H3K27me2 | Abcam Ab24684 | NM_001080424 |

HDME INHIBITION

| Compound Name | Compound # | KDM4C | KDM4A | KDM6B | KDM5B | KDM2A |
|---|---|---|---|---|---|---|
| N-{2-({[4-(diethylamino)butyl]amino}methyl)pyridin-4-yl]methyl}-2,2,2-trifluoroacetamide | 1 | ++ | | | +++ | |
| [2-({[4-(dimethylamino)butyl]amino}methyl)pyridin-4-yl]methanamine | 2 | ++ | | | +++ | |
| [2-({[3-(dimethylamino)propyl]amino}methyl)pyridin-4-yl]methanamine | 3 | + | | | +++ | |
| 2-({[4-(aminomethyl)pyridin-2-yl]methyl}amino)-N-[2-(dimethylamino)ethyl]-N-ethylacetamide | 4 | ++ | | + | +++ | |
| [2-({[4-(diethylamino)butyl]amino}methyl)pyridin-4-yl]methanamine | 5 | ++ | | | +++ | |
| N-[4-(diethylamino)butyl]-2,2,2-trifluoro-N-({4-[(trifluoroacetamido)methyl]pyridin-2-yl}methyl)acetamide | 6 | + | | | +++ | |
| [2-({[4-(azetidin-1-yl)butyl]amino}methyl)pyridin-4-yl]methanamine | 7 | + | | | +++ | |
| [2-({[5-(dimethylamino)pentyl]amino}methyl)pyridin-4-yl]methanamine | 8 | ++ | | | +++ | |
| 2-({[4-(aminomethyl)pyridin-2-yl]methyl}amino)-N-{1-[(2-methoxyphenyl)methyl]piperidin-4-yl}acetamide | 9 | + | + | | ++ | |
| N-{2-({[4-(dimethylamino)butyl]amino}methyl)pyridin-4-yl]methyl}cyclopropanamine | 10 | + | | | + | |
| N-{2-({[3-(2-methylpiperidin-1-yl)propyl]amino}methyl)pyridin-4-yl]methyl}cyclopropanamine | 11 | + | | | + | |
| N-({2-[(propylamino)methyl]pyridin-4-yl}methyl)cyclopropanamine | 12 | + | | | + | |
| 2-{[(4-{[(cyanomethyl)amino]methyl}pyridin-2-yl)methyl]amino}-N,N-dimethylacetamide | 13 | ++ | ++ | | ++ | |

-continued

| | | HDME INHIBITION | | | | |
|---|---|---|---|---|---|---|
| Compound Name | Compound # | KDM4C | KDM4A | KDM6B | KDM5B | KDM2A |
| 2-{[(4-{[(2-fluoroethyl)amino]methyl}pyridin-2-yl)methyl]amino}-N,N-dimethylacetamide | 14 | + | | | + | |
| 2-({4-({[2-(dimethylamino)ethyl]amino}methyl)pyridin-2-yl]methyl}amino)-N,N-dimethylacetamide | 15 | + | + | | ++ | |
| {[(2S)-1-benzylpyrrolidin-2-yl]methyl}[(4-{[(cyclopropylmethyl)amino]methyl}pyridin-2-yl)methyl]amine | 16 | | | | + | |
| benzyl(methyl){3-[({4-[(methylamino)methyl]pyridin-2-yl}methyl)amino]propyl}amine | 17 | + | | | + | |
| benzyl(3-{[(4-{[(2-methoxyethyl)amino]methyl}pyridin-2-yl)methyl]amino}propyl)methylamine | 19 | + | | | + | |
| 2-[({4-[(cyclopropylamino)methyl]pyridin-2-yl}methyl)amino]-N-{1-[(2-methoxyphenyl)methyl]piperidin-4-yl}acetamide | 20 | + | + | | ++ | |
| 2-cyclopropyl-2-({[2-({[2-(dimethylamino)ethyl]amino}methyl)pyridin-4-yl]methyl}amino)acetonitrile | 21 | + | | | ++ | |
| 2-({[2-({[3-(dimethylamino)propyl]amino}methyl)pyridin-4-yl]methyl}amino)propanenitrile | 22 | + | | | +++ | |
| 2-[({2-[({4-[benzyl(cyclopropyl)amino]butyl}amino)methyl]pyridin-4-yl}methyl)amino]acetonitrile | 23 | + | | | ++ | |
| 2-[2-({[3-(dimethylamino)propyl]amino}methyl)pyridin-4-yl]-2-(methylamino)acetonitrile | 24 | + | | + | +++ | |
| N-[(2-{[({[2-(dimethylamino)ethyl](ethyl)carbamoyl}methyl)amino]methyl}pyridin-4-yl)methyl]-2,2,2-trifluoroacetamide | 25 | | ++ | + | +++ | + |
| N-[(2-{[N-({[2-(dimethylamino)ethyl](ethyl)carbamoyl}methyl)-2,2,2-trifluoroacetamido]methyl}pyridin-4-yl)methyl]-2,2,2-trifluoroacetamide | 26 | ++ | | | +++ | |
| 2-[({4-[(N-cyclopropylcarboximidoyl]pyridin-2-yl}methyl)amino]-N,N-dimethylacetamide | 33 | ++ | | | ++ | |
| N,N-dimethyl-2-[({4-[[(3-phenylpropyl)imino]methyl]pyridin-2-yl}methyl)amino]acetamide | 34 | + | | | ++ | |
| N,N-dimethyl-2-[({4-[N-(2-methylcyclopropyl)carboximidoyl]pyridin-2-yl}methyl)amino]acetamide | 35 | ++ | | | ++ | |
| 2-[({4-[[(2-cyclohexylethyl)imino]methyl]pyridin-2-yl}methyl)amino]-N,N-dimethylacetamide | 36 | + | + | | ++ | |
| [3-(dimethylamino)propyl]({4-[{[3-(dimethylamino)propyl]imino}methyl]pyridin-2-yl}methyl)amine | 37 | ++ | | | +++ | |
| ({4-[{[2-(dimethylamino)ethyl]imino}methyl]pyridin-2-yl}methyl)[3-(dimethylamino)propyl]amine | 38 | + | | | +++ | |

-continued

| | | HDME INHIBITION | | | | |
|---|---|---|---|---|---|---|
| Compound Name | Compound # | KDM4C | KDM4A | KDM6B | KDM5B | KDM2A |
| N-{[2-({[2-(ethylsulfanyl)ethyl]amino}methyl)pyridin-4-yl]methylidene}cyclopropanamine | 39 | + | | | + | |
| N-{[2-({[2-(1-methylpyrrolidin-2-yl)ethyl]amino}methyl)pyridin-4-yl]methylidene}cyclopropanamine | 40 | ++ | | | +++ | |
| N-({2-[({3-[benzyl(methyl)amino]propyl}amino)methyl]pyridin-4-yl}methylidene)cyclopropanamine | 41 | ++ | + | | ++ | |
| N-{[2-({[3-(pyrrolidin-1-yl)propyl]amino}methyl)pyridin-4-yl]methylidene}cyclopropanamine | 42 | ++ | + | + | +++ | |
| N-{[2-({[(2E)-4-(dimethylamino)but-2-en-1-yl]amino}methyl)pyridin-4-yl]methylidene}cyclopropanamine | 43 | ++ | | | +++ | |
| N-{[2-({[4-(dimethylamino)butyl]amino}methyl)pyridin-4-yl]methylidene}cyclopropanamine | 45 | ++ | | | +++ | |
| N-[(2-{[({4-[(dimethylamino)methyl]cyclohexyl}methyl)amino]methyl}pyridin-4-yl)methylidene]cyclopropanamine | 46 | ++ | +++ | | +++ | |
| N-{[2-({[5-(dimethylamino)pentyl]amino}methyl)pyridin-4-yl]methylidene}cyclopropanamine | 47 | ++ | | | +++ | |
| 2-[({4-[N-cyclopropylcarboximidoyl]pyridin-2-yl}methyl)amino]-N-[4-(diethylamino)butyl]acetamide | 48 | + | | | + | |
| 2-[({4-[N-cyclopropylcarboximidoyl]pyridin-2-yl}methyl)amino]-1-[(2R)-2-(pyrrolidin-1-ylmethyl)pyrrolidin-1-yl]ethan-1-one | 49 | ++ | | | +++ | |
| N-(2-cyanoethyl)-2-[({4-[N-cyclopropylcarboximidoyl]pyridin-2-yl}methyl)amino]-N-ethylacetamide | 50 | + | | | ++ | |
| 2-[({4-[N-cyclopropylcarboximidoyl]pyridin-2-yl}methyl)amino]-N-[(1-ethylpyrrolidin-2-yl)methyl]acetamide | 51 | + | | | ++ | |
| 2-[({4-[N-cyclopropylcarboximidoyl]pyridin-2-yl}methyl)amino]-N-methyl-N-[3-(1H-pyrazol-1-yl)propyl]acetamide | 52 | + | | | ++ | |
| N-(1-benzylpyrrolidin-3-yl)-2-[({4-[N-cyclopropylcarboximidoyl]pyridin-2-yl}methyl)amino]acetamide | 53 | + | + | | ++ | |
| 2-[({4-[N-cyclopropylcarboximidoyl]pyridin-2-yl}methyl)amino]-1-(4-methylpiperazin-1-yl)ethan-1-one | 54 | + | | | ++ | |
| 1-(4-benzylpiperidin-1-yl)-2-[({4-[N-cyclopropylcarboximidoyl]pyridin-2-yl}methyl)amino]ethan-1-one | 55 | + | | | + | |
| 2-[({4-[N-cyclopropylcarboximidoyl]pyridin-2-yl}methyl)amino]-N-methyl-N-(prop-2-yn-1-yl)acetamide | 56 | + | | | + | |
| methyl 2-[({4-[N-cyclopropylcarboximidoyl]pyridin-2-yl}methyl)amino]acetate | 59 | + | | | + | |
| [4-(diethylamino)butyl]({4-[[(2-methoxyethyl)imino]methyl]pyridin-2-yl}methyl)amine | 60 | | ++ | | | |

-continued

| | | HDME INHIBITION | | | | |
|---|---|---|---|---|---|---|
| Compound Name | Compound # | KDM4C | KDM4A | KDM6B | KDM5B | KDM2A |
| 2-[{[2-({[4-(diethylamino)butyl]amino}methyl)pyridin-4-yl]methylidene}amino]ethan-1-ol | 61 | ++ | | | +++ | |
| {[2-({[4-(diethylamino)butyl]amino}methyl)pyridin-4-yl]methylidene}(2,2,3,3,3-pentafluoropropyl)amine | 62 | ++ | | | +++ | |
| 2-[({4-[[(2-cyclohexylethyl)imino]methyl]pyridin-2-yl}methyl)amino]-N-[2-(dimethylamino)ethyl]-N-ethylacetamide | 63 | ++ | | | +++ | |
| [3-(dimethylamino)propyl]({4-[(methoxyimino)methyl]pyridin-2-yl}methyl)amine | 64 | + | | | + | |
| [4-(diethylamino)butyl]({[4-(1-methylimidazolidin-2-yl)pyridin-2-yl]methyl})amine | 65 | + | | | +++ | |
| N-[2-(dimethylamino)ethyl]-N-ethyl-2-[({4-[(((2-hydroxyethyl)imino]methyl]pyridin-2-yl}methyl)amino]acetamide | 66 | ++ | | | +++ | |
| (2-cyclohexylethyl)({[2-({[4-(diethylamino)butyl]amino}methyl)pyridin-4-yl]methylidene})amine | 67 | ++ | | | +++ | |
| [4-(diethylamino)butyl]({[4-(1-methyl-1,3-diazinan-2-yl)pyridin-2-yl]methyl})amine | 68 | ++ | | | +++ | |
| 2-[({4-[5-benzyl-3-(trifluoroacetyl)-1,3-oxazinan-2-yl]pyridin-2-yl}methyl)amino]-N-[2-(dimethylamino)ethyl]-N-ethylacetamide | 90 | | +++ | + | +++ | |
| N-[2-(dimethylamino)ethyl]-N-ethyl-2-[({4-[7-(trifluoroacetyl)-5-oxa-7-azaspiro[2.5]octan-6-yl]pyridin-2-yl}methyl)amino]acetamide | 91 | | +++ | + | +++ | + |
| N-[(2-fluorophenyl)methyl]-2-[({4-[[(2-hydroxyethyl)imino]methyl]pyridin-2-yl}methyl)amino]-N-methylacetamide | 92 | + | | | + | + |
| 2-[({2-[({2-[2-(benzyloxy)phenyl]ethyl}amino)methyl]pyridin-4-yl}methylidene)amino]ethan-1-ol | 93 | + | | | + | + |
| N-(2-cyanoethyl)-N-ethyl-2-[({4-[[(2-hydroxyethyl)imino]methyl]pyridin-2-yl}methyl)amino]acetamide | 94 | + | | | ++ | + |
| (2S)-2-[({4-[[(2-hydroxyethyl)imino]methyl]pyridin-2-yl}methyl)amino]-4-methyl-1-(piperidin-1-yl)pentan-1-one | 95 | + | | | + | + |
| 2-[{4-[[(2-hydroxyethyl)imino]methyl]pyridin-2-yl}methyl)amino]-N-methyl-N-(2-phenylethyl)acetamide | 96 | + | | | + | + |
| 2-{[({4-[(dimethylamino)methyl]cyclohexyl}methyl)amino]methyl}pyridine-4-carbaldehyde | 97 | ++ | | | +++ | |
| 2-({[(2E)-4-(dimethylamino)but-2-en-1-yl]amino}methyl)pyridine-4-carbaldehyde | 98 | ++ | +++ | | +++ | |
| 2-({[(2Z)-4-(dimethylamino)but-2-en-1-yl]amino}methyl)pyridine-4-carbaldehyde | 99 | + | | | + | |
| 2-({[(1-methylpiperidin-4-yl)methyl]amino}methyl)pyridine-4-carbaldehyde | 100 | ++ | | | +++ | |

-continued

HDME INHIBITION

| Compound Name | Compound # | KDM4C | KDM4A | KDM6B | KDM5B | KDM2A |
|---|---|---|---|---|---|---|
| N-[2-(dimethylamino)ethyl]-N-ethyl-2-{[(4-formylpyridin-2-yl)methyl]amino}acetamide | 101 | ++ | ++ | + | +++ | |
| 2-[({2-oxo-2-[(2R)-2-(pyrrolidin-1-ylmethyl)pyrrolidin-1-yl]ethyl}amino)methyl]pyridine-4-carbaldehyde | 102 | ++ | ++ | | ++ | |
| 2-({[2-(4-methylpiperazin-1-yl)-2-oxoethyl]amino}methyl)pyridine-4-carbaldehyde | 103 | + | | | ++ | |
| N-[(1-ethylpyrrolidin-2-yl)methyl]-2-{[(4-formylpyridin-2-yl)methyl]amino}acetamide | 104 | + | | | ++ | |
| N,N-diethyl-2-{[(4-formylpyridin-2-yl)methyl]amino}acetamide | 105 | + | | | ++ | |
| 2-({[2-(4-benzylpiperidin-1-yl)-2-oxoethyl]amino}methyl)pyridine-4-carbaldehyde | 106 | + | | | + | |
| 2-({[4-(diethylamino)butyl]amino}methyl)pyridine-4-carbaldehyde | 107 | ++ | | + | +++ | |
| 2-({[4-(dimethylamino)butyl]amino}methyl)pyridine-4-carbaldehyde | 108 | ++ | | | +++ | |
| 2-[({4-[benzyl(cyclopropyl)amino]butyl}amino)methyl]pyridine-4-carbaldehyde | 109 | + | + | | ++ | |
| 2-({[2-(dimethylamino)ethyl]amino}methyl)pyridine-4-carbaldehyde | 110 | + | | | ++ | |
| 2-({[3-(pyrrolidin-1-yl)propyl]amino}methyl)pyridine-4-carbaldehyde | 111 | + | + | | +++ | |
| N-[4-(diethylamino)butyl]-2-{[(4-formylpyridin-2-yl)methyl]amino}acetamide | 112 | + | | | + | |
| N-(1-benzylpyrrolidin-3-yl)-2-{[(4-formylpyridin-2-yl)methyl]amino}acetamide | 113 | + | | | + | |
| 2-({[5-(dimethylamino)pentyl]amino}methyl)pyridine-4-carbaldehyde | 114 | + | | | +++ | |
| N-[4-(diethylamino)butyl]-2,2,2-trifluoro-N-[(4-formylpyridin-2-yl)methyl]acetamide | 115 | ++ | | | +++ | |
| N-[2-(dimethylamino)-2-methylpropyl]-N-ethyl-2-{[(4-formylpyridin-2-yl)methyl]amino}acetamide | 118 | ++ | | | +++ | |
| 2-({methyl[2-oxo-2-(piperidin-1-yl)ethyl]amino}methyl)pyridine-4-carbaldehyde | 120 | + | | | + | + |

(a)
+++: IC$_{50}$ < 250 nM;
++: 250 nM ≤ IC$_{50}$ ≤ 2500 nM;
+: IC$_{50}$ > 2500 nM

Example 5

Cell Proliferation Assays for EC50 Value Determination

This example demonstrates the ability of the compounds of the invention to inhibit the proliferation of a human breast cancer cell line.

General Method

MCF7 cells were seeded in multi well plates at a density optimized to give approximately 90% confluent cells at the time of harvest. Cells were incubated for 24 hours before addition of compound. Compounds were diluted in complete medium and added to the plates in duplicates. The final concentration of DMSO was maximum 0.5%. Complete medium used was DMEM with GlutaMAX containing 10% FBS and pen/strep.

120 hours after addition of compounds, the plates were harvested and analyzed by ATPlite 1 Step (Perkin Elmer, cat no 6016739) according to the manufactures recommendation.

| Compound Name | Compound # | EC50 |
|---|---|---|
| N-{[2-({[4-(diethylamino)butyl]amino}methyl)pyridin-4-yl]methyl}-2,2,2-trifluoroacetamide | 1 | +++ |
| [2-({[4-(dimethylamino)butyl]amino}methyl)pyridin-4-yl]methanamine | 2 | +++ |
| [2-({[3-(dimethylamino)propyl]amino}methyl)pyridin-4-yl]methanamine | 3 | +++ |
| 2-({[4-(aminomethyl)pyridin-2-yl]methyl}amino)-N-[2-(dimethylamino)ethyl]-N-ethylacetamide | 4 | +++ |
| [2-({[4-(diethylamino)butyl]amino}methyl)pyridin-4-yl]methanamine | 5 | +++ |
| N-[4-(diethylamino)butyl]-2,2,2-trifluoro-N-({4-[(trifluoroacetamido)methyl]pyridin-2-yl}methyl)acetamide | 6 | +++ |
| [2-({[4-(azetidin-1-yl)butyl]amino}methyl)pyridin-4-yl]methanamine | 7 | ++ |
| [2-({[5-(dimethylamino)pentyl]amino}methyl)pyridin-4-yl]methanamine | 8 | +++ |
| 2-({[4-(aminomethyl)pyridin-2-yl]methyl}amino)-N-{1-[(2-methoxyphenyl)methyl]piperidin-4-yl}acetamide | 9 | + |
| 2-({[2-({[3-(dimethylamino)propyl]amino}methyl)pyridin-4-yl]methyl}amino)propanenitrile | 22 | +++ |
| N-[2-{[({[2-(dimethylamino)ethyl](ethyl)carbamoyl}methyl)amino]methyl}pyridin-4-yl)methyl]-2,2,2-trifluoroacetamide | 25 | +++ |
| N-[(2-{[N-({[2-(dimethylamino)ethyl](ethyl)carbamoyl}methyl)-2,2,2-trifluoroacetamido]methyl}pyridin-4-yl)methyl]-2,2,2-trifluoroacetamide | 26 | +++ |
| ({[2-({[4-(diethylamino)butyl]amino}methyl)pyridin-4-yl]methyl}carbamoyl)formic acid | 27 | ++ |
| tert-butyl ({[2-({[4-(diethylamino)butyl]amino}methyl)pyridin-4-yl]methyl}carbamoyl)formate | 28 | ++ |
| ethyl 2-({[(2-{[({[2-(dimethylamino)ethyl](ethyl)carbamoyl}methyl)amino]methyl}pyridin-4-yl)methyl]carbamoyl}oxy)benzoate | 29 | ++ |
| N-[(2-{[({[2-(azetidin-1-yl)ethyl](ethyl)carbamoyl}methyl)amino]methyl}pyridin-4-yl)methyl]-2,2,2-trifluoroacetamide | 30 | +++ |
| N-[(2-{[({[2-(dimethylamino)ethyl](ethyl)carbamoyl}methyl)amino]methyl}pyridin-4-yl)methyl]-2,2,3,3,4,4,4-heptafluorobutanamide | 31 | ++ |
| N-[(2-{[({[2-(dimethylamino)ethyl](ethyl)carbamoyl}methyl)amino]methyl}pyridin-4-yl)methyl]-2,2-difluorobutanamide | 32 | + |
| N,N-dimethyl-2-[({4-[[(3-phenylpropyl)imino]methyl]pyridin-2-yl}methyl)amino]acetamide | 34 | + |
| 2-[({4-[[(2-cyclohexylethyl)imino]methyl]pyridin-2-yl}methyl)amino]-N,N-dimethylacetamide | 36 | ++ |
| [3-(dimethylamino)propyl]({4-[{[3-(dimethylamino)propyl]imino}methyl]pyridin-2-yl}methyl)amine | 37 | +++ |
| ({4-[{[2-(dimethylamino)ethyl]imino}methyl]pyridin-2-yl}methyl)[3-(dimethylamino)propyl]amine | 38 | +++ |
| N-{[2-({[2-(1-methylpyrrolidin-2-yl)ethyl]amino}methyl)pyridin-4-yl]methylidene}cyclopropanamine | 40 | ++ |
| N-{[2-({[3-(pyrrolidin-1-yl)propyl]amino}methyl)pyridin-4-yl]methylidene}cyclopropanamine | 42 | +++ |
| N-{[2-({[(2E)-4-(dimethylamino)but-2-en-1-yl]amino}methyl)pyridin-4-yl]methylidene}cyclopropanamine | 43 | +++ |
| N-{[2-({[4-(azetidin-1-yl)butyl]amino}methyl)pyridin-4-yl]methylidene}cyclopropanamine | 44 | +++ |
| N-[(2-{[({4-[(dimethylamino)methyl]cyclohexyl}methyl)amino]methyl}pyridin-4-yl)methylidene]cyclopropanamine | 46 | +++ |
| 2-[({4-[[(2-cyclohexylethyl)imino]methyl]pyridin-2-yl}methyl)amino]-N,N-diethylacetamide | 57 | + |
| N,N-diethyl-2-[({4-[(octylimino)methyl]pyridin-2-yl}methyl)amino]acetamide | 58 | + |
| [4-(diethylamino)butyl]({4-[[(2-methoxyethyl)imino]methyl]pyridin-2-yl}methyl)amine | 60 | +++ |
| 2-[{[2-({[4-(diethylamino)butyl]amino}methyl)pyridin-4-yl]methylidene}amino]ethan-1-ol | 61 | +++ |
| {[2-({[4-(diethylamino)butyl]amino}methyl)pyridin-4-yl]methylidene}(2,2,3,3,3-pentafluoropropyl)amine | 62 | +++ |
| 2-[({4-[[(2-cyclohexylethyl)imino]methyl]pyridin-2-yl}methyl)amino]-N-[2-(dimethylamino)ethyl]-N-ethylacetamide | 63 | +++ |
| [3-(dimethylamino)propyl]({4-[(methoxyimino)methyl]pyridin-2-yl}methyl)amine | 64 | + |
| [4-(diethylamino)butyl]({[4-(1-methylimidazolidin-2-yl)pyridin-2-yl]methyl})amine | 65 | +++ |
| N-[2-(dimethylamino)ethyl]-N-ethyl-2-[({4-[[(2-hydroxyethyl)imino]methyl]pyridin-2-yl}methyl)amino]acetamide | 66 | +++ |

| Compound Name | Compound # | EC50 |
|---|---|---|
| (2-cyclohexylethyl)({[2-({[4-(diethylamino)butyl]amino}methyl)pyridin-4-yl]methylidene})amine | 67 | +++ |
| [4-(diethylamino)butyl]({[4-(1-methyl-1,3-diazinan-2-yl)pyridin-2-yl]methyl})amine | 68 | +++ |
| N,N-diethyl-2-[({4-[{2-(4-methylphenyl)ethyl]imino}methyl]pyridin-2-yl}methyl)amino]acetamide | 69 | + |
| 4-[2-{[2-({[4-(diethylamino)butyl]amino}methyl)pyridin-4-yl]methylidene}hydrazin-1-yl]benzonitrile | 70 | ++ |
| 3-[{[2-({[4-(diethylamino)butyl]amino}methyl)pyridin-4-yl]methylidene}amino]propan-1-ol | 71 | +++ |
| [4-(diethylamino)butyl][(4-{7-oxa-9-azaspiro[4.5]decan-8-yl}pyridin-2-yl)methyl]amine | 72 | +++ |
| 2-[{[2-({[4-(diethylamino)butyl]amino}methyl)pyridin-4-yl]methylidene}amino]propan-1-ol | 73 | +++ |
| 1-[{[2-({[4-(diethylamino)butyl]amino}methyl)pyridin-4-yl]methylidene}amino]propan-2-ol | 74 | +++ |
| 2-[{[2-({[4-(diethylamino)butyl]amino}methyl)pyridin-4-yl]methylidene}amino]-2-phenylethan-1-ol | 75 | +++ |
| 3-[{[2-({[4-(diethylamino)butyl]amino}methyl)pyridin-4-yl]methylidene}amino]-2,2-dimethylpropan-1-ol | 76 | +++ |
| (1-{[{[2-({[4-(diethylamino)butyl]amino}methyl)pyridin-4-yl]methylidene}amino]methyl}cyclopropyl)methanol | 77 | +++ |
| N-[2-(dimethylamino)ethyl]-N-ethyl-2-[({4-[[(3-hydroxypropyl)imino]methyl]pyridin-2-yl}methyl)amino]acetamide | 78 | +++ |
| N-ethyl-2-[({4-[[(2-hydroxyethyl)imino]methyl]pyridin-2-yl}methyl)amino]-N-[(1-methylpyrrolidin-2-yl)methyl]acetamide | 79 | +++ |
| 2-{[{[2-({[4-(diethylamino)butyl]amino}methyl)pyridin-4-yl]methylidene}amino]methyl}-3-phenylpropan-1-ol | 80 | ++ |
| 2-[({4-[[(2-cyclohexyl-3-hydroxypropyl)imino]methyl]pyridin-2-yl}methyl)amino]-N-[2-(dimethylamino)ethyl]-N-ethylacetamide | 81 | +++ |
| N-[3-(dimethylamino)propyl]-N-ethyl-2-[({4-[[(2-hydroxyethyl)imino]methyl]pyridin-2-yl}methyl)amino]acetamide | 82 | +++ |
| N-[2-(dimethylamino)propyl]-N-ethyl-2-[({4-[[(2-hydroxyethyl)imino]methyl]pyridin-2-yl}methyl)amino]acetamide | 83 | +++ |
| 1-[{[2-({[4-(diethylamino)butyl]amino}methyl)pyridin-4-yl]methylidene}amino]-3-phenylpropan-2-ol | 84 | +++ |
| N-{[(1S,2S)-2-(dimethylamino)cyclopentyl]methyl}-N-ethyl-2-[({4-[[(2-hydroxyethyl)imino]methyl]pyridin-2-yl}methyl)amino]acetamide | 85 | ++ |
| 2-[({4-[{[3-(dimethylamino)-2-hydroxypropyl]imino}methyl]pyridin-2-yl}methyl)amino]-N-[2-(dimethylamino)ethyl]-N-ethylacetamide | 86 | +++ |
| 2-({[4-(5,5-dimethyl-1,3-oxazinan-2-yl)pyridin-2-yl]methyl}amino)-N-[2-(dimethylamino)ethyl]-N-ethylacetamide | 87 | +++ |
| N-[2-(dimethylamino)ethyl]-N-ethyl-2-[({4-[({[1-(hydroxymethyl)cyclopropyl]methyl}imino)methyl]pyridin-2-yl}methyl)amino]acetamide | 88 | +++ |
| 2-[({4-[[(2-benzyl-3-hydroxypropyl)imino]methyl]pyridin-2-yl}methyl)amino]-N-[2-(dimethylamino)ethyl]-N-ethylacetamide | 89 | +++ |
| 2-({4-[5-benzyl-3-(trifluoroacetyl)-1,3-oxazinan-2-yl]pyridin-2-yl}methyl)amino]-N-[2-(dimethylamino)ethyl]-N-ethylacetamide | 90 | +++ |
| N-[2-(dimethylamino)ethyl]-N-ethyl-2-[({4-[7-(trifluoroacetyl)-5-oxa-7-azaspiro[2.5]octan-6-yl]pyridin-2-yl}methyl)amino]acetamide | 91 | +++ |
| N-[(2-fluorophenyl)methyl]-2-[({4-[[(2-hydroxyethyl)imino]methyl]pyridin-2-yl}methyl)amino]-N-methylacetamide | 92 | + |
| 2-[({2-[({2-[2-(benzyloxy)phenyl]ethyl}amino)methyl]pyridin-4-yl}methylidene)amino]ethan-1-ol | 93 | + |
| N-(2-cyanoethyl)-N-ethyl-2-[({4-[[(2-hydroxyethyl)imino]methyl]pyridin-2-yl}methyl)amino]acetamide | 94 | + |
| (2S)-2-[({4-[[(2-hydroxyethyl)imino]methyl]pyridin-2-yl}methyl)amino]-4-methyl-1-(piperidin-1-yl)pentan-1-one | 95 | + |
| 2-{[({4-[(dimethylamino)methyl]cyclohexyl}methyl)amino]methyl}pyridine-4-carbaldehyde | 97 | ++ |
| 2-({[(2E)-4-(dimethylamino)but-2-en-1-yl]amino}methyl)pyridine-4-carbaldehyde | 98 | +++ |
| 2-({[(2Z)-4-(dimethylamino)but-2-en-1-yl]amino}methyl)pyridine-4-carbaldehyde | 99 | + |
| 2-({[(1-methylpiperidin-4-yl)methyl]amino}methyl)pyridine-4-carbaldehyde | 100 | +++ |
| N-[2-(dimethylamino)ethyl]-N-ethyl-2-{[(4-formylpyridin-2-yl)methyl]amino}acetamide | 101 | +++ |

-continued

| Compound Name | Compound # | EC50 |
|---|---|---|
| 2-[({2-oxo-2-[(2R)-2-(pyrrolidin-1-ylmethyl)pyrrolidin-1-yl]ethyl}amino)methyl]pyridine-4-carbaldehyde | 102 | ++ |
| 2-({[4-(diethylamino)butyl]amino}methyl)pyridine-4-carbaldehyde | 107 | +++ |
| 2-({[3-(pyrrolidin-1-yl)propyl]amino}methyl)pyridine-4-carbaldehyde | 111 | +++ |
| N-[4-(diethylamino)butyl]-2,2,2-trifluoro-N-[(4-formylpyridin-2-yl)methyl]acetamide | 115 | +++ |
| N-[2-(diethylamino)ethyl]-N-ethyl-2-{[(4-formylpyridin-2-yl)methyl]amino}acetamide | 116 | +++ |
| 2-[({[3-(dimethylamino)cyclopentyl]methyl}amino)methyl]pyridine-4-carbaldehyde | 117 | ++ |
| N-[2-(dimethylamino)-2-methylpropyl]-N-ethyl-2-{[(4-formylpyridin-2-yl)methyl]amino}acetamide | 118 | +++ |
| N-ethyl-2-{[(4-formylpyridin-2-yl)methyl]amino}-N-[(1-methylpyrrolidin-2-yl)methyl]acetamide | 119 | +++ |

(a) +++: $EC_{50}$ < 250 nM; ++: 250 nM ≤ $EC_{50}$ ≤ 2500 nM; +: $EC_{50}$ > 2500 nM

Example 6

Cell Proliferation Assays for EC50 Value Determination

This example demonstrates the ability of the compounds of the invention to inhibit the proliferation of a human cancer cell lines.

The assays were performed by the method of Example 5 by seeding the relevant cell line at a density optimized to give approximately 90% confluent cells at the time of harvest.

| | | INHIBITION OF CELL PROLIFERATION | | | | | |
|---|---|---|---|---|---|---|---|
| Cell Line | Cell Type | Compound #25 | Compound #42 | Compound #61 | Compound #81 | Compound #90 | Compound #107 |
| A375 | Melanoma | ++ | | | | | |
| AMO1 | Plasmacytoma | | | +++ | | | |
| ARPE19 | Retinal pigmented epithelium | + | + | + | | | + |
| BT474 | Mammary ductal carcinoma | | ++ | +++ | | | +++ |
| EJM | Myeloma | + | | + | | | |
| HCC1954 | Breast dutal carcinoma | + | | | | | |
| HEPG2 | Hepatocellular carcinoma | + | + | + | | | + |
| JJN3 | Plasma cell leukemia | | | + | | | |
| Jurkat Clone E6-1 | Acute T cell lymphoma | + | | | | | |
| K562 | Chronic myelogenous leukemia | ++ | | | | | |
| KARPAS620 | Plasma cell leukemia | | + | +++ | +++ | +++ | |
| KMS 12 BM | Myeloma | +++ | | | | | |
| L1236 | Hodgkin's lymphoma | + | | + | | | |
| L363 | Plasma cell leukemia | + | | + | | | |
| LP1 | Myeloma | | | + | | | |
| MDA MB 231 | Breast carcinoma | + | + | | | | + |
| MIA PACA2 | Pancreas epithelial carcinoma | | + | + | | | + |
| MM1R | Myeloma | | | | | +++ | |
| MM1S | Myeloma | +++ | | | | | |
| MOLP2 | Myeloma | ++ | | | | | + |

-continued

| Cell Line | Cell Type | Compound #25 | Compound #42 | Compound #61 | Compound #81 | Compound #90 | Compound #107 |
|---|---|---|---|---|---|---|---|
| MOLP8 | Myeloma | | | | +++ | +++ | |
| NALM6 | Lymphoblastic leukemia | | +++ | | | | +++ |
| NCIH929 | Myeloma | ++ | | + | | | |
| OPM2 | Myeloma | ++ | + | | | | ++ |
| OVCAR-3 | Ovary | + | | | | | |
| RAJI | Burkitt's lymphoma | + | + | + | | | + |
| RPMI8226 | Myeloma | | + | + | | ++ | + |
| SK MM2 | Plasma cell leukemia | | | ++ | | | |
| SK-MEL-28 | Melanoma | + | | | | | |
| SU DHL6 | B cell lymphoma | +++ | | | | | |
| U266 | Myeloma | | | + | | | |
| U2OS | Osteosarcoma | | + | | | | + |
| UH01 | Hodgkin's lymphoma | | | + | | | |

(a)
+++: $EC_{50} < 250$ nM;
++: $250$ nM $\leq EC_{50} \leq 2500$ nM;
+: $EC_{50} > 2500$ nM Example 7

Inhibition of Tumor Growth in Mouse Xenograft Model

This example demonstrates ability of compounds of the invention to inhibit tumor growth in vivo in the OPM-2 subcutaneous mouse xenograft model of multiple myeloma.

Method

Briefly, NOD/SCID mice γ-irradiated with $^{60}$Co (200 rad) (12 animals/group) were inoculated subcutaneously with 8×106 OPM-2 cells assisted with Matrigel. Dosing according to the table below started when tumors reached an average size of ~100 mm$^3$ (day 15). Dosing continued until the average size of tumors in the vehicle group reached ~2000 mm$^3$ (day 31).

Animals were 7 weeks old female NOD/SCID mice (Mus Musculus), supplied by Beijing HFK Bio-Technology Co. Ltd. (Beijing, china). Body weight was approx. 16-23 g. Before commencement of treatment, all animals were weighed and tumor volumes were measured, and mice were assigned into groups using randomized block design based upon their tumor volumes.

OPM-2 tumor cells were maintained in vitro in RPMI1640 medium supplemented with 20% fetal bovine serum at 37° C. in an atmosphere of 5% $CO_2$ in air. The tumor cells were routinely subcultured twice weekly. The cells growing in an exponential growth phase were harvested and counted for tumor inoculation.

Tumor sizes were measured three times weekly in two dimensions using a caliper, and the volume was expressed in mm$^3$ using the formula: $V=0.5a \times b^2$ where a and b were the long and short diameters of the tumor, respectively.

| Days after inoculation | Vehicle BID x 14 | Positive control Lenolidomide QDx4/week x 2 i.p. 20 mg/kg | Compound #61 BID x 14 i.p. 20 mg/kg | Compound #61 BID x 14 i.p. 10 mg/kg | Compound #61 BID x 14 i.p. 1 mg/kg |
|---|---|---|---|---|---|
| | | | Tumor Volume (mm$^3$) | | |
| 15 | 101 ± 11 | 101 ± 12 | 101 ± 12 | 101 ± 11 | 101 ± 12 |
| 17 | 276 ± 19 | 156 ± 26 | 188 ± 25 | 198 ± 28 | 249 ± 32 |
| 19 | 406 ± 36 | 178 ± 36 | 292 ± 50 | 276 ± 44 | 320 ± 45 |
| 21 | 643 ± 59 | 266 ± 56 | 440 ± 77 | 519 ± 67 | 577 ± 85 |
| 24 | 1047 ± 86 | 395 ± 92 | 766 ± 143 | 694 ± 92 | 951 ± 124 |
| 26 | 1313 ± 108 | 509 ± 116 | 1029 ± 196 | 928 ± 136 | 1259 ± 169 |
| 28 | 1776 ± 142 | 767 ± 169 | 1298 ± 236 | 1289 ± 178 | 1800 ± 202 |
| 31 | 2473 ± 213 | 1148 ± 175 | 1573 ± 261 | 1996 ± 302 | 2864 ± 334 |

LIST OF REFERENCES

Catchpole S et al., Int. J. Oncol. 38, 1267-77, 2011
Cloos, P. a. C. et al. (2008), Genes. Dev. 22; 115-1140
Cloos, P. Et al., Nature 442, 307-11, 2006
Fischle, W., et. Al., Curr. Opinion Cell Biol. 15, 172-83, 2003
Hayami S. et al. (2010) Mol. Cancer 9
He J et al., Blood 117 (14), 3869-80, 2011
He J et al. Nat Struct Mol Biol 15(11), 2008
Kelly, T. K. et al. (2010), "Epigenetic modifications as therapeutic targets", Nat. Biotechnol. 28; 1069-1078
Klose, R. J. et al., Nature 442, 312-16, 2006
Liu, G. Et al., Oncogene 28, 4491-500, 2009
Margueron, R., et al., Curr. Opinion Genet. Dev. 15, 163-76, 2005
Morton and Houghton, "Establishment of human tumor xenografts in immunodeficient mice", Nature Protocols, 2 (2) 247-250, 2007
Pfau R et al., PNAS 105(6), 1907-12, 2008
Queguiner, G. and Pastour, P., Comptes Rendus des Seances de l'Académie des Sciences, Série C: Sciences Chimiques, 268(2) 182-5, 1969.
Quina, A. S. et al. (2006), "Chromatin structure and epigenetics", Biochem. Pharmacol. 72; 1563-1569

Roy et al. PerkinElmer Technical Note: AlphaLISA #12, April 2011

Tzatsos A et al., PNAS 106 (8), 2641-6, 2009
Yamane K. et al., Mol. Cell 25, 801-12, 2007
Xiang Y. et al. (2007) PNAS 104

The invention claimed is:

1. A compound of the Formula (I)

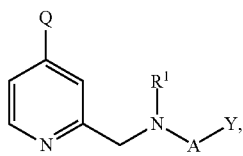

wherein

Q is selected from —CH=NR$^{12}$, —W, —CH$_2$NHR$^{13}$, —CH=O and —CH(OR$^{17}$)$_2$;

A is —CH$_2$C(O)—;

Y is —NR$^6$R$^7$;

R$^1$ is —H;

each R$^3$ is independently selected from C$_{1-6}$ alkyl, C$_{1-4}$ fluoroalkyl, C$_{1-4}$ hydroxyalkyl, C$_{2-6}$ alkenyl, C$_{2-6}$ alkynyl, C$_{3-10}$ cycloalkyl, —Z-heterocyclyl, —Z-aryl, —Z-heteroaryl, —Z—NR$^6$R$^7$, —Z—C(=O)—NR$^6$R$^7$, —Z—NR$^6$—C(=O)—R$^7$, —Z—C(=O)—R$^7$, —Z—OR$^7$, halogen, —Z—SR$^7$, —Z—SOR$^7$, —Z—SO$_2$R$^7$, —Z—SO$_2$NR$^6$R$^7$ and —Z—COOR$^7$, wherein any heterocyclyl may be substituted with one or more R$^4$, and wherein any heteroaryl and any aryl may be substituted with one or more R$^5$;

Z is selected from a single bond, C$_{1-4}$ alkylene, heterocyclylene and C$_{3-6}$ cycloalkylene;

each R⁴ is independently selected from C₁₋₆ alkyl, C₁₋₄ fluoroalkyl, C₁₋₄ hydroxyalkyl, C₁₋₄ alkoxy, C₃₋₁₀ cycloalkyl, —N(R¹⁰)₂, carbamoyl, and —OH;

each R⁵ is independently selected from C₁₋₆ alkyl, C₁₋₄ fluoroalkyl, C₁₋₄ hydroxyalkyl, C₁₋₄ alkoxy, C₃₋₆ cycloalkyl, —CN, —F, —Cl, —Br, carbamoyl and —OH;

each of R⁶ and R⁷ is independently selected from —H, C₁₋₈ alkyl, C₁₋₄ fluoroalkyl, C₁₋₄ perfluoroalkyl, C₁₋₄ hydroxyalkyl, C₂₋₈ alkenyl, C₂₋₈ alkynyl, C₃₋₁₀ cycloalkyl, —Z-heterocyclyl, —Z-heteroaryl and —Z-aryl, which alkyl, alkenyl, alkynyl, cycloalkyl, heterocyclyl, heteroaryl and aryl may optionally be substituted with one or more independently selected R⁸; or, alternatively, R⁶ and R⁷ may together with the N-atom to which they are attached form an N-heterocyclic ring optionally substituted with one or more independently selected R⁸;

each R⁸ is independently selected from C₁₋₆ alkyl, C₁₋₄ fluoroalkyl, C₁₋₄ hydroxyalkyl, C₂₋₆ alkenyl, C₂₋₆ alkynyl, C₃₋₁₀ cycloalkyl, —Z-heterocyclyl, —Z-heteroaryl, —Z-aryl, —Z—NR¹⁰R¹¹, —Z—C(=O)—NR¹⁰R¹¹, —Z—OR⁹, halogen, —CN, —Z—SR⁹, —Z—SOR⁹, —Z—SO₂R⁹ and —Z—COOR⁹, which alkyl, alkenyl, alkynyl, cycloalkyl, heterocyclyl, heteroaryl and aryl may optionally be substituted with one or more selected from C₁₋₄ alkyl, C₁₋₄ fluoroalkyl, C₁₋₄ hydroxyalkyl, C₃₋₆ cycloalkyl, —Z-heterocyclyl, —Z-heteroaryl, —Z-aryl, —Z—NR¹⁰R¹¹, —Z—C(=O)—NR¹⁰R¹¹, —Z—OR⁹, halogen, —CN, —Z—SR⁹, —Z—SOR⁹, —Z—SO₂R⁹ and —Z—COOR⁹; wherein any heterocyclyl may be further substituted with one or more R⁴ as defined above, and wherein any heteroaryl and any aryl may be further substituted with one or more R⁵ as defined above, and each R⁹ is independently selected from —H, C₁₋₈ alkyl, C₁₋₄ fluoroalkyl, C₁₋₄ hydroxyalkyl, C₂₋₈ alkenyl, C₂₋₈ alkynyl, C₃₋₁₀ cycloalkyl, —Z-heterocyclyl, —Z-aryl, and —Z-heteroaryl, wherein any heterocyclyl may be substituted with one or more R⁴ as defined above, and wherein any heteroaryl and any aryl may be substituted with one or more R⁵ as defined above;

each of R¹⁰ and R¹¹ is independently selected from —H, C₁₋₆ alkyl, C₁₋₄ fluoroalkyl, C₁₋₄ hydroxyalkyl, C₂₋₈ alkenyl, C₂₋₈ alkynyl, C₃₋₁₀ cycloalkyl, heterocyclyl, heteroaryl, and aryl, wherein any heterocyclyl may be substituted with one or more R⁴ as defined above, and wherein any heteroaryl and any aryl may be substituted with one or more R⁵ as defined above, or, alternatively, R¹⁰ and R¹¹ may together with the N-atom to which they are attached form an N-heterocyclic ring optionally substituted with one or more R⁴ as defined above;

when Q is —CH=NR¹², R¹² is selected from C₁₋₁₀ alkyl, C₂₋₁₀ alkenyl, C₂₋₁₀ alkynyl, C₃₋₁₀ cycloalkyl, —Z-heterocyclyl, —Z-aryl, —Z-heteroaryl, —Z—NR⁶R⁷, —Z—C(=O)—NR⁶R⁷, —Z—NR⁶—C(=O)—R⁷, —Z—C(=O)—R⁷, —Z—OR⁷, halogen, —Z—SR⁷, —Z—SOR⁷, —Z—SO₂R⁷ and —Z—COOR⁷, which alkyl, alkenyl, alkynyl, cycloalkyl, heterocyclyl, heteroaryl and aryl may optionally be substituted with one or more R³;

when Q is —CH₂NHR¹³, R¹³ is selected from hydrogen, —C(O)R⁷, —C(O)C(O)R⁷, —R⁷, —CR¹⁴R¹⁵—NR⁶R⁷, —CR¹⁴R¹⁵CN, —CR¹⁴R¹⁵OR⁷, wherein each of R¹⁴ and R¹⁵ is independently selected from —H, C₁₋₈ alkyl, C₂₋₈ alkenyl, C₂₋₈ alkynyl, C₃₋₁₀ cycloalkyl, heterocyclyl, heteroaryl and aryl, and wherein R¹⁴ and R¹⁵ together with the intervening carbon atom may designate a C₃₋₁₀ cycloalkyl or C₅₋₁₀-cycloalkenyl ring, which alkyl, alkenyl, alkynyl, cycloalkyl ring, cycloalkenyl ring, heterocyclyl, heteroaryl and aryl may optionally be substituted with one or more R³;

when Q is W, W is selected from an 1,3-diaza-C₅₋₇-cycloalk-2-yl group which is N-substituted with R¹⁶ and optionally further substituted with one or more R³, and an 1,3-oxaza-C₅₋₇-cycloalk-2-yl group which is N-substituted with R¹⁶ and optionally further substituted with one or more R³, wherein in both instances two R³'s on the same carbon atom may together form a spiro group R¹⁶ is selected from hydrogen, —C(O)R⁷, and —C(O)C(O)R⁷, and —C(O)C(O)R⁷;

when Q is —CH(OR¹⁷)₂, each R¹⁷ independently is R³, or wherein two R¹⁷ substituents together with the intervening —O—CH(-)—O— may form a heterocyclyl optionally substituted with one or more R³ and containing up to two oxo groups;

or an isomer or a mixture of isomers thereof, or a pharmaceutically acceptable salt or solvate thereof.

2. A compound having the structure

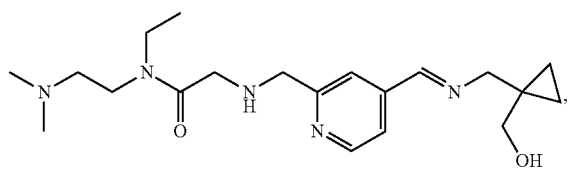 [SMILES: CCN(CCN(C)C)C(=O)CNCc1cc(/C=N/CC2(CO)CC2)ccn1]

or a salt or solvate thereof.

3. A compound having the structure

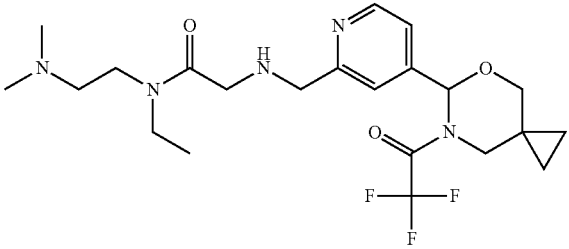

or a salt or solvate thereof.

4. A compound having the structure

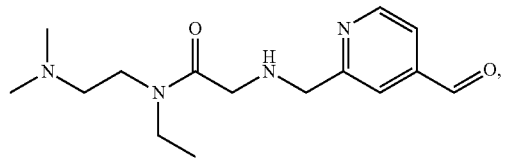 [SMILES: CCN(CCN(C)C)C(=O)CNCc1cc(C=O)ccn1]

or a salt or solvate thereof.

5. The compound of claim 1, wherein the compound is an acid addition salt.

6. The compound of claim 5, wherein the acid is selected from succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic, galacturonic, benzenesulfonic, p-toluenesulfonic, oxalic, methanesulfonic, and naphthalenesulfonic acid.

7. The compound of claim 6, wherein the acid is p-toluenesulfonic or oxalic.

8. The compound of claim 2, wherein the compound is an acid addition salt.

9. The compound of claim 8, wherein the acid is selected from succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic, galacturonic, benzenesulfonic, p-toluenesulfonic, oxalic, methanesulfonic, and naphthalenesulfonic acid.

10. The compound of claim 9, wherein the acid is p-toluenesulfonic or oxalic.

11. The compound of claim 3, wherein the compound is an acid addition salt.

12. The compound of claim 11, wherein the acid is selected from succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic, galacturonic, benzenesulfonic, p-toluenesulfonic, oxalic, methanesulfonic, and naphthalenesulfonic acid.

13. The compound of claim 12, wherein the acid is p-toluenesulfonic or oxalic.

14. The compound of claim 4, wherein the compound is an acid addition salt.

15. The compound of claim 14, wherein the acid is selected from succinic, maleic, acetic, fumaric, citric, tartaric, benzoic, trifluoroacetic, malic, lactic, formic, propionic, glycolic, gluconic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), ethanesulfonic, pantothenic, stearic, sulfinilic, alginic, galacturonic, benzenesulfonic, p-toluenesulfonic, oxalic, methanesulfonic, and naphthalenesulfonic acid.

16. The compound of claim 15, wherein the acid is p-toluenesulfonic or oxalic.

17. A pharmaceutical composition comprising a compound of claim 1 and one or more pharmaceutically acceptable excipients, diluents or carriers.

18. A method of treating cancer in a subject, comprising administering to said subject a therapeutically effective amount of at least one compound of claim 1, wherein the cancer is squamous cell carcinoma.

19. The method of claim 18, wherein the squamous cell carcinoma is located in the skin, lips, mouth, esophagus, urinary bladder, prostate, lungs, vagina, or cervix.

20. A method of treating cancer in a subject, comprising administering to said subject a therapeutically effective amount of at least one compound of claim 1, wherein the cancer is selected from the group consisting of leukemia, lymphoma, oral cancer, laryngeal cancer, esophageal cancer, prostate cancer, bladder cancer, renal cancer, uterine cancer, ovarian cancer, testicular cancer, rectal cancer, colon cancer, lung cancer, brain cancer, breast cancer, pancreatic cancer, stomach cancer, liver cancer, thyroid cancer, melanoma, and multiple myeloma.

21. A method for inhibiting a histone demethylase, comprising contacting a cell with a compound of claim 1 in an amount effective to produce a concentration sufficient to inhibit the demethylation of a histone in a cell.

22. The method of claim 21, wherein the histone demethylase is a member of the KDM6 family, KDM5 family, KDM4 family, KDM3 family, or KDM2 family.

23. The compound of claim 1, or an isomer or a mixture of isomers thereof, or a pharmaceutically acceptable salt or solvate thereof, wherein the compound is selected from the group consisting of:

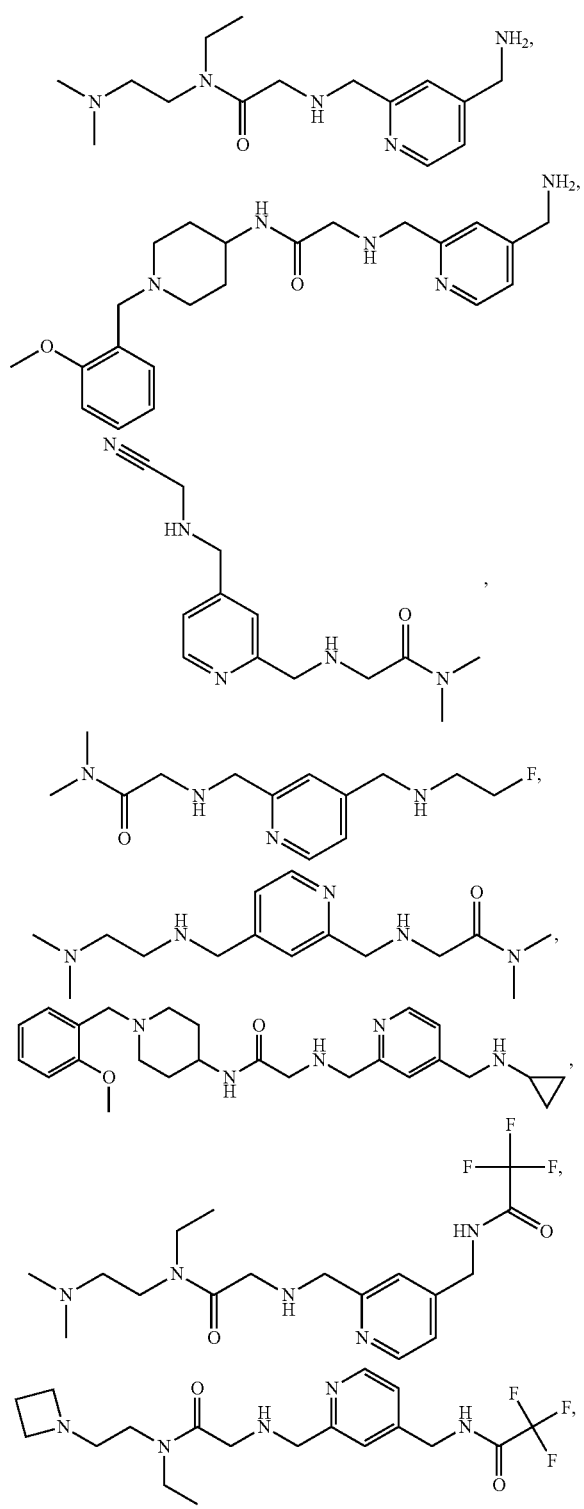

171
-continued
172
-continued
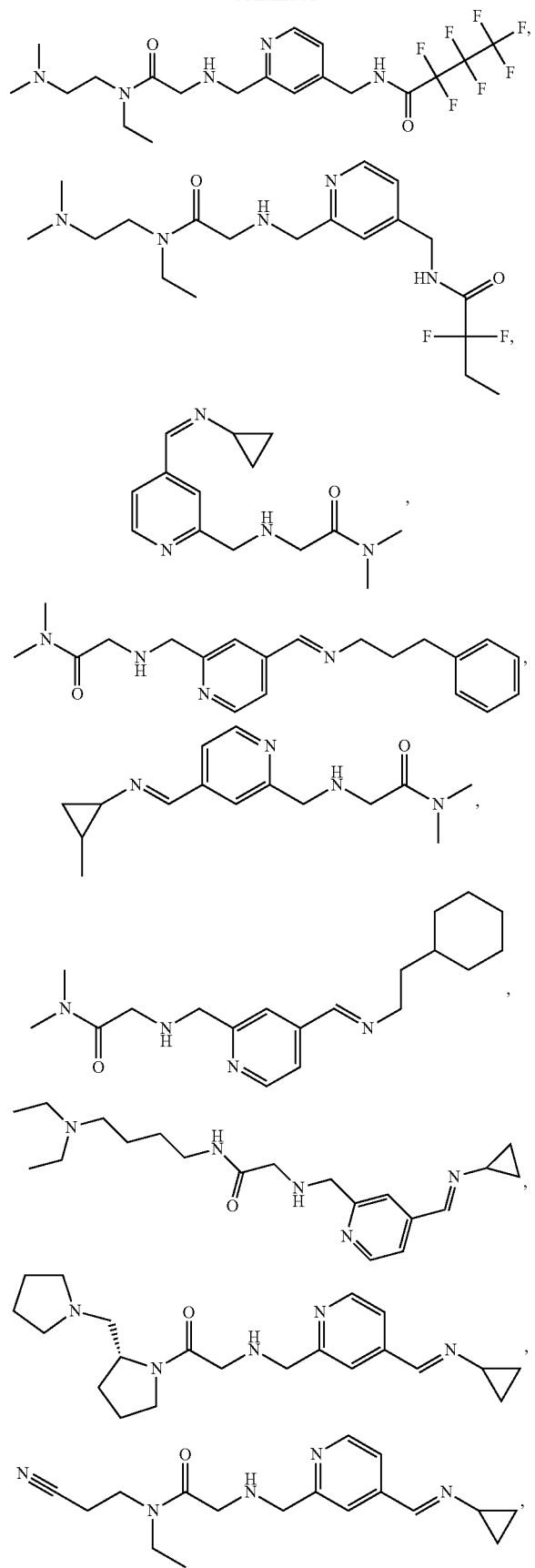
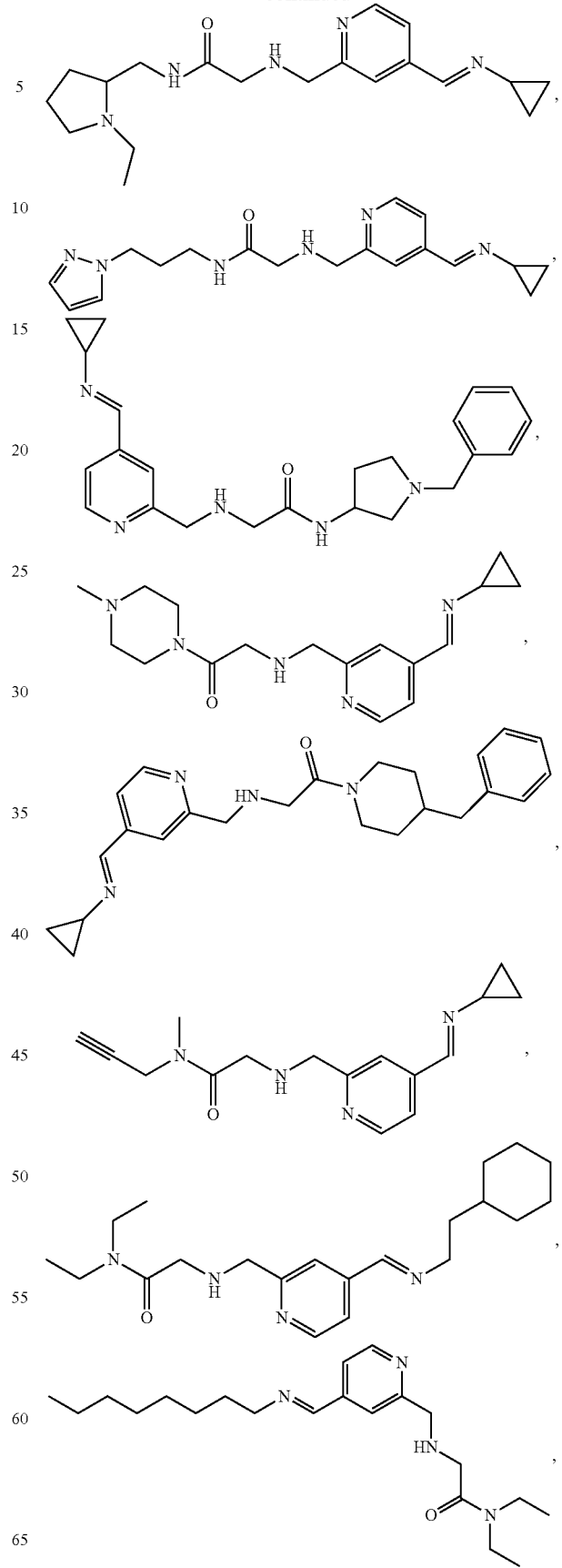

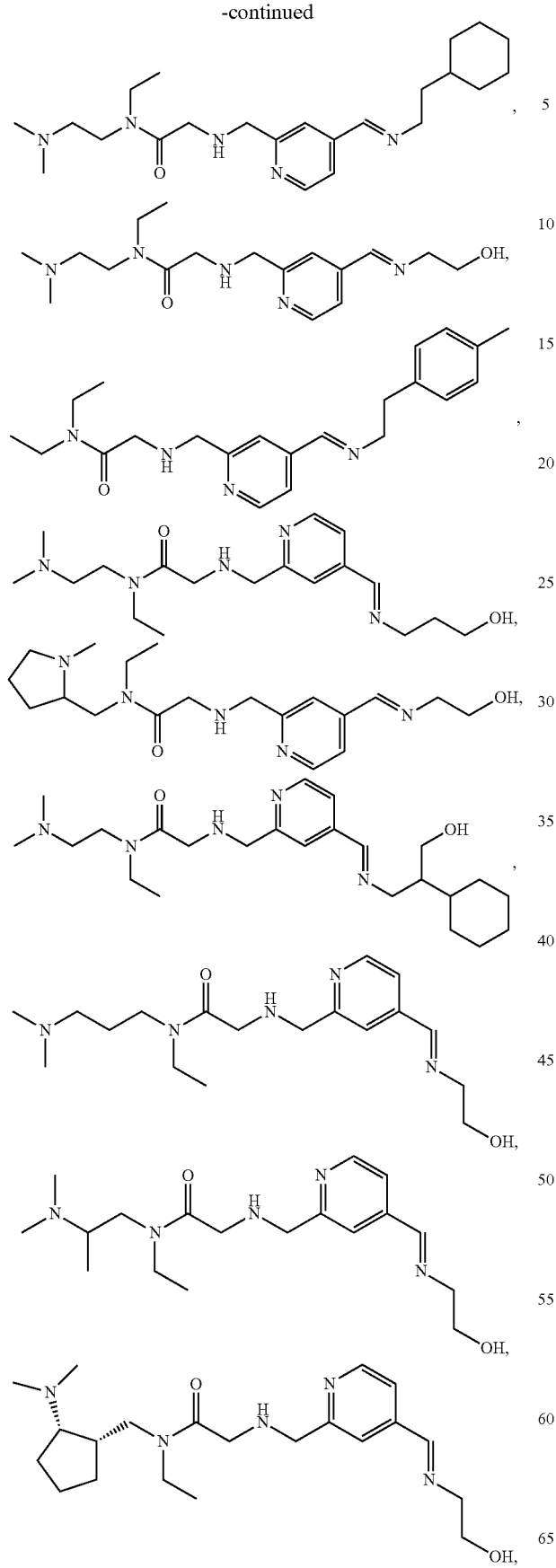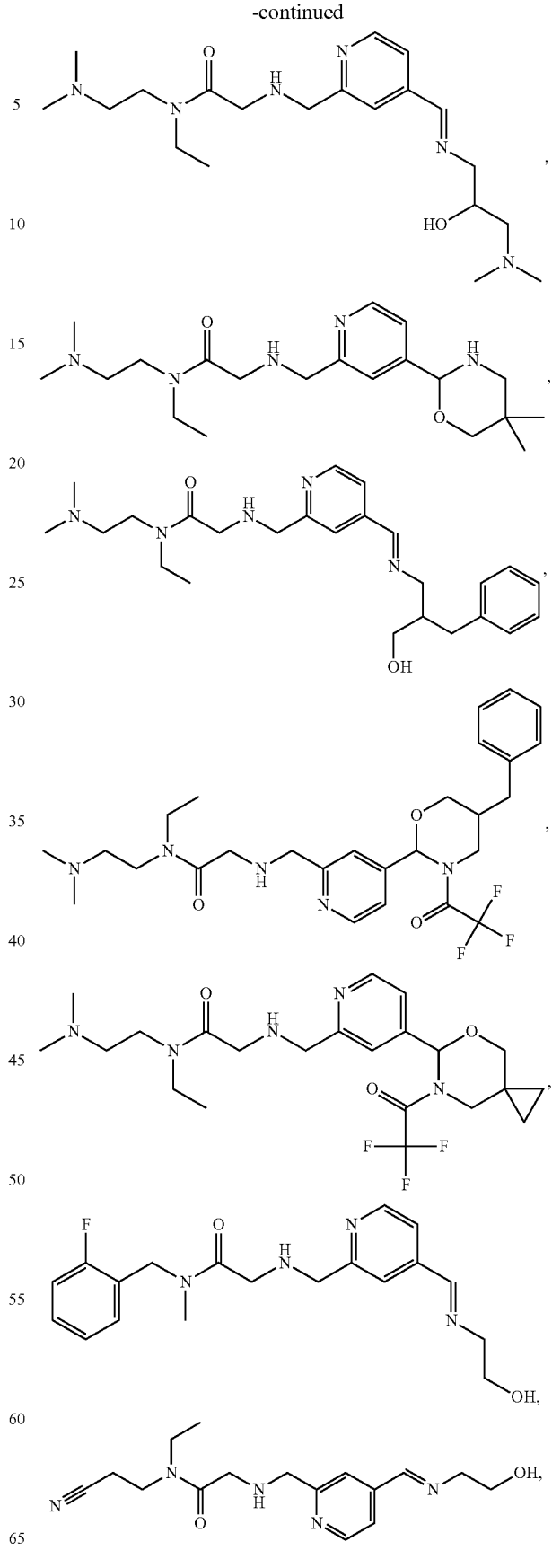

175
-continued
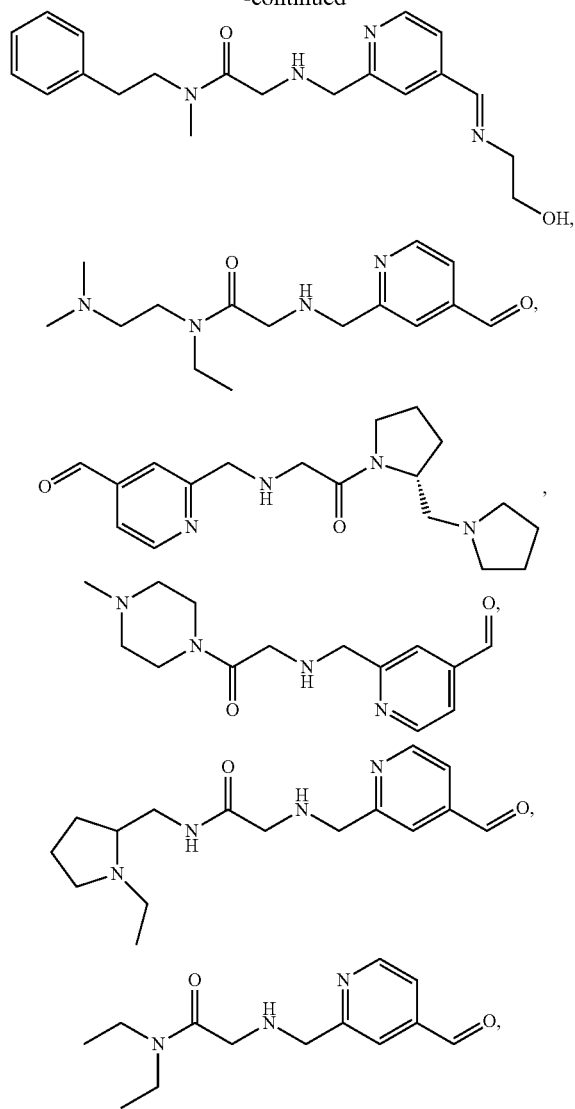
176
-continued
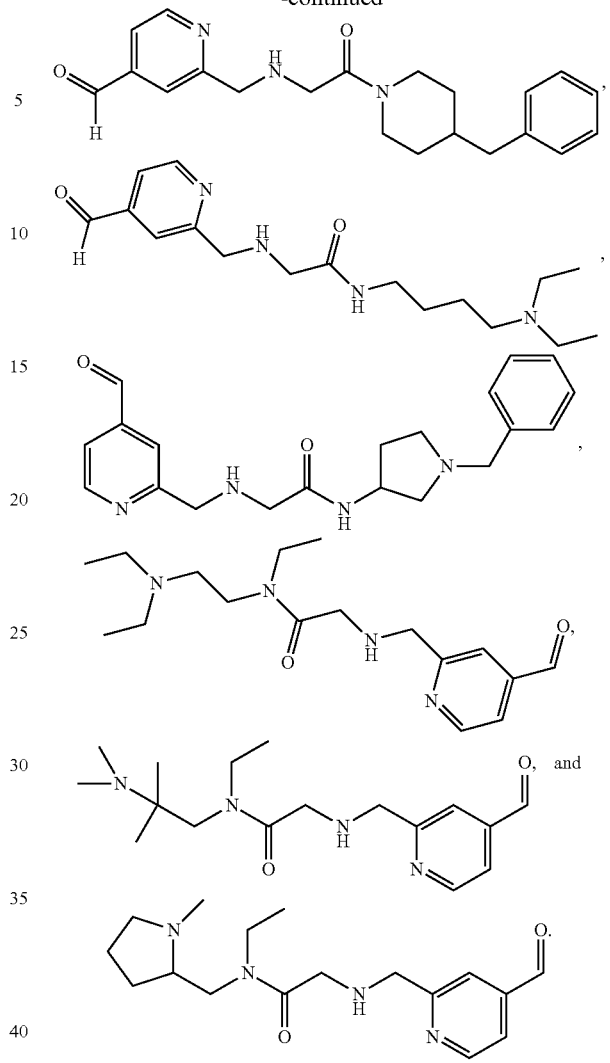
* * * * *